US012692236B2

(12) United States Patent
Schiltz et al.

(10) Patent No.: US 12,692,236 B2
(45) Date of Patent: Jul. 28, 2026

(54) SMALL MOLECULE MODULATORS OF SIGMA-1 AND SIGMA-2 RECEPTORS AND USES THEREOF

(71) Applicant: Northwestern University, Evanston, IL (US)

(72) Inventors: Gary E. Schiltz, Naperville, IL (US); Iredia D. Iyamu, Evanston, IL (US); Rama K. Mishra, Chicago, IL (US); Wei Lv, Evanston, IL (US); Neha Malik, Evanston, IL (US)

(73) Assignee: Northwestern University, Evanston, IL (US)

( * ) Notice: Subject to any disclaimer, the term of this patent is extended or adjusted under 35 U.S.C. 154(b) by 763 days.

(21) Appl. No.: 17/296,867

(22) PCT Filed: Nov. 26, 2019

(86) PCT No.: PCT/US2019/063357

§ 371 (c)(1),
(2) Date: May 25, 2021

(87) PCT Pub. No.: WO2020/112846

PCT Pub. Date: Jun. 4, 2020

(65) Prior Publication Data

US 2023/0041761 A1 Feb. 9, 2023

Related U.S. Application Data

(60) Provisional application No. 62/771,826, filed on Nov. 27, 2018.

(51) Int. Cl.

| | |
|---|---|
| *C07D 231/00* | (2006.01) |
| *A61K 31/416* | (2006.01) |
| *A61K 31/4178* | (2006.01) |
| *A61K 31/422* | (2006.01) |
| *A61K 31/437* | (2006.01) |
| *A61K 31/4439* | (2006.01) |
| *A61K 31/454* | (2006.01) |
| *A61K 31/4545* | (2006.01) |
| *A61K 31/4725* | (2006.01) |
| *A61K 31/496* | (2006.01) |
| *A61K 31/4985* | (2006.01) |
| *A61K 31/506* | (2006.01) |
| *A61K 31/5377* | (2006.01) |
| *A61K 31/551* | (2006.01) |
| *A61K 47/55* | (2017.01) |
| *A61K 47/64* | (2017.01) |
| *C07D 231/56* | (2006.01) |
| *C07D 401/12* | (2006.01) |
| *C07D 401/14* | (2006.01) |
| *C07D 403/12* | (2006.01) |
| *C07D 405/12* | (2006.01) |
| *C07D 413/12* | (2006.01) |
| *C07D 471/04* | (2006.01) |
| *C07D 487/04* | (2006.01) |

(52) U.S. Cl.

CPC .......... *C07D 231/56* (2013.01); *A61K 31/416* (2013.01); *A61K 31/4178* (2013.01); *A61K 31/422* (2013.01); *A61K 31/437* (2013.01); *A61K 31/4439* (2013.01); *A61K 31/454* (2013.01); *A61K 31/4545* (2013.01); *A61K 31/4725* (2013.01); *A61K 31/496* (2013.01); *A61K 31/4985* (2013.01); *A61K 31/506* (2013.01); *A61K 31/5377* (2013.01); *A61K 31/551* (2013.01); *A61K 47/55* (2017.08); *A61K 47/64* (2017.08); *C07D 401/12* (2013.01); *C07D 401/14* (2013.01); *C07D 403/12* (2013.01); *C07D 405/12* (2013.01); *C07D 413/12* (2013.01); *C07D 471/04* (2013.01); *C07D 487/04* (2013.01)

(58) Field of Classification Search

CPC ........... A61K 31/4409; A61K 31/4439; A61K 31/444; A61K 31/454; A61K 31/4545; C07D 231/56

See application file for complete search history.

(56) References Cited

U.S. PATENT DOCUMENTS

| | | |
|---|---|---|
| 3,989,816 A | 11/1976 | Rajadhyaksha |
| 4,444,762 A | 4/1984 | Rajadhyaksha |
| 5,770,581 A | 6/1998 | Weichselbaum et al. |

(Continued)

FOREIGN PATENT DOCUMENTS

| | | | |
|---|---|---|---|
| ES | 2251317 | 4/2006 | |
| ES | 2251317 B1 * | 3/2007 | ........... A61K 31/416 |
| WO | WO-2016179349 A1 * | 11/2016 | .............. A61P 35/00 |

OTHER PUBLICATIONS

Lyamu et al. Development of Tetrahydroindazole-Based Potent and Selective Sigma-2 Receptor Ligands. ChemMedChem. 2019, vol. 14, pp. 1248-1256. (Year: 2019).*

(Continued)

*Primary Examiner* — Jeanette M Lieb

(74) *Attorney, Agent, or Firm* — Casimir Jones, S.C.; Robert A. Goetz

(57) ABSTRACT

This invention is in the field of medicinal chemistry. In particular, the invention relates to anew class of small-molecules having a tetrahydroindazole structure which function as modulators (e.g., activators or inhibitors) of sigma-1 and/or sigma-2 receptors, and their use as therapeutics for the treatment of cancer and other diseases (e.g., neurological conditions) characterized with sigma-1 and/or sigma-2 receptor activity.

7 Claims, 48 Drawing Sheets

(56) References Cited

U.S. PATENT DOCUMENTS

| | | | | |
|---|---|---|---|---|
| 10,435,375 | B2 * | 10/2019 | Schiltz | C07D 401/14 |
| 2007/0249564 | A1 | 10/2007 | Erion et al. | |
| 2011/0015183 | A1 * | 1/2011 | Corbera Arjona | A61K 31/496 514/307 |
| 2018/0155295 | A1 * | 6/2018 | Schiltz | C07D 401/04 |

OTHER PUBLICATIONS

Iyamu, Id, et al. "Discovery of a novel class of potent and selective tetrahydroindazole-based sigma-1 receptor ligands". Bioorganic & Medicinal Chemistry, vol. 27, No. 9, May 1, 2019. (Year: 2019).*
Pubchem. N,N-Dimethyl-1-propyl-4,5,6,7-tetrahydroindazole-3-carboxamide. Jun. 12, 2019, p. 1-6 [online], [retrieved on Feb. 5, 2020]. Retrieved from the Internet ; p. 2. (Year: 2019).*
Rodriguez-Munoz, M et al., The ON:OFF switch, σ1R-HINT1 protein, controls GPCR-NMDA receptor cross-regulation: Implications in neurological disorders, Oncotarget 2015, 6(34), 35458-77.
Sabino V, et al., Sigma Receptors and Substance Use Disorders, Adv Exp Med Biol. 2017; 964: 177-199.
Sabino, V. et al., Sigma-1 receptor knockout mice display a depressive-like phenotype, Behavioural brain research 2009, 198(2), 472-476.
Sachau J, et al., Patient Reported Outcome Measures in Chronic Neuropathic Pain Clinical Trials - A Systematic Literature Review, The Journal of Pain, 24(1), 2023: pp. 38-54.
Sadeghzadeh M, et al., Radioiodination and preclinical evaluation of 4-benzyl-1-(3-[1251]-iodobenzylsulfonyl)piperidine as a breast tumor imaging tracer in mouse, Ann Nucl Med. May 2017;31(4): 335-346.
Sahn, J. J. et al., Sigma 2 Receptor/Tmem97 Agonists Produce Long Lasting Antineuropathic Pain Effects in Mice, ACS chemical neuroscience 2017, 8(8): 1801-1811.
Sahn, J. J. et al., Norbenzomorphan Scaffold: Chemical Tool for Modulating Sigma Receptor-Subtype Selectivity, Acs Med Chem Lett 2017, 8(4), 455-460.
Sahn, J. J. et al., Norbenzomorphan Framework as a Novel Scaffold for Generating Sigma 2 Receptor/PGRMC1 Subtype Selective Ligands, ChemMedChem 2016, 11(6): 556-61.
Salvino JM, et al., Novel small molecule guanidine Sigma1 inhibitors for advanced prostate cancer, Bioorg Med Chem Lett. May 15, 2017; 27(10): 2216-2220.
Schrock, J. M. et al., Sequential Cytoprotective Responses to Sigma1 Ligand-Induced Endoplasmic Reticulum Stress, Mol Pharmacol 2013, 84(5), 751-62.
Scott LL, et al., Small molecule modulators of o2R/Tmem97 reduce alcohol withdrawal-induced behaviors, Neuropsychopharmacology. Aug. 2018; 43(9):1867-1875.
Seth, P. et al., Expression pattern of the type 1 sigma receptor in the brain and identity of critical anionic amino acid residues in the ligand-binding domain of the receptor, Biochimica et biophysica acta 2001, 1540 (1), 59-67.
Sun D, et al., Potential Roles of Mitochondria-Associated ER Membranes (MAMs) in Traumatic Brain Injury, Cell Mol Neurobiol. Nov. 2017; 37(8): 1349-1357.
Sun YT, et al., Synthesis and pharmacological evaluation of 6,7-dimethoxy-1,2,3,4-tetrahydroisoquinoline derivatives as sigma-2 receptor ligands, Eur J Med Chem. Mar. 10, 2017;147:227-237.
Sun, H. et al., Development of Novel Alkoxyisoxazoles as Sigma-1 Receptor Antagonists with Anti-Nociceptive Efficacy, J Med Chem 2016, 59 (13), 6329-43.
Tadić V, et al., Sigma 1 receptor activation modifies intracellular calcium exchange in the G93AhSOD1 ALS model, Neuroscience. Sep. 17, 2017; 359:105-118.
Tejada MÁ, et al., Targeting immune-driven opioid analgesia by sigma-1 receptors:Opening the door to novel perspectives for the analgesic use ofsigma-1 antagonists, Pharmacol Res. May 2018; 131:224-230.
Thomas JD, et al., Sigma1 Targeting to Suppress Aberrant Androgen Receptor Signaling in Prostate Cancer, Cancer Res. May 1, 2017;77(9):2439-2452.
Uchida N, et al., A Variant of the Sigma Receptor Type-1 Gene Is a Protective Factor for Alzheimer Disease, Am J Geriatr Psychiatry 13:12, Dec. 2005: 1062-6.
Valenza M, et al., Ethanol-related behaviors in mice lacking the sigma-1 receptor, Behavioural Brain Research 297 (2016) 196-203.
Vázquez-Rosa E, et al., Neuroprotective Efficacy of a Sigma 2 Receptor/TMEM97 Modulator (DKR-1677) after Traumatic Brain Injury; ACS Chem Neurosci. Nov. 13, 2018; 1595-1602.
Vilner, B. J. et al., Sigma-i and Sigma-2 Receptors Are Expressed in a Wide Variety of Human and Rodent Tumor Cell Lines, Cancer Res. 1995, 55 (2), 408-13.
Wang X, et al., Sigma 1 receptor mediated HMGB1 expression in spinal cord is involved in the development of diabetic neuropathic pain, Neurosci Lett. Mar. 6, 2018; 668: 164-168.
Weng TY, Roles of sigma-1 receptors on mitochondrial functions relevant to neurodegenerative diseases, Journal of Biomedical Science (2017) 24:74, 14 pgs.
Wheeler, K. T. et al., Sigma-2 receptors as a biomarker of proliferation in solid tumours, British journal of cancer 2000, 82 (6), 1223-32.
Xu Q, et al., Sigma-1 receptor (01R) is downregulated in hepatic malignant tumors and regulates HepG2 cell proliferation, migration and apoptosis, Oncology Reports 39: 1405-1413, 2018.
Xu, J. et al., Identification of the PGRMC1 protein complex as the putative sigma-2 receptor binding site, Nat Commun; 2: 380, 2013.
Yamamoto, H. et al., Amino acid residues in the transmembrane domain of the type 1 sigma receptor critical for ligand binding, FEBS Letters 445 (1999) 1922.
Yang D, et al., Design and Investigation of a [18F]-Labeled Benzamide Derivative as a High Affinity Dual Sigma Receptor Subtype Radioligand for Prostate Tumor Imaging, Mol Pharm. Mar. 6, 2017;14(3): 770-780.
Yi, B. et al., Small molecule modulator of sigma 2 receptor is neuroprotective and reduces cognitive deficits and neuro-inflammation in experimental models of Alzheimer's disease, Journal of neurochemistry 2017, 140 (4), 561-575.
Zeng, C. et al., Sigma-2 ligands induce tumour cell death by multiple signalling pathways, British Journal of Cancer (2012) 106, 693-701.
International Search Report and Written Opinion; International Application No. PCT/US19/63357; mailed Apr. 9, 2020; pp. 1-12.
Alon, A. et al., Identification of the gene that codes for the o2 receptor, Proceedings of the National Academy of Sciences 2017, 114 (27), 7160-7165.
Al-Saif, A et al., A Mutation in Sigma-1 Receptor Causes Juvenile Amyotrophic Lateral Sclerosis, Annals of neurology 2011, 70 (6), 913-9.
Bai, S. et al., Synthesis and Structure-Activity Relationship Studies of Conformationally Flexible Tetrahydroisoquinolinyl Triazole Carboxamide and Triazole Substituted Benzamide Analogues as 02 Receptor Ligands, J Med Chem 2014, 57 (10), 4239-51.
Baum E, et al., PET Imaging Evaluation of Four s1 Radiotracers in Nonhuman Primates, J Nucl Med. Jun. 2017; 58 (6):982-988.
Benarroch EE., Sigma-1 receptor and amyotrophic lateral sclerosis, Neurology. Oct. 16, 2018;91(16):743-747.
Blasio A, et al., Sigma-1 Receptor Mediates Acquisition of Alcohol Drinking and Seeking behavior in Alcohol-Preferring Rats, Behav Brain Res. 2015; 287:315-22.
Borroto-Escuela DO, et al., Cocaine self-administration specifically increases A2AR-D2R and D2R-sigma1R heteroreceptor complexes in the rat nucleus accumbens shell. Relevance for cocaine use disorder, Pharmacol Biochem Behav. Apr. 2017; 155:24-31.
Bruna J, et al., Sigma-1 receptor: a new player in neuroprotection against chemotherapy-induced peripheral neuropathy, Neural Regen Res. May 2018; 13(5):775-778.
Castany S, et al., Critical role of sigma-1 receptors in central neuropathic pain-related behaviours after mild spinal cord injury in mice, Sci Rep. Mar. 1, 2018; 8(1):3873, 13 pages.

(56) References Cited

OTHER PUBLICATIONS

Chien, C. C. et al., Selective Antagonism of Opioid Analgesia by a Sigma System1, The Journal of pharmacology and experimental therapeutics 1994, 271 (3), 1583-90.
Colabufo, N. A. et al., Correlation between sigma2 receptor protein expression and histopathologic grade in human bladder cancer, Cancer letters 2006, 237 (1), 83-8.
Diaz, J. L. et al., Synthesis and Biological Evaluation of the 1-Arylpyrazole Class of 01 Receptor Antagonists: Identification of 4-{2-[5-Methyl-1-(naphthalen-2-yl)-1H-pyrazol-3-yloxy]ethyl}morpholine (S1RA, E-52862), J Med Chem 2012, 55 (19), 8211-24.
Diaz, J. L. et al., Synthesis and Structure-Activity Relationship (SAR) Study of a New Series of Selective #1 Receptor Ligands for the Treatment of Pain: 4-Aminotriazoles., J Med Chem 2015, 58 (5), 2441-51.
Diaz, J. L. et al., Pyrazoloij3,4-d]pyrimidines as sigma-1 receptor ligands for the treatment of pain. Part 1: 4-acylamino derivatives, MedChemComm 2017, 8 (6), 1235-1245.
Diaz, J. L. et al., Pyrazoloij3,4-d]pyrimidines as sigma-1 receptor ligands for the treatment of pain. Part 2: Introduction of cyclic substituents in position 4, MedChemComm 2017, 8 (6), 1246-1254.
Dong H, et al., Sigma-1 Receptor Modulates Neuroinflammation After Traumatic Brain Injury, Cell Mol Neurobiol. Jul. 2016; 36(5):639-45.
Dreser A, et al., The ALS-linked E102Q mutation in Sigma receptor-1 leads to ER stress-mediated defects in protein homeostasis and dysregulation of RNA-binding proteins, Cell Death Differ. Oct. 2017; 24(10): 1655-1671.
Fukunaga K, et al., Stimulation of the Sigma-1 Receptor and the Effects on Neurogenesis and Depressive Behaviors in Mice, Adv Exp Med Biol. 2017; 964:201-211.
Gueguinou M, et al., The SigmaR1 chaperone drives breast and colorectal cancer cell migration by tuning SK3- dependent Ca2+ homeostasis, Oncogene. Jun. 22, 2017; 36(25):3640-3647.
Hall H, et al., AF710B, an M1/sigma-1 receptor agonist with long-lasting disease-modifying properties in a transgenic rat model of Alzheimer's disease, Alzheimers Dement. 2017;14(6):811-823.
Hanner, M. et al., Purification, molecular cloning, and expression of the mammalian sigma1-binding site, Proc Natl Acad Sci, 1996, 93(15), 8072-7.
Hayashi, T. et al., Regulating ankyrin dynamics: roles of signma-1 receptors, Proc Natl Acad Sci, 2001, 98(2), 491-6.
Iyamu, Id.; et al., Discovery of a novel class of potent and selective tetrahydroindazole-based signma-1 receptor ligands. Bioorganic & Medicinal Chemistry, vol. 27, No. 9, May 1, 2019, abstract only.
Izzo, N. J. et al., Alzheimer's Therapeutics Targeting Amyloid Beta 1-42 Oligomers II: Sigma-2/PGRMC1 Receptors Mediate Abeta 42 Oligomer Binding and Synaptotoxicity, PloS One 2014, 9(11), e111899, 15 pages.
Kashiwagi, H. et al., Selective sigma-2 ligands preferentially bind to pancreatic adenocarcinomas: applications in diagnostic imaging and therapy, Molecular cancer 2007, 6:48, 12 pages.
Kim, F. J. et al., 01 Receptor Modulation of G-Protein-Coupled Receptor Signaling: Potentiation of Opioid Transduction Independent from Receptor Binding, Mol Pharmacol 2010, 77(4), 695-703.
Kranz M, et al., Bridging from Brain to Tumor Imaging: (S)-(•)-and(R)-(+)-[18F]Fluspidine for Investigation of Sigma-1 Receptors in Tumor-Bearing Mice, Molecules. Mar. 20, 2018; 23(3), 13 pags.
Lan, Y. et al., Synthesis and Biological Evaluation of Novel Sigma-1 Receptor Antagonists Based on Pyrimidine Scaffold As Agents for Treating Neuropathic Pain, J Med Chem 2014, 57(24), 10404-23.
Langa, F et al., Generation and phenotypic analysis of sigma receptor type I knockout mice, The European journal of neuroscience 2003, 18(8), 2188-96.
Lever JR, et al., A Selective Sigma-2 Receptor Ligand Antagonizes Cocaine-Induced Hyperlocomotion in Mice, Synapse. Feb. 2014; 68(2): 73-84.
Lever JR, et al., Cocaine Occupancy of Sigma1 Receptors and Dopamine Transporters in Mice, Synapse. Mar. 2016; 0 (3):98-111.
Stanhewicz et al., Sex differences in endothelial function important to vascular health and overall cardiovascular disease risk across the lifespan, Am J Physiol Heart Circ Physiol. Sep. 14, 2018, 315: H1569-H1588.
Luty, A. A. et al., Sigma Nonopioid Intracellular Receptor 1 Mutations Cause Frontotemporal Lobar Degeneration—Motor Neuron Disease, Annals of neurology 2010, 68(5), 639-49.
Mach, R. H. et al., O2 Receptors as Potential Biomarkers of Proliferation in Breast Cancer, Cancer Res., 1997, 57(1), 156-61.
Maher, C. M. et al., Small-molecule Sigma1 Modulator Induces Autophagic Degradation of PD-L1, Molecular cancer researchm 2018, 16 (2), 243-255.
Mancuso R. et al., Sigma-1 Receptor in Motoneuron Disease, Adv Exp Med Biol. 2017; 964:235-254.
Mandelli L. et al., The Impact of a Single Nucleotide Polymorphism in SIGMAR1 on Depressive Symptoms in Major Depressive Disorder and Bipolar Disorder, Adv Ther. Mar. 2017;34(3):713-724.
McDonald ES. et al., Sigma-2 ligands and PARP inhibitors synergistically trigger cell death in breast cancer cells, Biochem Biophys Res Commun. May 6, 2017;486(3):788-795.
Mei, J. et al., Receptor Modulation of Opioid Analgesia in the Mouse, The Journal of pharmacology and experimental therapeutics 2002, 300(4), 1070-4.
Mir, S. U. R. et al., Progesterone receptor membrane component 1/Sigma-2 receptor associates with MAP1LC3B and promotes autophagy, Autophagy 2013, 9(10), 1566-1578.
Mishra, R. K. et al., Discovery and characterization of novel small-molecule CXCR4 receptor agonists and antagonists, Sci Rep 2016, 6:30155, 9 pages.
Mondal, S. et al., High-Content Microfluidic Screening Platform Used To Identify 02R/Tmem97 Binding Ligands that Reduce Age-Dependent Neurodegeneration in C. elegans SC_APP Model, ACS chemical neuroscience 2018, 9(5), 1014-1026.
Navarro, G. et al., Direct involvement of 0-1 receptors in the dopamine D1 receptor-mediated effects of cocaine, 2Proc Natl Acad Sci, 2010, 107(43), 18676-81.
Nguyen L, et al., Sigma-1 Receptors and Neurodegenerative Diseases: Towards a Hypothesis of Sigma-1 Receptors as Amplifiers of Neurodegeneration and Neuroprotection, Adv Exp Med Biol. 2017; 964:133-152.
Ortíz-Rentería M, et al., TRPV1 channels and the progesterone receptor Sig-1R interact to regulate pain, Proc Natl Acad Sci. Feb. 13, 2018;115(7):E1657-E1666.
Pati ML, et al., Sigma-2 receptor agonist derivatives of 1-Cyclohexyl-4-[3-(5-methoxy-1,2,3,4-tetrahydronaphthalen-1-yl)propyl]piperazine (PB28) induce cell death via mitochondrial superoxide production and caspase activation in pancreatic cancer, BMC Cancer. Jan. 13, 2017; 17:51, 12 pgs.
Prause, J. et al., Altered localization, abnormal modification and loss of function of Sigma receptor-1 in amyotrophic lateral sclerosis, Human molecular genetics 2013, 22(8): 1581-600.
PUBCHEM. N,N-Dimethyl-1-propyl-4,5,6,7-tetrahydroindazole-3-carboxamide. Jun. 12, 2019, 1 page 1-6 [online], [retrieved on Feb. 5, 2020]. Retrieved from the Internet <URL: https://pubchem.ncbi.nlm.nih.gov/ compound/141634603>; page 2.
Rodríguez-Muñoz M, et al., Cannabidiol enhances morphine antinociception, diminishes NMDAmediated seizures and reduces stroke damage via the sigma 1 receptor, Mol Brain. Sep. 17, 2018;11:51: 12 pages.

* cited by examiner

FIG. 1A

| Molecule Name | Structure | Analytical data | Sigma-1 Binding | Sigma-2 Binding | Ki Legend: +++ = < 1 uM; ++ = between 1-10 uM; Blank = > 10 uM |
|---|---|---|---|---|---|
| NUCC-0200625 | 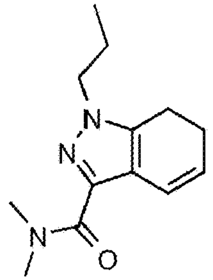 | $^1$H NMR (500 MHz, $CDCl_3$) δ 6.23 (dt, $J$ = 9.6, 1.9 Hz, 1H), 5.80 (dt, $J$ = 9.6, 4.3 Hz, 1H), 4.08 (t, $J$ = 7.3 Hz, 2H), 3.11 (s, 3H), 3.02 (s, 3H), 2.78 (t, $J$ = 8.3 Hz, 2H), 2.43 (tdd, $J$ = 8.3, 4.3, 1.9 Hz, 2H), 1.82 (h, $J$ = 7.4 Hz, 2H), 0.89 (t, $J$ = 7.4 Hz, 3H). $^{13}$C NMR (126 MHz, $CDCl_3$) δ 163.16, 147.35, 130.21, 125.96, 118.79, 115.39, 51.93, 38.70, 30.20, 24.17, 24.13, 20.99, 11.27. | | | |
| NUCC-0200626 | 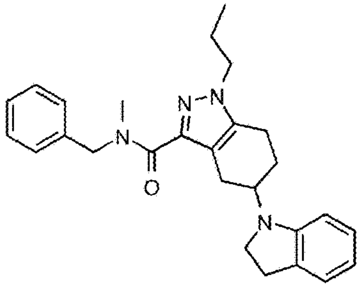 | $^1$H NMR (500 MHz, $CDCl_3$) δ 7.32 (d, J = 5.3 Hz, 5H), 7.11 – 6.99 (m, 3H), 6.62 (t, J = 7.3 Hz, 2H), 6.44 (t, J = 6.5 Hz, 2H), 5.07 – 4.93 (m, 2H), 4.72 (q, J = 14.6 Hz, 1H), 3.93 (dt, J = 25.5, 7.1 Hz, 3H), 3.88 – 3.76 (m, 2H), 3.49 (dq, J = 16.6, 8.5 Hz, 2H), 3.39 (dq, J = 12.7, 8.1, 5.7 Hz, 2H), 3.22 (s, 2H), 3.08 – 2.92 (m, 8H), 2.81 (dd, J = 16.7, 11.1 Hz, 3H), 2.70 (ddd, J = 21.6, 12.0, 6.7 Hz, 2H), 2.18 – 2.09 (m, 2H), 1.93 (tt, J = 11.9, 5.8 Hz, 2H), 1.81 (dh, J = 28.9, 7.1 Hz, 4H), 0.93 (t, J = 7.4 Hz, 2H), 0.87 (t, J = 7.4 Hz, 3H). MS. ESIMS m/z $[M + H]^+$ 429.57 | | | |
| NUCC-0200627 | 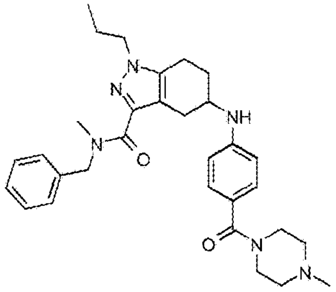 | MS: ESIMS m/z $[M + H]^+$ 529.7 | | | |

FIG. 1B

| | | | | | |
|---|---|---|---|---|---|
| NUCC-0200628 | 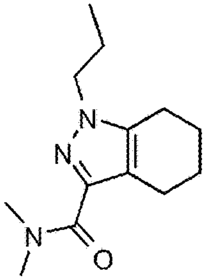 | $^1$H NMR (500 MHz, $CDCl_3$) δ 3.92 (t, $J$ = 7.2 Hz, 2H), 3.26 (s, 3H), 3.06 (s, 3H), 2.65 (t, $J$ = 6.1 Hz, 2H), 2.55 (t, $J$ = 6.3 Hz, 2H), 1.86 – 1.75 (m, 4H), 1.74 – 1.67 (m, 2H), 0.90 (t, $J$ = 7.4 Hz, 3H). 13C NMR (126 MHz, $CDCl_3$) δ 165.71, 142.42, 138.76, 118.04, 50.64, 39.09, 35.66, 23.65, 23.02, 22.65, 21.64, 21.26, 11.32. MS: ESIMS m/z $[M + H]^+$ 236.4 | | | |
| NUCC-0200630 | 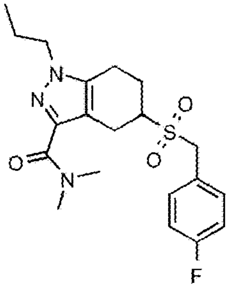 | $^1$H NMR (500 MHz, $CDCl_3$) δ 7.62 – 7.55 (m, 2H), 7.30 – 7.23 (m, 2H), 4.44 (s, 2H), 4.12 (t, J = 7.2 Hz, 2H), 3.80 (qdd, J = 7.6, 4.9, 2.7 Hz, 1H), 3.52 (s, 3H), 3.27 (s, 3H), 3.17 (dd, J = 16.1, 5.1 Hz, 1H), 2.93 (dd, J = 15.8, 7.0 Hz, 1H), 2.88 – 2.80 (m, 1H), 2.23 (dtq, J = 12.3, 6.0, 3.1, 2.6 Hz, 1H), 2.18 – 2.10 (m, 1H), 2.02 (qd, J = 7.3, 1.4 Hz, 2H), 1.59 – 1.50 (m, 1H), 1.47 (d, J = 9.5 Hz, 1H), 1.11 (t, J = 7.4 Hz, 3H). $^{13}C$ NMR (126 MHz, $CDCl_3$) δ 164.87, 164.07, 142.50, 137.42, 132.66, 125.39, 115.96, 115.79, 115.46, 59.22, 50.92, 50.13, 39.15, 35.93, 29.63, 29.05, 23.52, 18.85, 11.28. | | | |
| NUCC-0200631 | 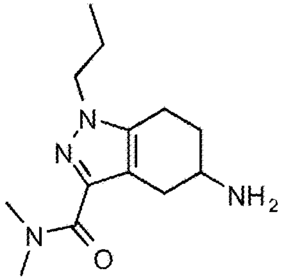 | $^1$H NMR (500 MHz, $CDCl_3$) δ 3.91 (t, $J$ = 7.2 Hz, 2H), 3.56 (p, $J$ = 7.3 Hz, 1H), 3.29 (s, 3H), 3.18 (dd, $J$ = 15.9, 5.0 Hz, 1H), 3.03 (s, 3H), 2.92 – 2.84 (m, 1H), 2.80 (dt, $J$ = 16.4, 5.0 Hz, 1H), 2.67 (pd, $J$ = 12.2, 9.5, 4.1 Hz, 1H), 2.38 – 2.28 (m, 1H), 2.16 – 2.03 (m, 1H), 1.81 (h, $J$ = 7.4 Hz, 2H), 0.90 (t, $J$ = 7.4 Hz, 3H). $^{13}C$ NMR (126 MHz, $CDCl_3$) δ 167.19, 165.05, 141.85, 137.49, 114.70, 51.07, 47.60, 39.28, 36.12, 26.64, 26.56, 23.46, 19.25, 11.31. ESIMS m/z $[M + H]^+$ 236.4 251.3 | | | |

FIG. 1C

| | | | | | |
|---|---|---|---|---|---|
| NUCC-0200632 | 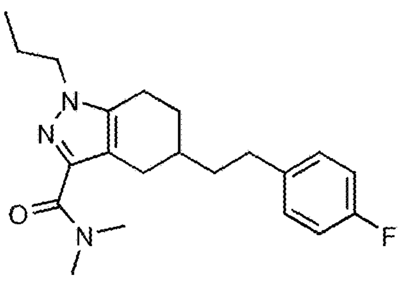 | $^{1}$H NMR (500 MHz,CDCl$_3$) δ 7.16 – 7.10 (m, 2H), 6.99 – 6.92 (m, 2H), 3.92 (dd, *J* = 7.7, 6.6 Hz, 2H), 3.29 (s, 3H), 3.08 (s, 3H), 2.97 (dd, *J* = 16.0, 3.8 Hz, 1H), 2.73 (dt, *J* = 14.4, 7.5 Hz, 1H), 2.65 (ddt, *J* = 12.7, 6.4, 3.2 Hz, 2H), 2.52 (ddd, *J* = 16.2, 10.8, 5.8 Hz, 1H), 2.28 (dd, *J* = 16.0, 8.6 Hz, 1H), 1.97 (dt, *J* = 13.6, 3.5 Hz, 1H), 1.81 (h, *J* = 7.3 Hz, 2H), 1.73 – 1.69 (m, 1H), 1.67 – 1.62 (m, 1H), 1.49 (dtd, *J* = 12.9, 10.7, 5.6 Hz, 1H), 0.91 (t, *J* = 7.4 Hz, 3H). $^{13}$C NMR (126 MHz, CDCl$_3$) δ 165.45, 160.19, 142.13, 138.66, 138.19, 129.65, 118.00, 115.10, 50.64, 37.98, 33.92, 32.52, 29.71, 29.13, 27.43, 23.52, 21.12, 11.19. ESIMS m/z [M + H]$^+$ 358.3 | | | |
| NUCC-0200633 | 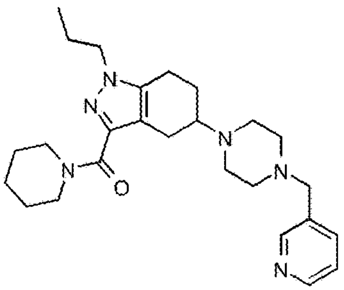 | $^{1}$H NMR (500 MHz, CDCl$_3$ ) δ 8.52 (d, J = 3.4 Hz, 2H), 8.33 (s, 2H, FA), 7.68 (dt, J = 7.9, 1.9 Hz, 1H), 7.30 (dd, J = 7.8, 4.8 Hz, 1H), 3.94 – 3.73 (m, 4H), 3.65 (t, J = 5.3 Hz, 2H), 3.58 (s, 2H), 3.43 – 3.30 (m, 1H), 3.12 (ddd, J = 22.2, 14.1, 5.9 Hz, 5H), 2.74 (dt, J = 14.0, 9.4 Hz, 6H), 2.69 – 2.53 (m, 1H), 2.42 (ddd, J = 12.7, 5.3, 2.5 Hz, 1H), 1.90 – 1.70 (m, 3H), 1.70 – 1.45 (m, 6H), 0.87 (t, J = 7.4 Hz, 3H); $^{13}$C NMR (126 MHz,CDCl$_3$) δ 166.08, 163.17, 149.63, 148.41, 142.31, 137.40, 137.29, 132.90, 123.77, 115.11, 77.28, 77.03, 76.78, 61.05, 60.40, 59.15, 50.90, 50.34, 48.19, 43.39, 26.79, 25.76, 24.88, 24.73, 23.39, 21.20, 21.05, 20.71, 14.20, 11.14. MS. ESIMS *m/z* [M + H]$^+$ 451. | | | |
| NUCC-0200634 | 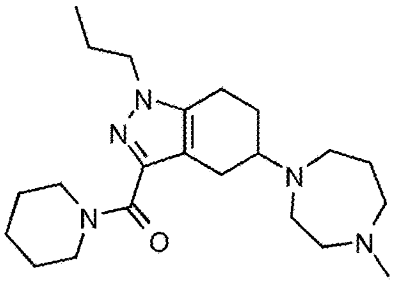 | $^{1}$H NMR (500 MHz, CDCl$_3$) δ 8.71 – 8.29 (m, 2H, FA), 3.87 (td, J = 7.0, 1.4 Hz, 2H), 3.78 (d, J = 6.1 Hz, 2H), 3.65 (d, J = 5.7 Hz, 2H), 3.13 (dt, J = 25.7, 4.0 Hz, 3H), 3.07 – 2.82 (m, 7H), 2.78 – 2.68 (m, 1H), 2.66 (s, 3H), 2.62 – 2.41 (m, 2H), 2.16 – 2.02 (m, 3H), 1.76 (q, J = 7.3 Hz, 2H), 1.70 – 1.40 (m, 7H), 0.87 (t, J = 7.4 Hz, 3H); $^{13}$C NMR (126 MHz, CDCl$_3$) δ 171.14, 167.74, 163.61, 142.38, 137.67, 116.66, 77.30, 77.04, 76.79, 61.36, 60.38, 57.67, 54.38, 50.77, 49.39, 48.19, 45.92, 44.13, 43.26, 26.83, 25.75, 25.09, 24.76, 24.29, 23.45, 23.32, 21.18, 21.04, 14.19, 11.16. ESIMS *m/z* [M + H]$^+$ 388. | | | |

FIG. 1D

| | | | | | |
|---|---|---|---|---|---|
| NUCC-0200635 | 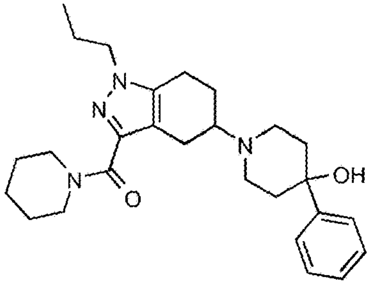 | $^1$H NMR (500 MHz, CDCl$_3$) δ 8.40 (s, 2H, FA), 7.48 – 7.40 (m, 2H), 7.31 (t, J = 7.6 Hz, 2H), 7.26 – 7.19 (m, 1H), 4.03 – 3.73 (m, 4H), 3.59 (ddd, J = 17.1, 8.8, 4.7 Hz, 4H), 3.42 – 3.24 (m, 3H), 3.18 (dd, J = 14.9, 4.9 Hz, 1H), 2.89 – 2.68 (m, 3H), 2.59 (dddd, J = 29.2, 14.8, 10.9, 3.6 Hz, 3H), 2.03 – 1.84 (m, 3H), 1.79 (q, J = 7.3 Hz, 2H), 1.63 (dq, J = 26.7, 7.4, 6.3 Hz, 6H), 0.89 (t, J = 7.4 Hz, 3H); $^{13}$C NMR (126 MHz, CDCl$_3$) δ 166.88, 163.06, 146.29, 142.09, 137.36, 128.53, 127.52, 124.41, 115.04, 69.59, 61.54, 53.43, 50.97, 48.31, 47.52, 43.56, 41.92, 35.75, 35.50, 26.74, 25.77, 24.93, 24.69, 23.38, 20.70, 11.16. ESIMS *m/z* [M + H]$^+$ 451. | | | |
| NUCC-0200636 | 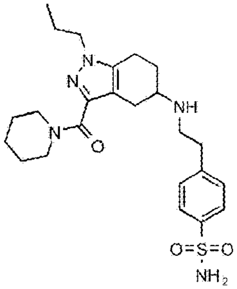 | $^1$H NMR (500 MHz, CDCl$_3$) δ 7.77 – 7.70 (m, 2H), 7.27 – 7.21 (m, 2H), 3.82 (td, J = 7.1, 1.9 Hz, 2H), 3.74 – 3.46 (m, 4H), 2.98 – 2.66 (m, 6H), 2.58 (dt, J = 16.2, 5.3 Hz, 1H), 2.47 (ddd, J = 15.9, 9.4, 6.0 Hz, 1H), 2.25 (dd, J = 16.8, 9.5 Hz, 1H), 1.95 – 1.80 (m, 1H), 1.72 (q, J = 7.3 Hz, 2H), 1.66 – 1.39 (m, 7H), 0.83 (t, J = 7.4 Hz, 3H); $^{13}$C NMR (126 MHz, CDCl$_3$) δ 163.89, 145.26, 142.37, 140.24, 137.94, 129.33, 126.60, 115.84, 77.30, 77.04, 76.79, 53.45, 50.70, 48.21, 47.92, 43.27, 36.30, 29.01, 27.78, 26.81, 25.73, 24.74, 23.45, 19.69, 11.21. ESIMS *m/z* [M + H]$^+$ 474. | | | |
| NUCC-0200638 | 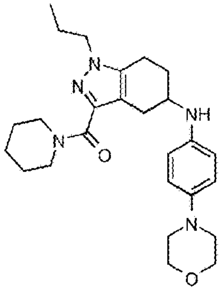 | $^1$H NMR (500 MHz, CDCl$_3$) δ 8.09 (s, 1H, FA), 6.84 (d, J = 8.3 Hz, 2H), 6.62 (d, J = 8.3 Hz, 2H), 4.08 – 3.77 (m, 6H), 3.77 – 3.47 (m, 5H), 3.25 – 2.84 (m, 5H), 2.81 – 2.35 (m, 3H), 2.13 (dd, J = 12.2, 5.7 Hz, 1H), 1.82 (tq, J = 14.4, 7.3 Hz, 3H), 1.71 – 1.31 (m, 6H), 0.90 (t, J = 7.4 Hz, 3H); $^{13}$C NMR (126 MHz, CDCl$_3$) δ 163.94, 163.56, 143.36, 142.51, 141.20, 137.80, 118.61, 115.49, 115.13, 77.29, 77.03, 76.78, 66.90, 51.30, 50.75, 49.70, 48.27, 43.38, 28.21, 27.68, 26.78, 25.69, 24.69, 23.47, 19.31, 11.19. ESIMS *m/z* [M + H]$^+$ 452. | | | |

FIG. 1E

| | | | | | |
|---|---|---|---|---|---|
| NUCC-0200644 | 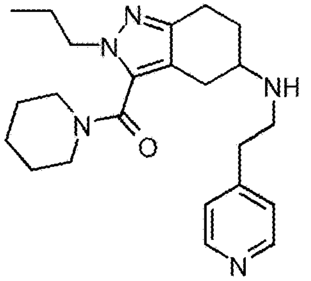 | $^1$H NMR (500 MHz, $CDCl_3$) δ 8.58 – 8.47 (m, 2H), 8.26 (s, 2H, FA), 7.22 – 7.14 (m, 2H), 4.19 – 3.70 (m, 2H), 3.56 – 3.12 (m, 6H), 3.12 – 2.99 (m, 2H), 2.88 (dd, J = 29.2, 16.0 Hz, 2H), 2.77 – 2.50 (m, 2H), 2.29 (s, 1H), 2.02 – 1.87 (m, 1H), 1.78 (h, J = 7.4 Hz, 2H), 1.54 (d, J = 91.6 Hz, 6H), 0.85 (t, J = 7.4 Hz, 3H); $^{13}$C NMR (126 MHz, $CDCl_3$) δ 166.34, 161.20, 149.25, 146.91, 145.49, 133.80, 124.33, 52.19, 47.81, 45.64, 43.12, 32.21, 26.96, 25.59, 24.53, 24.31, 23.85, 11.15. ESIMS *m/z* $[M + H]^+$ 396. | | | |
| NUCC-0200645 | 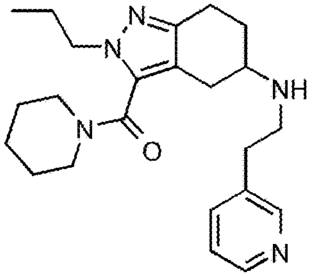 | $^1$H NMR (500 MHz,$CDCl_3$) δ 8.51 – 8.47 (m, 1H), 8.47 – 8.42 (m, 1H), 8.27 (s, 2H, FA), 7.62 (dt, J = 7.7, 1.9 Hz, 1H), 7.27 (dd, J = 7.8, 4.9 Hz, 1H), 3.91 (d, J = 36.2 Hz, 3H), 3.55 – 3.11 (m, 6H), 3.06 (t, J = 8.1 Hz, 2H), 3.01 – 2.79 (m, 2H), 2.77 – 2.53 (m, 2H), 2.30 (s, 1H), 2.07 – 1.88 (m, 1H), 1.76 (p, J = 7.4 Hz, 2H), 1.54 (d, J = 95.2 Hz, 6H), 0.85 (t, J = 7.4 Hz, 3H); $^{13}$C NMR (126 MHz, $CDCl_3$) δ 166.44, 161.18, 149.10, 147.72, 145.48, 137.25, 133.78, 132.96, 124.05, 52.18, 46.31, 43.10, 30.07, 26.95, 25.60, 24.47, 24.31, 23.86, 11.15. ESIMS *m/z* $[M + H]^+$ 396. | | | |
| NUCC-0200648 | 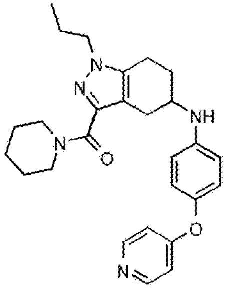 | $^1$H NMR (500 MHz, $CDCl_3$) δ 8.52 – 8.32 (m, 2H), 8.18 (s, 1H, FA), 6.98 – 6.80 (m, 4H), 6.70 – 6.58 (m, 2H), 3.94 (t, J = 7.2 Hz, 2H), 3.84 – 3.57 (m, 5H), 3.14 (dd, J = 15.9, 4.9 Hz, 1H), 2.80 – 2.61 (m, 2H), 2.58 (dd, J = 15.9, 7.4 Hz, 1H), 2.14 (ddd, J = 11.7, 6.0, 3.5 Hz, 1H), 2.01 – 1.88 (m, 1H), 1.82 (h, J = 7.4 Hz, 2H), 1.73 – 1.46 (m, 6H), 0.91 (t, J = 7.4 Hz, 3H); $^{13}$C NMR (126 MHz, $CDCl_3$) δ 167.83, 164.25, 163.87, 148.19, 145.41, 144.04, 142.47, 137.70, 121.92, 115.61, 114.19, 112.25, 50.80, 48.80, 48.30, 43.43, 28.40, 27.64, 26.80, 25.73, 24.70, 23.47, 19.29, 11.20. ESIMS *m/z* $[M + H]^+$ 460. | | | |

FIG. 1F

| | | | | | |
|---|---|---|---|---|---|
| NUCC-0200649 | 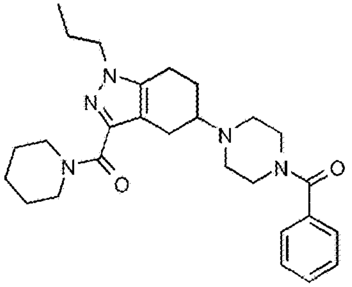 | $^1$H NMR (500 MHz, $CDCl_3$) δ 8.04 (s, 2H), 7.34 – 7.18 (m, 5H), 3.92 – 3.59 (m, 6H), 3.49 (t, J = 5.3 Hz, 4H), 3.08 (tdd, J = 11.6, 5.1, 2.2 Hz, 1H), 2.99 – 2.68 (m, 5H), 2.68 – 2.37 (m, 3H), 2.16 (dq, J = 10.0, 2.5 Hz, 1H), 1.77 – 1.56 (m, 3H), 1.56 – 1.30 (m, 6H), 0.72 (t, J = 7.4 Hz, 3H); $^{13}$C NMR (126 MHz, $CDCl_3$) δ 170.51, 165.24, 163.35, 142.16, 137.55, 134.56, 130.29, 128.69, 127.17, 115.47, 61.32, 50.89, 48.28, 43.51, 26.78, 25.75, 25.12, 24.68, 23.40, 21.35, 20.80, 11.14. ESIMS *m/z* $[M + H]^+$ 465. | | | |
| NUCC-0200650 | 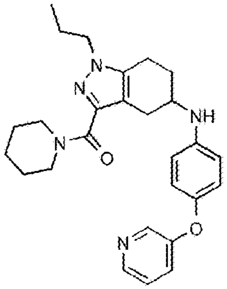 | $^1$H NMR (500 MHz, $CDCl_3$) δ 8.32 (dd, J = 2.3, 1.2 Hz, 1H), 8.26 (dd, J = 3.9, 2.1 Hz, 1H), 8.10 (s, 1H, FA), 7.24 (d, J = 2.8 Hz, 2H), 6.92 – 6.80 (m, 2H), 6.66 – 6.52 (m, 2H), 4.06 – 3.84 (m, 3H), 3.84 – 3.70 (m, 3H), 3.67 (d, J = 6.5 Hz, 2H), 3.13 (dd, J = 15.9, 5.0 Hz, 1H), 2.79 – 2.62 (m, 2H), 2.57 (dd, J = 15.9, 7.4 Hz, 1H), 2.19 – 2.08 (m, 1H), 1.85 (ddt, J = 36.0, 14.5, 6.7 Hz, 3H), 1.70 – 1.41 (m, 6H), 0.91 (td, J = 7.4, 2.1 Hz, 3H); $^{13}$C NMR (126 MHz, $CDCl_3$) δ 163.83, 163.06, 155.97, 146.30, 144.44, 142.58, 141.97, 138.89, 137.70, 124.44, 124.31, 121.31, 115.61, 114.34, 64.64, 50.78, 48.97, 48.26, 43.38, 28.46, 27.68, 26.82, 25.73, 24.73, 23.48, 19.31, 11.21. ESIMS *m/z* $[M + H]^+$ 460. | | +++ | |
| NUCC-0200651 | 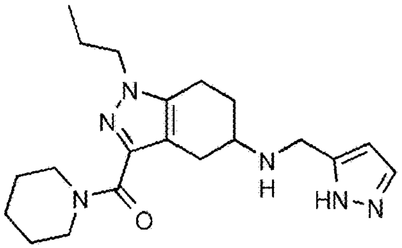 | $^1$H NMR (500 MHz, $CDCl_3$) δ 8.18 (s, 2H, FA), 7.24 (d, J = 2.2 Hz, 1H), 6.16 (d, J = 2.3 Hz, 1H), 4.08 (d, J = 13.5 Hz, 1H), 3.93 (d, J = 13.5 Hz, 1H), 3.64 (t, J = 7.0 Hz, 4H), 3.42 (q, J = 6.4 Hz, 2H), 3.31 (dq, J = 8.5, 4.7, 3.5 Hz, 1H), 3.02 (dd, J = 15.8, 4.9 Hz, 1H), 2.82 (dd, J = 15.8, 8.4 Hz, 1H), 2.63 (dt, J = 16.5, 5.2 Hz, 1H), 2.57 – 2.36 (m, 1H), 2.15 – 1.92 (m, 2H), 1.61 – 1.18 (m, 8H), 0.67 (t, J = 7.4 Hz, 3H); $^{13}$C NMR (126 MHz, $CDCl_3$) δ 167.32, 163.29, 142.10, 141.16, 137.32, 131.29, 113.86, 106.40, 52.95, 50.80, 48.26, 43.38, 41.27, 26.71, 25.73, 25.50, 24.65, 24.02, 23.17, 19.06, 11.11. ESIMS *m/z* $[M + H]^+$ 371. | | | |

FIG. 1G

| | | | | | |
|---|---|---|---|---|---|
| NUCC-0200653 | 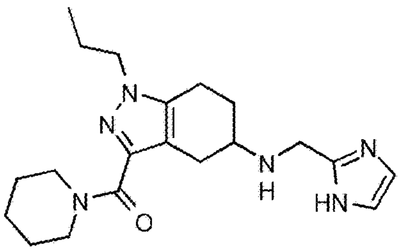 | $^{1}$H NMR (500 MHz, $CDCl_3$) δ 8.49 (s, 2H, FA), 7.24 (s, 2H), 4.74 – 4.49 (m, 2H), 4.05 (t, J = 7.2 Hz, 2H), 3.97 (d, J = 5.9 Hz, 2H), 3.78 (t, J = 5.4 Hz, 2H), 3.56 – 3.31 (m, 2H), 3.07 – 2.89 (m, 2H), 2.82 (dt, J = 12.3, 6.3 Hz, 1H), 2.52 (d, J = 12.8 Hz, 1H), 2.28 – 2.13 (m, 1H), 1.94 (q, J = 7.2 Hz, 2H), 1.79 (ddt, J = 30.2, 10.9, 5.9 Hz, 6H), 1.05 (t, J = 7.4 Hz, 3H); $^{13}$C NMR (126 MHz,$CDCl_3$) δ 167.77, 163.24, 141.95, 139.07, 137.25, 122.07, 114.21, 53.81, 50.88, 48.30, 43.51, 40.07, 26.69, 25.73, 25.56, 24.63, 24.46, 23.31, 19.44, 11.14. ESIMS *m/z* $[M + H]^+$ 371 . | | | |
| NUCC-0200696 | 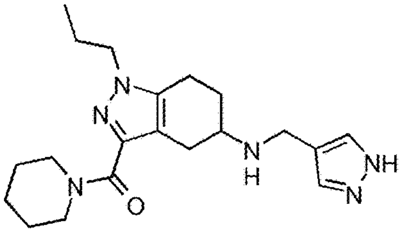 | $^{1}$H NMR (500 MHz, $CDCl_3$) δ 8.25 (s, 2H, FA), 7.55 (s, 2H), 4.17 – 3.98 (m, 2H), 3.91 – 3.74 (m, 4H), 3.64 (q, J = 4.4 Hz, 2H), 3.37 (d, J = 13.0 Hz, 1H), 3.19 (dd, J = 15.3, 5.0 Hz, 1H), 2.83 – 2.66 (m, 2H), 2.61 (td, J = 10.6, 5.4 Hz, 1H), 2.31 (d, J = 12.1 Hz, 1H), 2.03 – 1.87 (m, 1H), 1.75 (p, J = 7.3 Hz, 2H), 1.61 (tt, J = 19.2, 6.4 Hz, 6H), 0.87 (t, J = 7.4 Hz, 3H); $^{13}$C NMR (126 MHz,$CDCl_3$) δ 166.57, 163.44, 141.81, 137.45, 135.05, 114.17, 53.45, 50.89, 48.39, 43.59, 39.07, 26.70, 25.75, 25.37, 24.63, 24.43, 23.29, 19.54, 11.14. ESIMS *m/z* $[M + H]^+$ 371. | | | |
| NUCC-0200697 | 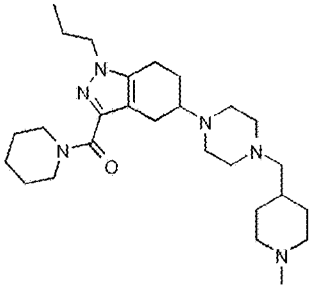 | $^{1}$H NMR (500 MHz, $CDCl_3$) δ 8.35 (s, 3H, FA), 3.83 (dq, J = 28.4, 6.2, 5.6 Hz, 4H), 3.62 (t, J = 5.3 Hz, 2H), 3.45 (d, J = 11.3 Hz, 2H), 3.28 (q, J = 7.5, 6.8 Hz, 1H), 3.17 – 2.96 (m, 5H), 2.82 – 2.53 (m, 12H), 2.34 (d, J = 6.3 Hz, 3H), 1.88 (t, J = 11.0 Hz, 2H), 1.76 (dt, J = 14.6, 7.0 Hz, 3H), 1.70 – 1.44 (m, 9H), 0.85 (t, J = 7.4 Hz, 3H); $^{13}$C NMR (126 MHz, $CDCl_3$) δ 167.17, 163.25, 142.20, 137.51, 115.19, 62.12, 61.02, 53.90, 51.00, 50.88, 48.23, 47.69, 43.41, 30.82, 27.50, 26.77, 25.76, 24.77, 24.70, 23.38, 21.45, 20.66, 11.14. ESIMS *m/z* $[M + H]^+$ 471. | | | |

FIG. 1H

| | | | | | |
|---|---|---|---|---|---|
| NUCC-0200698 | 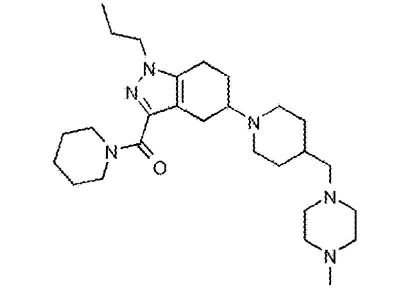 | $^1$H NMR (500 MHz, $CDCl_3$) δ 8.36 (s, 3H, FA), 3.88 (tt, J = 7.1, 3.9 Hz, 4H), 3.63 (t, J = 5.3 Hz, 2H), 3.55 (dd, J = 5.1, 2.2 Hz, 1H), 3.47 - 3.35 (m, 2H), 3.18 - 2.85 (m, 5H), 2.75 (tdd, J = 15.6, 13.6, 12.4, 5.0 Hz, 4H), 2.64 (d, J = 15.1 Hz, 8H), 2.54 - 2.44 (m, 1H), 2.31 (d, J = 6.4 Hz, 2H), 1.88 (dt, J = 18.2, 9.9 Hz, 3H), 1.82 - 1.44 (m, 12H), 0.87 (t, J = 7.4 Hz, 3H); $^{13}$C NMR (126 MHz, $CDC_{l3}$) δ 166.91, 162.97, 142.15, 137.35, 114.90, 62.09, 61.49, 53.35, 50.96, 50.51, 48.22, 45.74, 43.49, 43.35, 31.80, 27.56, 27.32, 26.77, 25.79, 24.89, 24.70, 23.36, 20.66, 11.12. ESIMS *m/z* [M + H]$^+$ 471. | | | |
| NUCC-0200699 | 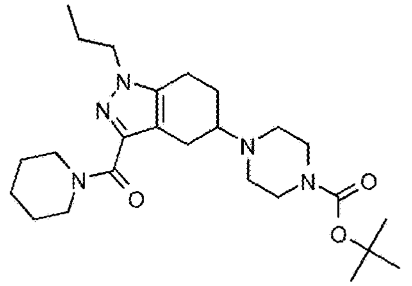 | $^1$H NMR (500 MHz, $CDCl_3$) δ 8.25 (s, 2H, FA), 3.95 - 3.76 (m, 4H), 3.65 (dd, J = 12.8, 7.3 Hz, 6H), 3.37 (dd, J = 5.1, 2.2 Hz, 1H), 3.14 - 2.91 (m, 5H), 2.84 - 2.58 (m, 3H), 2.39 (dq, J = 10.9, 2.5 Hz, 1H), 1.91 - 1.72 (m, 3H), 1.72 - 1.50 (m, 6H), 1.44 (s, 9H), 0.87 (t, J = 7.4 Hz, 3H); $^{13}$C NMR (126 MHz, $CDCl_3$) δ 165.78, 163.21, 153.95, 142.20, 137.42, 115.10, 80.83, 61.48, 50.92, 48.24, 47.97, 43.47, 28.32, 26.77, 25.75, 24.90, 24.69, 23.38, 21.08, 20.72, 11.13. ESIMS *m/z* [M + H]$^+$ 461. | | | |
| NUCC-0200700 | 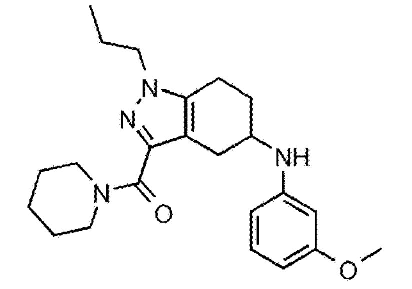 | $^1$H NMR (500 MHz,$CD_3OD$) δ 7.07 (t, J = 8.1 Hz, 1H), 6.27 (dt, J = 8.1, 2.2 Hz, 2H), 6.21 (t, J = 2.3 Hz, 1H), 3.97 (d, J = 12.0 Hz, 1H), 3.77 (s, 4H), 3.68 (dq, J = 11.9, 5.4 Hz, 4H), 3.40 (s, 1H), 3.01 (dd, J = 15.7, 5.0 Hz, 1H), 2.71 (td, J = 15.6, 14.8, 8.9 Hz, 2H), 2.54 (dd, J = 15.8, 7.5 Hz, 1H), 2.24 - 2.09 (m, 1H), 1.96 - 1.78 (m, 3H), 1.75 - 1.45 (m, 6H), 0.93 (t, J = 7.4 Hz, 3H); $^{13}$C NMR (126 MHz, $CD_3OD$) δ 164.27, 160.73, 148.62, 142.27, 138.26, 129.97, 115.30, 106.41, 102.27, 99.24, 54.98, 50.65, 48.39, 43.30, 27.84, 27.42, 26.62, 25.58, 24.47, 23.36, 19.22, 10.94. ESIMS *m/z* [M + H]$^+$ 397. | | | |

FIG. 1I

| | | | | | |
|---|---|---|---|---|---|
| NUCC-0200701 | 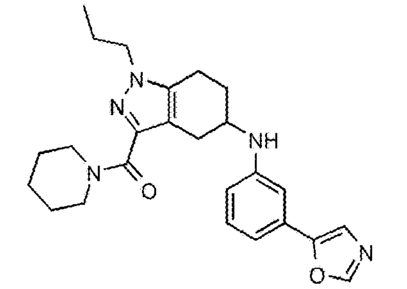 | $^1$H NMR (500 MHz, $CDCl_3$) δ 7.87 (s, 1H), 7.28 (s, 1H), 7.19 (t, J = 7.9 Hz, 1H), 6.96 (dt, J = 7.7, 1.1 Hz, 1H), 6.87 (t, J = 2.0 Hz, 1H), 6.58 (dd, J = 8.1, 2.3 Hz, 1H), 3.93 (t, J = 7.2 Hz, 2H), 3.85 (qd, J = 5.0, 2.4 Hz, 1H), 3.76 (q, J = 7.5, 6.5 Hz, 2H), 3.71 – 3.60 (m, 2H), 3.13 (dd, J = 15.9, 5.0 Hz, 1H), 2.68 (td, J = 6.3, 3.9 Hz, 2H), 2.60 (dd, J = 16.0, 7.2 Hz, 1H), 2.19 – 2.10 (m, 1H), 1.98 – 1.87 (m, 1H), 1.82 (q, J = 7.3 Hz, 2H), 1.70 – 1.50 (m, 6H), 0.92 (t, J = 7.4 Hz, 3H); $^{13}$C NMR (126 MHz, $CDCl_3$) δ 163.74, 152.00, 150.23, 147.53, 142.72, 137.62, 129.94, 128.65, 121.27, 115.52, 113.59, 108.71, 50.79, 48.38, 48.22, 43.31, 28.51, 27.53, 26.83, 25.72, 24.75, 23.49, 19.20, 11.22. ESIMS *m/z* $[M + H]^+$ 434. | | | |
| NUCC-0200703 | 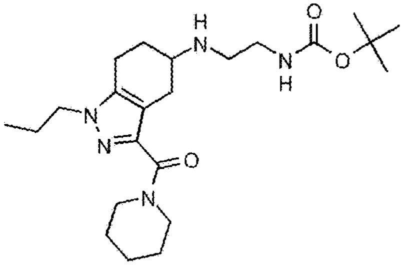 | $^1$H NMR (500 MHz, $CDCl_3$) δ 8.34 (s, 1H), 3.88 (td, J = 7.0, 1.6 Hz, 2H), 3.79 (q, J = 6.1 Hz, 2H), 3.70 – 3.52 (m, 2H), 3.52 – 3.27 (m, 4H), 3.26 – 3.05 (m, 3H), 2.76 (ddt, J = 12.5, 9.7, 5.0 Hz, 2H), 2.63 (td, J = 10.6, 5.3 Hz, 1H), 2.41 – 2.27 (m, 1H), 1.97 (dt, J = 15.5, 8.1 Hz, 1H), 1.76 (p, J = 7.3 Hz, 2H), 1.61 (ddt, J = 25.4, 13.4, 6.2 Hz, 6H), 1.38 (s, 9H), 0.87 (t, J = 7.4 Hz, 3H); $^{13}$C NMR (126 MHz,$CDCl_3$) δ 167.34, 163.19, 156.57, 142.07, 137.22, 114.25, 79.71, 54.18, 50.88, 50.64, 48.26, 45.37, 43.46, 37.46, 28.36, 26.71, 25.74, 25.57, 24.67, 24.60, 23.34, 19.55, 11.14. ESIMS *m/z* $[M + H]^+$ 435. | | | |
| NUCC-0200704 | 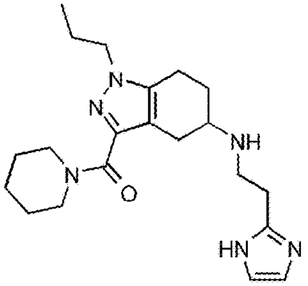 | $^1$H NMR (500 MHz, $CDCl_3$) δ 8.34 (s, 2H, FA), 7.04 (s, 2H), 3.94 – 3.73 (m, 4H), 3.69 – 3.55 (m, 3H), 3.48 (d, J = 24.6 Hz, 4H), 3.31 (d, J = 12.3 Hz, 1H), 3.21 (dd, J = 15.5, 4.9 Hz, 1H), 2.84 – 2.70 (m, 2H), 2.63 (ddd, J = 16.7, 11.0, 6.0 Hz, 1H), 2.44 – 2.29 (m, 1H), 1.97 (dd, J = 11.9, 5.8 Hz, 1H), 1.76 (p, J = 7.3 Hz, 2H), 1.71 – 1.49 (m, 6H), 0.87 (t, J = 7.4 Hz, 3H); $^{13}$C NMR (126 MHz, $CDCl_3$) δ 167.78, 163.09, 143.40, 141.90, 137.25, 119.78, 114.52, 55.06, 50.89, 48.27, 43.50, 43.20, 26.70, 25.77, 25.57, 24.65, 24.28, 23.62, 23.34, 19.64, 11.14. ESIMS *m/z* $[M + H]^+$ 385. | | | |

FIG. 1J

| | | | | | |
|---|---|---|---|---|---|
| NUCC-0200705 | 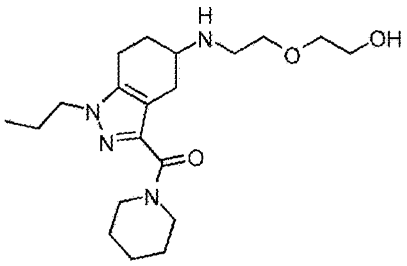 | $^{1}$H NMR (500 MHz, $CDCl_3$) δ 8.38 (s, 1H), 3.88 (td, J = 7.0, 1.9 Hz, 2H), 3.84 – 3.71 (m, 4H), 3.71 – 3.51 (m, 6H), 3.37 (td, J = 11.5, 5.4 Hz, 1H), 3.33 – 3.20 (m, 2H), 3.15 (ddd, J = 12.9, 5.8, 3.3 Hz, 1H), 2.77 (dq, J = 9.8, 5.9 Hz, 2H), 2.64 (ddd, J = 16.4, 10.5, 6.0 Hz, 1H), 2.37 (dt, J = 13.9, 3.8 Hz, 1H), 2.04 (tt, J = 11.2, 5.6 Hz, 1H), 1.78 (h, J = 7.3 Hz, 2H), 1.72 – 1.46 (m, 6H), 0.88 (t, J = 7.4 Hz, 3H); $^{13}$C NMR (126 MHz, $CDCl_3$) δ 167.70, 163.31, 142.09, 137.29, 114.16, 73.00, 66.14, 61.22, 54.06, 50.88, 48.27, 45.24, 43.41, 26.73, 25.81, 25.75, 24.69, 24.39, 23.34, 19.55, 11.15. ESIMS *m/z* $[M+H]^+$ 379. | | | |
| NUCC-0200706 | 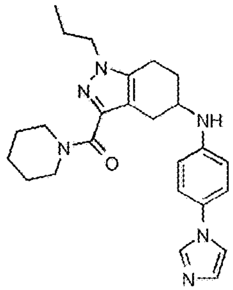 | $^{1}$H NMR (500 MHz, $CDCl_3$) δ 8.22 (s, 1H), 7.92 (t, J = 1.3 Hz, 1H), 7.19 (d, J = 1.3 Hz, 1H), 7.17 – 7.08 (m, 3H), 6.69 – 6.57 (m, 2H), 3.93 (t, J = 7.2 Hz, 2H), 3.86 – 3.71 (m, 3H), 3.66 (t, J = 5.3 Hz, 2H), 3.14 (dd, J = 15.9, 4.9 Hz, 1H), 2.75 – 2.65 (m, 2H), 2.60 (dd, J = 15.9, 7.3 Hz, 1H), 2.18 – 2.07 (m, 1H), 1.99 – 1.87 (m, 1H), 1.82 (p, J = 7.3 Hz, 2H), 1.73 – 1.45 (m, 6H), 0.91 (t, J = 7.4 Hz, 3H); $^{13}$C NMR (126 MHz, $CDCl_3$) δ 164.23, 163.73, 147.25, 142.59, 137.57, 135.29, 127.27, 126.77, 123.69, 119.38, 115.49, 113.47, 50.80, 48.51, 48.25, 43.38, 28.38, 27.41, 26.82, 25.73, 24.73, 23.48, 19.18, 11.21. ESIMS *m/z* $[M+H]^+$ 433. | | | |
| NUCC-0200707 | 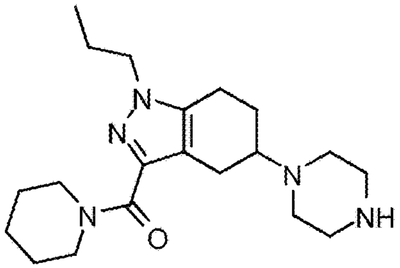 | $^{1}$H NMR (500 MHz, $CDCl_3$) δ 3.89 (d, J = 7.7 Hz, 2H), 3.74 (d, J = 22.1 Hz, 6H), 3.63 (t, J = 10.2 Hz, 6H), 3.19 (dd, J = 15.4, 4.7 Hz, 1H), 2.85 (t, J = 14.8 Hz, 2H), 2.69 (s, 1H), 2.46 – 2.35 (m, 1H), 1.99 (dd, J = 11.9, 5.8 Hz, 1H), 1.78 (q, J = 7.3 Hz, 2H), 1.71 – 1.49 (m, 6H), 0.87 (t, J = 7.4 Hz, 3H). ESIMS *m/z* $[M+H]^+$ 360. | | | |

FIG. 1K
| | | | | | |
|---|---|---|---|---|---|
| NUCC-0200708 | 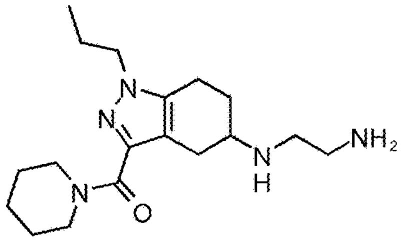 | $^{1}$H NMR (500 MHz, $CDCl_3$) δ 3.96 – 3.65 (m, 4H), 3.65 – 3.29 (m, 7H), 3.11 (dd, J = 15.7, 5.1 Hz, 1H), 2.86 – 2.52 (m, 3H), 2.39 – 2.23 (m, 1H), 1.98 (dt, J = 11.5, 5.4 Hz, 1H), 1.75 (p, J = 7.3 Hz, 2H), 1.69 – 1.37 (m, 6H), 0.87 (t, J = 7.4 Hz, 3H); $^{13}$C NMR (126 MHz, $CDCl_3$) δ 163.41, 141.58, 137.35, 113.36, 55.08, 50.92, 48.47, 43.70, 42.67, 36.48, 26.56, 25.54, 25.07, 24.45, 24.24, 23.20, 19.22, 11.02. ESIMS *m/z* $[M + H]^+$ 334. | | | |
| NUCC-0200710 | 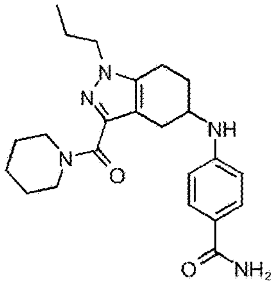 | ESIMS *m/z* $[M + H]^+$ 410. | | | |
| NUCC-0200711 | 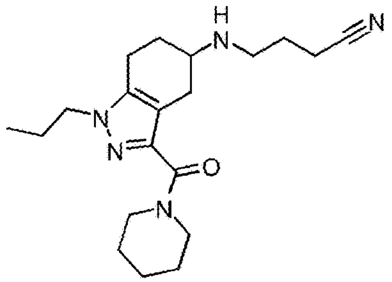 | $^{1}$H NMR (500 MHz, $CDCl_3$) δ 8.34 (s, 1H, FA), 3.93 – 3.83 (m, 2H), 3.78 (tq, J = 12.7, 6.4, 4.8 Hz, 2H), 3.60 (q, J = 5.3, 4.7 Hz, 2H), 3.31 (tt, J = 8.5, 2.6 Hz, 1H), 3.23 – 2.99 (m, 3H), 2.83 – 2.68 (m, 2H), 2.61 (ddd, J = 16.5, 10.8, 5.9 Hz, 1H), 2.51 (t, J = 7.1 Hz, 2H), 2.33 (dq, J = 10.3, 3.5 Hz, 1H), 2.07 (dq, J = 10.6, 6.8 Hz, 2H), 2.00 – 1.85 (m, 1H), 1.76 (h, J = 7.3 Hz, 2H), 1.69 – 1.45 (m, 6H), 0.86 (t, J = 7.4 Hz, 3H); $^{13}$C NMR (126 MHz, $CDCl_3$) δ 167.30, 163.24, 141.88, 137.42, 118.66, 114.24, 54.39, 50.89, 48.31, 43.77, 43.50, 26.69, 25.75, 25.64, 24.66, 24.62, 23.31, 22.53, 19.62, 14.84, 11.13. ESIMS *m/z* $[M + H]^+$ 358. | | | |

FIG. 1L

| | | | | | |
|---|---|---|---|---|---|
| NUCC-0200712 | 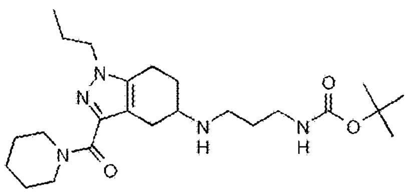 | $^1H$ NMR (500 MHz, $CDCl_3$) δ 3.87 (td, J = 7.0, 1.9 Hz, 2H), 3.78 (tt, J = 13.8, 8.9 Hz, 2H), 3.61 (p, J = 6.6, 6.0 Hz, 2H), 3.31 (dt, J = 14.9, 6.1 Hz, 1H), 3.25 – 3.13 (m, 3H), 3.10 (dt, J = 12.1, 7.2 Hz, 1H), 3.00 (dt, J = 12.5, 6.8 Hz, 1H), 2.82 – 2.67 (m, 2H), 2.62 (ddd, J = 16.6, 10.9, 5.8 Hz, 1H), 2.42 – 2.30 (m, 1H), 1.92 (dp, J = 21.2, 7.2, 6.3 Hz, 3H), 1.76 (h, J = 7.3 Hz, 2H), 1.69 – 1.48 (m, 6H), 1.38 (s, 9H), 0.87 (t, J = 7.4 Hz, 3H); $^{13}C$ NMR (126 MHz, $CDCl_3$) δ 167.37, 163.21, 157.05, 142.02, 137.29, 114.29, 79.68, 54.36, 50.87, 48.27, 43.44, 42.50, 37.19, 28.39, 26.80, 26.72, 25.75, 25.69, 24.67, 24.45, 23.34, 19.68, 11.15. ESIMS *m/z* $[M + H]^+$ 448. | | | |
| NUCC-0200713 | 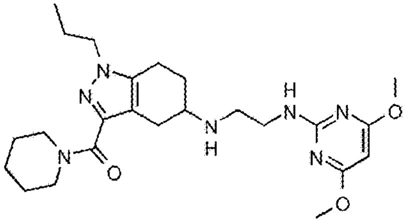 | $^1H$ NMR (500 MHz, $CDCl_3$) δ 8.16 (s, 1H), 3.86 (td, J = 7.0, 3.2 Hz, 2H), 3.75 (d, J = 17.5 Hz, 10H), 3.67 – 3.54 (m, 2H), 3.52 – 3.39 (m, 2H), 3.39 – 3.31 (m, 1H), 3.25 (dd, J = 15.4, 5.1 Hz, 1H), 2.86 – 2.69 (m, 2H), 2.61 (ddd, J = 16.8, 10.9, 6.1 Hz, 1H), 2.37 (ddd, J = 12.3, 6.3, 3.0 Hz, 1H), 2.03 (ddq, J = 17.2, 10.9, 5.9 Hz, 1H), 1.76 (h, J = 7.3 Hz, 2H), 1.71 – 1.48 (m, 6H), 0.87 (t, J = 7.4 Hz, 3H); $^{13}C$ NMR (126 MHz, $CDCl_3$) δ 172.14, 164.76, 163.35, 162.61, 162.33, 161.01, 142.02, 137.18, 117.79, 115.46, 113.89, 78.03, 54.54, 54.10, 50.88, 48.30, 45.01, 43.48, 38.46, 26.69, 25.72, 25.66, 24.64, 24.16, 23.31, 19.57, 11.12. ESIMS *m/z* $[M + H]^+$ 472. | | | |
| NUCC-0200714 | 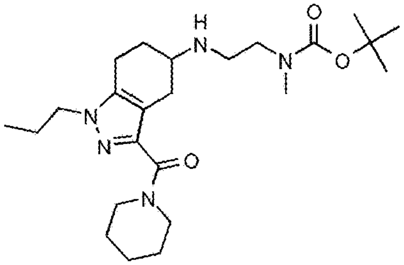 | $^1H$ NMR (500 MHz, $CDCl_3$) δ 8.34 (s, 2H, FA), 3.93 – 3.84 (m, 2H), 3.84 – 3.71 (m, 2H), 3.62 (t, J = 5.2 Hz, 2H), 3.59 – 3.29 (m, 3H), 3.18 (dd, J = 15.6, 5.3 Hz, 3H), 2.85 (s, 3H), 2.75 (tp, J = 10.5, 3.4 Hz, 2H), 2.63 (dq, J = 16.1, 8.9, 7.4 Hz, 1H), 2.38 – 2.25 (m, 1H), 2.07 – 1.89 (m, 1H), 1.77 (h, J = 7.3 Hz, 2H), 1.70 – 1.50 (m, 6H), 1.40 (s, 11H), 0.87 (t, J = 7.4 Hz, 3H); $^{13}C$ NMR (126 MHz, $CDCl_3$) δ 166.92, 163.26, 157.03, 142.16, 137.25, 114.22, 80.74, 53.71, 50.86, 48.24, 46.25, 43.67, 43.40, 35.77, 28.33, 26.73, 26.11, 25.75, 24.69, 24.51, 23.36, 19.46, 11.15. ESIMS *m/z* $[M + H]^+$ 448. | | | |

FIG. 1M
| | | | | | |
|---|---|---|---|---|---|
| NUCC-0200715 | 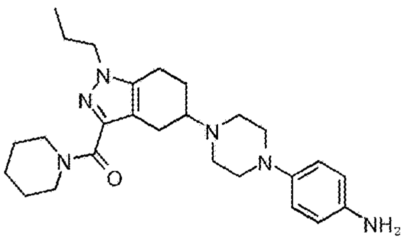 | ESIMS *m/z* [M + H]$^+$ 451.3. | | | |
| NUCC-0200716 | 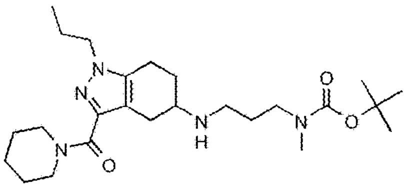 | $^1$H NMR (500 MHz, $CDCl_3$) δ 8.40 (s, 2H, FA), 3.88 (td, J = 7.0, 2.8 Hz, 2H), 3.78 (q, J = 5.8 Hz, 2H), 3.63 (dq, J = 12.0, 6.7, 5.8 Hz, 2H), 3.51 (s, 1H), 3.33 (d, J = 12.5 Hz, 1H), 3.21 (dd, J = 15.5, 5.1 Hz, 2H), 3.03 (q, J = 5.9, 5.5 Hz, 1H), 2.92 (q, J = 6.2 Hz, 1H), 2.81 (s, 4H), 2.76 (dd, J = 6.1, 2.7 Hz, 1H), 2.73 – 2.58 (m, 2H), 2.43 (s, 1H), 1.95 (dqd, J = 18.9, 10.6, 9.5, 4.9 Hz, 3H), 1.76 (p, J = 7.3 Hz, 2H), 1.69 – 1.47 (m, 6H), 1.41 (s, 10H), 0.88 (t, J = 7.4 Hz, 3H); $^{13}$C NMR (126 MHz, $CDCl_3$) δ 167.12, 163.21, 157.67, 142.19, 137.30, 114.19, 81.00, 54.32, 50.87, 48.21, 44.78, 43.32, 41.70, 34.39, 28.41, 26.77, 26.51, 25.76, 24.72, 24.16, 23.38, 19.74, 11.15. ESIMS m/z [M + H]$^+$ 463. | | +++ | |
| NUCC-0200717 | 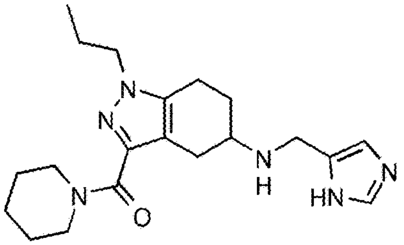 | $^1$H NMR (500 MHz, $CDCl_3$) δ 8.28 (s, 2H, FA), 7.76 (s, 1H), 7.18 (s, 1H), 4.27 (d, J = 13.5 Hz, 1H), 4.17 (d, J = 13.6 Hz, 1H), 3.94 – 3.73 (m, 4H), 3.62 (td, J = 13.4, 11.2, 6.4 Hz, 2H), 3.33 (d, J = 12.2 Hz, 1H), 3.23 (dd, J = 15.3, 5.1 Hz, 1H), 2.84 – 2.70 (m, 2H), 2.63 (ddd, J = 16.5, 11.0, 5.8 Hz, 1H), 2.38 (d, J = 12.4 Hz, 1H), 2.08 – 1.91 (m, 1H), 1.78 (h, J = 7.3 Hz, 2H), 1.62 (ddt, J = 23.4, 11.3, 5.1 Hz, 6H), 0.88 (t, J = 7.4 Hz, 3H); $^{13}$C NMR (126 MHz, $CDCl_3$) δ 167.36, 163.28, 141.87, 137.33, 135.86, 126.59, 121.47, 114.28, 53.67, 50.92, 48.35, 43.55, 39.92, 26.70, 25.76, 25.45, 24.63, 24.52, 23.33, 19.64, 11.16. ESIMS m/z [M + H]$^+$ 371 . | | | |

FIG. 1N

| | | | | | |
|---|---|---|---|---|---|
| NUCC-0200818 | 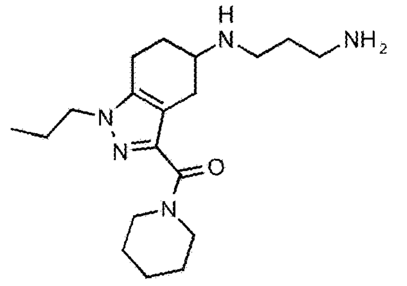 | $^1$H NMR (500 MHz, $CDCl_3$) δ 3.86 (q, J = 7.4 Hz, 2H), 3.82 – 3.65 (m, 2H), 3.65 – 3.50 (m, 2H), 3.34 (d, J = 41.5 Hz, 2H), 3.23 – 2.96 (m, 4H), 2.75 (dd, J = 16.1, 10.7 Hz, 2H), 2.68 – 2.51 (m, 1H), 2.37 – 2.13 (m, 3H), 1.96 (d, J = 20.7 Hz, 1H), 1.76 (h, J = 7.4 Hz, 2H), 1.70 – 1.44 (m, 6H), 0.87 (t, J = 7.4 Hz, 3H). ESIMS m/z $[M + H]^+$ 348. | | ++ | |
| NUCC-0200819 | 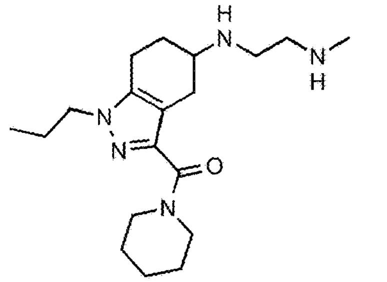 | $^1$H NMR (500 MHz, $CDCl_3$) δ 3.97 – 3.72 (m, 4H), 3.72 – 3.34 (m, 7H), 3.20 (dd, J = 15.3, 4.9 Hz, 1H), 2.89 – 2.55 (m, 6H), 2.42 – 2.23 (m, 1H), 2.04 (dd, J = 12.5, 6.0 Hz, 1H), 1.78 (h, J = 7.4 Hz, 2H), 1.63 (ddt, J = 34.8, 11.3, 6.0 Hz, 6H), 0.88 (t, J = 7.4 Hz, 3H); $^{13}$C NMR (126 MHz, $CDCl_3$) δ 163.42, 162.31, 141.52, 137.30, 117.37, 115.04, 113.54, 55.15, 50.99, 48.53, 45.80, 43.79, 41.44, 33.64, 26.61, 25.67, 25.35, 24.49, 24.15, 23.24, 19.28, 11.09. ESIMS m/z $[M + H]^+$ 348. | | | |
| NUCC-0200821 | 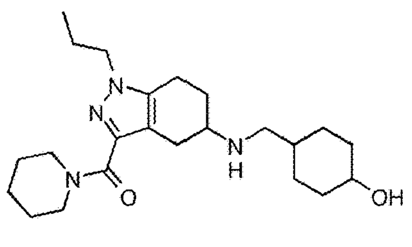 | $^1$H NMR (500 MHz, $CDCl_3$) δ 8.36 (s, 1H, FA), 3.96 – 3.71 (m, 4H), 3.62 (tq, J = 13.1, 7.4, 5.9 Hz, 2H), 3.48 (ddd, J = 10.9, 6.6, 4.1 Hz, 1H), 3.40 – 3.15 (m, 2H), 2.88 (dd, J = 12.3, 7.2 Hz, 1H), 2.84 – 2.68 (m, 3H), 2.62 (td, J = 11.7, 5.9 Hz, 1H), 2.48 – 2.37 (m, 1H), 2.05 – 1.82 (m, 4H), 1.77 (h, J = 7.3 Hz, 2H), 1.72 – 1.38 (m, 9H), 1.19 (t, J = 12.2 Hz, 1H), 1.01 (dp, J = 16.4, 7.0, 5.0 Hz, 1H), 0.87 (t, J = 7.4 Hz, 3H); $^{13}$C NMR (126 MHz, $CDCl_3$) δ 167.03, 163.25, 141.98, 137.35, 114.42, 69.97, 65.69, 54.98, 54.88, 50.88, 50.75, 50.46, 48.31, 43.47, 34.57, 34.54, 34.35, 33.88, 31.56, 31.52, 29.00, 28.89, 26.72, 25.77, 25.63, 24.67, 24.47, 24.30, 23.35, 19.90, 11.16. ESIMS m/z $[M + H]^+$ 403. | | ++ | |

FIG. 10O
| | | | | | |
|---|---|---|---|---|---|
| NUCC-0200822 | 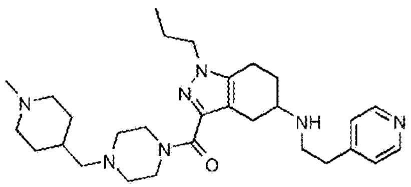 | | | ++ | |
| NUCC-0200823 | 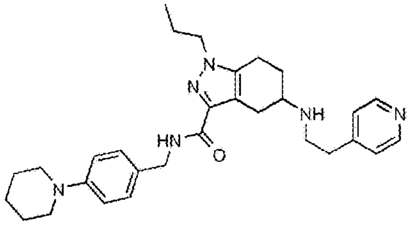 | $^1$H NMR (500 MHz, MeOD) δ 8.86 (d, $J$ = 6.3 Hz, 2H), 8.16 (d, $J$ = 6.1 Hz, 2H), 7.70 (d, $J$ = 8.7 Hz, 2H), 7.57 (d, $J$ = 8.3 Hz, 2H), 4.57 (s, 2H), 4.04 (t, $J$ = 7.1 Hz, 2H), 3.62 (dt, $J$ = 14.0, 6.6 Hz, 7H), 3.54 – 3.42 (m, 5H), 2.96 (ddd, $J$ = 16.5, 5.8, 3.4 Hz, 1H), 2.83 (qd, $J$ = 12.7, 11.4, 5.6 Hz, 2H), 2.46 (dd, $J$ = 11.0, 5.9 Hz, 1H), 2.15 – 2.00 (m, 5H), 1.87 (h, $J$ = 7.2 Hz, 3H), 1.18 (t, $J$ = 7.0 Hz, 2H), 0.92 (t, $J$ = 7.4 Hz, 3H). $^{13}$C NMR (126 MHz, MeOD) δ 165.07, 160.14, 143.47, 142.69, 142.49, 141.95, 140.18, 130.49, 129.16, 122.37, 114.66, 66.89, 58.45, 56.19, 52.08, 45.31, 42.75, 33.33, 26.37, 25.91, 24.83, 24.25, 22.08, 20.34, 15.44, 11.36. | | | |
| NUCC-0200824 | 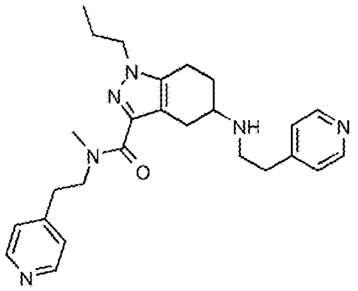 | $^1$H NMR (500 MHz, MeOD) δ 8.89 – 8.83 (m, 2H), 8.78 (t, $J$ = 5.0 Hz,21H), 8.17 (d, $J$ = 6.5 Hz, 2H), 8.08 (d, $J$ = 5.6 Hz, 1H), 7.97 (d, $J$ = 6.0 Hz, 1H), 4.30 (t, $J$ = 7.2 Hz, 1H), 4.03 (t, $J$ = 7.1 Hz, 1H), 3.61 (t, $J$ = 8.2 Hz, 2H), 3.49 (q, $J$ = 7.0 Hz, 3H), 3.37 (d, $J$ = 21.0 Hz, 2H), 3.20 (dd, $J$ = 15.6, 5.2 Hz, 1H), 3.14 (s, 1H), 3.02 – 2.89 (m, 1H), 2.75 (dtd, $J$ = 48.8, 15.5, 13.3, 7.7 Hz, 1H), 2.45 (d, $J$ = 13.0 Hz, 1H), 1.82 (dp, $J$ = 14.4, 7.2 Hz, 1H), 1.60 (s, 2H), 1.18 (t, $J$ = 7.0 Hz, 3H). | | ++ | |

FIG. 1P

| | | | | | |
|---|---|---|---|---|---|
| NUCC-0200825 | 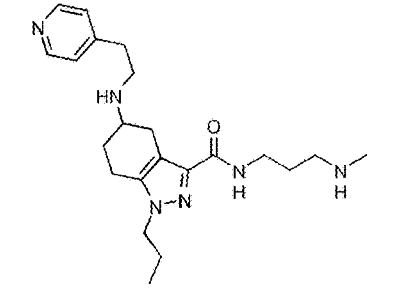 | $^1$H NMR (500 MHz, MeOD) δ 8.86 (d, J = 6.0 Hz, 2H), 8.17 (d, J = 6.0 Hz, 2H), 4.04 (t, J = 7.1 Hz, 2H), 3.62 (dtt, J = 12.7, 8.4, 4.8 Hz, 3H), 3.47 (ddd, J = 16.8, 10.0, 4.6 Hz, 7H), 3.04 (t, J = 7.4 Hz, 2H), 2.96 (ddd, J = 16.7, 5.6, 3.4 Hz, 1H), 2.84 (ddd, J = 24.8, 16.4, 10.0 Hz, 2H), 2.72 (s, 3H), 2.46 (dd, J = 11.6, 5.2 Hz, 1H), 2.05 (tt, J = 11.2, 5.5 Hz, 1H), 1.96 (p, J = 6.8 Hz, 2H), 1.87 (h, J = 7.3 Hz, 2H), 1.60 (s, 2H), 1.18 (t, J = 7.0 Hz, 2H), 0.92 (t, J = 7.4 Hz, 3H). | | | |
| NUCC-0200826 | 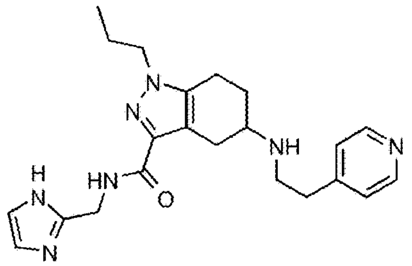 | $^1$H NMR (500 MHz, MeOD) δ 7.28 – 7.18 (m, 2H), 6.48 – 6.41 (m, 2H), 3.22 (d, J = 1.7 Hz, 2H), 2.47 (t, J = 7.1 Hz, 2H), 2.02 (q, J = 8.5, 8.0 Hz, 3H), 1.89 – 1.77 (m, 3H), 1.74 (p, J = 1.7 Hz, 2H), 1.44 – 1.31 (m, 1H), 1.30 – 1.17 (m, 2H), 0.89 – 0.78 (m, 1H), 0.44 (dtd, J = 12.7, 10.6, 5.8 Hz, 1H), 0.30 (h, J = 7.3 Hz, 2H), -0.65 (t, J = 7.4 Hz, 3H). | | | |
| NUCC-0200827 | 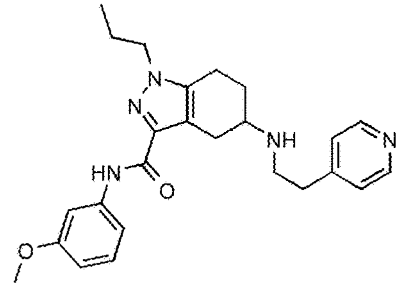 | $^1$H NMR (500 MHz, MeOD) δ 8.38 – 8.27 (m, 2H), 7.59 – 7.52 (m, 2H), 6.93 (t, J = 2.2 Hz, 1H), 6.79 – 6.67 (m, 2H), 6.21 (ddd, J = 8.0, 2.5, 1.2 Hz, 1H), 3.59 (t, J = 7.2 Hz, 2H), 3.31 (s, 3H), 3.20 – 3.08 (m, 3H), 3.08 – 2.97 (m, 1H), 2.91 (ddt, J = 8.9, 6.6, 3.6 Hz, 2H), 2.83 (p, J = 1.7 Hz, 1H), 2.47 (ddd, J = 16.6, 6.1, 3.9 Hz, 1H), 2.35 (ddd, J = 26.2, 16.5, 7.8 Hz, 2H), 1.94 (ddd, J = 13.7, 6.2, 3.0 Hz, 1H), 1.54 (dtd, J = 12.7, 10.8, 5.9 Hz, 1H), 1.46 – 1.35 (m, 2H), 0.46 (t, J = 7.4 Hz, 3H). | ++ | +++ | |

FIG. 1Q
| | | | | | |
|---|---|---|---|---|---|
| NUCC-0200828 | 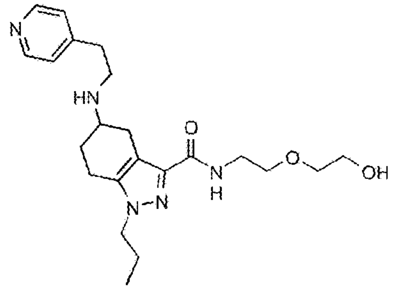 | $^1$H NMR (500 MHz, $CD_3OD$) δ 9.30 (d, $J$ = 5.8 Hz, 2H), 8.51 (dd, $J$ = 6.2, 3.3 Hz, 2H), 7.91 (s, 0H), 5.08 (t, $J$ = 4.5 Hz, 1H), 4.87 (s, 6H), 4.53 – 4.44 (m, 2H), 4.35 (t, $J$ = 4.6 Hz, 1H), 4.33 – 4.25 (m, 1H), 4.24 – 3.89 (m, 10H), 3.47 – 3.31 (m, 2H), 3.28 (ddd, $J$ = 16.6, 10.6, 6.0 Hz, 1H), 2.97 (dd, $J$ = 11.7, 5.5 Hz, 1H), 2.56 (qt, $J$ = 11.1, 5.0 Hz, 1H), 2.38 (hd, $J$ = 7.3, 2.4 Hz, 2H), 1.48 (t, $J$ = 7.4 Hz, 3H). | | | |
| NUCC-0200830 | 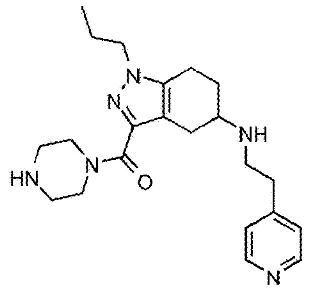 | ESIMS m/z $[M + H]^+$ 397.4. | | | |
| NUCC-0200831 | 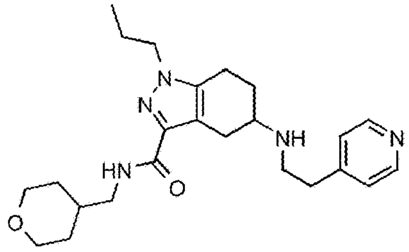 | ESIMS m/z $[M + H]^+$ 426.3 | | ++ | |

FIG. 1R

| | | | | | |
|---|---|---|---|---|---|
| NUCC-0200832 | 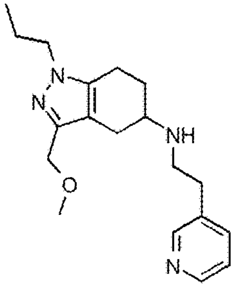 | $^{1}$H NMR (500 MHz, $CDCl_3$) δ 8.71 – 8.11 (m, 1H), 7.58 (dt, J = 7.9, 1.9 Hz, 0H), 7.28 – 7.13 (m, 1H), 4.35 (s, 1H), 3.86 (d, J = 4.6 Hz, 0H), 3.30 (s, 1H), 3.27 – 3.14 (m, 1H), 3.14 – 2.88 (m, 1H), 2.72 (ddd, J = 16.2, 5.7, 2.9 Hz, 0H), 2.60 (qd, J = 11.0, 9.8, 4.9 Hz, 1H), 2.38 – 2.20 (m, 0H), 1.92 (qd, J = 11.2, 5.8 Hz, 0H), 1.77 (q, J = 7.3 Hz, 1H), 0.87 (t, J = 7.4 Hz, 1H). $^{13}$C NMR (126 MHz, $CDCl_3$) δ 167.79, 149.89, 148.30, 145.20, 137.42, 136.55, 133.55, 123.81, 111.50, 67.22, 58.10, 54.42, 50.65, 46.82, 31.09, 27.12, 24.85, 23.67, 20.05, 11.30. ESIMS m/z [M + H]$^+$ 329.24. | | | |
| NUCC-0200833 | 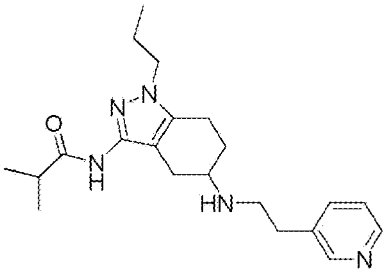 | 1H NMR (500 MHz, CDCl3) δ 8.47 (s, 2H), 8.39 (s, 1H), 7.77 (s, 1H), 7.59 (d, J = 7.8 Hz, 1H), 7.23 (dd, J = 7.8, 4.9 Hz, 1H), 3.77 (t, J = 7.2 Hz, 2H), 3.15 (ddp, J = 32.4, 17.1, 5.9, 5.5 Hz, 2H), 2.99 (ddd, J = 27.3, 15.0, 6.5 Hz, 2H), 2.72 (dt, J = 16.4, 4.9 Hz, 1H), 2.65 – 2.55 (m,2H), 2.52 (q, J = 6.9 Hz, 1H), 2.32 – 2.19 (m, 1H), 1.96 (td, J = 9.8, 5.0 Hz, 1H), 1.74 (q, J = 7.3 Hz, 2H), 1.25 (s, 1H), 1.21 (dd, J = 6.9, 3.0 Hz, 6H), 0.87 (t, J = 7.4 Hz, 3H). 13C NMR (126 MHz, CDCl3) δ 175.67, 167.35, 149.91, 148.14, 142.49, 138.23, 136.73, 133.80, 123.80, 106.31, 54.08, 50.51, 46.96, 35.80, 31.35, 29.84, 26.83, 26.26, 23.52, 19.89, 19.80, 19.70, 11.31. ESIMS m/z [M + H]+ 370.37. | | | |
| NUCC-0200834 | 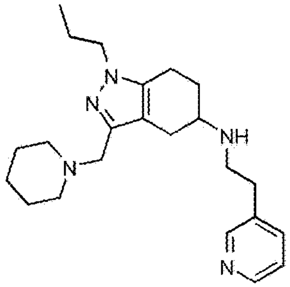 | $^{1}$H NMR (500 MHz, CDCl3) δ 8.48 (dd, J = 16.7, 7.4 Hz, 2H), 8.39 (s, 2H), 7.67 (d, J = 7.6 Hz, 1H), 4.05 (d, J = 9.5 Hz, 1H), 3.96 (dt, J = 14.4, 6.5 Hz, 1H), 3.89 (td, J = 7.0, 4.2 Hz, 2H), 3.37 (s, 1H), 3.24 (s, 2H), 3.04 (d, J = 46.4 Hz, 6H), 2.86 – 2.74 (m, 2H), 2.59 (dd, J = 33.7, 12.0 Hz, 1H), 2.26 (s, 1H), 2.02 (d, J = 17.1 Hz, 1H), 1.78 (h, J = 7.5 Hz, 2H), 1.56 (s, 2H), 0.89 (t, J = 7.4 Hz, 3H). $^{13}$C NMR (126 MHz, CDCl3) δ 167.34, 149.73, 147.96, 138.23, 137.44, 137.13, 133.56, 123.95, 113.85, 53.98, 52.76, 51.73, 51.02, 46.74, 33.34, 30.50, 25.55, 24.39, 23.51, 22.90, 22.16, 19.34, 11.29. ESIMS m/z [M + H]$^+$ 382.3 | | | |

FIG. 1S

| | | | | | |
|---|---|---|---|---|---|
| NUCC-0200835 | 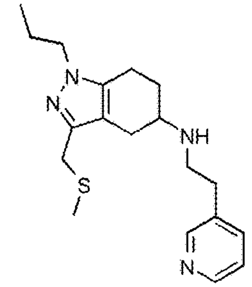 | $^{1}$H NMR (500 MHz, $CDCl_3$) δ 8.56 – 8.42 (m, 2H), 7.58 (dt, J = 7.9, 1.9 Hz, 1H), 7.24 (dd, J = 7.8, 4.7 Hz, 1H), 4.35 (s, 2H), 3.86 (d, J = 4.6 Hz, 2H), 3.30 (s, 3H), 3.24 – 3.14 (m, 2H), 3.14 – 2.94 (m, 4H), 2.72 (ddd, J = 16.2, 5.7, 2.9 Hz, 1H), 2.60 (qd, J = 11.0, 9.8, 4.9 Hz, 2H), 2.35 – 2.26 (m, 1H), 1.92 (qd, J = 11.2, 5.8 Hz, 1H), 1.77 (q, J = 7.3 Hz, 2H), 0.87 (t, J = 7.4 Hz, 3H). $^{13}$C NMR (126 MHz, $CDCl_3$) δ 167.37, 149.72, 148.15, 145.08, 137.42, 136.85, 133.25, 123.92, 110.20, 54.53, 50.52, 46.54, 30.40, 29.51, 26.46, 24.29, 23.67, 19.99, 15.10, 11.26. ESIMS m/z $[M + H]^+$ 345.23 | | | |
| NUCC-0200836 | 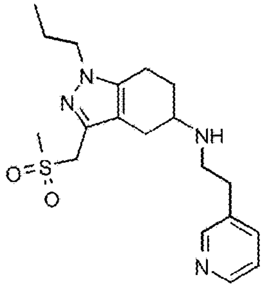 | $^{1}$H NMR (500 MHz, $CDCl_3$) δ 8.49 (d, J = 2.2 Hz, 1H), 8.47 (dd, J = 4.9, 1.5 Hz, 1H), 8.32 (s, 2H), 7.63 (dt, J = 7.7, 1.9 Hz, 1H), 4.21 (q, J = 14.6 Hz, 2H), 3.89 (td, J = 7.0, 4.5 Hz, 2H), 3.35 (d, J = 6.7 Hz, 1H), 3.33 – 3.24 (m, 1H), 3.18 (td, J = 11.2, 10.5, 5.8 Hz, 1H), 3.11 – 2.98 (m, 3H), 2.83 (s, 3H), 2.81 – 2.72 (m, 2H), 2.66 (ddd, J = 16.1, 9.5, 6.7 Hz, 1H), 2.35 – 2.26 (m, 1H), 2.05 (tdd, J = 16.9, 12.4, 7.2 Hz, 1H), 1.79 (p, J = 7.3 Hz, 2H), 0.89 (t, J = 7.4 Hz, 3H). $^{13}$C NMR (126 MHz, $CDCl_3$) δ 166.73, 149.49, 147.95, 138.22, 137.17, 137.09, 133.32, 124.05, 113.20, 54.04, 53.63, 50.95, 46.68, 39.19, 30.54, 26.27, 24.22, 23.60, 19.50, 11.28. $[M + H]^+$ 377.2 | | | |
| NUCC-0200837 | 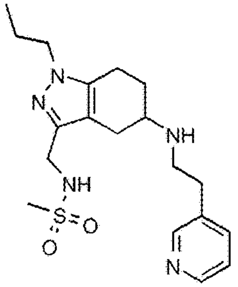 | $^{1}$H NMR (500 MHz, CDCl3) δ 8.51 (s, 1H), 8.47 (d, J = 4.5 Hz, 1H), 8.02 (s, 1H), 7.59 (d, J = 8.0 Hz, 1H), 4.23 (d, J = 5.3 Hz, 2H), 3.85 (t, J = 7.2 Hz, 2H), 3.49 (s, 1H), 3.10 (s, 1H), 2.96 (s, 1H), 2.93 (s, 3H), 2.59 (d, J = 7.9 Hz, 1H), 1.77 (q, J = 7.3 Hz, 1H), 1.26 (s, 1H), 0.88 (t, J = 7.4 Hz, 3H). | | | |

FIG. 1T

| | | | | | |
|---|---|---|---|---|---|
| NUCC-0200838 | 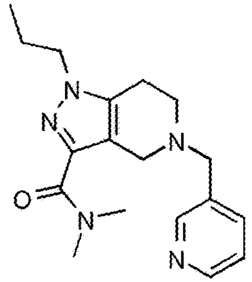 | $^1$H NMR (500 MHz, $CDCl_3$) δ 8.60 (d, J = 2.2 Hz, 1H), 8.53 (dd, J = 4.6, 2.1 Hz, 1H), 8.27 – 8.13 (m, 1H), 7.87 – 7.77 (m, 1H), 7.33 (tt, J = 7.5, 4.5 Hz, 1H), 3.92 (td, J = 9.8, 8.5, 3.7 Hz, 2H), 3.84 (d, J = 11.9 Hz, 1H), 3.79 (d, J = 14.4 Hz, 3H), 3.35 (d, J = 4.5 Hz, 3H), 3.03 (d, J = 4.5 Hz, 3H), 2.87 (q, J = 7.8, 6.8 Hz, 1H), 2.82 (q, J = 5.6 Hz, 1H), 2.72 (p, J = 5.8 Hz, 2H), 1.81 (dtp, J = 11.1, 7.3, 3.4 Hz, 2H), 0.95 – 0.85 (m, 3H). $^{13}$C NMR (126 MHz, $CDCl_3$) δ 164.70, 149.40, 147.73, 141.26, 138.38, 137.80, 136.63, 136.36, 123.85, 117.09, 58.65, 50.86, 49.90, 48.91, 38.94, 35.99, 23.41, 21.82, 11.17. ESIMS m/z $[M + H]^+$ 327.8 | | | |
| NUCC-0200839 | 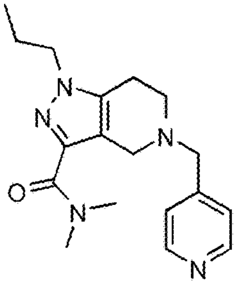 | $^1$H NMR (500 MHz, $CDCl_3$) δ 8.42 – 8.31 (m, 2H), 8.01 (s, 1H), 7.25 (d, J = 2.0 Hz, 1H), 3.74 (t, J = 7.1 Hz, 2H), 3.64 (s, 2H), 3.58 (s, 2H), 3.17 (s, 3H), 2.83 (s, 3H), 2.66 (t, J = 5.7 Hz, 2H), 2.54 (t, J = 5.7 Hz, 2H), 1.64 (p, J = 7.3 Hz, 2H), 0.71 (td, J = 7.4, 1.9 Hz, 3H). $^{13}$C NMR (126 MHz, $CDCl_3$) δ 164.65, 164.34, 148.85, 147.89, 141.21, 136.52, 124.70, 116.85, 60.11, 50.94, 49.91, 49.31, 39.03, 36.10, 23.44, 21.74, 11.20. ESIMS m/z $[M + H]^+$ 328.2 | | | |
| NUCC-0200840 | 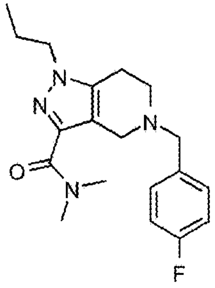 | $^1$H NMR (500 MHz, $CDCl_3$) δ 8.48 (s, 1H), 7.66 – 7.58 (m, 2H), 7.26 (t, J = 8.6 Hz, 2H), 4.24 (s, 2H), 4.20 (s, 2H), 4.15 (t, J = 7.1 Hz, 2H), 3.59 (s, 3H), 3.34 (t, J = 5.9 Hz, 2H), 3.24 (s, 3H), 3.09 (t, J = 5.9 Hz, 2H), 2.03 (h, J = 7.3 Hz, 2H), 1.11 (t, J = 7.4 Hz, 3H). $^{13}$C NMR (126 MHz, $CDCl_3$) δ 166.23, 163.94, 163.86, 161.96, 141.65, 135.62, 132.25, 132.18, 128.86, 128.84, 115.95, 115.78, 114.83, 59.53, 51.08, 48.73, 48.51, 38.98, 36.18, 23.38, 20.49, 11.15. ESIMS m/z $[M + H]^+$ 345.5 | | | |

FIG. 1U
| | | | | | |
|---|---|---|---|---|---|
| NUCC-0200841 | 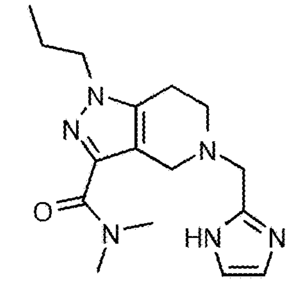 | $^1H$ NMR (500 MHz, $CDCl_3$) δ 8.54 (s, 1H), 7.26 (s, 1H), 4.35 (s, 2H), 4.15 – 4.05 (m, 4H), 3.55 (s, 3H), 3.19 (s, 5H), 2.97 (t, J = 5.7 Hz, 2H), 1.98 (h, J = 7.3 Hz, 2H), 1.06 (t, J = 7.4 Hz, 3H). $^{13}C$ NMR (126 MHz, $CDCl_3$) δ 167.29, 164.03, 141.94, 141.36, 135.78, 121.39, 114.89, 51.09, 51.04, 49.44, 48.47, 39.00, 36.21, 23.34, 20.43, 11.17. ESIMS m/z $[M + H]^+$ 317.5 | | | |
| NUCC-0200842 | 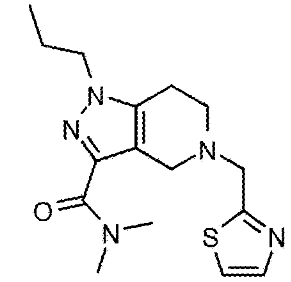 | $^1H$ NMR (500 MHz, $CDCl_3$) δ 8.09 (s, 1H), 7.69 (d, J = 3.3 Hz, 1H), 4.10 (s, 2H), 3.89 (d, J = 6.9 Hz, 4H), 3.32 (s, 3H), 3.00 (s, 3H), 2.91 (t, J = 5.7 Hz, 2H), 2.69 (t, J = 5.7 Hz, 2H), 1.78 (h, J = 7.3 Hz, 2H), 0.86 (t, J = 7.4 Hz, 3H). $^{13}C$ NMR (126 MHz, $CDCl_3$) δ 169.19, 164.46, 164.01, 142.37, 141.30, 136.63, 120.09, 116.99, 57.53, 50.92, 49.91, 49.07, 39.04, 36.10, 23.48, 21.72, 11.24. | | | |
| NUCC-0200843 | 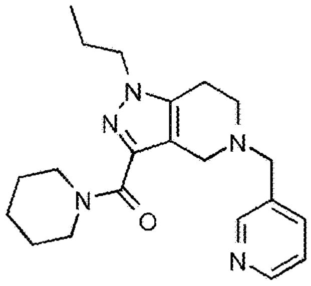 | $^1H$ NMR (500 MHz, $CDCl_3$) δ 8.62 (d, J = 2.3 Hz, 1H), 8.60 – 8.54 (m, 1H), 8.20 (s, 1H), 7.88 (dt, J = 7.9, 2.0 Hz, 1H), 7.38 (dd, J = 7.9, 4.9 Hz, 1H), 3.99 – 3.88 (m, 6H), 3.84 (s, 2H), 3.63 (d, J = 7.0 Hz, 2H), 2.94 (t, J = 5.8 Hz, 2H), 2.76 (t, J = 5.8 Hz, 2H), 1.81 (h, J = 7.4 Hz, 2H), 1.65 (q, J = 5.8, 5.0 Hz, 2H), 1.62 – 1.52 (m, 4H), 0.90 (t, J = 7.4 Hz, 3H). $^{13}C$ NMR (126 MHz, $CDCl_3$) δ 164.84, 162.84, 149.20, 147.89, 141.43, 138.77, 136.29, 132.58, 124.28, 116.00, 58.21, 51.00, 49.56, 48.93, 48.19, 43.73, 26.83, 25.88, 24.81, 23.49, 21.41, 11.26. ESIMS m/z $[M + H]^+$ 368.3 | | | |

FIG. 1V

| | | | | | |
|---|---|---|---|---|---|
| NUCC-0200844 | 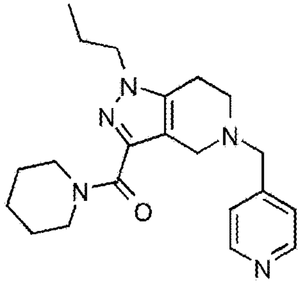 | $^1H$ NMR (500 MHz, $CDCl_3$) δ 8.43 – 8.35 (m, 2H), 8.01 (s, 1H), 7.27 (d, J = 1.6 Hz, 1H), 3.75 (t, J = 7.1 Hz, 4H), 3.65 (s, 2H), 3.58 (s, 2H), 3.51 – 3.37 (m, 2H), 2.66 (t, J = 5.8 Hz, 2H), 2.55 (t, J = 5.8 Hz, 2H), 1.64 (p, J = 7.3 Hz, 2H), 1.46 (q, J = 5.5 Hz, 2H), 1.44 – 1.32 (m, 4H), 0.73 (t, J = 7.4 Hz, 3H). $^{13}C$ NMR (126 MHz, $CDCl_3$) δ 164.57, 162.95, 148.86, 148.02, 141.29, 136.53, 124.71, 116.65, 60.20, 50.95, 49.94, 49.37, 48.18, 43.70, 26.84, 25.86, 24.80, 23.51, 21.84, 11.27. | | | |
| NUCC-0200845 | 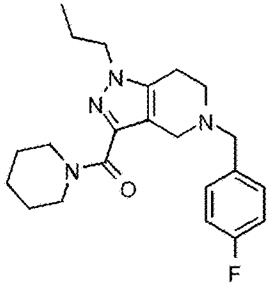 | $^1H$ NMR (500 MHz, $CDCl_3$) δ 8.48 (s, 1H), 7.64 – 7.57 (m, 2H), 7.28 (s, 1H), 4.24 – 4.09 (m, 8H), 3.84 (d, J = 7.0 Hz, 2H), 3.29 (td, J = 5.9, 2.6 Hz, 2H), 3.06 (t, J = 5.9 Hz, 2H), 2.04 (hept, J = 7.0 Hz, 2H), 1.87 (dt, J = 10.7, 5.1 Hz, 2H), 1.11 (t, J = 7.4 Hz, 3H). $^{13}C$ NMR (126 MHz, $CDCl_3$) δ 166.21, 163.90, 162.55, 161.93, 141.73, 135.80, 135.77, 132.13, 132.11, 132.06, 115.93, 115.76, 115.02, 59.78, 59.76, 51.07, 48.86, 48.84, 48.60, 48.12, 43.73, 26.81, 25.90, 24.82, 23.47, 20.80, 20.77, 11.24. ESIMS m/z $[M + H]^+$ 385.3 | | | |
| NUCC-0200846 | 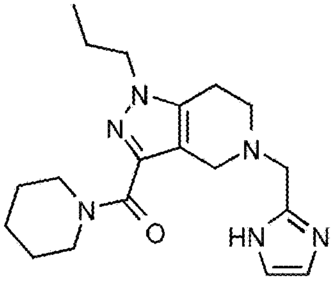 | $^1H$ NMR (500 MHz, $CDCl_3$) δ 8.52 (s, 1H), 7.26 (s, 1H), 4.40 (d, J = 13.0 Hz, 2H), 4.20 (d, J = 14.2 Hz, 2H), 4.12 (dq, J = 13.8, 6.6 Hz, 3H), 3.80 (dt, J = 11.4, 5.2 Hz, 2H), 3.51 (t, J = 6.0 Hz, 1H), 3.31 (q, J = 7.3 Hz, 1H), 3.24 (t, J = 5.9 Hz, 1H), 3.18 (t, J = 6.0 Hz, 1H), 3.02 (t, J = 5.9 Hz, 1H), 2.06 – 1.95 (m, 2H), 1.85 (dq, J = 10.7, 5.0 Hz, 2H), 1.82 – 1.72 (m, 4H), 1.54 (t, J = 7.3 Hz, 1H), 1.08 (td, J = 7.4, 2.6 Hz, 3H). $^{13}C$ NMR (126 MHz, $CDCl_3$) δ 167.08, 162.30, 141.18, 135.33, 134.82, 121.84, 114.11, 113.18, 51.11, 51.00, 50.64, 49.42, 48.63, 48.06, 47.80, 43.67, 26.67, 25.78, 24.65, 23.30, 20.00, 19.52, 11.13, 9.71. ESIMS m/z $[M + H]^+$ 357.5 | | | |

FIG. 1W

| | | | | | |
|---|---|---|---|---|---|
| NUCC-0200847 | 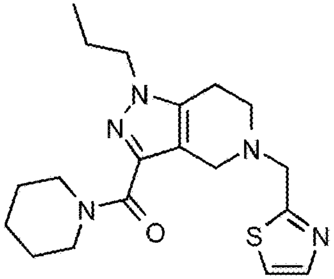 | $^1$H NMR (500 MHz, $CDCl_3$) δ 8.09 (s, 1H), 7.68 (d, J = 3.4 Hz, 1H), 4.09 (s, 2H), 3.87 (dd, J = 14.0, 6.8 Hz, 5H), 3.57 (d, J = 21.0 Hz, 2H), 2.89 (t, J = 5.8 Hz, 2H), 2.68 (t, J = 5.7 Hz, 2H), 1.78 (tq, J = 14.6, 7.3 Hz, 2H), 1.59 (t, J = 5.0 Hz, 3H), 1.56 (s, 3H), 0.86 (t, J = 7.4 Hz, 3H). $^{13}$C NMR (126 MHz, $CDCl_3$) δ 169.22, 164.15, 163.10, 142.41, 141.35, 136.63, 120.10, 116.67, 57.63, 50.91, 49.87, 49.14, 48.26, 43.66, 26.85, 25.86, 24.83, 23.52, 21.81, 11.27. ESIMS m/z $[M + H]^+$ 373.6 | | | |
| NUCC-0200848 | 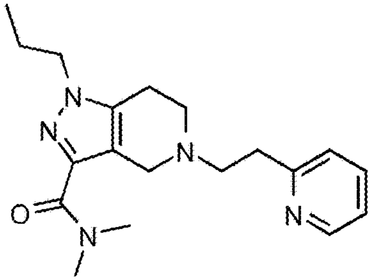 | $^1$H NMR (500 MHz, $CDCl_3$) δ 8.50 (dt, J = 5.0, 2.3 Hz, 1H), 8.27 (d, J = 3.1 Hz, 1H), 7.65 (tt, J = 7.8, 2.6 Hz, 1H), 7.18 (dd, J = 7.7, 4.5 Hz, 1H), 4.24 (d, J = 3.1 Hz, 2H), 3.95 (td, J = 7.1, 3.2 Hz, 2H), 3.49 – 3.35 (m, 5H), 3.30 (ddt, J = 15.8, 10.4, 4.8 Hz, 4H), 3.05 (d, J = 2.9 Hz, 3H), 2.97 (q, J = 5.9, 4.7 Hz, 2H), 1.83 (qd, J = 7.3, 3.2 Hz, 2H), 0.90 (td, J = 7.3, 3.2 Hz, 3H). $^{13}$C NMR (126 MHz, $CDCl_3$) δ 166.27, 163.68, 157.44, 148.94, 141.96, 137.48, 135.23, 124.09, 122.25, 114.06, 55.42, 51.22, 49.21, 49.02, 38.99, 36.30, 33.12, 23.43, 19.94, 11.21. ESIMS m/z $[M + H]^+$ 342.2 | | | |
| NUCC-0200849 | 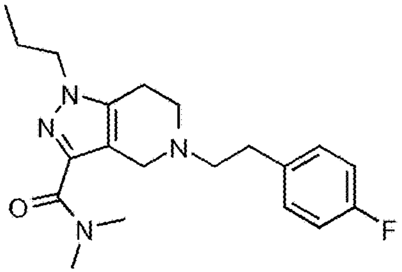 | $^1$H NMR (500 MHz, $CDCl_3$) δ 8.58 (s, 1H), 7.50 – 7.42 (m, 2H), 7.28 (s, 1H), 4.48 (s, 2H), 4.23 (t, J = 7.1 Hz, 2H), 3.72 (s, 3H), 3.53 (t, J = 6.0 Hz, 2H), 3.45 – 3.38 (m, 2H), 3.38 – 3.27 (m, 5H), 3.23 (t, J = 5.9 Hz, 2H), 2.12 (h, J = 7.3 Hz, 2H), 1.19 (t, J = 7.4 Hz, 3H). $^{13}$C NMR (126 MHz, $CDCl_3$) δ 166.62, 163.73, 141.93, 135.39, 133.37, 133.35, 130.42, 130.36, 115.77, 114.43, 58.04, 51.21, 49.65, 48.71, 39.00, 36.31, 30.93, 23.45, 20.24, 11.22. ESIMS m/z $[M + H]^+$ 359.5 | | | |

FIG. 1X

| | | | | | |
|---|---|---|---|---|---|
| NUCC-0200850 | 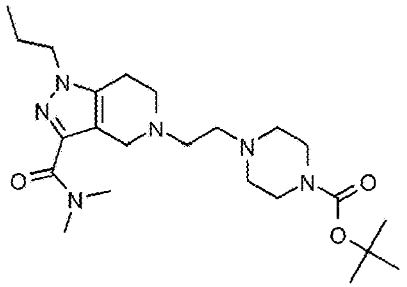 | $^{1}$H NMR (500 MHz, $CDCl_3$) δ 4.06 (s, 2H), 3.93 (t, J = 7.1 Hz, 2H), 3.49 (t, J = 5.0 Hz, 4H), 3.40 (s, 3H), 3.20 (t, J = 5.9 Hz, 2H), 3.09 (t, J = 6.4 Hz, 2H), 3.04 (s, 3H), 2.88 (dt, J = 17.1, 6.1 Hz, 4H), 2.67 (t, J = 5.0 Hz, 4H), 1.81 (h, J = 7.3 Hz, 2H), 1.42 (s, 9H), 0.88 (t, J = 7.4 Hz, 3H). $^{13}$C NMR (126 MHz, $CDCl_3$) δ 166.25, 163.84, 154.53, 141.67, 135.56, 114.72, 80.32, 53.47, 52.76, 52.04, 51.13, 49.73, 49.17, 39.01, 36.30, 28.43, 23.41, 20.31, 11.20. ESIMS m/z $[M + H]^+$ 449.4 | | | |
| NUCC-0200851 | 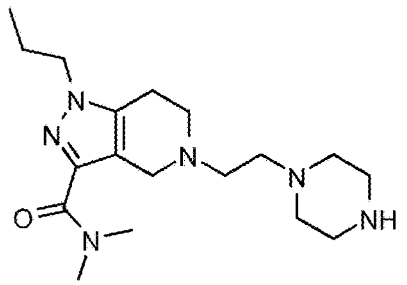 | $^{1}$H NMR (500 MHz, $CDCl_3$) δ 4.46 (s, 1H), 3.95 (t, J = 7.1 Hz, 1H), 3.59 (s, 1H), 3.48 – 3.39 (m, 1H), 3.33 (t, J = 5.6 Hz, 1H), 3.19 (s, 1H), 3.10 – 2.97 (m, 2H), 2.87 (d, J = 4.8 Hz, 1H), 2.78 (s, 1H), 1.82 (h, J = 7.1 Hz, 1H), 0.88 (td, J = 7.4, 1.7 Hz, 1H). $^{13}$C NMR (126 MHz, $CDCl_3$) δ 163.31, 142.02, 134.19, 117.85, 115.52, 111.73, 52.05, 51.38, 51.21, 49.82, 49.48, 49.09, 43.44, 39.01, 36.45, 23.28, 18.70, 11.07. ESIMS m/z $[M + H]^+$ 349.3 | | | |
| NUCC-0200852 | 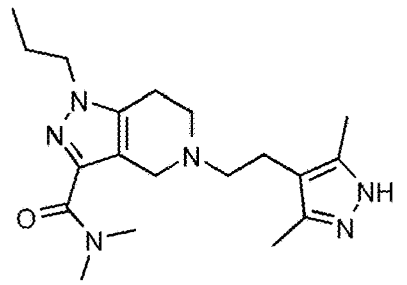 | $^{1}$H NMR (500 MHz, $CDCl_3$) δ 8.28 (s, 1H), 4.10 (s, 2H), 3.95 (t, J = 7.1 Hz, 2H), 3.43 (s, 3H), 3.16 (t, J = 5.9 Hz, 2H), 3.07 (s, 3H), 2.91 (t, J = 5.9 Hz, 2H), 2.88 – 2.80 (m, 2H), 2.78 (dt, J = 8.1, 5.3 Hz, 2H), 2.20 (s, 6H), 1.84 (h, J = 7.3 Hz, 2H), 0.91 (t, J = 7.4 Hz, 3H). $^{13}$C NMR (126 MHz, $CDCl_3$) δ 166.50, 163.97, 142.32, 141.82, 135.84, 115.18, 112.09, 56.80, 51.17, 49.77, 48.77, 39.06, 36.30, 23.49, 20.75, 19.75, 11.26, 10.75. ESIMS m/z $[M + H]^+$ d 359.3 | | | |

FIG. 1Y

| | | | | | |
|---|---|---|---|---|---|
| NUCC-0200853 | 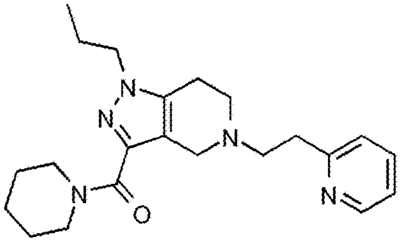 | $^{1}$H NMR (500 MHz, $CDCl_3$) δ 8.50 (dd, J = 5.0, 1.7 Hz, 1H), 8.28 (s, 1H), 7.64 (td, J = 7.7, 1.9 Hz, 1H), 7.24 (s, 1H), 7.20 – 7.12 (m, 1H), 4.18 (s, 2H), 4.00 (t, J = 5.5 Hz, 2H), 3.93 (t, J = 7.2 Hz, 2H), 3.64 (dd, J = 7.5, 3.8 Hz, 2H), 3.36 (dd, J = 10.1, 5.9 Hz, 2H), 3.27 (q, J = 4.4, 3.1 Hz, 4H), 2.93 (t, J = 5.9 Hz, 2H), 1.82 (h, J = 7.3 Hz, 2H), 1.67 (dt, J = 9.5, 4.5 Hz, 2H), 1.64 – 1.53 (m, 4H), 0.90 (t, J = 7.4 Hz, 3H). $^{13}$C NMR (126 MHz, $CDCl_3$) δ 166.28, 162.23, 157.70, 148.97, 141.89, 137.26, 135.33, 123.91, 122.08, 114.19, 55.56, 51.09, 49.25, 48.99, 47.98, 43.69, 33.40, 26.77, 25.86, 24.78, 23.40, 20.15, 11.18. ESIMS m/z $[M + H]^+$ 381.7 | | | |
| NUCC-0200854 | 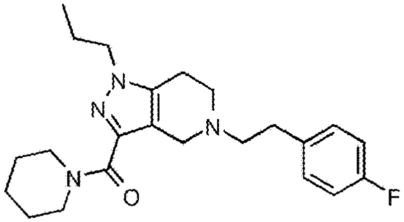 | $^{1}$H NMR (500 MHz, $CDCl_3$) δ 8.39 (s, 1H), 7.30 – 7.23 (m, 2H), 7.06 (t, J = 8.6 Hz, 2H), 4.27 (s, 2H), 4.12 (t, J = 5.3 Hz, 2H), 4.03 (t, J = 7.1 Hz, 2H), 3.74 (t, J = 5.3 Hz, 2H), 3.33 (t, J = 5.9 Hz, 2H), 3.26 – 3.18 (m, 2H), 3.16 – 3.09 (m, 2H), 3.03 (t, J = 5.9 Hz, 2H), 1.91 (h, J = 7.3 Hz, 2H), 1.77 (dt, J = 10.4, 4.7 Hz, 2H), 1.74 – 1.64 (m, 4H), 0.99 (t, J = 7.4 Hz, 3H). $^{13}$C NMR (126 MHz, $CDCl_3$) δ 166.59, 162.19, 141.92, 135.32, 133.32, 130.39, 130.32, 115.74, 115.57, 114.27, 58.10, 51.14, 49.73, 48.73, 48.01, 43.76, 30.97, 26.80, 25.91, 24.80, 23.44, 20.29, 11.20. ESIMS m/z $[M + H]^+$ 399.2 | +++ | ++ | |
| NUCC-0200855 | 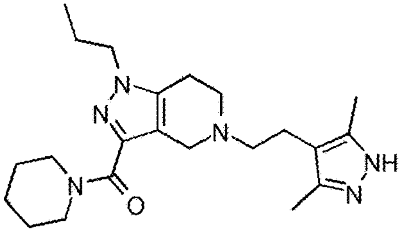 | $^{1}$H NMR (500 MHz, $CDCl_3$) δ 8.24 (s, 1H), 4.28 (s, 2H), 4.06 (t, J = 5.4 Hz, 2H), 3.95 (t, J = 7.1 Hz, 2H), 3.66 (t, J = 5.3 Hz, 2H), 3.35 (t, J = 5.9 Hz, 2H), 2.99 (t, J = 6.2 Hz, 4H), 2.88 – 2.80 (m, 2H), 2.19 (s, 6H), 1.83 (h, J = 7.3 Hz, 2H), 1.68 (td, J = 6.5, 5.7, 3.2 Hz, 2H), 1.63 (t, J = 5.7 Hz, 4H), 0.91 (t, J = 7.4 Hz, 3H). $^{13}$C NMR (126 MHz, $CDCl_3$) δ 165.99, 162.04, 142.42, 142.05, 135.14, 113.68, 111.08, 56.41, 51.26, 49.97, 48.67, 48.07, 43.88, 26.83, 25.97, 24.83, 23.46, 20.14, 19.09, 11.20, 10.62. ESIMS m/z $[M + H]^+$ 399.3 | | ++ | |

FIG. 1Z

| | | | | | |
|---|---|---|---|---|---|
| NUCC-0200856 | 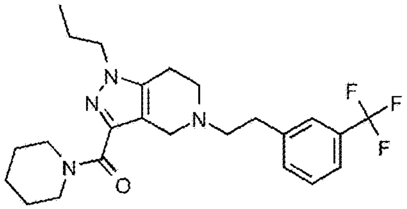 | $^1$H NMR (500 MHz, $CDCl_3$) δ 8.12 (s, 1H), 7.34 – 7.29 (m, 2H), 7.25 (d, J = 2.1 Hz, 1H), 3.94 (s, 2H), 3.85 (t, J = 5.4 Hz, 2H), 3.78 (t, J = 7.1 Hz, 2H), 3.50 (t, J = 5.2 Hz, 2H), 3.00 (t, J = 5.9 Hz, 2H), 2.93 (s, 4H), 2.74 (t, J = 5.9 Hz, 2H), 1.67 (h, J = 7.4 Hz, 2H), 1.52 (dt, J = 10.7, 3.8 Hz, 2H), 1.45 (dd, J = 11.9, 6.1 Hz, 4H), 0.75 (t, J = 7.4 Hz, 3H). $^{13}$C NMR (126 MHz, $CDCl_3$) δ 166.36, 162.43, 141.84, 139.25, 135.69, 132.39, 129.28, 125.55, 125.51, 123.69, 123.66, 115.00, 58.04, 51.11, 49.86, 48.93, 48.06, 43.74, 32.09, 26.85, 25.93, 24.85, 23.49, 20.75, 11.23. ESIMS m/z [M + H]$^+$ 449.7 | ++ | +++ | |
| NUCC-0200857 | 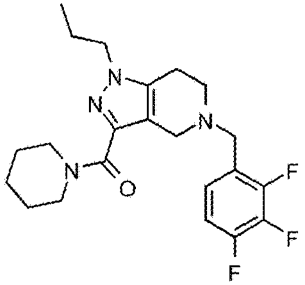 | $^1$H NMR (500 MHz, $CDCl_3$) δ 8.14 (s, 1H), 7.25 – 7.18 (m, 1H), 6.96 (tdd, J = 9.1, 6.9, 2.0 Hz, 1H), 4.02 – 3.88 (m, 6H), 3.84 (s, 2H), 3.65 (s, 2H), 2.96 (t, J = 5.9 Hz, 2H), 2.77 (t, J = 5.8 Hz, 2H), 1.82 (h, J = 7.3 Hz, 2H), 1.66 (d, J = 5.5 Hz, 2H), 1.61 (d, J = 12.5 Hz, 4H), 0.91 (t, J = 7.4 Hz, 3H). $^{13}$C NMR (126 MHz, $CDCl_3$) δ 164.65, 162.91, 141.50, 136.29, 125.59, 125.56, 125.53, 116.18, 112.46, 112.43, 112.32, 112.29, 53.04, 51.02, 49.22, 48.86, 48.22, 43.77, 26.87, 25.93, 24.87, 23.53, 21.48, 11.29. ESIMS m/z [M + H]$^+$ 421.4 | | ++ | |
| NUCC-0200858 | 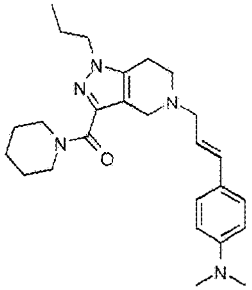 | 1H NMR (500 MHz, CDCl3) δ 8.24 (s, 2H), 7.26 (dd, J = 9.8, 8.1 Hz, 2H), 6.69 – 6.59 (m, 3H), 6.03 (dt, J = 15.4, 7.4 Hz, 1H), 4.32 (d, J = 8.8 Hz, 2H), 4.00 (d, J = 5.0 Hz, 2H), 3.92 (t, J = 7.1 Hz, 2H), 3.86 (d, J = 7.4 Hz, 2H), 3.61 (t, J = 5.5 Hz, 2H), 3.48 – 3.35 (m, 2H), 3.02 (t, J = 6.0 Hz, 2H), 2.95 (s, 5H), 2.93 – 2.81 (m, 3H), 1.80 (h, J = 7.4 Hz, 2H), 1.70 – 1.62 (m, 2H), 1.59 (d, J = 4.8 Hz, 4H), 0.88 (t, J = 7.4 Hz, 3H). 13C NMR (126 MHz, CDCl3) δ 165.89, 161.84, 151.01, 142.14, 140.56, 134.66, 128.31, 123.28, 112.88, 112.22, 111.19, 58.59, 51.30, 48.20, 48.04, 47.95, 43.87, 40.43, 26.76, 25.90, 24.77, 23.41, 19.54, 11.17. ESIMS m/z [M + H]$^+$ 436.3 | ++ | ++ | |

FIG. 1AA

| | | | | | |
|---|---|---|---|---|---|
| NUCC-0200859 | 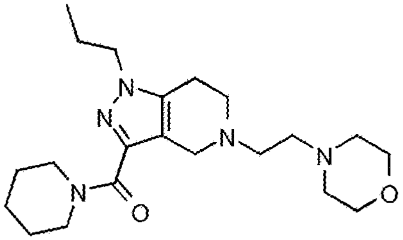 | 1H NMR (500 MHz, CDCl3) δ 8.31 (s, 1H), 4.00 (t, J = 5.3 Hz, 2H), 3.97 – 3.89 (m, 4H), 3.76 (t, J = 4.7 Hz, 4H), 3.65 (t, J = 5.3 Hz, 2H), 3.10 (dt, J = 8.9, 4.4 Hz, 2H), 2.99 (td, J = 6.7, 2.4 Hz, 2H), 2.87 – 2.79 (m, 4H), 2.69 (t, J = 4.5 Hz, 4H), 1.82 (h, J = 7.4 Hz, 2H), 1.67 (dt, J = 10.3, 5.1 Hz, 2H), 1.65 – 1.53 (m, 4H), 0.91 (t, J = 7.4 Hz, 3H). 13C NMR (126 MHz, CDCl3) δ 166.54, 162.63, 141.70, 136.03, 115.59, 66.19, 54.79, 53.54, 52.71, 51.06, 50.03, 49.47, 48.11, 43.72, 26.89, 25.95, 24.89, 23.52, 21.03, 11.29. ESIMS m/z [M + H]+ 389.8 | | | |
| NUCC-0200860 | 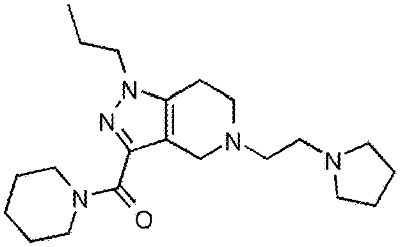 | 1H NMR (500 MHz, CDCl3) δ 8.35 (s, 1H), 3.98 (t, J = 5.3 Hz, 2H), 3.91 (t, J = 7.2 Hz, 2H), 3.71 (s, 2H), 3.64 (t, J = 5.3 Hz, 2H), 3.30 (d, J = 6.5 Hz, 3H), 3.25 (t, J = 6.4 Hz, 2H), 2.98 (t, J = 6.4 Hz, 2H), 2.88 (t, J = 5.7 Hz, 2H), 2.69 (t, J = 5.7 Hz, 2H), 2.08 – 1.96 (m, 4H), 1.81 (h, J = 7.3 Hz, 2H), 1.66 (p, J = 5.2, 4.4 Hz, 2H), 1.63 – 1.52 (m, 4H), 0.90 (t, J = 7.4 Hz, 3H). 13C NMR (126 MHz, CDCl3) δ 166.73, 163.06, 141.15, 136.98, 116.76, 54.07, 52.77, 52.35, 50.91, 50.21, 49.47, 48.15, 43.66, 26.87, 25.91, 24.86, 23.49, 23.16, 21.70, 11.27. ESIMS m/z [M + H]+ 374.3 | | ++ | |
| NUCC-0200861 | 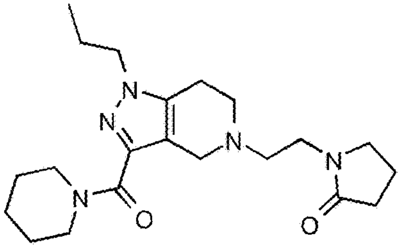 | 1H NMR (500 MHz, CDCl3) δ 8.17 (s, 1H), 4.23 – 4.15 (m, 2H), 4.03 – 3.96 (m, 2H), 3.93 (t, J = 7.1 Hz, 2H), 3.64 (q, J = 6.5 Hz, 4H), 3.46 (t, J = 7.1 Hz, 2H), 3.32 (q, J = 8.8, 7.1 Hz, 2H), 3.15 (t, J = 6.3 Hz, 2H), 2.91 (t, J = 5.8 Hz, 2H), 2.38 (t, J = 8.1 Hz, 2H), 2.03 (h, J = 8.4, 7.7 Hz, 2H), 1.82 (h, J = 7.3 Hz, 2H), 1.67 (td, J = 6.5, 5.8, 2.9 Hz, 2H), 1.64 – 1.54 (m, 4H), 0.90 (t, J = 7.3 Hz, 3H). 13C NMR (126 MHz, CDCl3) δ 176.37, 165.02, 162.25, 141.88, 135.20, 113.88, 52.53, 51.18, 49.72, 48.72, 48.08, 47.68, 43.82, 38.83, 30.73, 26.80, 25.90, 24.81, 23.45, 20.09, 17.90, 11.22. ESIMS m/z [M + H]+ 387.9 | | | |

FIG. 1BB

| | | | | | |
|---|---|---|---|---|---|
| NUCC-0200862 | 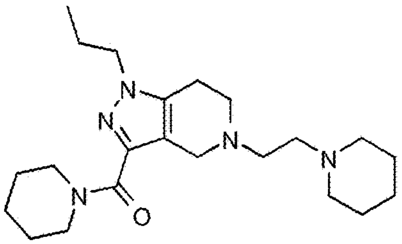 | 1H NMR (500 MHz, CDCl3) δ 8.37 – 8.33 (m, 1H), 3.97 (dt, J = 12.0, 6.1 Hz, 2H), 3.91 (t, J = 7.2 Hz, 2H), 3.73 (s, 2H), 3.64 (t, J = 5.4 Hz, 2H), 3.21 – 3.09 (m, 5H), 3.02 (t, J = 6.3 Hz, 2H), 2.89 (t, J = 5.7 Hz, 2H), 2.70 (t, J = 5.7 Hz, 2H), 1.83 (dq, J = 24.8, 7.3, 6.6 Hz, 5H), 1.72 – 1.64 (m, 2H), 1.64 – 1.53 (m, 6H), 0.90 (t, J = 7.4 Hz, 3H). 13C NMR (126 MHz, CDCl3) δ 166.47, 163.04, 141.18, 136.91, 116.60, 53.77, 51.51, 50.95, 49.87, 49.60, 48.17, 43.70, 26.88, 25.93, 24.87, 23.50, 22.90, 22.21, 21.56, 11.28, 11.20. ESIMS m/z [M + H]+ 388.9 | ++ | ++ | |
| NUCC-0200863 | 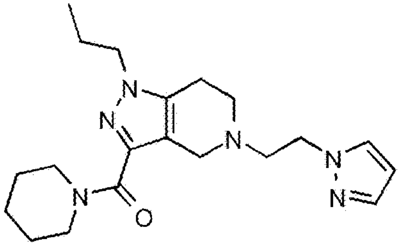 | $^1$H NMR (500 MHz, $CDCl_3$) δ 8.16 (s, 1H), 7.56 – 7.48 (m, 2H), 6.25 (t, J = 2.1 Hz, 1H), 4.51 (t, J = 6.6 Hz, 2H), 4.04 (s, 2H), 3.98 (t, J = 5.3 Hz, 2H), 3.92 (t, J = 7.1 Hz, 2H), 3.65 (t, J = 5.3 Hz, 2H), 3.34 (t, J = 6.7 Hz, 2H), 2.99 (t, J = 5.9 Hz, 2H), 2.80 (t, J = 5.9 Hz, 2H), 1.67 (dt, J = 10.6, 5.0 Hz, 2H), 1.61 (q, J = 6.4 Hz, 4H), 0.90 (t, J = 7.4 Hz, 3H). $^{13}$C NMR (126 MHz, $CDCl_3$) δ 164.87, 164.84, 162.45, 141.78, 139.97, 135.58, 130.46, 114.83, 106.05, 55.66, 51.09, 49.79, 49.51, 48.56, 48.10, 43.80, 26.84, 25.91, 24.83, 23.47, 20.60, 11.23. ESIMS m/z [M + H]+ 371.5. | | | |
| NUCC-0200864 | 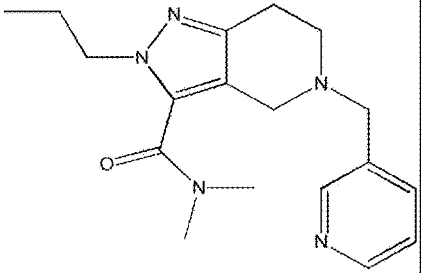 | $^1$H NMR (500 MHz, $CDCl_3$) δ 8.55 (t, J = 3.2 Hz, 1H), 8.50 (d, J = 5.1 Hz, 1H), 7.79 – 7.70 (m, 1H), 7.28 (dd, J = 6.6, 4.0 Hz, 1H), 4.02 (q, J = 7.2, 6.0 Hz, 2H), 3.70 (d, J = 8.8 Hz, 2H), 3.43 (d, J = 8.5 Hz, 2H), 3.02 (s, 3H), 2.95 (d, J = 16.7 Hz, 3H), 2.78 (tp, J = 8.2, 4.4, 3.4 Hz, 4H), 1.85 – 1.71 (m, 2H), 0.85 (t, J = 7.4 Hz, 3H). $^{13}$C NMR (126 MHz, $CDCl_3$) δ 162.91, 149.75, 149.63, 148.40, 145.29, 137.01, 133.87, 131.76, 123.65, 113.10, 58.91, 52.01, 50.46, 48.87, 37.99, 34.89, 23.96, 23.24, 11.13. ESIMS m/z [M + H]+ 328.5. | | | |

FIG. 1CC
| | | | | | |
|---|---|---|---|---|---|
| NUCC-0200865 | 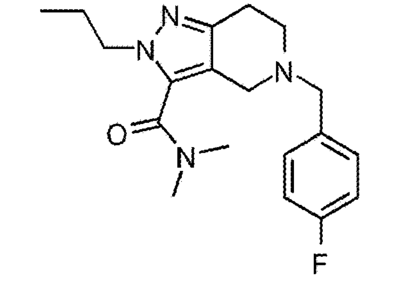 | $^1$H NMR (500 MHz, $CDCl_3$) δ 7.61 – 7.54 (m, 2H), 7.28 (d, J = 2.2 Hz, 1H), 7.24 (s, 1H), 4.29 (t, J = 7.3 Hz, 2H), 3.99 (s, 2H), 3.78 (s, 2H), 3.29 (s, 3H), 3.21 (d, J = 17.0 Hz, 3H), 3.13 (d, J = 6.0 Hz, 2H), 3.06 (t, J = 5.9 Hz, 2H), 2.05 (h, J = 7.4 Hz, 2H), 1.12 (t, J = 7.4 Hz, 3H). $^{13}$C NMR (126 MHz, $CDCl_3$) δ 166.04, 163.38, 162.89, 161.43, 144.97, 132.53, 132.12, 131.05, 115.53, 112.47, 60.19, 52.17, 49.85, 48.35, 38.10, 35.00, 24.05, 22.66, 11.22. | | | |
| NUCC-0200866 | 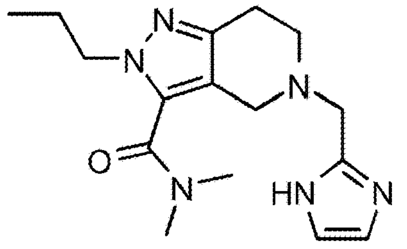 | $^1$H NMR (500 MHz, $CDCl_3$) δ 9.53 (s, 2H), 8.60 (s, 1H), 4.28 (t, J = 7.3 Hz, 2H), 4.23 (s, 2H), 3.80 (s, 2H), 3.28 (s, 3H), 3.24 – 3.15 (m, 5H), 3.10 (t, J = 5.9 Hz, 2H), 2.04 (h, J = 7.3 Hz, 2H), 1.10 (t, J = 7.4 Hz, 3H). $^{13}$C NMR (126 MHz, $CDCl_3$) δ 167.40, 162.61, 144.25, 143.43, 132.35, 122.24, 111.39, 53.43, 52.29, 50.55, 48.71, 38.10, 35.07, 24.04, 22.60, 11.23. ESIMS m/z [M + H]$^+$ 316.5 | | | |
| NUCC-0200867 | 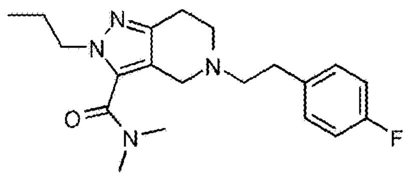 | $^1$H NMR (500 MHz, $CDCl_3$) δ 7.20 – 7.12 (m, 2H), 7.02 – 6.92 (m, 2H), 4.05 (t, J = 7.3 Hz, 2H), 3.61 (s, 2H), 3.07 (s, 3H), 3.01 (s, 3H), 2.96 (t, J = 5.9 Hz, 2H), 2.92 – 2.78 (m, 6H), 1.81 (p, J = 7.3 Hz, 2H), 0.87 (t, J = 7.5 Hz, 3H). $^{13}$C NMR (126 MHz, $CDCl_3$) δ 166.37, 162.84, 162.49, 160.55, 144.80, 135.07, 132.07, 130.11, 115.21, 112.24, 58.63, 52.11, 50.42, 48.64, 38.07, 34.93, 32.72, 23.95, 22.66, 11.13. ESIMS m/z [M + H]$^+$ 359.1 | ++ | | |

FIG. 1DD
| | | | | | |
|---|---|---|---|---|---|
| NUCC-0200868 | 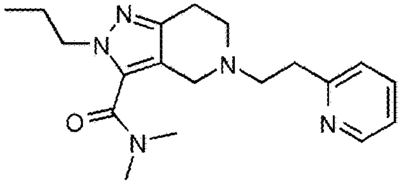 | $^1$H NMR (500 MHz, $CDCl_3$) δ 8.50 (dd, J = 4.9, 1.6 Hz, 1H), 8.26 (s, 1H), 7.63 (td, J = 7.7, 1.9 Hz, 1H), 7.16 (dd, J = 7.5, 5.0 Hz, 1H), 4.05 (t, J = 7.5 Hz, 2H), 3.89 (s, 2H), 3.27 (dd, J = 8.7, 4.9 Hz, 2H), 3.24 – 3.16 (m, 3H), 3.13 – 2.98 (m, 6H), 2.96 (t, J = 6.1 Hz, 2H), 1.81 (p, J = 7.4 Hz, 2H), 0.87 (t, J = 7.4 Hz, 3H). $^{13}$C NMR (126 MHz, $CDCl_3$) δ 166.14, 162.40, 158.04, 149.07, 143.51, 137.19, 132.71, 123.82, 122.05, 110.05, 55.24, 52.33, 49.94, 48.14, 38.18, 35.04, 33.99, 23.95, 21.41, 11.19. ESIMS m/z $[M + H]^+$ 341.7 | | | |
| NUCC-0200869 | 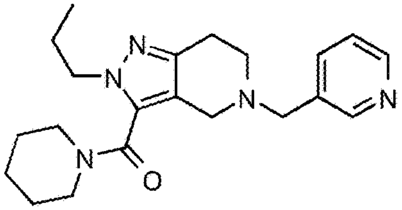 | $^1$H NMR (500 MHz, $CDCl_3$) δ 8.60 (d, J = 2.1 Hz, 1H), 8.58 (dd, J = 4.9, 1.7 Hz, 1H), 8.18 (s, 2H), 7.89 (dt, J = 8.0, 2.0 Hz, 1H), 7.40 (dd, J = 7.9, 4.9 Hz, 1H), 4.07 (s, 2H), 3.87 (s, 2H), 3.60 (s, 2H), 2.96 (s, 2H), 2.86 (t, J = 6.0 Hz, 2H), 1.82 (h, J = 7.4 Hz, 2H), 1.52 (s, 3H), 0.88 (t, J = 7.4 Hz, 3H). $^{13}$C NMR (126 MHz, $CDCl_3$) δ 164.67, 161.19, 149.01, 147.92, 144.36, 138.80, 132.68, 132.44, 124.40, 111.35, 57.73, 52.24, 49.91, 48.28, 43.18, 26.90, 25.78, 24.43, 24.04, 22.26, 11.28. ESIMS m/z $[M + H]^+$ 368.3 | | | |
| NUCC-0200870 | 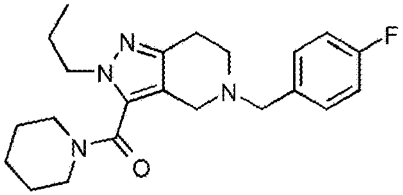 | $^1$H NMR (500 MHz, $CDCl_3$) δ 8.43 (s, 2H), 7.62 – 7.53 (m, 2H), 4.26 (s, 2H), 4.20 (s, 2H), 4.14 – 3.80 (m, 2H), 3.52 (s, 5H), 3.15 (d, J = 6.9 Hz, 2H), 2.02 (h, J = 7.3 Hz, 2H), 1.92 – 1.80 (m, 2H), 1.72 (s, 3H), 1.08 (t, J = 7.4 Hz, 3H). $^{13}$C NMR (126 MHz, $CDCl_3$) δ 165.86, 164.15, 160.76, 143.00, 133.07, 132.33, 128.41, 116.16, 109.10, 58.01, 52.40, 48.75, 47.03, 43.59, 27.23, 25.92, 24.37, 23.96, 20.77, 11.26. | ++ | | |

FIG. 1EE
| | | | | | |
|---|---|---|---|---|---|
| NUCC-0200871 | 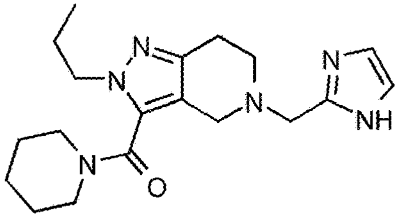 | $^1$H NMR (500 MHz, $CDCl_3$) δ 8.46 (s, 2H), 4.47 (s, 2H), 4.33 – 4.11 (m, 2H), 3.91 (s, 2H), 3.81 – 3.38 (m, 3H), 3.31 (t, J = 6.1 Hz, 2H), 3.12 (t, J = 5.9 Hz, 2H), 1.97 (h, J = 7.3 Hz, 2H), 1.88 – 1.78 (m, 2H), 1.70 (s, 4H), 1.04 (td, J = 7.4, 2.2 Hz, 3H). $^{13}$C NMR (126 MHz, $CDCl_3$) δ 167.01, 160.69, 142.95, 140.68, 132.74, 122.33, 109.04, 52.40, 51.35, 50.08, 48.06, 43.09, 27.23, 25.90, 24.37, 23.95, 21.56, 11.25. | | | |
| NUCC-0200872 | 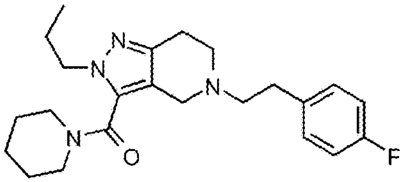 | $^1$H NMR (500 MHz, $CDCl_3$) δ 8.55 (s, 1H), 7.54 (d, J = 1.9 Hz, 1H), 7.49 – 7.39 (m, 2H), 7.28 (s, 1H), 4.31 (d, J = 38.4 Hz, 3H), 4.10 (s, 2H), 3.88 – 3.43 (m, 5H), 3.37 (dd, J = 11.1, 5.5 Hz, 2H), 3.33 – 3.15 (m, 4H), 2.11 (h, J = 7.4 Hz, 2H), 1.96 (s, 2H), 1.17 (t, J = 7.4 Hz, 3H). $^{13}$C NMR (126 MHz, $CDCl_3$) δ 165.97, 162.80, 160.56, 142.65, 133.06, 130.26, 115.73, 115.56, 108.57, 56.16, 52.34, 49.27, 47.50, 43.16, 31.00, 26.79, 25.78, 24.29, 23.83, 20.44, 11.16. | +++ | | |
| NUCC-0200873 | 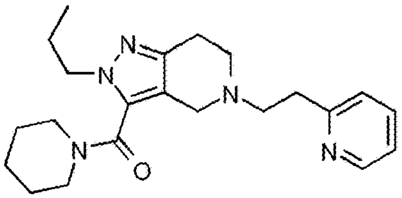 | $^1$H NMR (500 MHz, $CDCl_3$) δ 8.47 (d, J = 5.0 Hz, 1H), 8.22 (d, J = 1.6 Hz, 2H), 7.69 – 7.59 (m, 1H), 7.24 (d, J = 5.0 Hz, 1H), 7.16 (dd, J = 7.5, 5.0 Hz, 1H), 4.21 – 3.68 (m, 4H), 3.49 – 3.27 (m, 6H), 3.23 (dd, J = 9.6, 6.2 Hz, 3H), 3.06 – 2.88 (m, 2H), 1.79 (h, J = 7.3 Hz, 2H), 0.85 (td, J = 7.4, 1.5 Hz, 3H). $^{13}$C NMR (126 MHz, $CDCl_3$) δ 165.97, 160.62, 157.24, 148.85, 142.68, 137.60, 133.07, 124.11, 122.37, 108.57, 54.35, 52.42, 49.52, 47.79, 43.19, 33.19, 27.21, 25.61, 24.39, 23.93, 20.61, 11.24. | | | |

FIG. 1FF

| | | | | | |
|---|---|---|---|---|---|
| NUCC-0200877 | 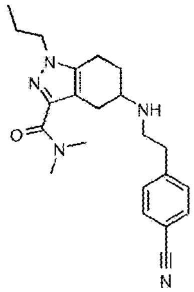 | $^1$H NMR (500 MHz, $CDCl_3$) δ 8.30 (s, 2H), 7.48 (d, J = 7.7 Hz, 2H), 7.24 (s, 1H), 3.82 (t, J = 7.4 Hz, 2H), 3.22 (d, J = 24.9 Hz, 6H), 3.13 (td, J = 10.8, 4.3 Hz, 1H), 3.10 – 2.97 (m, 2H), 2.94 (s, 3H), 2.82 – 2.65 (m, 2H), 2.62 – 2.48 (m, 1H), 2.37 – 2.25 (m, 1H), 1.91 (q, J = 8.9, 6.0 Hz, 1H), 1.72 (p, J = 7.4 Hz, 2H), 0.80 (t, J = 7.4 Hz, 3H). $^{13}$C NMR (126 MHz, $CDCl_3$) δ 167.23, 164.66, 142.57, 141.94, 137.38, 132.64, 129.78, 118.72, 114.89, 111.15, 54.49, 51.07, 46.10, 39.24, 36.06, 32.81, 25.81, 25.00, 23.45, 19.75, 11.25. ESIMS m/z $[M + H]^+$ 379.7 | | | |
| NUCC-0200879 | 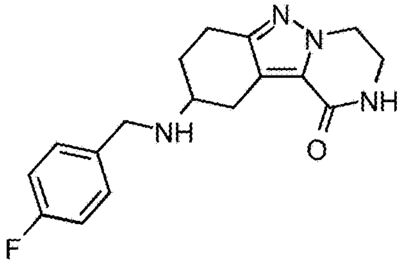 | $^1$H NMR (500 MHz, DMSO-$d_6$) δ 8.24 (s, 1H), 8.03 (t, $J$ = 2.7 Hz, 1H), 7.50 – 7.41 (m, 2H), 4.16 (dd, $J$ = 7.1, 5.0 Hz, 2H), 3.89 (s, 2H), 3.53 (td, $J$ = 6.1, 5.2, 2.8 Hz, 2H), 3.08 (dd, $J$ = 16.3, 5.0 Hz, 1H), 2.95 (tdd, $J$ = 8.3, 5.1, 2.4 Hz, 1H), 2.71 (dt, $J$ = 16.2, 4.9 Hz, 1H), 2.58 – 2.43 (m, 4H), 2.07 (dd, $J$ = 12.8, 6.0 Hz, 1H), 1.65 (dtd, $J$ = 12.8, 10.1, 5.4 Hz, 1H). $^{13}$C NMR (126 MHz, DMSO-$d_6$) δ 164.09, 162.30, 159.40, 147.10, 134.97, 130.44, 129.47, 116.30, 114.99, 52.40, 48.65, 45.76, 39.12, 27.63, 26.88, 20.80. ESIMS m/z $[M + H]^+$ 315.1 | +++ | | |
| NUCC-0200880 | 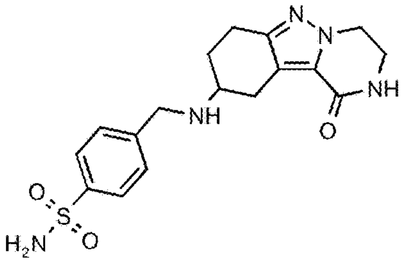 | $^1$H NMR (500 MHz, DMSO-$d_6$) δ 8.19 (s, 1H), 8.00 (t, $J$ = 2.7 Hz, 1H), 7.80 – 7.74 (m, 2H), 7.55 (d, $J$ = 8.1 Hz, 2H), 7.29 (s, 2H), 4.15 (dd, $J$ = 7.1, 5.0 Hz, 2H), 3.89 (s, 2H), 3.53 (ddd, $J$ = 7.8, 4.9, 2.7 Hz, 2H), 3.02 (dd, $J$ = 16.3, 4.9 Hz, 1H), 2.83 (tdd, $J$ = 8.4, 6.6, 5.0, 2.4 Hz, 1H), 2.74 – 2.64 (m, 1H), 2.43 (dd, $J$ = 16.3, 8.4 Hz, 1H), 2.05 – 1.93 (m, 1H), 1.60 (dtd, $J$ = 12.8, 9.8, 5.5 Hz, 1H). $^{13}$C NMR (126 MHz, DMSO-$d_6$) δ 163.58, 159.46, 147.28, 144.71, 142.45, 129.43, 128.34, 125.49, 116.74, 52.27, 49.41, 45.74, 39.94, 28.25, 27.59, 20.78. ESIMS m/z $[M + H]^+$ 376.2 | | | |

FIG. 1GG

| | | | | | |
|---|---|---|---|---|---|
| NUCC-0200881 | 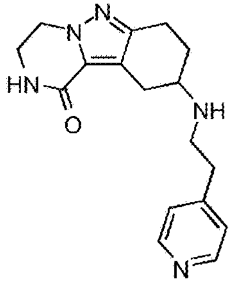 | $^{1}$H NMR (500 MHz, Methanol-$d_4$) δ 8.56 – 8.49 (m, 2H), 8.28 (s, 3H), 7.48 – 7.39 (m, 2H), 4.28 (dd, $J$ = 7.1, 5.2 Hz, 2H), 3.70 (dd, $J$ = 7.1, 5.2 Hz, 2H), 3.59 (ddt, $J$ = 12.8, 10.3, 2.7 Hz, 1H), 3.44 (dt, $J$ = 16.6, 6.7 Hz, 3H), 3.11 (tt, $J$ = 9.0, 4.1 Hz, 2H), 2.92 (ddd, $J$ = 16.6, 5.7, 3.6 Hz, 1H), 2.80 (qd, $J$ = 10.7, 10.0, 4.3 Hz, 2H), 2.38 (dtd, $J$ = 12.8, 5.2, 2.8 Hz, 1H), 2.03 – 1.91 (m, 1H). $^{13}$C NMR (126 MHz, Methanol-$d_4$) δ 166.91, 161.71, 150.43, 148.56, 148.37, 131.28, 125.81, 116.03, 55.77, 47.15, 46.22, 40.73, 32.72, 26.94, 25.59, 21.88. ESIMS m/z [M + H]$^+$ 312.3 | | | |
| NUCC-0200882 | 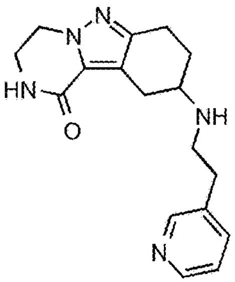 | $^{1}$H NMR (500 MHz, Methanol-$d_4$) δ 8.52 (s, 1H), 8.47 (d, $J$ = 7.0 Hz, 3H), 7.84 (d, $J$ = 7.9 Hz, 1H), 7.45 (dd, $J$ = 7.7, 5.1 Hz, 1H), 4.28 (t, $J$ = 6.2 Hz, 2H), 3.70 (t, $J$ = 6.2 Hz, 2H), 3.52 (d, $J$ = 12.4 Hz, 1H), 3.40 (dt, $J$ = 16.0, 6.9 Hz, 4H), 3.07 (t, $J$ = 8.1 Hz, 2H), 2.91 (dt, $J$ = 16.6, 4.6 Hz, 1H), 2.78 (td, $J$ = 16.3, 7.7 Hz, 2H), 2.35 (d, $J$ = 12.9 Hz, 1H), 2.04 (s, 1H), 1.92 (qd, $J$ = 11.4, 5.5 Hz, 1H). $^{13}$C NMR (126 MHz, Methanol-$d_4$) δ 169.25, 161.77, 150.38, 148.95, 148.48, 138.63, 134.74, 131.28, 125.52, 116.26, 55.73, 47.21, 47.15, 40.74, 30.99, 27.22, 25.93, 21.90. ESIMS m/z [M + H]$^+$ 312.2 | | ++ | |
| NUCC-0200918 | 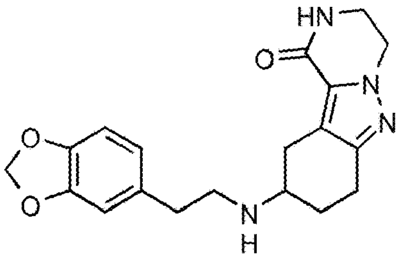 | $^{1}$H NMR (500 MHz, DMSO-$d_6$) δ 8.32 (s, 2H), 8.08 (s, 1H), 6.87 (s, 1H), 6.83 (d, $J$ = 8.0 Hz, 1H), 6.72 (d, $J$ = 7.9 Hz, 1H), 5.97 (s, 2H), 4.16 (d, $J$ = 6.1 Hz, 2H), 3.54 (d, $J$ = 12.4 Hz, 2H), 3.23 – 3.14 (m, 2H), 3.12 (d, $J$ = 5.0 Hz, 1H), 3.03 (dd, $J$ = 10.5, 6.5 Hz, 2H), 2.79 (t, $J$ = 8.0 Hz, 2H), 2.77 – 2.68 (m, 1H), 2.58 (dq, $J$ = 16.1, 8.4, 6.9 Hz, 2H), 2.14 (d, $J$ = 12.6 Hz, 1H), 1.71 (qd, $J$ = 11.5, 5.5 Hz, 1H). $^{13}$C NMR (126 MHz, DMSO-$d_6$) δ 164.88, 159.30, 147.29, 146.77, 145.71, 132.29, 129.57, 121.57, 115.44, 109.07, 108.20, 100.73, 53.04, 46.63, 45.79, 39.13, 33.08, 26.48, 25.55, 20.80. ESIMS m/z [M + H]$^+$ 355.2 | ++ | ++ | |

FIG. 1HH

| | | | | | |
|---|---|---|---|---|---|
| NUCC-0200919 | 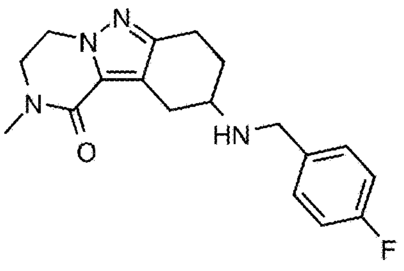 | $^1$H NMR (500 MHz, $CDCl_3$) δ 8.08 (s, 3H), 7.26 (dd, J = 8.5, 5.2 Hz, 2H), 6.79 (t, J = 8.5 Hz, 2H), 4.09 (dd, J = 7.4, 5.2 Hz, 2H), 3.98 (d, J = 13.1 Hz, 1H), 3.87 (d, J = 13.1 Hz, 1H), 3.56 – 3.45 (m, 2H), 3.20 (dd, J = 16.0, 5.2 Hz, 1H), 3.06 (ddd, J = 14.4, 10.2, 4.1 Hz, 1H), 2.87 (s, 3H), 2.70 (dd, J = 16.1, 10.2 Hz, 1H), 2.61 (ddd, J = 16.6, 5.5, 2.9 Hz, 1H), 2.40 (ddd, J = 16.9, 11.5, 5.6 Hz, 1H), 2.05 – 1.95 (m, 1H), 1.63 (qd, J = 11.9, 5.5 Hz, 1H). $^{13}$C NMR (126 MHz, $CDCl_3$) δ 167.00, 162.06, 158.66, 147.68, 132.22, 129.94, 127.24, 116.04, 115.40, 53.02, 47.51, 45.72, 33.69, 25.98, 24.31, 21.34. ESIMS m/z $[M + H]^+$ 329.2 | ++ | ++ | |
| NUCC-0200920 | 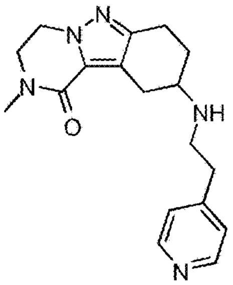 | $^1$H NMR (500 MHz, $CDCl_3$) δ 8.48 (d, J = 5.9 Hz, 2H), 8.30 (s, 3H), 7.25 (d, J = 5.8 Hz, 2H), 4.26 (t, J = 6.2 Hz, 2H), 3.67 (dd, J = 7.3, 5.1 Hz, 2H), 3.41 (d, J = 13.2 Hz, 2H), 3.37 – 3.25 (m, 2H), 3.13 (t, J = 8.2 Hz, 2H), 3.01 (s, 3H), 2.93 (dd, J = 12.5, 5.2 Hz, 1H), 2.91 – 2.82 (m, 1H), 2.69 (ddd, J = 16.8, 11.3, 5.6 Hz, 1H), 2.36 (d, J = 12.6 Hz, 1H), 1.98 (ddd, J = 16.8, 11.3, 5.3 Hz, 1H). $^{13}$C NMR (126 MHz, $CDCl_3$) δ 166.48, 158.54, 148.83, 147.57, 147.39, 129.99, 124.65, 115.21, 54.51, 47.49, 45.75, 45.46, 33.66, 31.94, 25.98, 24.74, 21.29. ESIMS m/z $[M + H]^+$ 326.2 | | | |
| NUCC-0200921 | 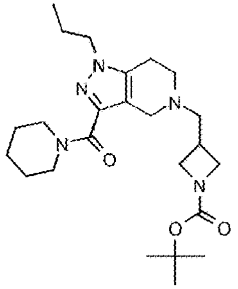 | $^1$H NMR (500 MHz, $CDCl_3$) δ 4.06 (t, J = 8.0 Hz, 2H), 3.95 (dt, J = 26.7, 7.9 Hz, 4H), 3.86 – 3.78 (m, 2H), 3.65 (tt, J = 8.6, 4.3 Hz, 4H), 2.96 (q, J = 4.0, 3.4 Hz, 5H), 2.80 (d, J = 5.8 Hz, 2H), 1.81 (h, J = 7.4 Hz, 2H), 1.67 (q, J = 6.4, 5.8 Hz, 2H), 1.64 – 1.55 (m, 4H), 1.42 (s, 9H), 0.90 (t, J = 7.4 Hz, 3H). $^{13}$C NMR (126 MHz, $CDCl_3$) δ 165.11, 162.70, 156.39, 141.65, 136.07, 115.77, 79.68, 64.65, 60.88, 51.02, 50.04, 49.42, 48.12, 43.70, 30.62, 28.51, 26.88, 26.24, 25.93, 24.88, 23.51, 21.22, 11.28. ESIMS m/z $[M + H]^+$ 446.6 | | | |

FIG. 1II
| | | | | | |
|---|---|---|---|---|---|
| NUCC-0200922 | 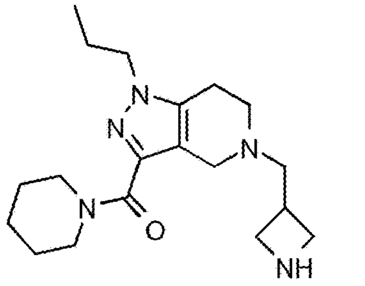 | $^1$H NMR (500 MHz, $CDCl_3$) δ 4.29 (d, J = 20.3 Hz, 4H), 4.08 (s, 2H), 4.01 (d, J = 6.2 Hz, 2H), 3.94 (t, J = 7.1 Hz, 2H), 3.68 – 3.49 (m, 5H), 3.47 (s, 2H), 3.00 (t, J = 5.7 Hz, 2H), 1.81 (h, J = 7.3 Hz, 2H), 1.67 (q, J = 5.8 Hz, 2H), 1.61 (q, J = 5.7 Hz, 4H), 0.88 (t, J = 7.4 Hz, 3H). $^{13}$C NMR (126 MHz, $CDCl_3$) δ 161.88, 141.79, 134.39, 117.87, 115.55, 111.90, 57.39, 51.33, 49.74, 49.55, 49.43, 48.11, 43.96, 28.08, 26.71, 25.88, 24.71, 23.29, 19.12, 11.07. ESIMS m/z $[M + H]^+$ 346.3 | | | |
| NUCC-0201114 | 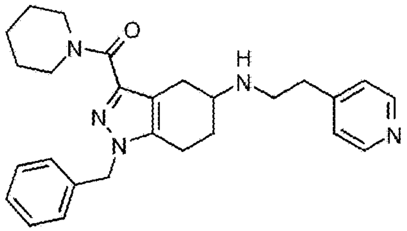 | ESIMS m/z $[M + H]^+$ 444.2 | +++ | | |
| NUCC-0201118 | 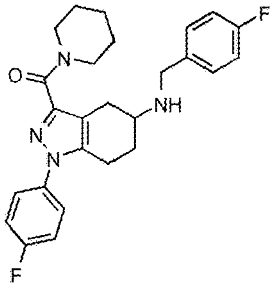 | ESIMS m/z $[M + H]^+$ 451.6 | | | |

FIG. 1JJ
| | | | | | |
|---|---|---|---|---|---|
| NUCC-0201119 | 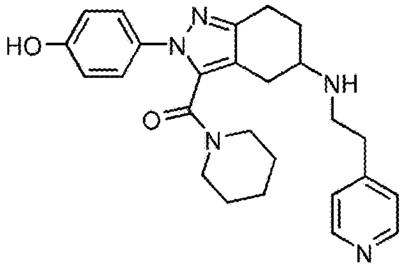 | ESIMS m/z [M + H]$^+$ 446.6 | | | |
| NUCC-0201120 | 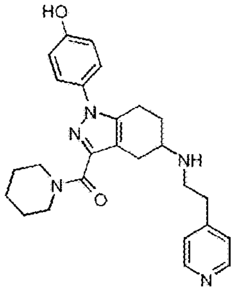 | ESIMS m/z [M + H]$^+$ 446.6 | | | |
| NUCC-0201121 | 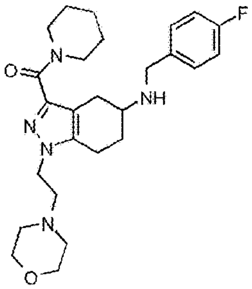 | ESIMS m/z [M + H]+ 470.6 | | | |

FIG. 1KK
| | | | | | |
|---|---|---|---|---|---|
| NUCC-0201122 | 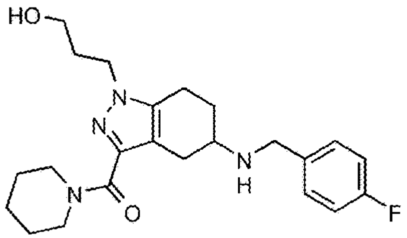 | ESIMS m/z $[M + H]^+$ 415.5 | | | |
| NUCC-0201123 | 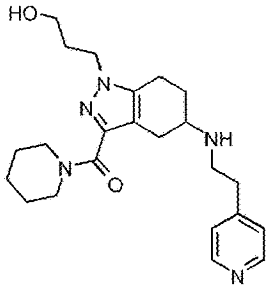 | ESIMS m/z $[M + H]^+$ 412.4 | | | |
| NUCC-0201124 | 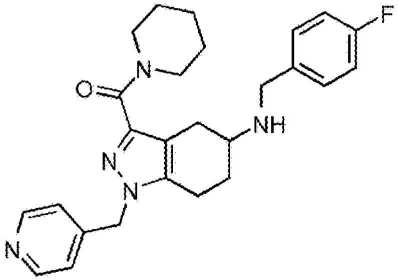 | ESIMS m/z $[M + H]^+$ 447.6 | | | |

FIG. 1LL
| | | | | | |
|---|---|---|---|---|---|
| NUCC-0201125 | 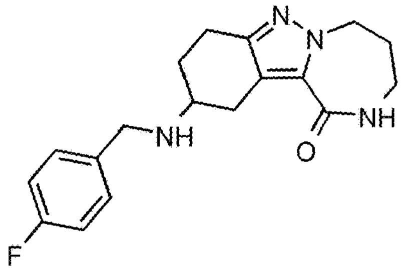 | $^1$H NMR (500 MHz, $CDCl_3$) δ 8.30 (s, 2H), 7.91 (t, J = 5.1 Hz, 1H), 7.52 – 7.38 (m, 2H), 7.02 (t, J = 8.3 Hz, 2H), 4.34 (t, J = 6.7 Hz, 2H), 4.21 (t, J = 10.2 Hz, 2H), 3.43 – 3.21 (m, 4H), 2.95 (dd, J = 15.3, 10.1 Hz, 1H), 2.88 (ddd, J = 16.6, 5.5, 2.4 Hz, 1H), 2.63 (ddd, J = 16.9, 12.0, 5.6 Hz, 1H), 2.40 – 2.30 (m, 1H), 2.26 – 2.11 (m, 2H), 1.92 (qd, J = 12.2, 5.5 Hz, 1H). $^{13}$C NMR (126 MHz, $CDCl_3$) δ 166.85, 164.22, 162.24, 146.62, 132.22, 132.15, 127.22, 116.26, 116.08, 53.52, 50.48, 47.80, 40.13, 28.68, 26.09, 25.39, 21.58. | +++ | | |
| NUCC-0201126 | 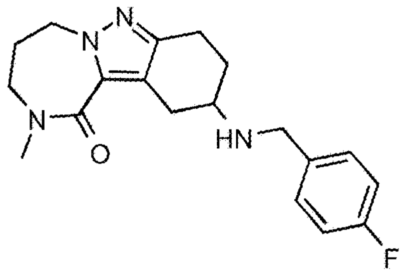 | $^1$H NMR (500 MHz, $CDCl_3$) δ 8.50 (s, 2H), 7.75 – 7.64 (m, 2H), 7.28 (s, 1H), 4.55 (hept, J = 7.2 Hz, 2H), 4.42 (d, J = 13.1 Hz, 1H), 4.30 (d, J = 13.0 Hz, 1H), 3.70 – 3.60 (m, 2H), 3.58 (d, J = 5.2 Hz, 1H), 3.57 – 3.49 (m, 2H), 3.37 (s, 3H), 3.17 – 3.09 (m, 1H), 3.06 (ddd, J = 16.5, 5.6, 2.8 Hz, 1H), 2.86 (ddd, J = 16.8, 11.6, 5.6 Hz, 1H), 2.51 (p, J = 6.7 Hz, 2H), 2.47 – 2.39 (m, 1H), 2.07 (qd, J = 11.8, 5.3 Hz, 1H). $^{13}$C NMR (126 MHz, $CDCl_3$) δ 166.51, 164.07, 162.75, 146.12, 133.86, 132.18, 126.98, 116.20, 116.05, 53.29, 47.93, 47.61, 47.55, 34.90, 28.39, 26.16, 23.99, 21.20. | +++ | | |
| NUCC-0201127 | 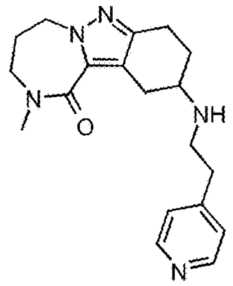 | ESIMS m/z $[M + H]^+$ 340.4 | | | |

FIG. 1MM
| | | | | | |
|---|---|---|---|---|---|
| NUCC-0201128 | 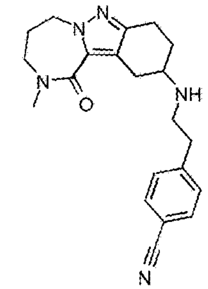 | $^1$H NMR (500 MHz, $CDCl_3$) δ 8.20 (s, 2H), 7.48 (d, J = 8.1 Hz, 2H), 7.24 (s, 1H), 4.20 (t, J = 6.9 Hz, 2H), 3.37 – 3.24 (m, 3H), 3.18 (dddd, J = 33.7, 17.0, 11.6, 5.1 Hz, 3H), 3.09 – 3.02 (m, 2H), 2.99 (s, 3H), 2.76 (ddt, J = 16.3, 10.3, 4.7 Hz, 2H), 2.59 (ddd, J = 16.1, 12.7, 6.3 Hz, 1H), 2.31 – 2.23 (m, 1H), 2.15 (h, J = 6.4 Hz, 2H), 1.94 – 1.83 (m, 1H). $^{13}$C NMR (126 MHz, $CDCl_3$) δ 166.57, 163.21, 162.63, 147.04, 145.97, 142.23, 133.90, 132.57, 129.67, 118.59, 118.12, 116.05, 111.06, 66.73, 54.59, 48.01, 47.62, 45.96, 34.90, 32.51, 28.35, 26.27, 24.33, 21.14. | | ++ | |
| NUCC-0201129 | 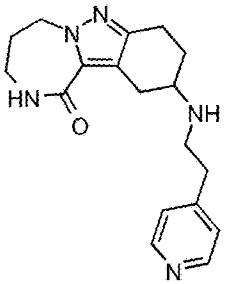 | $^1$H NMR (500 MHz, $CD_3OD$) δ 8.46 (d, J = 5.1 Hz, 2H), 8.31 (s, 2H), 7.42 – 7.37 (m, 2H), 4.35 (td, J = 6.7, 1.4 Hz, 2H), 3.58 – 3.49 (m, 1H), 3.40 (t, J = 8.2 Hz, 2H), 3.29 – 3.23 (m, 3H), 3.08 (tt, J = 9.2, 4.4 Hz, 2H), 2.85 (ddd, J = 16.5, 5.8, 3.7 Hz, 1H), 2.73 (ddd, J = 16.8, 13.2, 7.7 Hz, 2H), 2.34 (dq, J = 12.2, 3.6, 3.1 Hz, 1H), 2.19 (p, J = 6.5 Hz, 2H), 2.00 – 1.87 (m, 1H). $^{13}$C NMR (126 MHz, $CD_3OD$) δ 167.73, 165.68, 150.35, 148.67, 147.50, 134.87, 125.83, 118.22, 55.84, 50.85, 46.16, 40.36, 32.67, 30.08, 26.96, 25.81, 21.78. | | ++ | |
| NUCC-0201130 | 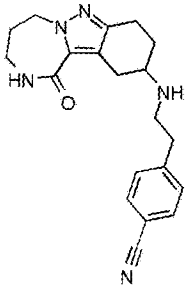 | $^1$H NMR (500 MHz, DMSO-$d_6$) δ 8.25 (s, 2H), 8.09 (t, J = 5.3 Hz, 1H), 7.80 – 7.76 (m, 2H), 7.49 (d, J = 8.2 Hz, 2H), 4.27 (t, J = 6.7 Hz, 2H), 3.18 – 3.09 (m, 3H), 3.09 – 3.00 (m, 3H), 2.94 (t, J = 7.7 Hz, 2H), 2.69 (dt, J = 16.0, 4.8 Hz, 1H), 2.55 (dt, J = 11.4, 5.6 Hz, 1H), 2.49 – 2.42 (m, 1H), 2.06 (p, J = 6.5 Hz, 3H), 1.72 – 1.59 (m, 1H). $^{13}$C NMR (126 MHz, DMSO-$d_6$) δ 164.20, 163.26, 145.93, 144.99, 133.22, 132.28, 129.83, 118.94, 117.75, 109.17, 53.23, 49.16, 46.02, 38.56, 33.80, 28.70, 26.87, 26.18, 20.68. | ++ | +++ | |

FIG. 1NN
| | | | | | |
|---|---|---|---|---|---|
| NUCC-0201131 | 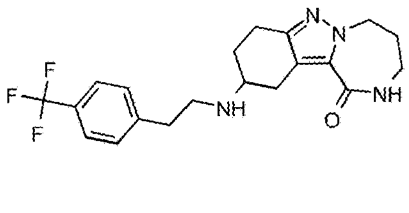 | $^1$H NMR (500 MHz, $CDCl_3$) δ 8.31 (s, 3H), 7.87 (t, J = 5.0 Hz, 1H), 7.51 (d, J = 8.0 Hz, 2H), 7.31 (d, J = 8.0 Hz, 2H), 4.39 (td, J = 6.6, 3.0 Hz, 2H), 3.39 (pt, J = 9.1, 5.4 Hz, 3H), 3.26 (q, J = 6.2, 4.5 Hz, 3H), 3.22 – 3.06 (m, 2H), 2.96 – 2.85 (m, 2H), 2.70 (ddd, J = 16.8, 11.7, 5.6 Hz, 1H), 2.45 – 2.37 (m, 1H), 2.24 (p, J = 6.4 Hz, 2H), 1.92 (qd, J = 12.0, 5.4 Hz, 1H). $^{13}$C NMR (126 MHz, $CDCl_3$) δ 166.69, 164.34, 146.63, 141.00, 132.76, 129.27, 125.92, 125.89, 125.86, 125.83, 118.62, 54.86, 50.92, 46.31, 40.38, 32.47, 28.55, 26.30, 25.22, 21.49. | ++ | | |
| NUCC-0201132 | 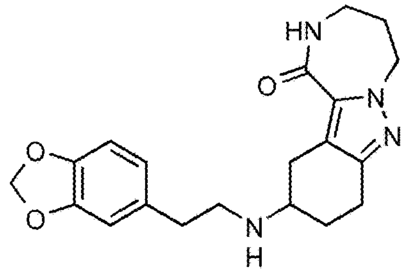 | $^1$H NMR (500 MHz, $CD_3OD$) δ 8.33 (s, 2H), 6.82 (d, *J* = 1.5 Hz, 1H), 6.81 – 6.74 (m, 2H), 5.93 (s, 2H), 4.39 (td, *J* = 6.8, 1.6 Hz, 2H), 3.58 – 3.47 (m, 1H), 3.32 (d, *J* = 8.4 Hz, 5H), 3.29 – 3.25 (m, 1H), 2.99 – 2.92 (m, 2H), 2.92 – 2.85 (m, 1H), 2.75 (ddd, *J* = 16.2, 10.6, 6.6 Hz, 2H), 2.40 – 2.31 (m, 1H), 2.23 (p, *J* = 6.5 Hz, 2H), 1.92 (dtd, *J* = 12.8, 11.2, 5.7 Hz, 1H). $^{13}$C NMR (126 MHz, $CD_3OD$) δ 167.65, 165.70, 149.53, 148.27, 147.52, 134.88, 131.41, 122.92, 118.26, 109.97, 109.48, 102.44, 55.76, 50.90, 47.79, 40.40, 33.23, 30.07, 26.97, 25.85, 21.81. | +++ | | |
| NUCC-0201133 | 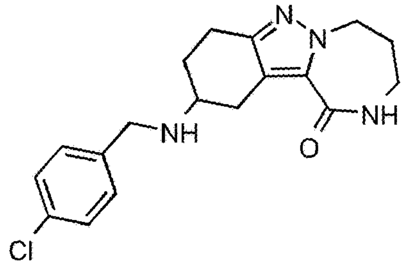 | $^1$H NMR (500 MHz, $CDCl_3$) δ 8.29 (s, 2H), 7.84 (s, 1H), 7.38 (d, J = 8.0 Hz, 2H), 7.27 (d, J = 4.9 Hz, 1H), 4.32 (t, J = 6.6 Hz, 2H), 4.25 – 4.10 (m, 2H), 3.45 – 3.28 (m, 2H), 3.28 – 3.15 (m, 2H), 3.00 – 2.82 (m, 2H), 2.63 (ddd, J = 16.9, 11.9, 5.5 Hz, 1H), 2.41 – 2.29 (m, 1H), 2.17 (dt, J = 20.1, 7.3 Hz, 2H), 1.92 (ddp, J = 17.6, 12.1, 6.1, 5.4 Hz, 1H). $^{13}$C NMR (126 MHz, $CDCl_3$) δ 166.84, 146.58, 135.43, 132.65, 131.60, 129.87, 129.28, 129.15, 53.79, 50.59, 47.87, 40.19, 28.50, 25.93, 25.47, 21.53. | +++ | | |

FIG. 10O

| | | | | | |
|---|---|---|---|---|---|
| NUCC-0201134 | 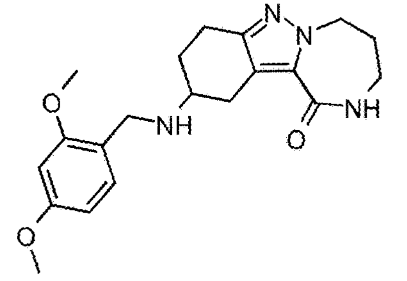 | $^1$H NMR (500 MHz, $CDCl_3$) δ 8.38 (s, 2H), 8.07 (s, 1H), 6.49 – 6.34 (m, 2H), 4.33 (t, J = 6.7 Hz, 2H), 4.24 (d, J = 13.0 Hz, 1H), 4.14 (d, J = 13.2 Hz, 1H), 3.75 (s, 3H), 3.73 (s, 3H), 3.40 – 3.30 (m, 1H), 3.24 (hept, J = 8.2 Hz, 3H), 2.96 – 2.84 (m, 2H), 2.61 (ddd, J = 16.9, 12.0, 5.5 Hz, 1H), 2.44 – 2.33 (m, 1H), 2.16 (p, J = 6.7 Hz, 2H), 1.96 (qd, J = 12.1, 5.3 Hz, 1H). $^{13}$C NMR (126 MHz, $CDCl_3$) δ 167.24, 164.59, 162.08, 159.15, 146.53, 133.01, 132.81, 118.53, 111.96, 104.79, 98.46, 55.50, 52.99, 50.06, 42.82, 39.78, 28.91, 25.76, 25.52, 21.65. | | | |
| NUCC-0201135 | 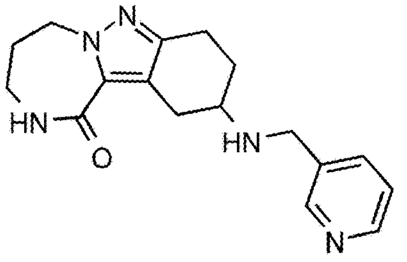 | $^1$H NMR (500 MHz, $CDCl_3$) δ 8.68 (d, J = 2.2 Hz, 1H), 8.51 (dd, J = 4.9, 1.5 Hz, 1H), 8.30 (s, 2H), 7.93 (dt, J = 7.9, 1.9 Hz, 1H), 7.87 (t, J = 5.3 Hz, 1H), 7.30 (dd, J = 7.9, 4.9 Hz, 1H), 4.33 (td, J = 6.6, 1.7 Hz, 2H), 4.28 – 4.19 (m, 2H), 3.37 – 3.20 (m, 4H), 2.98 – 2.89 (m, 1H), 2.89 – 2.80 (m, 1H), 2.63 (ddd, J = 16.8, 11.6, 5.6 Hz, 1H), 2.37 – 2.27 (m, 1H), 2.18 (h, J = 7.1, 6.5 Hz, 2H), 1.90 (qd, J = 11.9, 5.4 Hz, 1H). $^{13}$C NMR (126 MHz, $CDCl_3$) δ 166.95, 164.53, 150.52, 149.69, 146.66, 138.36, 132.83, 128.97, 124.05, 118.68, 53.76, 50.33, 46.10, 39.99, 28.75, 26.48, 25.72, 21.48. | | | |
| NUCC-0201232 | 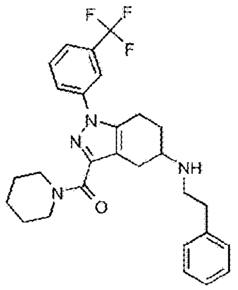 | $^1$H NMR (500 MHz, $CDCl_3$) δ 7.72 (s, 1H), 7.63 (d, J = 7.4 Hz, 1H), 7.60 – 7.50 (m, 2H), 7.27-7.18 (m, 5H), 3.80 (t, J = 5.4 Hz, 2H), 3.63 (q, J = 5.3 Hz, 2H), 3.44 (dt, J = 15.5, 8.2 Hz, 1H), 3.25 (dt, J = 14.5, 6.9 Hz, 2H), 3.19 – 3.10 (m, 1H), 3.04 (s, 2H), 2.85 (d, J = 10.4 Hz, 3H), 2.36 (s, 1H), 2.01 (d, J = 11.3 Hz, 1H), 1.63 (dq, J = 28.9, 5.5 Hz, 6H); $^{13}$C NMR (126 MHz, $CDCl_3$) δ 162.55, 144.79, 139.69, 138.20, 137.18, 132.06, 131.79, 129.96, 128.79, 128.73, 126.95, 126.00, 124.55, 124.06, 122.39, 119.96, 117.08, 53.55, 48.31, 46.93, 43.41, 33.17, 26.72, 26.33, 25.74, 25.01, 24.62, 21.55. ESIMS m/z $[M + H]^+$ 497. | | | |

FIG. 1PP
| | | | | | |
|---|---|---|---|---|---|
| NUCC-0201233 | 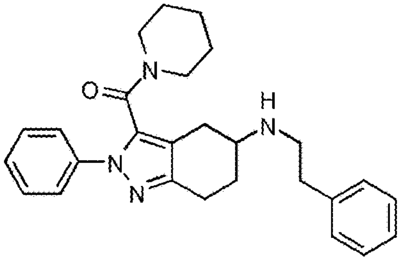 | $^{1}H$ NMR (500 MHz, $CDCl_3$) δ 7.44 (d, J = 8.0 Hz, 2H), 7.39 (t, J = 7.8 Hz, 2H), 7.35-7.25 (m, 3H), 7.25-7.17 (m, 3H), 3.78 (td, J = 20.8, 17.2, 10.4 Hz, 1H), 3.49-2.63 (m, 12H), 2.43 (s, 1H), 2.14-1.90 (m, 1H), 1.53 (s, 1H), 1.42 (p, J = 5.9 Hz, 2H), 1.32 (s, 1H), 1.27-1.11 (m, 1H), 0.60 (d, J = 12.4 Hz, 1H); $^{13}C$ NMR (126 MHz, $CDCl_3$) δ 167.03, 161.11, 148.38, 139.60, 136.69, 133.73, 129.31, 129.11, 128.89, 128.74, 128.67, 127.71, 127.12, 122.76, 114.08, 54.40, 48.91, 47.43, 46.76, 42.80, 32.91, 32.72, 27.06, 25.54, 25.05, 24.09, 23.64, 21.61. ESIMS m/z $[M + H]^+$ 430. | | | |
| NUCC-0201234 | 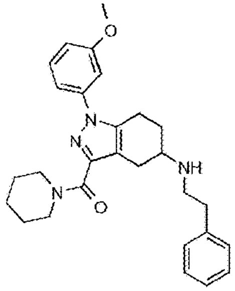 | ESIMS m/z $[M + H]^+$ 459.74 | | | |
| NUCC-0201235 | 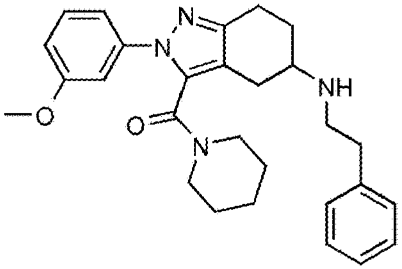 | ESIMS m/z $[M + H]^+$ 459.74 | | | |

FIG. 1QQ
| | | | | | |
|---|---|---|---|---|---|
| NUCC-0201236 | 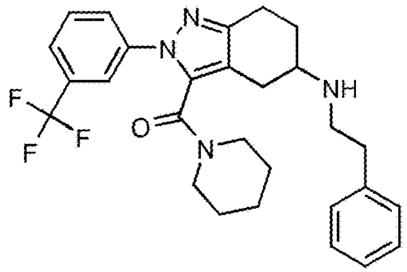 | $^1$H NMR (500 MHz, $CDCl_3$) δ 7.74 (d, J = 1.9 Hz, 1H), 7.67 (dt, J = 7.8, 1.6 Hz, 1H), 7.53 (dt, J = 15.6, 7.8 Hz, 2H), 7.29 (t, J = 7.3 Hz, 2H), 7.21 (t, J = 6.4 Hz, 3H), 3.81 (s, 1H), 3.45 (q, J = 5.8, 5.3 Hz, 1H), 3.28 (d, J = 41.8 Hz, 2H), 3.19 – 2.88 (m, 7H), 2.71 (d, J = 44.7 Hz, 2H), 2.51 – 2.26 (m, 1H), 2.02 (s, 1H), 1.75 – 1.15 (m, 5H), 0.80 (s, 1H); $^{13}$C NMR (126 MHz, $CDCl_3$) δ 160.77, 149.23, 140.02, 132.02, 131.76, 129.93, 128.87, 128.68, 127.04, 125.51, 124.55, 124.00, 122.39, 119.39, 70.94, 70.10, 62.75, 54.17, 47.45, 42.84, 25.96, 25.04, 24.09, 21.58. ESIMS m/z $[M + H]^+$ 497. | | | |
| NUCC-0201237 | 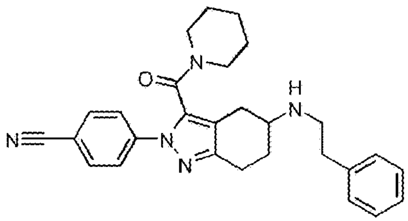 | $^1$H NMR (500 MHz, $CDCl_3$) δ 7.69 (d, J = 8.6 Hz, 2H), 7.61 (d, J = 8.4 Hz, 2H), 7.31-7.18 (m, 5H), 3.78 (s, 1H), 3.51 – 2.59 (m, 12H), 2.41 (s, 1H), 2.17 – 1.94 (m, 1H), 1.55 (d, J = 38.2 Hz, 3H), 1.37 (d, J = 37.6 Hz, 2H), 0.85 (s, 1H). ESIMS m/z $[M + H]^+$ 454. | | | |
| NUCC-0201238 | 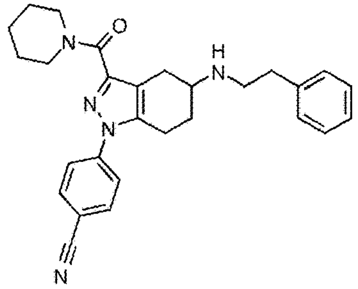 | ESIMS m/z $[M + H]^+$ 454. | | | |

FIG. 1RR
| | | | | | |
|---|---|---|---|---|---|
| NUCC-0201239 | 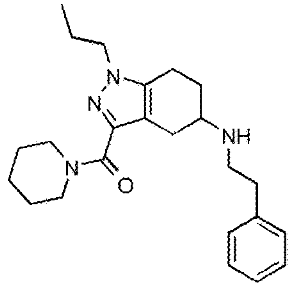 | ESIMS m/z [M + H]$^+$ 395.6 | | | |
| NUCC-0201240 | 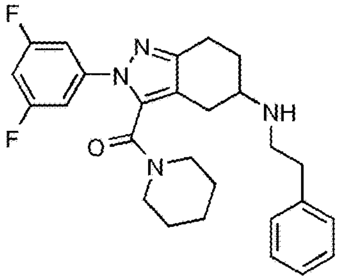 | $^1$H NMR (500 MHz, $CDCl_3$) δ 7.29 (t, J = 7.3 Hz, 2H), 7.22 (d, J = 15.4 Hz, 3H), 7.07 (dd, J = 7.6, 2.2 Hz, 2H), 6.74 (tt, J = 8.7, 2.3 Hz, 1H), 3.85 (s, 1H), 3.37 (s, 1H), 3.26 (d, J = 23.4 Hz, 1H), 3.20 – 2.85 (m, 7H), 2.74 (t, J = 31.1 Hz, 2H), 2.42 (d, J = 11.7 Hz, 1H), 2.11 – 1.89 (m, 1H), 1.50 (q, J = 46.0, 39.5 Hz, 5H), 0.92 (s, 1H); $^{13}$C NMR (126 MHz, $CDCl_3$) δ 164.10, 163.99, 162.12, 162.00, 160.64, 149.27, 128.90, 128.67, 127.12, 105.72, 105.49, 102.90, 102.69, 54.20, 47.48, 46.96, 42.93, 27.12, 26.07, 25.18, 24.13, 21.52. ESIMS m/z [M + H]$^+$ 465. | | | |
| NUCC-0201241 | 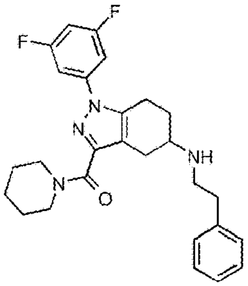 | $^1$H NMR (500 MHz, $CDCl_3$) δ 7.25 (d, J = 7.8 Hz, 2H), 7.19 (t, J = 8.7 Hz, 3H), 7.03 (dt, J = 7.5, 3.7 Hz, 2H), 6.81 – 6.72 (m, 1H), 3.79 (t, J = 5.3 Hz, 2H), 3.62 (tt, J = 6.3, 4.1, 3.4 Hz, 2H), 3.42 (dq, J = 20.4, 8.6, 7.4 Hz, 1H), 3.25 (dq, J = 11.0, 6.0, 5.6 Hz, 2H), 3.15 (td, J = 11.7, 11.2, 5.1 Hz, 1H), 3.04 (qt, J = 12.8, 5.2 Hz, 2H), 2.87 (ttd, J = 16.3, 13.8, 10.7, 4.9 Hz, 3H), 2.38 (d, J = 11.7 Hz, 1H), 2.09 – 1.94 (m, 1H), 1.72 – 1.53 (m, 6H). ESIMS m/z [M + H]$^+$ 465. | | | |

FIG. 1SS

| | | | | | |
|---|---|---|---|---|---|
| NUCC-0201245 | 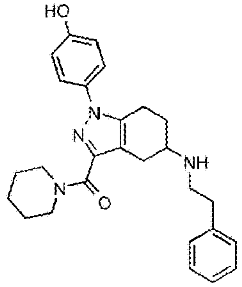 | $^1$H NMR (500 MHz, $CDCl_3$) δ 8.43 (s, 1H, FA), 7.31 (t, J = 7.5 Hz, 2H), 7.23 (q, J = 9.5, 8.2 Hz, 5H), 6.88 (d, J = 8.3 Hz, 2H), 3.84 (t, J = 5.4 Hz, 2H), 3.67 (q, J = 5.4 Hz, 2H), 3.52 - 3.40 (m, 1H), 3.22 (ddd, J = 36.2, 12.9, 5.4 Hz, 3H), 3.13 - 2.88 (m, 2H), 2.75 (dq, J = 15.5, 9.3, 7.2 Hz, 3H), 2.31 (d, J = 12.6 Hz, 1H), 1.95 (d, J = 10.4 Hz, 1H), 1.63 (dtd, J = 34.1, 10.5, 9.9, 4.9 Hz, 6H); $^{13}$C NMR (126 MHz, $CDCl_3$) δ 167.59, 163.29, 157.16, 142.93, 138.18, 136.48, 130.79, 128.81, 128.57, 127.10, 125.17, 115.81, 114.90, 53.76, 46.49, 43.48, 32.46, 26.62, 25.89, 25.65, 24.43, 24.15, 20.76. ESIMS m/z [M + H]$^+$ 445. | | | |
| NUCC-0201668 | 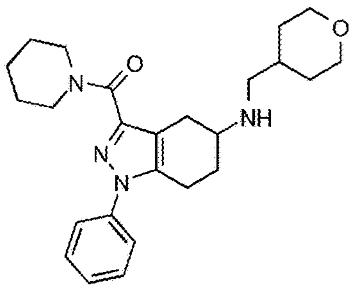 | $^1$H NMR (500 MHz, $CDCl_3$) δ 8.20 (s, 1H, FA), 7.32-7.21 (m, 4H), 7.17 (t, J = 6.9 Hz, 1H), 3.85-3.62 (m, 4H), 3.48 (t, J = 5.3 Hz, 2H), 3.30-3.05 (m, 4H), 2.83-2.56 (m, 5H), 2.29-2.17 (m, 1H), 1.82 (dddd, J = 34.1, 14.6, 6.4, 3.5 Hz, 2H), 1.66-1.34 (m, 8H), 1.14 (qt, J = 12.2, 4.7 Hz, 2H); $^{13}$C NMR (126 MHz, $CDCl_3$) δ 167.35, 162.83, 143.89, 139.13, 137.94, 129.33, 127.71, 123.20, 116.54, 67.21, 67.18, 54.58, 50.95, 48.35, 43.47, 32.82, 30.69, 26.76, 26.12, 25.79, 24.66, 24.58, 21.81. ESIMS m/z [M + H]$^+$ 423. | +++ | +++ | |
| NUCC-0201669 | 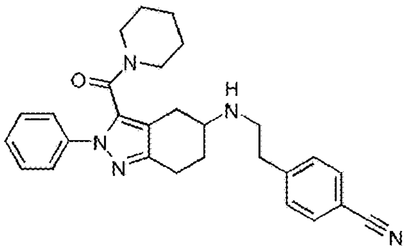 | $^1$H NMR (500 MHz, $CDCl_3$) δ 8.33 (s, 1H, FA), 7.58 (d, J = 7.8 Hz, 2H), 7.50-7.36 (m, 4H), 7.36-7.27 (m, 3H), 3.76 (t, J = 10.4 Hz, 1H), 3.46-3.06 (m, 6H), 3.04-2.58 (m, 6H), 2.37 (d, J = 31.1 Hz, 1H), 2.01 (t, J = 16.3 Hz, 1H), 1.52 (s, 1H), 1.42 (p, J = 5.8 Hz, 2H), 1.32 (s, 1H), 1.20 (t, J = 13.9 Hz, 1H), 0.58 (s, 1H); $^{13}$C NMR (126 MHz, $CDCl_3$) δ 167.02, 161.13, 148.36, 142.50, 139.53, 133.64, 132.63, 129.57, 129.36, 127.81, 122.72, 118.58, 114.21, 111.16, 54.59, 47.44, 46.24, 42.83, 33.22, 33.05, 27.34, 25.47, 25.02, 24.06, 23.93, 21.65, 21.31. ESIMS m/z [M + H]$^+$ 454. | | | |

FIG. 1TT

| | | | | | |
|---|---|---|---|---|---|
| NUCC-0201672 | 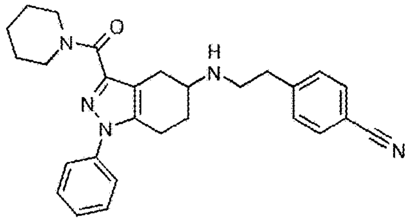 | $^1$H NMR (500 MHz, $CDCl_3$) δ 8.23 (s, 1H, FA), 7.38 (d, J = 7.9 Hz, 2H), 7.32–7.21 (m, 4H), 7.17 (dd, J = 16.7, 7.6 Hz, 3H), 3.70 (t, J = 5.3 Hz, 2H), 3.45 (t, J = 5.5 Hz, 2H), 3.27 (ddt, J = 9.3, 6.0, 3.3 Hz, 1H), 3.11 (ddd, J = 17.0, 13.3, 5.7 Hz, 2H), 2.97 (dtd, J = 37.8, 11.1, 5.6 Hz, 3H), 2.77–2.57 (m, 3H), 2.25–2.05 (m, 1H), 1.89–1.71 (m, 1H), 1.47 (dq, J = 26.9, 5.5, 5.1 Hz, 6H); $^{13}$C NMR (126 MHz, $CDCl_3$) δ 167.38, 162.79, 143.86, 142.70, 139.10, 137.91, 132.53, 129.65, 129.32, 127.74, 123.19, 118.63, 116.38, 110.99, 53.95, 48.33, 46.15, 43.48, 33.00, 26.74, 26.20, 25.78, 25.00, 24.62, 21.50. ESIMS m/z [M + H]$^+$ 454. | +++ | +++ | |
| NUCC-0201673 | 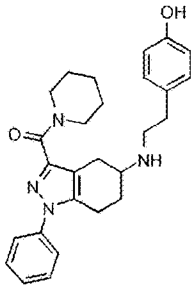 | $^1$H NMR (500 MHz, $CDCl_3$) δ 8.08 (s, 1H, FA), 7.49–7.36 (m, 4H), 7.34 (dt, J = 7.2, 1.7 Hz, 1H), 6.84 (d, J = 8.0 Hz, 2H), 6.72 (d, J = 8.1 Hz, 2H), 3.86 (s, 2H), 3.67 (d, J = 31.1 Hz, 2H), 3.49 (s, 1H), 3.29 (d, J = 15.2 Hz, 1H), 3.14 (d, J = 17.9 Hz, 1H), 3.09–2.69 (m, 6H), 2.45 (s, 1H), 2.08 (d, J = 10.2 Hz, 1H), 1.63 (d, J = 21.3 Hz, 6H). ESIMS m/z [M + H]$^+$ 445. | | | |
| NUCC-0201674 | 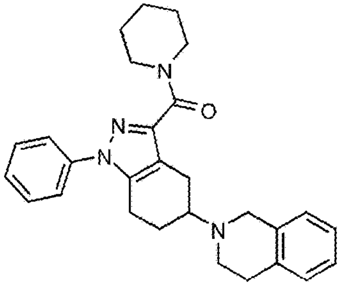 | $^1$H NMR (500 MHz, $CDCl_3$) δ 8.05 (s, 1H, FA), 7.32–7.21 (m, 4H), 7.14 (ddd, J = 8.7, 5.4, 3.2 Hz, 1H), 7.01–6.89 (m, 3H), 6.88–6.80 (m, 1H), 4.07–3.88 (m, 2H), 3.75–3.60 (m, 2H), 3.49 (t, J = 5.2 Hz, 2H), 3.37–3.22 (m, 1H), 3.15–2.98 (m, 3H), 2.93 (dt, J = 12.9, 6.3 Hz, 1H), 2.83 (dt, J = 16.8, 5.6 Hz, 1H), 2.77–2.57 (m, 3H), 2.33–2.15 (m, 1H), 1.75 (dt, J = 11.8, 6.0 Hz, 1H), 1.54–1.31 (m, 6H); $^{13}$C NMR (126 MHz, $CDCl_3$) δ 166.44, 163.01, 144.28, 139.30, 138.24, 132.64, 130.76, 129.27, 128.71, 127.54, 127.25, 126.80, 126.53, 123.19, 117.48, 60.00, 49.87, 48.31, 46.52, 43.40, 27.21, 26.83, 25.80, 25.63, 24.72, 22.87, 21.80. ESIMS m/z [M + H]$^+$ 441. | ++ | ++ | |

FIG. 1UU
| | | | | | |
|---|---|---|---|---|---|
| NUCC-0201675 | 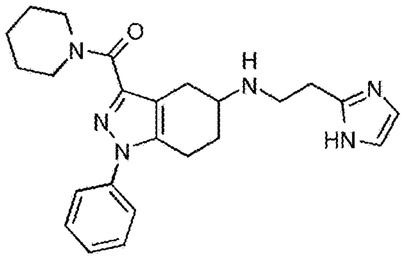 | | ++ | +++ | |
| NUCC-0201677 | 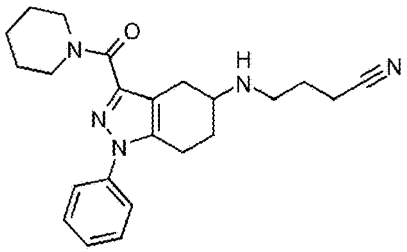 | $^1$H NMR (500 MHz, $CDCl_3$) δ 8.19 (s, 1H, FA), 7.24 (d, J = 4.3 Hz, 4H), 7.15 (q, J = 4.6 Hz, 1H), 3.66 (t, J = 5.4 Hz, 2H), 3.56–3.36 (m, 2H), 3.19–3.08 (m, 1H), 3.05 (dd, J = 15.6, 5.3 Hz, 1H), 2.87 (dddd, J = 19.2, 14.7, 9.7, 6.0 Hz, 2H), 2.74–2.51 (m, 3H), 2.35 (td, J = 7.1, 4.0 Hz, 2H), 2.06 (dd, J = 10.1, 5.0 Hz, 1H), 1.88 (p, J = 7.3 Hz, 2H), 1.79–1.65 (m, 1H), 1.44 (ddt, J = 23.7, 10.8, 5.1 Hz, 6H); $^{13}$C NMR (126 MHz, $CDCl_3$) δ 162.94, 144.01, 139.25, 138.10, 129.27, 127.59, 123.26, 118.91, 116.66, 53.88, 48.33, 44.28, 43.44, 26.77, 26.70, 25.78, 24.67, 23.53, 21.52, 14.98. ESIMS m/z [M + H]$^+$ 392. | | | |
| NUCC-0201680 | 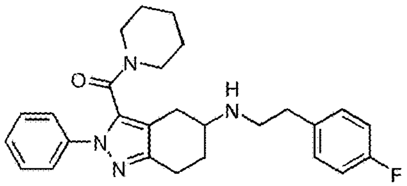 | | | | |

FIG. 1VV
| | | | | | |
|---|---|---|---|---|---|
| NUCC-0201682 | 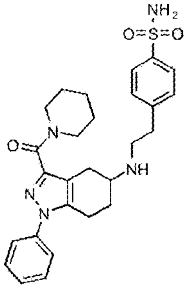 | $^1H$ NMR (500 MHz, $CD_3OD$) δ 8.33 (s, 1H, FA), 7.94–7.89 (m, 2H), 7.57–7.48 (m, 4H), 7.45 (dd, J = 11.5, 7.4 Hz, 3H), 3.94 (d, J = 5.8 Hz, 2H), 3.75 (t, J = 5.4 Hz, 2H), 3.51 – 3.40 (m, 2H), 3.30 – 3.06 (m, 4H), 2.93 (dd, J = 8.0, 4.8 Hz, 2H), 2.78 (dd, J = 15.7, 9.3 Hz, 1H), 2.45–2.31 (m, 1H), 2.09–1.92 (m, 1H), 1.84 – 1.60 (m, 6H); 13C NMR (126 MHz, $CD_3OD$) δ 162.29, 159.14, 139.70, 138.02, 137.48, 134.98, 134.24, 125.41, 125.37, 123.92, 122.71, 119.32, 112.08, 49.79, 44.48, 42.31, 39.56, 28.85, 22.72, 22.48, 21.74, 20.76, 20.54, 17.29. ESIMS m/z $[M + H]^+$ 508. | | | |
| NUCC-0201686 | 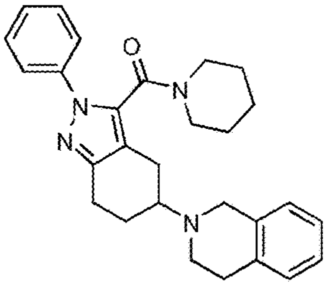 | ESIMS m/z $[M + H]^+$ 441. | | | |

SMALL MOLECULE MODULATORS OF SIGMA-1 AND SIGMA-2 RECEPTORS AND USES THEREOF

CROSS-REFERENCE TO RELATED APPLICATIONS

The present application is a U.S. 371 national phase entry of International Patent Application No. PCT/US2019/063357, filed Nov. 26, 2019, which claims priority to U.S. Provisional Patent Application No. 62/771,826, filed Nov. 27, 2018, hereby incorporated by reference in their entireties.

STATEMENT REGARDING FEDERALLY SPONSORED RESEARCH OR DEVELOPMENT

This invention was made with government support under grant numbers CA06553, CA189074, and HHSN271201300017C awarded by the National Institutes of Health. The government has certain rights in the invention.

FIELD OF THE INVENTION

This invention is in the field of medicinal chemistry. In particular, the invention relates to a new class of small-molecules having a tetrahydroindazole structure which function as modulators (e.g., activators or inhibitors) of sigma-1 and/or sigma-2 receptors, and their use as therapeutics for the treatment of cancer and other diseases (e.g., neurological conditions) characterized with sigma-1 and/or sigma-2 receptor activity

INTRODUCTION

The sigma receptors are classified into two subtypes, sigma-1 and sigma-2. Sigma-1 was first cloned in 1997 (see, Hanner, M.; et al., Proc Natl Acad Sci USA 1996, 93 (15), 8072-7) and is translated into a 25 kD protein with no other mammalian protein homologs. The most closely related protein is yeast C8-C7 sterol isomerase (see, Hanner, M.; et al., Proc Natl Acad Sci USA 1996, 93 (15), 8072-7); however, replacement of sterol isomerase by sigma-1 fails to reproduce isomerase function in yeast, indicating important functional differences exist between the two proteins. In sigma-1 knockout mice, animals grow normally with no overt phenotype (see, Langa, F et al., The European journal of neuroscience 2003, 18 (8), 2188-96), although they have been shown to display a mild depressive-like behavior (see, Sabino, V.; et al., Behavioural brain research 2009, 198 (2), 472-6). Sigma-1 is highly expressed in the CNS as well as in peripheral tissues.

The sigma-1 receptor has been shown to potentiate the activity of opioid receptors by physical association (see, Kim, F. J.; et al., Mol Pharmacol 2010, 77 (4), 695-703), possibly explaining the observed effects on opioid analgesia in vivo (see, Chien, C. C.; et al., The Journal of pharmacology and experimental therapeutics 1994, 271 (3), 1583-90; Mei, J.; et al., The Journal of pharmacology and experimental therapeutics 2002, 300 (3), 1070-4). Besides neurodegenerative disorders, sigma-1 ligands have also shown efficacy in animal models of pain (see, Sahn, J. J.; et al., ACS chemical neuroscience 2017, 8 (8), 1801-1811) and alcohol abuse (see, Scott, L. L.; et al., Neuropsychopharmacology: official publication of the American College of Neuropsychopharmacology 2018), indicating application to a potentially wide range of CNS diseases. Mutation studies have helped identify several negatively-charged amino acids (see, Seth, P.; et al., Biochimica et biophysica acta 2001, 1540 (1), 59-67) and non-polar transmembrane amino acids (see, Yamamoto, H.; et al., EBS letters 1999, 445 (1), 19-22) essential for sigma-1 ligand binding.

Sigma-2 antagonists have been suggested as potential Alzheimer's disease therapeutics based on their ability to prevent Abeta oligomer binding to neurons their effects on synapse loss and cognition in mouse models (see, Izzo, N. J.; et al., PloS one 2014, 9 (11), e111899). It has been shown that sigma-2 antagonists can prevent neurodegeneration in Alzheimer's mouse models (see, Yi, B.; et al., Journal of neurochemistry 2017, 140 (4), 561-575) and sigma-1 has been implicated in amyotrophic lateral sclerosis (see, Prause, J.; et al., Human molecular genetics 2013, 22 (8), 1581-600; Al-Saif, A.; et al., Annals of neurology 2011, 70 (6), 913-9; Luty, A. A.; et al., Annals of neurology 2010, 68 (5), 639-49).

Previously, it was believed that the sigma-2 receptor was the progesterone receptor membrane component 1 (PGRMC1) protein using data obtained from photoaffinity labeling and imaging studies (see, Xu, J.; et al., Nat Commun 2011, 2, 380). However, it was recently established that sigma-2 is actually the endoplasmic reticulum (ER) transmembrane protein TMEM97 (see, Alon, A.; et al., Proceedings of the National Academy of Sciences 2017, 114 (27), 7160-7165). The sigma-2 receptor has been shown to be a biomarker for rapidly dividing cells and is overexpressed in multiple tumor types (see, Vilner, B. J.; et al., Cancer Res. 1995, 55 (2), 408-13; Mach, R. H.; et al., Cancer Res. 1997, 57 (1), 156-61; Colabufo, N. A.; et al., Cancer letters 2006, 237 (1), 83-8; Kashiwagi, H.; et al., Molecular cancer 2007, 6, 48; Wheeler, K. T.; et al., British journal of cancer 2000, 82 (6), 1223-32).

One of the most well-supported hypotheses of the biological function of the sigma receptors is that they primarily act as protein chaperones that modulate the function of those proteins with which they associate. In support of this paradigm, it has been shown that sigma-1 regulates a variety of protein functions by direct binding, including those of TRPV1 (see, Ortiz-Renteria, M.; et al., Proc Natl Acad Sci USA 2018, 115 (7), E1657-e1666), dopamine receptors (see, Navarro, G.; et al., Proc Natl Acad Sci USA 2010, 107 (43), 18676-81), opioid receptors (see, Kim, F. J.; et al., Mol Pharmacol 2010, 77 (4), 695-703), potassium channels (see, Gueguinou, M.; et al., Oncogene 2017, 36 (25), 3640-3647), and others (see, Hayashi, T.; et al., Proc Natl Acad Sci USA 2001, 98 (2), 491-6; Rodriguez-Munoz, M.; et al., Oncotarget 2015, 6 (34), 35458-77) to potentiate their functions. Sigma-1 was also shown to be involved in mediating intracellular calcium levels in breast and colon cancer cells through its association to potassium channels (see, Gueguinou, M.; et al., Oncogene 2017, 36 (25), 3640-3647). In the context of cancer, it has been shown that sigma-1 ligands reduce breast cancer cell line proliferation by inducing ER stress (see, Schrock, J. M.; et al., Mol Pharmacol 2013, 84 (5), 751-62).

Because of the important roles of sigma-1 in CNS diseases and cancer, there have been a number of efforts aimed at developing potent and selective ligands. Among the sigma receptor ligands that have been developed are series of alkoxyisoxazoles (see, Sun, H.; et al., J Med Chem 2016, 59 (13), 6329-43) and alkoxypyazoles (see, Diaz, J. L.; et al., J Med Chem 2012, 55 (19), 8211-24) that displayed potent binding to sigma-1 and good selectivity against sigma-2. These compounds showed significant analgesic effects in mouse models of pain (see, Sun, H.; et al., J Med Chem 2016, 59 (13), 6329-43; Diaz, J. L.; et al., J Med Chem 2012, 55 (19), 8211-24). A series of sigma-1-selective ligands based on an aminotriazole scaffold was also reported with in vivo antinociceptive efficacy (see, Diaz, J. L.; et al., J Med Chem 2015, 58 (5), 2441-51). Another report of sigma-1 ligands with efficacy in the formalin analgesia assay was derived from substituted pyrimidines (see, Lan, Y.; et al., J Med Chem 2014, 57 (24), 10404-23). There have been other scaffolds developed as potent and selective sigma-1 ligands for CNS and cancer indications as well (FIG. 1) (see, Sahn, J. J.; et al., Acs Med Chem Lett 2017, 8 (4), 455-460; Sahn, J. J.; et al., ChemMedChem 2016, 11 (6), 556-61; Yi, B.; et al., Journal of neurochemistry 2017, 140 (4), 561-575; Mondal, S.; et al., ACS chemical neuroscience 2018, 9 (5), 1014-1026; Diaz, J. L.; et al., MedChemComm 2017, 8 (6), 1235-1245; Diaz, J. L.; et al., MedChemComm 2017, 8 (6), 1246-1254; Maher, C. M.; et al., Molecular cancer research: MCR 2018, 16 (2), 243-255).

Although there has been less attention on sigma-2 than sigma-1, it has been shown that sigma-2 plays a critical role in cancer cell survival and neuronal cell signaling. Modulation of its function causes cell death through autophagy (see, Mir, S. U. R.; et al., Autophagy 2013, 9 (10), 1566-1578) and other mechanisms (see, Zeng, C.; et al., British journal of cancer 2012, 106, 693). Recent work has sought to develop potent and selective sigma-2 ligands for use in studying various diseases, including tetrahydroisoquinolines and triazoles to afford potent sigma-2 ligands (see, Bai, S.; et al., J Med Chem 2014, 57 (10), 4239-51). Selective sigma-2 ligands based on a norbenzomorphans scaffold have also been shown to be effective in mouse models of Alzheimer's disease (see, Sahn, J. J.; et al., ChemMedChem 2016, 11 (6), 556-61; Yi, B.; et al., Journal of neurochemistry 2017, 140 (4), 561-575).

These efforts have advanced the progress towards development of chemical probes and therapeutics for sigma-1 and -2. However, it has been difficult to clearly establish specific roles of each of these proteins. While others have developed ligands selective for either sigma-1 or sigma-1, each of these compounds were derived from unique scaffolds. It is therefore likely that each of these compounds has greatly varied off-target effects, making it difficult to fully differentiate the roles of these two proteins.

A more useful set of ligands would be those that are closely related structurally but are potent and selective for the two different sigma receptors. Importantly, there have been no reports of the development of ligands selective for sigma-1 and sigma-2 that were derived from the sample molecular scaffold.

The present invention addresses this need.

SUMMARY OF THE INVENTION

Experiments conducted during the course of developing embodiments for the present invention developed a single chemotype of tetrahydroindazoles that are highly potent ligands for sigma-1 and sigma-2 receptors. Previous experiments conducted on the biological activity of a class of tetrahydroindazoles (see, Mishra, R. K.; et al., Sci Rep 2016, 6, 30155) and it was noted that one compound possessed moderate affinity for both the sigma-1 and sigma-2 receptors. As these receptors have been shown to be involved in multiple important diseases, additional experiments were conducted that initiated a thorough assessment of the structure-activity relationships (SAR) around this class of compounds. Such experiments resulted in the synthesis and characterization of a series of potent ligands based on a single chemotype where sigma-1 and sigma-2 potency can be tuned through structural modifications. Through modulation (e.g., activation or inhibition) of sigma-1 and/or sigma-2 receptor activity, such compounds can serve as therapeutics for neurological diseases, cancer, and other conditions, as well provide useful new tool compounds for studying the roles of these two proteins.

As such, the present invention relates to a new class of small-molecules having a tetrahydroindazole structure (or similar) which function as modulators (e.g., activators or inhibitors) of sigma-1 and/or sigma-2 receptors, and their use as therapeutics for the treatment of disorders and/or conditions and/or diseases associated with sigma-1 receptor activity and/or sigma-2 receptor activity.

Accordingly, the present invention contemplates that exposure of animals (e.g., humans) suffering from conditions related to sigma-1 and/or sigma-2 receptor activity (e.g., neurological conditions (e.g., traumatic brain injury, depression, stroke, pain, alcohol addiction, substance abuse, ALS, Alzheimer's disease), cancer (e.g., liver cancer, esophageal cancer, prostate cancer, breast cancer, pancreatic cancer, colon cancer)) to therapeutically effective amounts of drug(s) having a tetrahydroindazole (or similar) structure that modulate (e.g., activate or inhibit) the activity of the sigma-1 receptor and/or the sigma-2 receptor will inhibit the growth of cancer cells or supporting cells outright and/or render such cells as a population more susceptible to the cell death-inducing activity of cancer therapeutic drugs or radiation therapies.

The present invention contemplates that modulators (e.g., activators or inhibitors) of sigma-1 receptor and/or the sigma-2 receptor activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain tetrahydroindazole (or structurally similar) compounds function as modulators (e.g., activators or inhibitors) of sigma-1 receptor and/or the sigma-2 receptor activity, and serve as therapeutics for the treatment of cancer (e.g., liver cancer, esophageal cancer, prostate cancer, breast cancer, pancreatic cancer, colon cancer) and other diseases (e.g., CNS related conditions characterized with sigma-1 and/or sigma-2 receptor activity) (e.g., neurological conditions characterized with sigma-1 and/or sigma-2 receptor activity (e.g., traumatic brain injury, depression, stroke, pain, alcohol addiction, substance abuse, ALS, Alzheimer's disease). Thus, the present invention relates to tetrahydroindazole (or similar) compounds useful for modulating (e.g., activating or inhibiting) sigma-1 receptor and/or the sigma-2 receptor activity (e.g., thereby facilitating cell apoptosis), and increasing the sensitivity of cells to inducers of apoptosis and/or cell cycle arrest. Certain tetrahydroindazole (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, tetrahydroindazole (or similar) compounds encompassed within Formulas I, II, III, IV, V and VI are provided:

(Formula I)

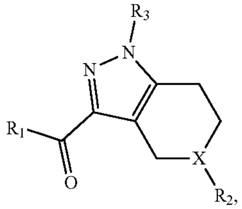

(Formula II)

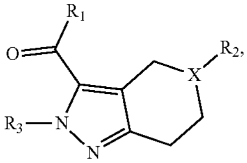

(Formula III)

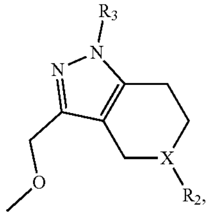

(Formula IV)

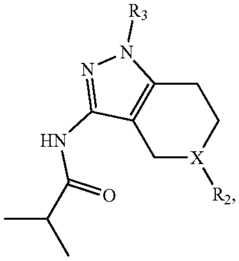

(Formula V)

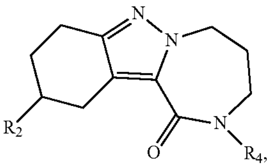

and

-continued (Formula VI)

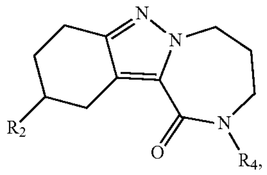

including pharmaceutically acceptable salts, solvates, and/or prodrugs thereof.

Formulas I, II, III, IV, V and VI are not limited to a particular chemical moiety for X, R1, R2, R3, and R4. In some embodiments, the particular chemical moiety for X, R1, R2, R3, and R4 independently include any chemical moiety that permits the resulting compound to modulate (e.g., activate or inhibit) sigma-1 receptor activity, and/or modulate (e.g., activate or inhibit) sigma-2 receptor activity.

In some embodiments, X is either Carbon or Nitrogen.

In some embodiments, R1 is selected from

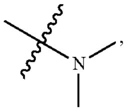

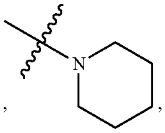

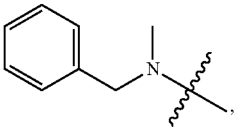

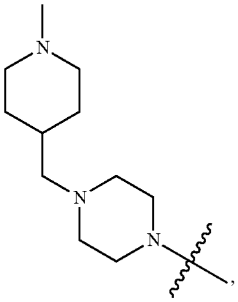

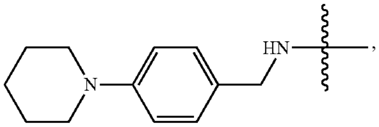

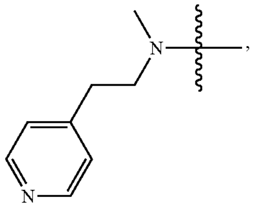

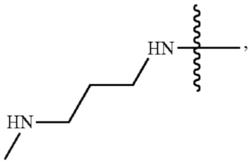

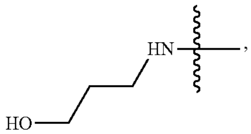

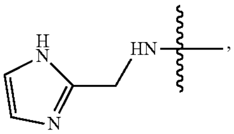

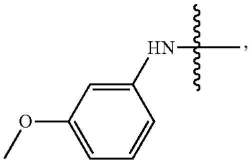

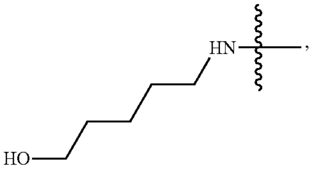

-continued
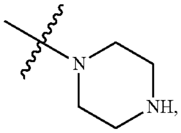
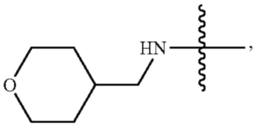
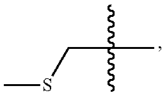
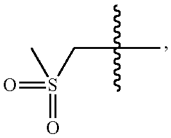
and
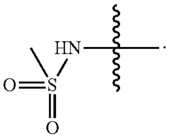
In some embodiments, R2 is selected from Hydrogen,
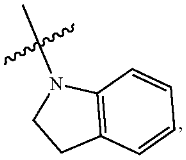
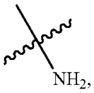
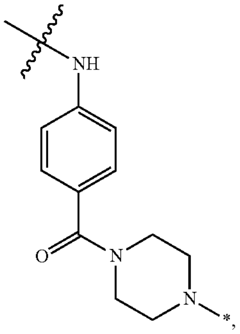
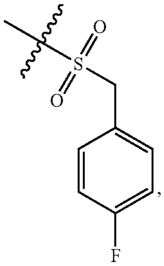
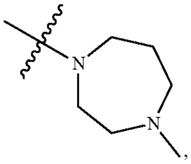
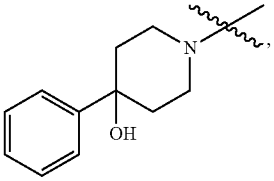
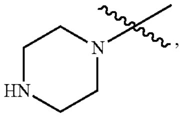
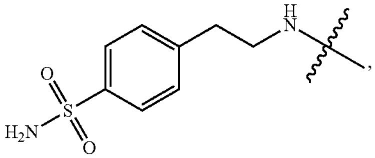
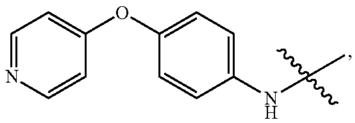
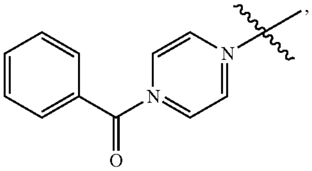
-continued
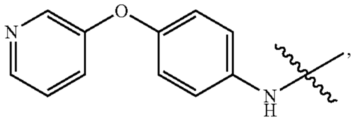
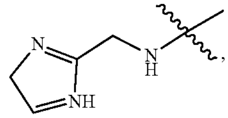
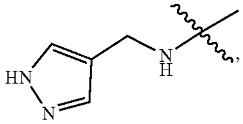
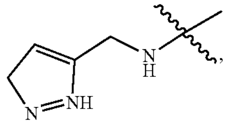
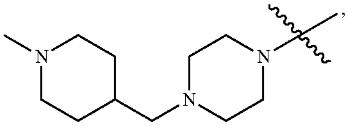
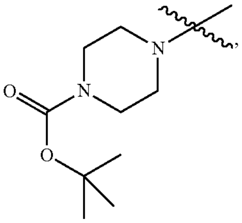
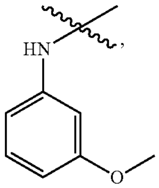
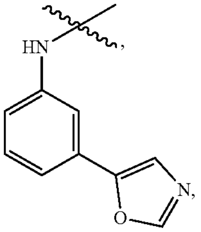
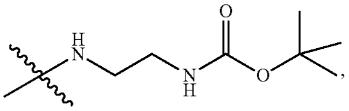
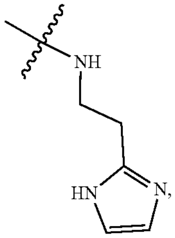
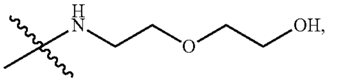
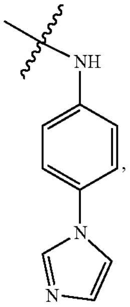
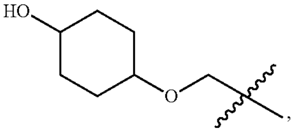
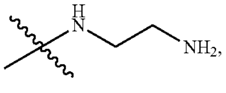

-continued
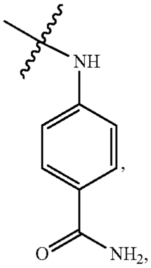
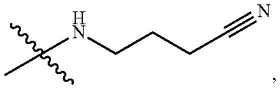
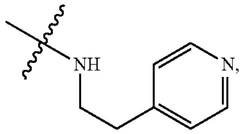
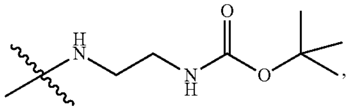
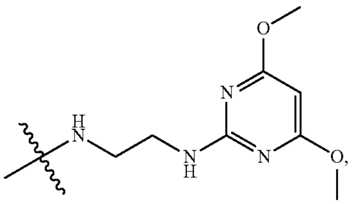
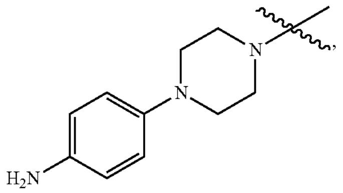
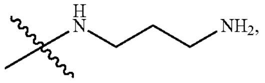
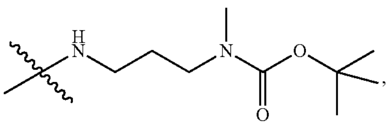
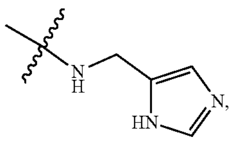
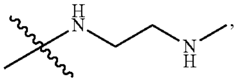
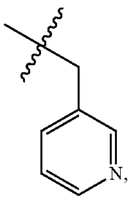
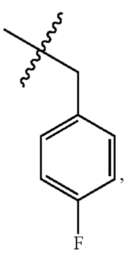
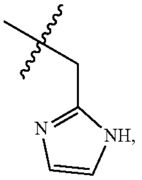
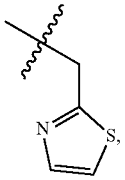
-continued
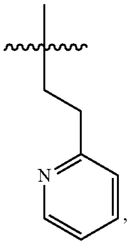
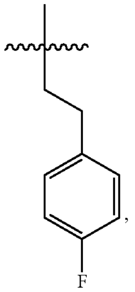
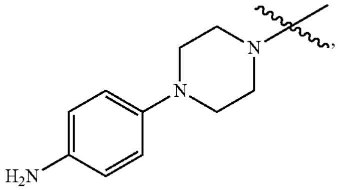
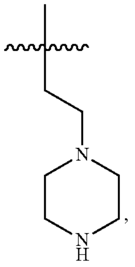
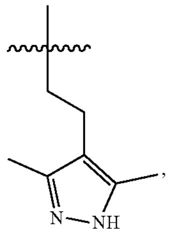
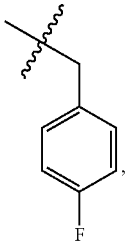
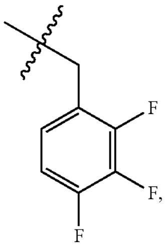
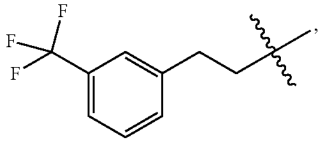
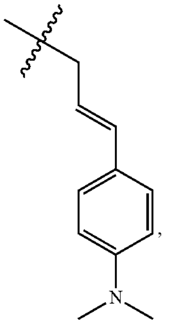
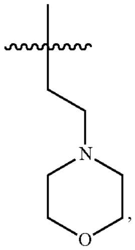
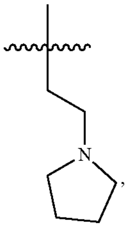
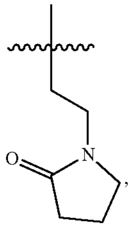
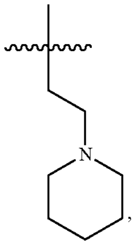
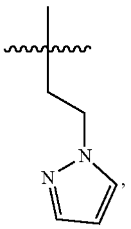
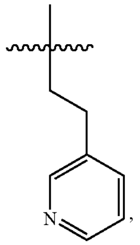

-continued
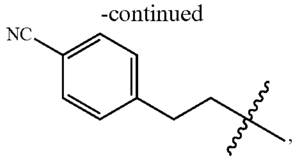
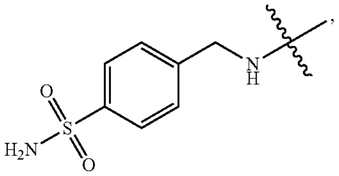
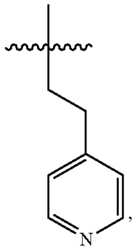
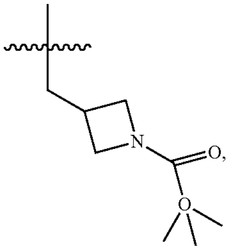
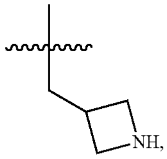
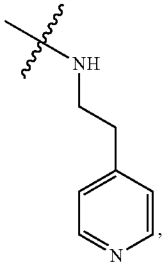
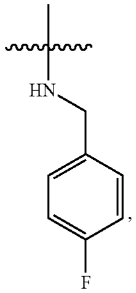
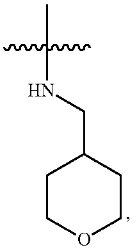
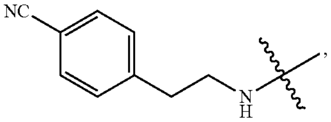
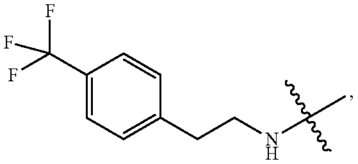
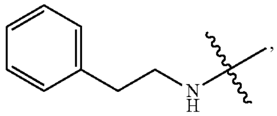
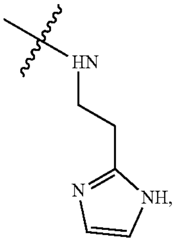
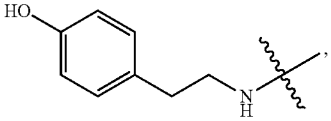
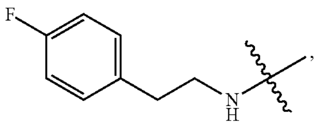
-continued
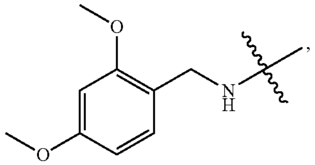
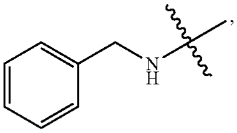
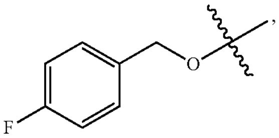
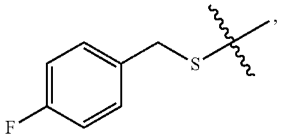
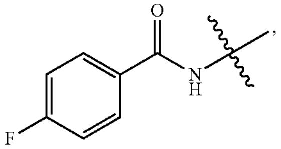
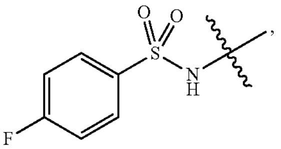
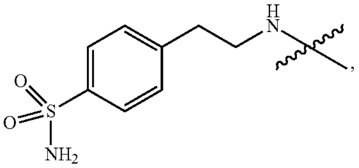
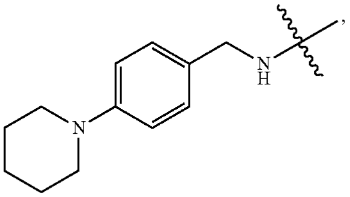
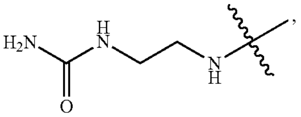
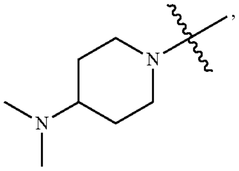
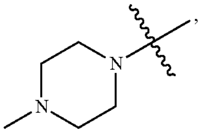
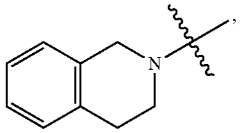
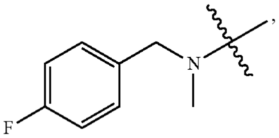
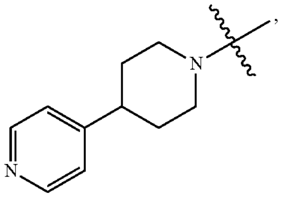
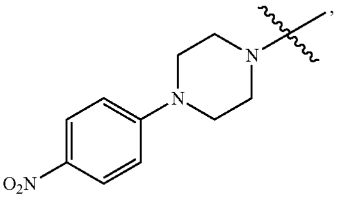
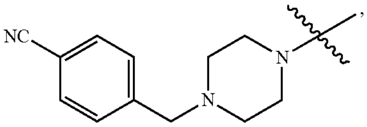

-continued

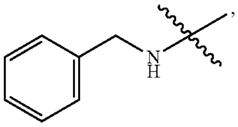,
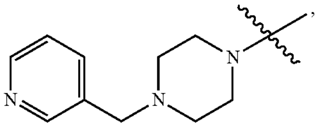,
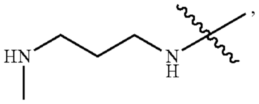,
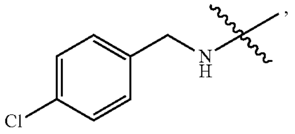,
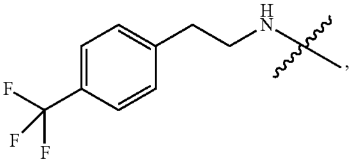,
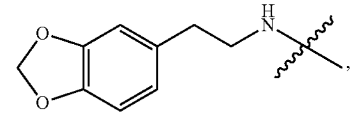,
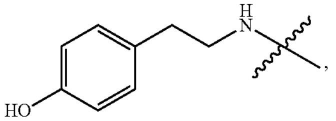,
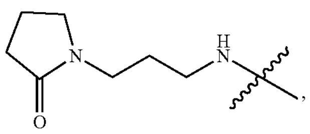,
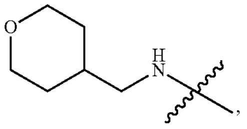,
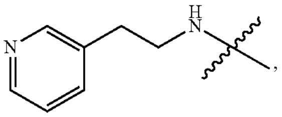,
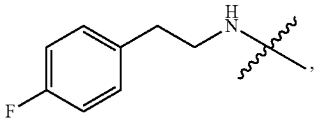,
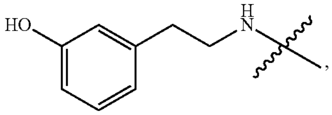, and
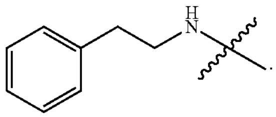.

In some embodiments, R3 is selected from

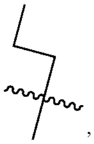,
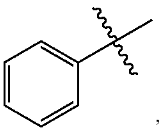,
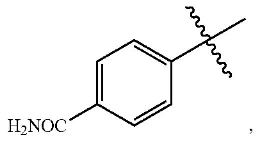,
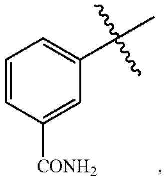,
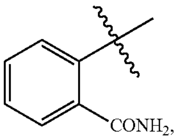,
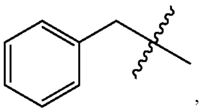,

-continued

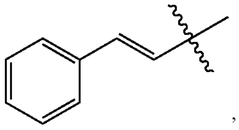,
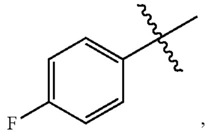, and
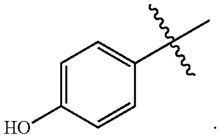.

In some embodiments, R4 is Hydrogen or methyl.

In some embodiments, compounds shown in Tables II, III and IV and FIG. 1 are contemplated for Formulas I, II, III, IV, V and VI.

Example I describes the binding affinities ($K_i$ values) for sigma-1 and sigma-2 various compounds encompassed within Formulas I, II, III, IV, V and VI (see, Table II, III and IV and FIG. 1).

The invention further provides processes for preparing any of the compounds of the present invention through following at least a portion of the techniques recited in the experimental section.

The compounds of the invention are useful for the treatment, amelioration, or prevention of disorders characterized with sigma-1 receptor activity and/or sigma-2 receptor activity (e.g., neurological conditions) (e.g., CNS conditions) (e.g., Alzheimer's disease; amyotrophic lateral sclerosis (ALS); pain; mental health (e.g., psychiatric) conditions; and substance abuse conditions).

For example, in some embodiments, such small-molecules having a tetrahydroindazole structure (or similar) which function as modulators (e.g., activators or inhibitors) of sigma-1 and/or sigma-2 receptors can be used as therapeutics for traumatic brain injury (see, e.g., Vazquez-Rosa E, et al., ACS Chem Neurosci. 2018 Nov. 13; Sun D, et al., Cell Mol Neurobiol. 2017 November; 37(8):1349-1357; Dong H, et al., Cell Mol Neurobiol. 2016 July; 36(5):639-45).

In some embodiments, such small-molecules having a tetrahydroindazole structure (or similar) which function as modulators (e.g., activators or inhibitors) of sigma-1 and/or sigma-2 receptors can be used as therapeutics for mood disorders (e.g., depression) (see, e.g., Liu X, et al., Am J Physiol Heart Circ Physiol. 2018 Sep. 14; Fukunaga K, Moriguchi S. Adv Exp Med Biol. 2017; 964:201-211; Mandelli L, et al., Adv Ther. 2017 March; 34(3):713-724).

In some embodiments, such small-molecules having a tetrahydroindazole structure (or similar) which function as modulators (e.g., activators or inhibitors) of sigma-1 and/or sigma-2 receptors can be used as therapeutics for stroke (see, e.g., Rodriguez-Muñoz M, et al., Mol Brain. 2018 Sep. 17; 11(1):51).

In some embodiments, such small-molecules having a tetrahydroindazole structure (or similar) which function as modulators (e.g., activators or inhibitors) of sigma-1 and/or sigma-2 receptors can be used as therapeutics for pain (see, e.g., Sachau J, et al., J Pain. 2018 Sep. 25. pii: 51526-5900 (18)30618-7; Castany S, et al., Sci Rep. 2018 Mar. 1; 8(1):3873; Bruna J, Velasco R. Neural Regen Res. 2018 May; 13(5):775-778; Tejada M Á, et al., Pharmacol Res. 2018 May; 131:224-230; Wang X, et al., Neurosci Lett. 2018 Mar. 6; 668:164-168; Ortiz-Renteria M, et al., Proc Natl Acad Sci USA. 2018 Feb. 13; 115(7):E1657-E1666).

In some embodiments, such small-molecules having a tetrahydroindazole structure (or similar) which function as modulators (e.g., activators or inhibitors) of sigma-1 and/or sigma-2 receptors can be used as therapeutics for alcohol addiction (see, e.g., Scott L L, et al., Neuropsychopharmacology. 2018 August; 43(9):1867-1875; Valenza M, et al., Behav Brain Res. 2016 Jan. 15; 297:196-203; Blasio A, et al., Behav Brain Res. 2015; 287:315-22).

In some embodiments, such small-molecules having a tetrahydroindazole structure (or similar) which function as modulators (e.g., activators or inhibitors) of sigma-1 and/or sigma-2 receptors can be used as therapeutics for substance abuse (see, e.g., Sabino V, et al., Adv Exp Med Biol. 2017; 964:177-199; Borroto-Escuela D O, et al., Pharmacol Biochem Behav. 2017 April; 155:24-31; Lever J R, et al., Synapse. 2016 March; 70(3):98-111; Lever J R, et al., Synapse. 2014 February; 68(2):73-84).

In some embodiments, such small-molecules having a tetrahydroindazole structure (or similar) which function as modulators (e.g., activators or inhibitors) of sigma-1 and/or sigma-2 receptors can be used as therapeutics for Alzheimer's disease (see, e.g., Hall H, et al., Alzheimers Dement. 2018 June; 14(6):811-823; Uchida N, et al., Am J Geriatr Psychiatry. 2005 December; 13(12):1062-6).

In some embodiments, such small-molecules having a tetrahydroindazole structure (or similar) which function as modulators (e.g., activators or inhibitors) of sigma-1 and/or sigma-2 receptors can be used as therapeutics for amyotrophic lateral sclerosis (ALS) (see, e.g., Benarroch E E. Neurology. 2018 Oct. 16; 91(16):743-747; Weng T Y, Tsai S A, Su T P. J Biomed Sci. 2017 Sep. 16; 24(1):74; Tadić V, et al., Neuroscience. 2017 Sep. 17; 359:105-118; Dreser A, et al., Cell Death Differ. 2017 October; 24(10):1655-1671; Mancuso R, Navarro X. Adv Exp Med Biol. 2017; 964:235-254; Nguyen L, et al., Adv Exp Med Biol. 2017; 964:133-152).

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like).

In certain embodiments, the cancer is any type of cancer characterized with sigma-1 receptor activity and/or sigma-2 receptor activity (e.g., liver cancer, esophageal cancer, prostate cancer, breast cancer, pancreatic cancer, colon cancer). Indeed, in some embodiments, such small-molecules having a tetrahydroindazole structure (or similar) which function as modulators (e.g., activators or inhibitors) of sigma-1 and/or sigma-2 receptors can be used as therapeutics for liver cancer, esophageal cancer, breast cancer, prostate cancer, colon cancer, and/or pancreatic cancer (see, e.g., Sun Y T, et al., Eur J Med Chem. 2018 Mar. 10; 147:227-237; Xu Q, et al., Oncol Rep. 2018 March; 39(3):1405-1413; Maher C M, et al., Mol Cancer Res. 2018 February; 16(2):243-255; Salvino J M, et al., 2017 May 15; 27(10):2216-2220; Thomas J D, et al., Cancer Res. 2017 May 1; 77(9):2439-2452; McDonald E S, et al., Biochem Biophys Res Commun. 2017 May 6; 486(3):788-795; Gueguinou M, et al., Oncogene. 2017 Jun. 22; 36(25):3640-3647; Pati M L, et al., BMC Cancer. 2017 Jan. 13; 17(1):51).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents, e.g., therapeutic agents useful in treating neurological conditions (e.g., Alzheimer's disease; amyotrophic lateral sclerosis (ALS); pain; mental health (e.g., psychiatric) conditions; and substance abuse conditions).

The present disclosure further provides bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited. An exemplary advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer and neurological conditions (e.g., Alzheimer's disease; amyotrophic lateral sclerosis (ALS); pain; mental health (e.g., psychiatric) conditions; and substance abuse conditions).

In an additional aspect, the disclosure provides bifunctional or PROTAC compounds, which comprise an E3 Ubiquitin Ligase binding moiety (e.g., a ligand for an E3 Ubiquitin Ligase or "ULM" group), and a moiety that binds a target protein (e.g., a protein/polypeptide targeting ligand or "PTM" group) (e.g., a sigma-1 receptor modulator and/or a sigma-2 receptor modulator) such that the target protein/polypeptide is placed in proximity to the ubiquitin ligase to effect degradation (and inhibition) of that protein (e.g., modulate sigma-1 receptor activity and/or sigma-2 receptor activity). In certain embodiments, the PTM is any of the compounds as described herein showing modulatory activity against sigma-1 receptor activity and/or sigma-2 receptor activity. In some embodiments, the ULM is a von-Hippel-Lindau (VHL) ligase, cereblon, mouse double minute 2 (MDM2), and/or inhibitor of apoptosis protein (IAP) E3 ligase binding moiety. For example, the structure of the bifunctional compound can be depicted as PTM-ULM.

The respective positions of the PTM and ULM moieties, as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as PTM-L-ULM, where PTM is a protein/polypeptide targeting moiety (e.g., any of the compounds as described herein showing modulatory activity against sigma-1 receptor activity and/or sigma-2 receptor activity), L is a linker, and ULM is a VHL, cereblon, MDM2, or IAP E3 ligase binding moiety binding moiety.

In some embodiments, the ULM is selected from

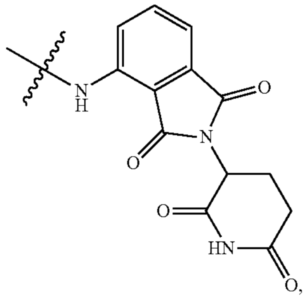

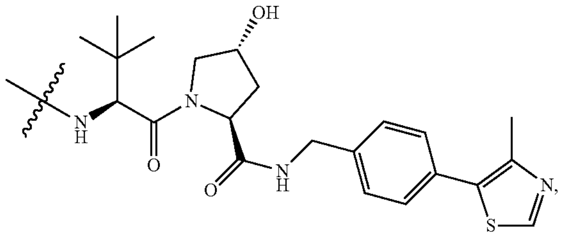

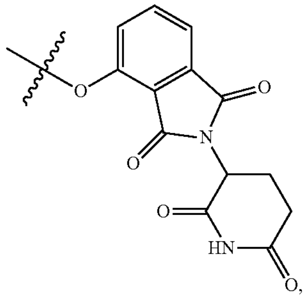

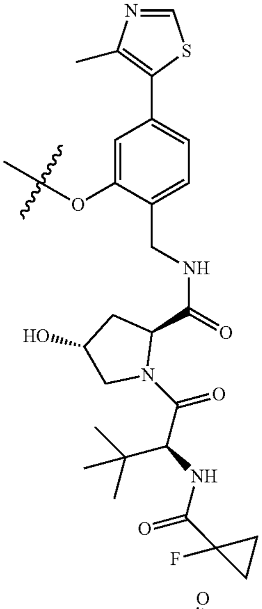

, and

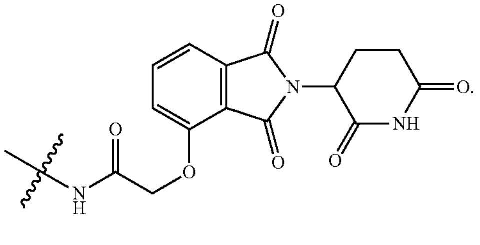

Such embodiments are not limited to a specific type of linker.

In some embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical. In some embodiments, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ULM group and PTM group may be covalently linked to the linker group through any group which is appropriate and stable to the chemistry of the linker. In exemplary aspects of the present invention, the linker is independently covalently bonded to the ULM group and the PTM group in certain embodiments through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain aspects where the PTM group is a ULM group, the target protein for degradation may be the ubiquitin ligase itself. In certain exemplary aspects, the linker may be linked to an optionally substituted alkyl, alkylene, alkene or alkyne group, an aryl group or a heterocyclic group on the ULM and/or PTM groups.

In some embodiments, the linker group is $-A_1 \ldots A_q-$; wherein $A_1$ to $A_q$ are each independently selected from the group consisting of a bond, $CR^{L1}R^{L2}$, O, S, S═O, $S(═O)_2$, $NR^{L3}$, $S(═O)_2NR^{L3}$, $S(═O)NR^{L3}$, $C(═O)NR^{L3}$, $NR^{L3}C(═O)NR^{L4}$, $NR^{L3}S(═O)_2NR^{L4}$, C(═O), $CR^{L1}═CR^{L2}$, $SiR^{L1}R^{L2}$, $P(═O)R^{L1}$, $P(═O)OR^{L1}$, $NR^{L3}C(═N—CN)NR^{L4}$, $NR^{L3}C(═N—CN)$, $NR^{L3}C(═C—NO_2)NR^{L4}$, $C_{3-11}$ cycloalkyl optionally substituted with 0-6 substituents selected from the group consisting of $R^{L1}$ and $R^{L2}$, $C_{3-11}$heterocyclyl optionally substituted with 0-6 substituents selected from the group consisting of $R^{L1}$ and $R^{L2}$, aryl optionally substituted with 0-6 substituents selected from the group consisting of $R^{L1}$ and $R^{L2}$, and heteroaryl optionally substituted with 0-6 substituents selected from the group consisting of $R^{L1}$ and $R^{L2}$, wherein: $R^{L1}$ and $R^{L2}$ each independently can be linked to other A groups to form a cycloalkyl or heterocyclyl moeity that can be further optionally substituted with 0-4 $R^{L5}$ groups; $R^{L1}$, $R^{L2}$, $R^{L3}$, $R^{L4}$ and $R^{L5}$ are each independently selected from the group consisting of H, halo, $C_{1-8}$ alkyl, $O(C_{1-8}$ alkyl), $S(C_{1-8}$ alkyl), $NH(C_{1-8}$ alkyl), $N(C_{1-8}alkyl)_2$, $C_{3-11}$ cycloalkyl, aryl, heteroaryl, $C_{3-11}$ heterocyclyl, $O(C_{1-8}$ cycloalkyl), $S(C_{1-8}$ cycloalkyl), $NH(C_{1-8}$ cycloalkyl), $N(C_{1-8}cycloalkyl)_2$, $N(C_{1-8}$ cycloalkyl)$(C_{1-8}$ alkyl), OH, $NH_2$, SH, $SO_2(C_{1-8}$ alkyl), $P(═O)(OC_{1-8}$ alkyl)$(C_{1-8}$ alkyl), $P(═O)(OC_{1-8}$ alkyl$)_2$, $C≡C—(C_{1-8}$ alkyl), C≡CH, $CH═CH(C_{1-8}$ alkyl), $C(C_{1-8}$ alkyl)$═CH(C_{1-8}$ alkyl), $C(C_{1-8}alkyl)═C(C_{1-8}alkyl)_2$, $Si(OH)_3$, $Si(C_{1-8}alkyl)_3$, $Si(OH)(C_{1-8}alkyl)_2$, $C(═O)(C_{1-8}$ alkyl), $CO_2H$, halogen, CN, $CF_3$, $CHF_2$, $CH_2F$, $NO_2$, $SF_5$, $SO_2NH(C_{1-8}$ alkyl), $SO_2N(C_{1-8}alkyl)_2$, S(═O)

$NH(C_{1-8}$ alkyl), $S(=O)N(C_{1-8}alkyl)_2$, $C(=O)NH(C_{1-8}$ alkyl), $C(=O)N(C_{1-8}alkyl)_2$, $N(C_{1-8}$ alkyl)$C(=O)NH(C_{1-8}$ alkyl), $N(C_{1-8}$ alkyl)$C(=O)N(C_{1-8}alkyl)_2$, $NHC(=O)NH(C_{1-8}$ alkyl), $NHC(=O)N(C_{1-8}alkyl)_2$, $NHC(=O)NH_2$, $N(C_{1-8}$ alkyl)$SO_2NH(C_{1-8}$ alkyl), $N(C_{1-8}alkyl)SO_2N(C_{1-8}alkyl)_2$, $NHSO_2NH(C_{1-8}$ alkyl), $NHSO_2N(C_{1-8}alkyl)_2$, and $NHSO_2NH_2$; and q is an integer greater than or equal to 1.

In certain embodiments, the compounds as described herein comprise multiple ULMs, multiple PTMs, multiple chemical linkers, or any combinations thereof.

In certain embodiments, the compound is selected from the group consisting of:

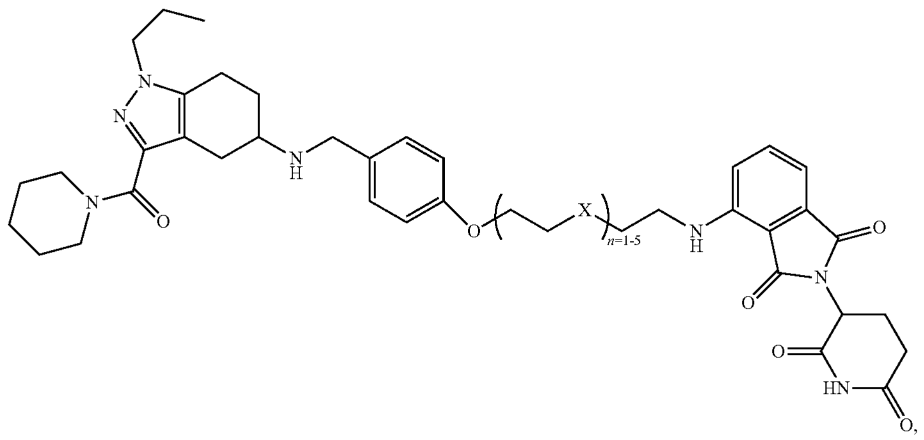

X = O, N

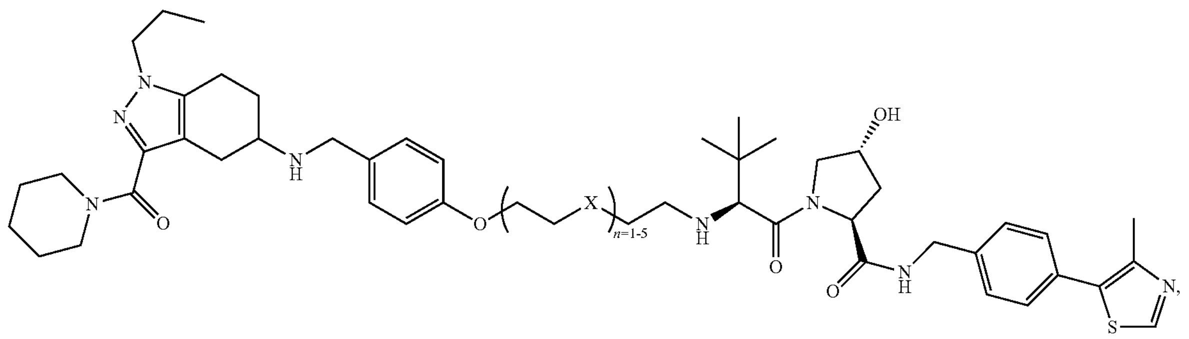

X = O, N

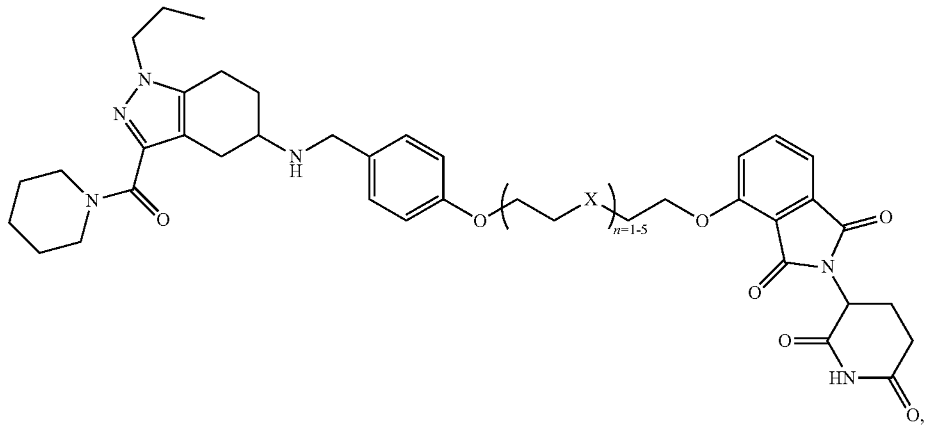

X = O, N

-continued
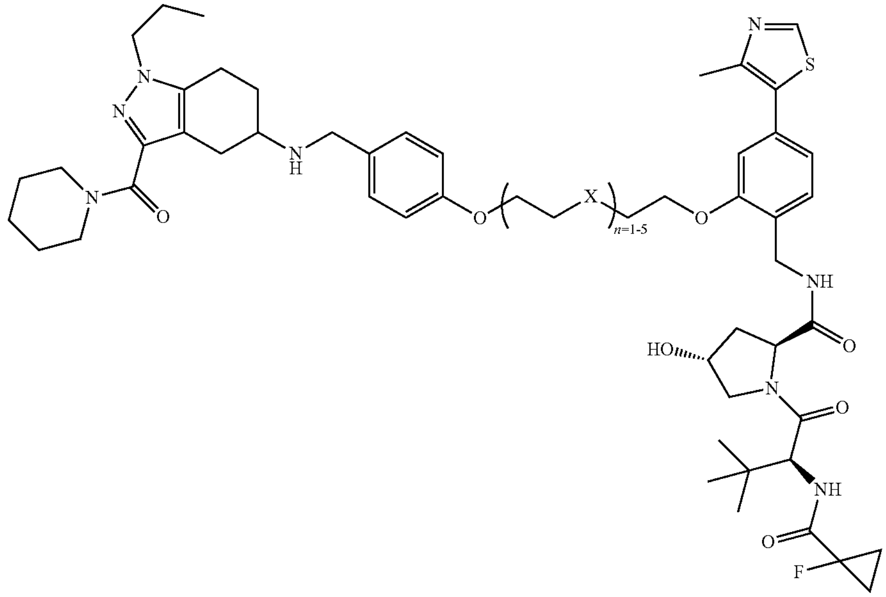
,
X = O, N
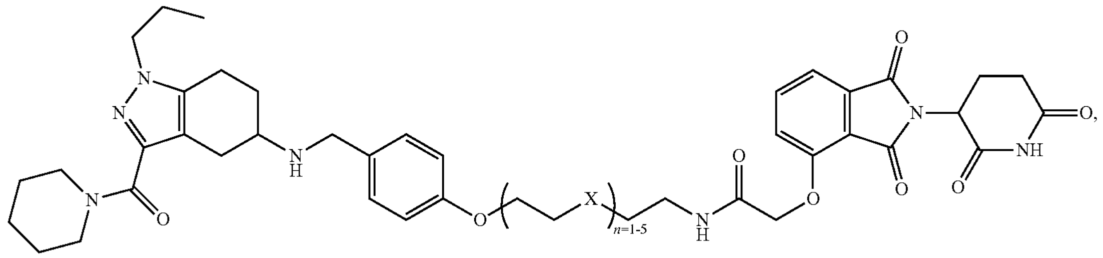
X = O, N
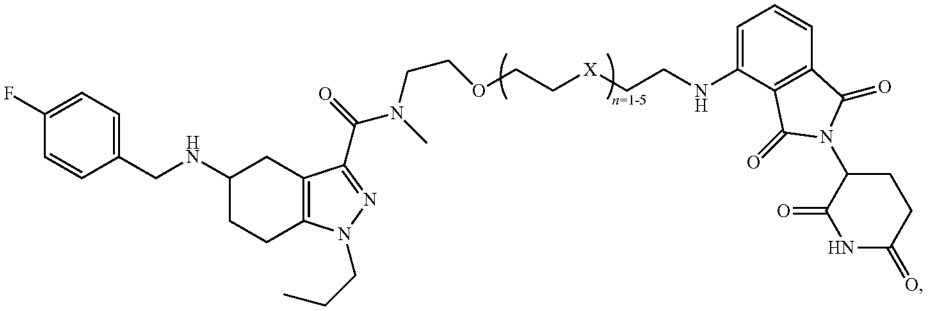
X = O, N
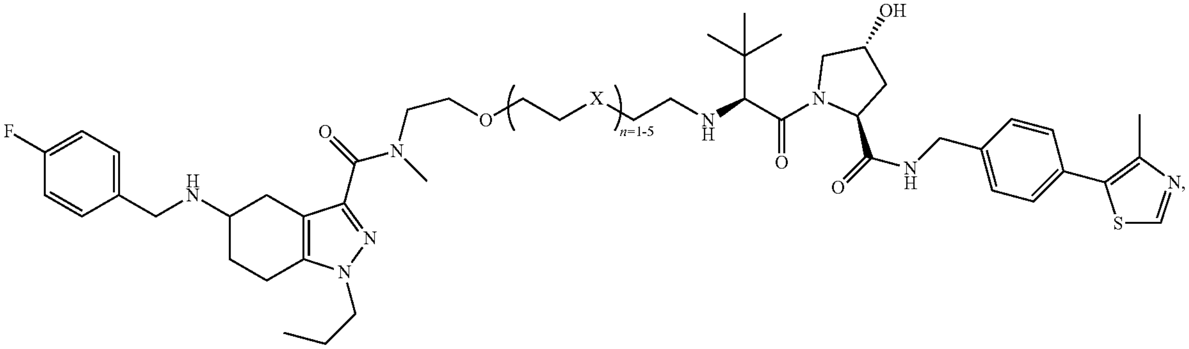
X = O, N -continued

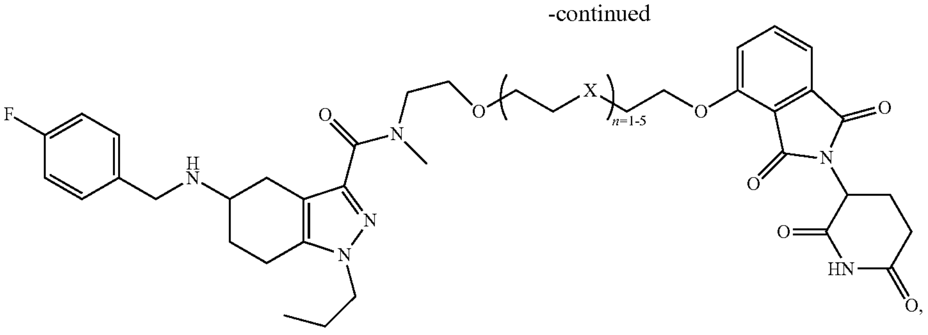

X = O, N

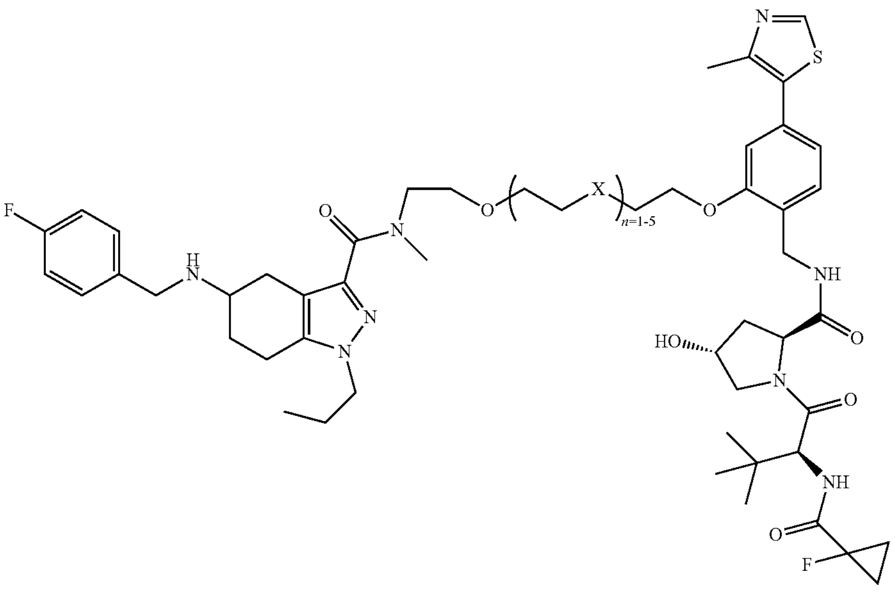

, and

X = O, N

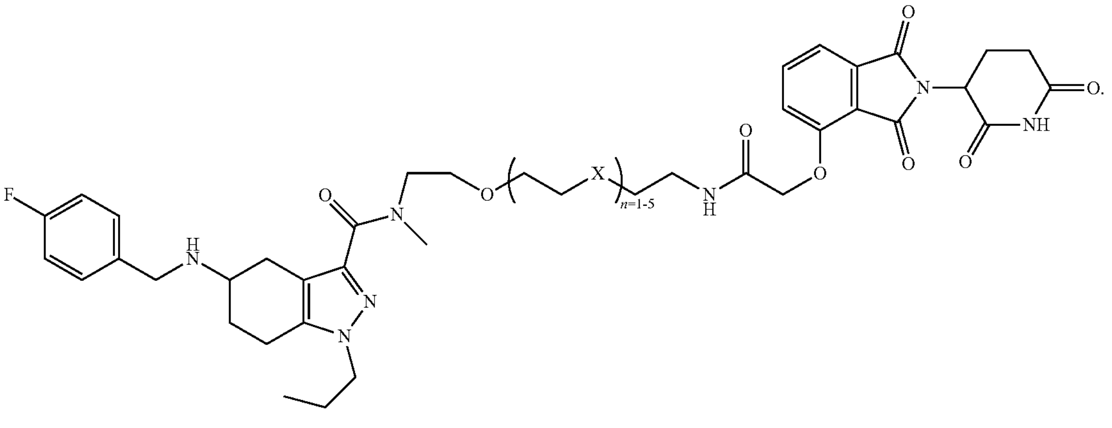

X = O, N

In some embodiments, the present invention provides a method of ubiquitinating/degrading sigma-1 receptor activity and/or sigma-2 receptor activity in a cell comprising administering a bifunctional compound as described herein comprising an ULM and a PTM, in certain embodiments linked through a linker moiety, as otherwise described herein, wherein the ULM is coupled to the PTM and wherein the ULM recognizes a ubiquitin pathway protein (e.g., any of the compounds as described herein showing modulatory activity against sigma-1 receptor activity and/or sigma-2 receptor activity) and the PTM recognizes the target protein such that degradation of the target protein occurs when the target protein (e.g., sigma-1 receptor and/or sigma-2 receptor) is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In certain embodiments, the compounds of the present invention (e.g., the compounds shown in Tables II, III and IV and FIG. 1) can be manipulated to serve as imaging agents (see, e.g., Kranz M, et al., Molecules. 2018 Mar. 20; 23(3); Sadeghzadeh M, et al., Ann Nucl Med. 2017 May; 31(4):335-346; Baum E, et al., J Nucl Med. 2017 June; 58(6):982-988; Yang D, et al., Mol Pharm. 2017 Mar. 6; 14(3):770-780).

BRIEF DESCRIPTION OF DRAWINGS

FIG. 1: Representative compounds of the present invention and, where applicable, analytical data, sigma-1 receptor binding activity, and sigma-2 receptor binding activity (wheren Ki Legend: +++=<1 uM; ++=between 1-10 uM; Blank=>10 uM).

DEFINITIONS

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, CA (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a tetrahydroindazole (or similar) compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

As used herein, the term "PROTAC" refers to proteolysis targeting chimeras.

The term "VCB E3 Ubiquitin Ligase", "Hippel-Lindau E3 Ubiquitin Ligase" or "Ubiquitin Ligase" is used to describe a target enzyme(s) binding site of ubiquitin ligase moieties in the bifunctional (chimeric) compounds according to the present invention. VCB E3 is a protein that, in combination with an E2 ubiquitin-conjugating enzyme, causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further, different lysines on ubiquitin can be targeted by an E3 to make chains. The most common lysine is Lys48 on the ubiquitin chain, which is used to make polyubiquitin, which is recognized by the proteasome.

The term "protein target moiety" or PTM is used to describe a small molecule that binds to a target protein or other protein or polypeptide of interest and places/presents that protein or polypeptide in proximity to an ubiquitin ligase, such that degradation of the protein or polypeptide by ubiquitin ligase may occur. Non-limiting examples of small molecule target protein binding moieties include any of the compounds as described herein showing modulatory activity against sigma-1 receptor activity and/or sigma-2 receptor activity.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to ULM groups through linker groups L.

Target proteins that may be bound to the protein target moiety and degraded by the ligase to which the ubiquitin ligase binding moiety is bound include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others. As described herein, in some embodiments, the target proteins are sigma-1 receptor and/or the sigma-2 receptor.

DETAILED DESCRIPTION OF THE INVENTION

The sigma-1 and sigma-2 receptors have been shown to play important roles in CNS diseases and cancer. Previous findings suggest that targeting these proteins with small molecule modulators may be of important therapeutic value. Development of ligands to help better define the individual roles of sigma-1 and -2 has been hampered by the inability to develop compounds that are both potent and selective for each target protein. Experiments conducted during the course of developing embodiments for the present invention describe the development of a single chemotype of tetrahydroindazoles (and similarly structured compounds) that are highly potent ligands for sigma-1 and sigma-2 for which selectivity can be tuned by structural modification (e.g., sigma-1 ligands having a $K_i$ of 17 nM and >500× selectivity towards sigma-2) (e.g., analogs having a $K_i$ of 19 nM for sigma-2 and >500× selectivity towards sigma-1). Such experiments also describe the application of a highly useful Chan-Lam coupling approach for the synthesis of various N-aryl tetrahydroindazole analogs. Such results indicate the feasibility of developing potent and selective ligands for the sigma-1 and sigma-2 receptors from a single chemotype. The compounds described herein will be useful in the development of new chemical probes for these receptors and to aid in future therapeutic development.

As such, the present invention relates to a new class of small-molecules having a tetrahydroindazole structure which function as modulators of sigma-1 and/or sigma-2 receptors, and their use as therapeutics for the treatment of cancer and other diseases (e.g., neurological conditions characterized with sigma-1 and/or sigma-2 receptor activity (e.g., Alzheimer's disease; amyotrophic lateral sclerosis (ALS); pain; mental health (e.g., psychiatric) conditions; and substance abuse conditions)).

In a particular embodiment, tetrahydroindazole (or similar) compounds encompassed within Formulas I, II, III, IV, V and VI are provided:

(Formula I)

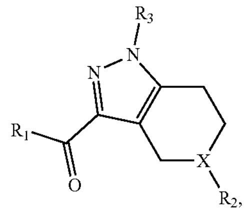

(Formula II)

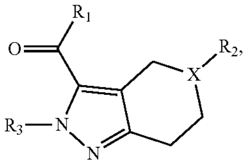

(Formula III)

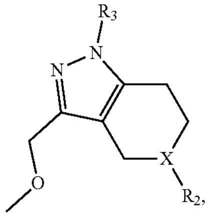

(Formula IV)

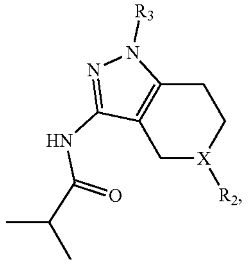

(Formula V)

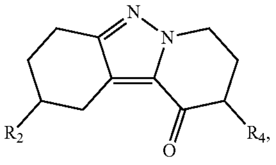

-continued (Formula VI)

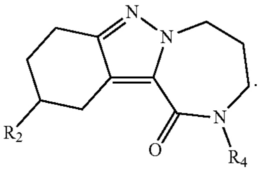

including pharmaceutically acceptable salts, solvates, and/or prodrugs thereof

Formulas I, II, III, IV, V and VI are not limited to a particular chemical moiety for X, R1, R2, R3, and R4. In some embodiments, the particular chemical moiety for X, R1, R2, R3, and R4 independently include any chemical moiety that permits the resulting compound to modulate (e.g., activate or inhibit) sigma-1 receptor activity, and/or modulate (e.g., activate or inhibit) sigma-2 receptor activity.

In some embodiments, X is either Carbon or Nitrogen.

In some embodiments, R1 is selected from

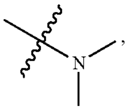,
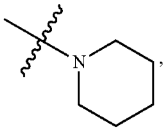,
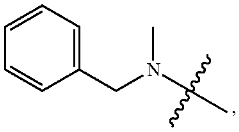
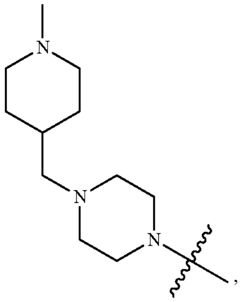,
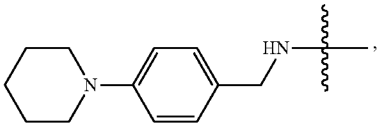,
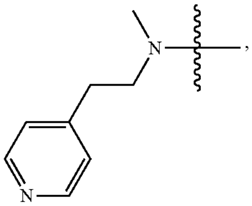,
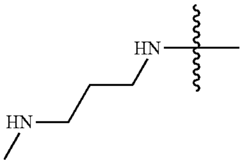,
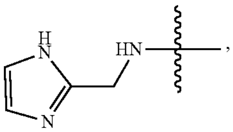,
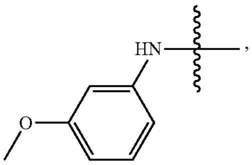,
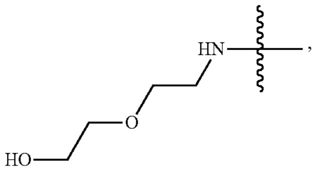,
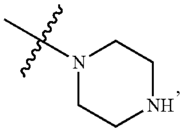

-continued

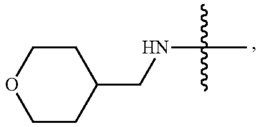,
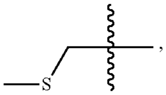,
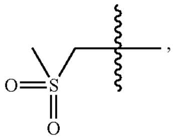, and
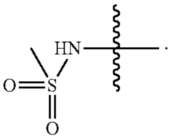.

In some embodiments, R2 is selected from Hydrogen,

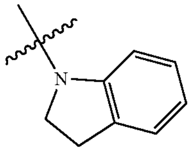,
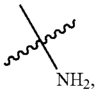,
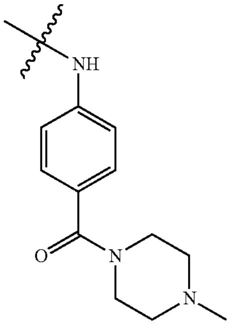,
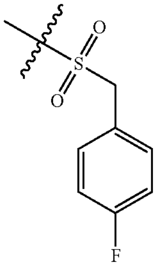,
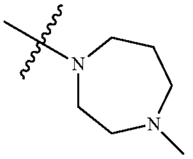,
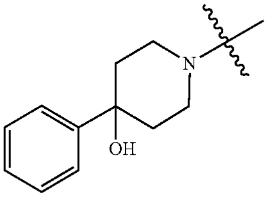,
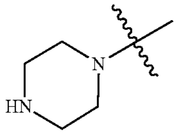,
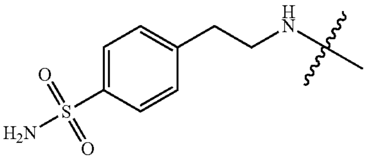,
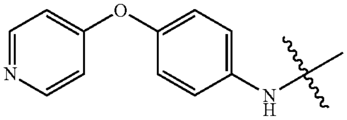,
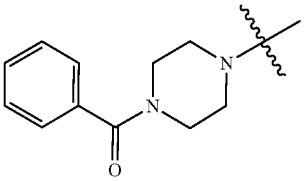, -continued
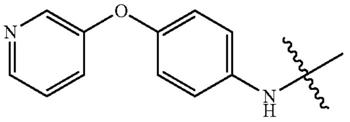
,
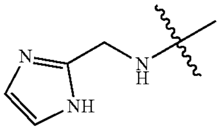
,
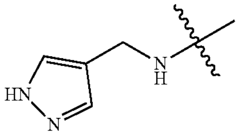
,
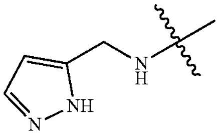
,
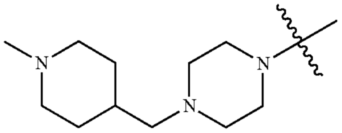
,
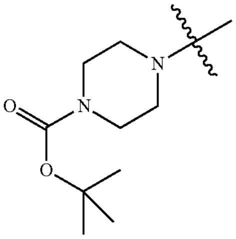
,
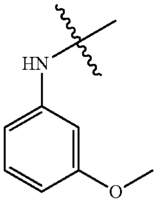
,
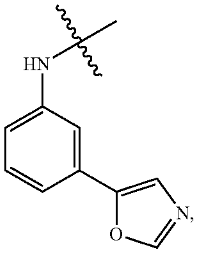
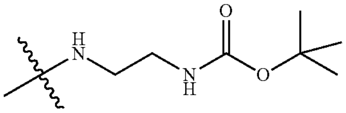
,
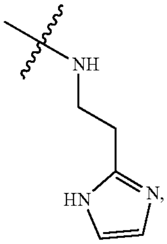
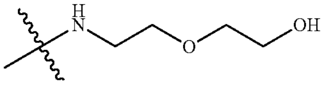
,
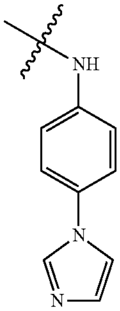
,
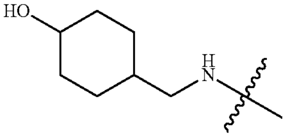
,
-continued
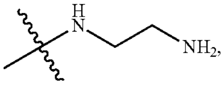
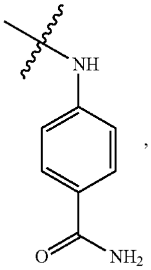
,
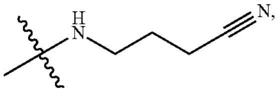
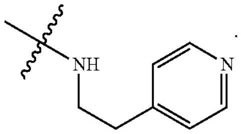
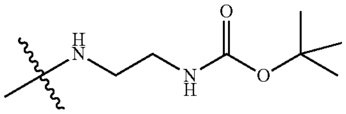
,
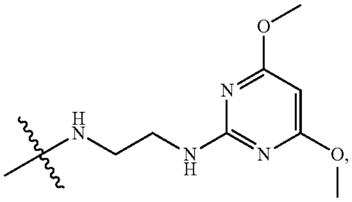
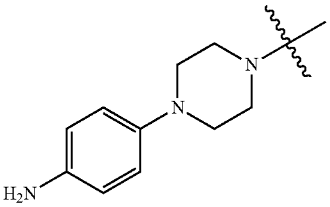
,
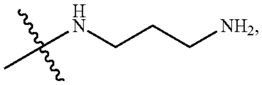
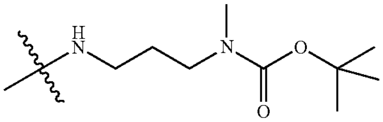
,
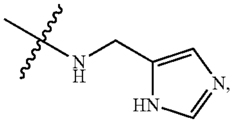
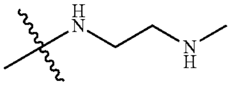
,
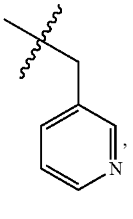
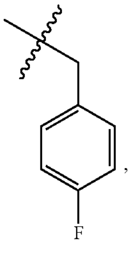
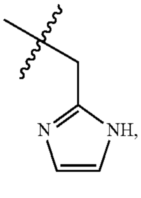
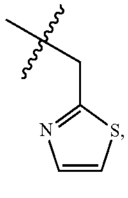

-continued
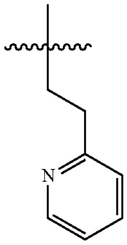 , 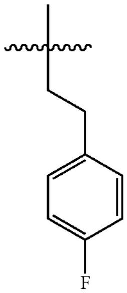 ,
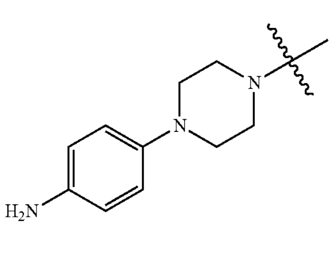 , 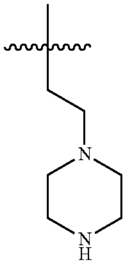 ,
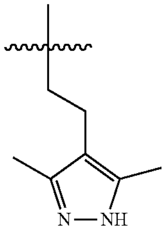 , 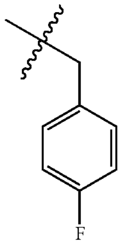 ,
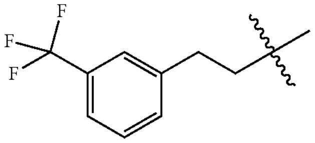 , 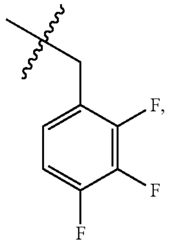
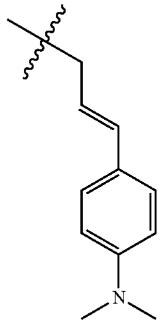 , 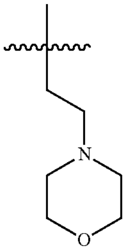 , 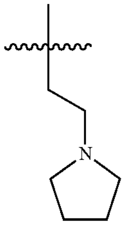 ,
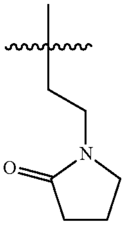 , 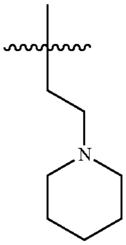 , 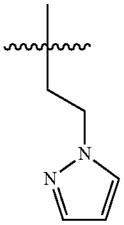 ,
-continued
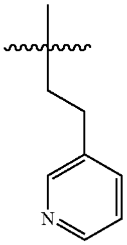 , 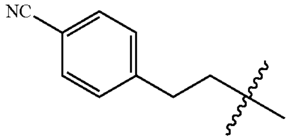 ,
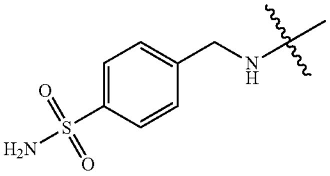 , 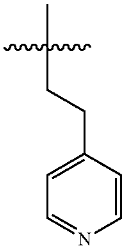 ,
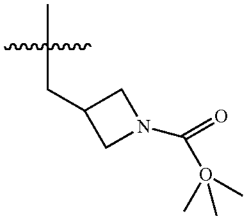 , 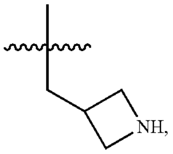
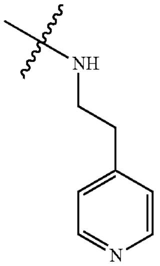 , 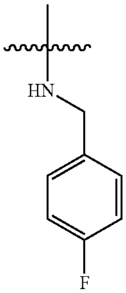 , 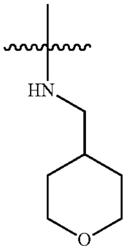 ,
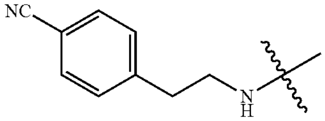 ,
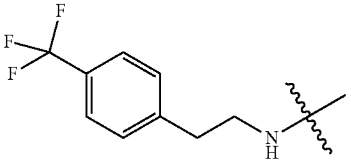 ,
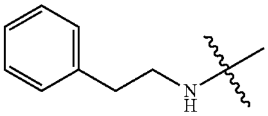 ,
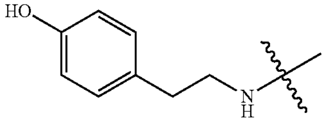 , 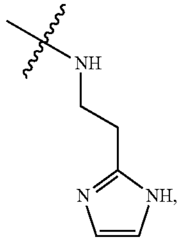

-continued
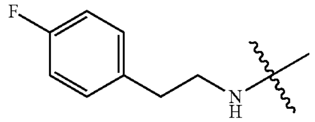,
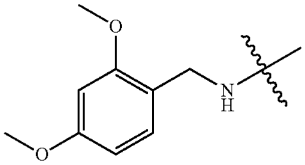, 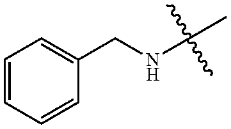,
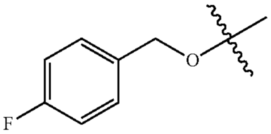, 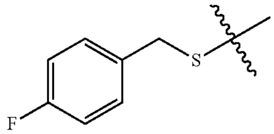,
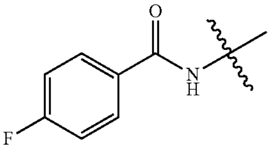, 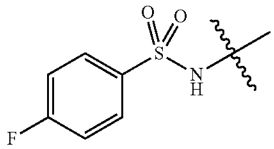,
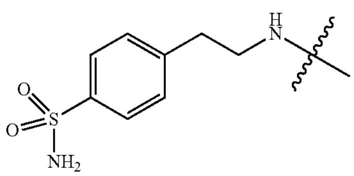,
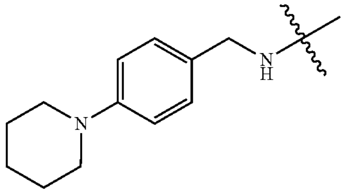,
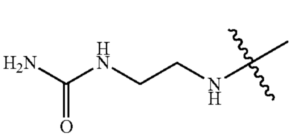, 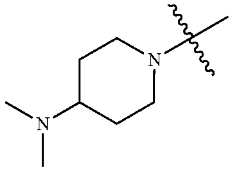,
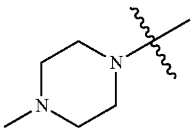, 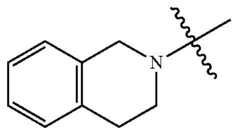,
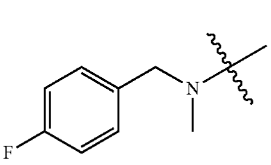, 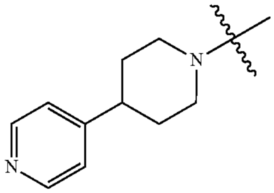,
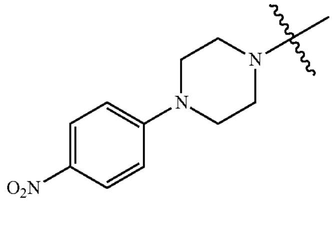,
-continued
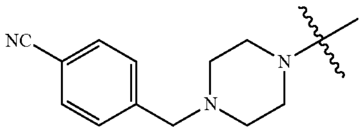,
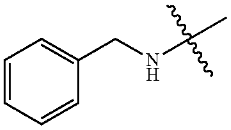, 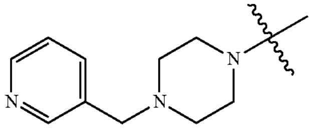,
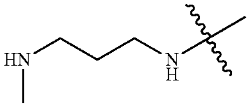, 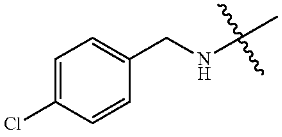,
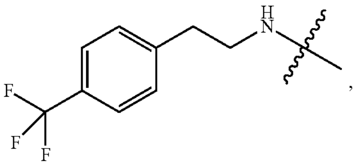,
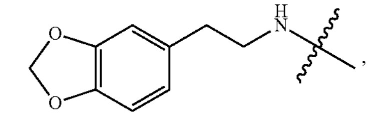,
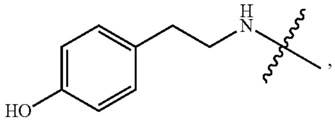,
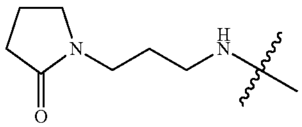, 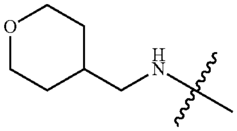,
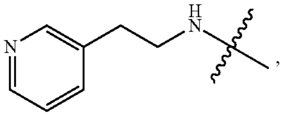,
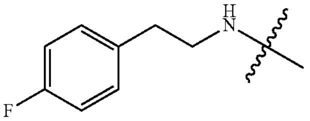,
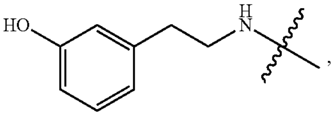, and
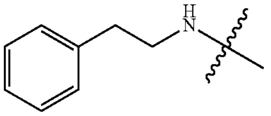.
In some embodiments, R3 is selected from
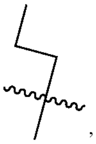, 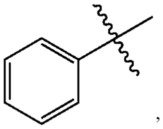, 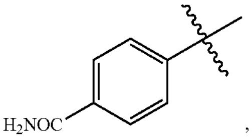, -continued

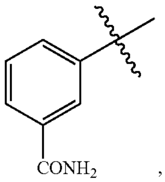,
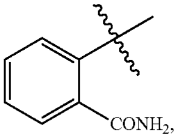,
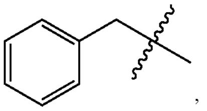,
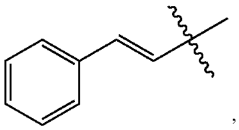,
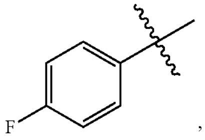, and
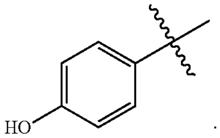.

In some embodiments, R4 is Hydrogen or methyl.

In some embodiments, compounds shown in Tables II, III and IV and FIG. 1 are contemplated for Formulas I, II, III, IV, V and VI.

Example I describes the binding affinities ($K_i$ values) for sigma-1 and sigma-2 various compounds encompassed within Formulas I, II, III, IV, V and VI (see, Tables II, III and IV and FIG. 1).

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The sigma-1 receptor and/or the sigma-2 receptor modulators (e.g., inhibitors or activators) of the present invention (e.g., tetrahydroindazole (or similar) compounds) can be used to induce apoptosis in any disorder that can be treated, ameliorated, or prevented by the induction of apoptosis. In one embodiment, the modulators (e.g., inhibitors or activators) can be used to induce apoptosis in cells comprising functional sigma-1 and/or sigma-2 receptors.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, central nervous system (CNS) related conditions characterized with sigma-1 and/or sigma-2 receptor activity, neurological conditions characterized with sigma-1 and/or sigma-2 receptor activity (e.g., Alzheimer's disease; amyotrophic lateral sclerosis (ALS); pain; mental health (e.g., psychiatric) conditions; substance abuse conditions), pancreatic cancer, breast cancer, prostate cancer, lymphoma, skin cancer, colon cancer, melanoma, malignant melanoma, ovarian cancer, brain cancer, primary brain carcinoma, head and neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having sigma-1 receptor activity and/or the sigma-2 receptor activity.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

In a particular embodiment, the additional therapeutic agent(s) is an agent useful in treating neurological conditions and/or CNS conditions (e.g., Alzheimer's disease; amyotrophic lateral sclerosis (ALS); pain; mental health (e.g., psychiatric) conditions; substance abuse conditions).

In a particular embodiment, the additional therapeutic agent(s) is an anticancer agent. A number of suitable anticancer agents are contemplated for use in the methods of the present invention. Indeed, the present invention contemplates, but is not limited to, administration of numerous anticancer agents such as: agents that induce apoptosis; polynucleotides (e.g., antisense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-$\alpha$) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethimide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N",N",-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |

TABLE 1-continued

| | | |
|---|---|---|
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |

TABLE 1-continued

| | | |
|---|---|---|
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7]indolizino[1,2-b] quinoline-3,14(4H,12H) dione hydrochloride trihydrate) | Camptosar | Pharmacia & Upjohn Company |

TABLE 1-continued

| | | |
|---|---|---|
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S{\bullet}HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asia Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |

TABLE 1-continued

| | | |
|---|---|---|
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}•H_2SO_4$) | Velban | Eli Lilly |
| Vincristine ($C_{46}H_{56}N_4O_{10}•H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

In certain embodiments, the present invention provides compositions comprising a bifunctional compound of chemical structure: ULM-L-PTM, wherein ULM is a small molecule ubiquitin ligase binding moiety selected from VHL, cereblon, MDM2, and IAP E3 ligase binding moiety binding moiety, wherein L is a bond or a chemical linker that is chemically linked to the ULM and the PTM; and wherein PTM is a small-molecule having a tetrahydroindazole (or similar) structure which functions as a modulator (e.g., inhibitor or activator) of sigma-1 and/or sigma-2 receptor activity. In some embodiments, the PTM is capable of modulating (e.g., inhibiting or activating) sigma-1 receptor activity and/or sigma-2 receptor activity.

In certain embodiments, the method of treating, ameliorating, or preventing a disease or condition characterized with sigma-1 receptor activity, sigma-2 receptor activity or both sigma-1 receptor activity and sigma-2 receptor activity, comprising administering to said patient a therapeutically effective amount of such a composition comprising a bifunctional compound of chemical structure: ULM-L-PTM. In some embodiments, the disease or condition is a neurological or CNS disease or condition. In some embodiments, the neurological or CNS disease or condition is one or more of Alzheimer's disease; amyotrophic lateral sclerosis (ALS); pain; mental health (e.g., psychiatric) conditions; and substance abuse conditions. In some embodiments, the disease or condition is a hyperproliferative disease or condition. In some embodiments, the hyperproliferative disease is any type of cancer characterized with sigma-1 and/or sigma-2 receptor activity. In some embodiments, the patient is a human patient. In some embodiments, such methods further comprises administering to said patient one or more anticancer agents, wherein said anticancer agent one or more of a chemotherapeutic agent, and radiation therapy.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes synthetic routes for compounds described herein.

Chemistry. The synthetic route to access the compounds 7a-7x is shown in Scheme 1. Commercially available 1,4-dioxaspiro[4.5]decan-8-one 1 was acylated with diethyloxalate in the presence of LDA at −78° C. to afford 2. Cyclization with propyl hydrazine afforded the pyrazole 3. Hydrolysis of the ester afforded the acid 4 which was coupled to respective amines to afford amides 5a and 5b. Removal of the ketal protecting group, followed by reductive amination gave the final compounds (Scheme 1).

Scheme 1. Synthesis of dimethyl amide analogs[a]

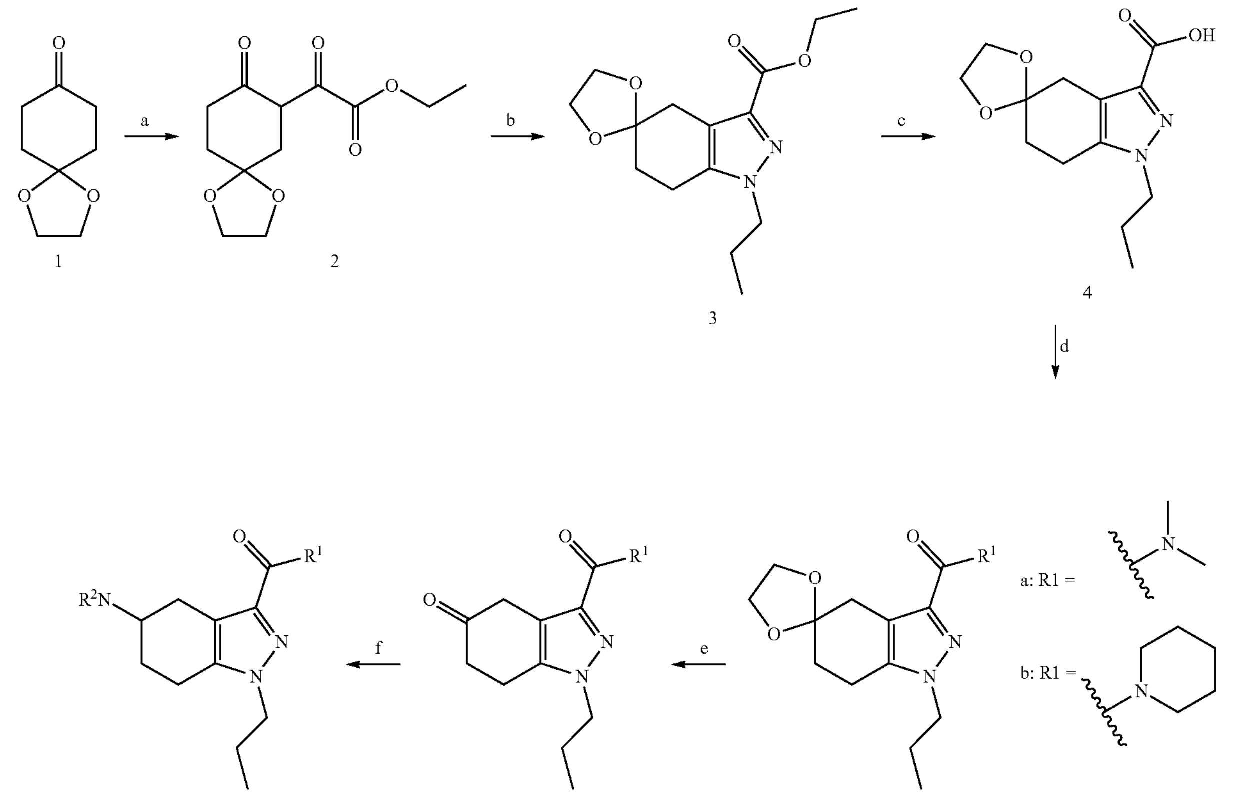

7a - 7x 6a - 6b 5a - 5b

[a]Reagents and conditions: a) diethyloxalate, LDA, THF, -78° C. to rt; b) propyl hydrazine, $K_2CO_3$, EtOH; c) NaOH, MeOH; d) $Me_2NH$, EDC, HOTt, TEA, DCM; e) 3N HCl, THF, 50° C.; f) $RNH_2$, AcOH, $NaBH(OAc)_3$, 1,2-DCE.

For indazoles with different C5-connections, sodium borohydride reduction of the ketone 6 afforded the alcohol which was alkylated to compound 9. Alternatively, the alcohol 8 was converted to a tosyl group 10 which was displaced with a thiol to afford the sulphide 11. The tosyl group was also displaced with an azide and subsequently reduced to the amine 12 which was coupled with and acid or sulfonyl chloride to afford 13 and 14 respectively (Scheme 2).

Scheme 2. Synthesis of indazole analogs with different C5 connections[a]

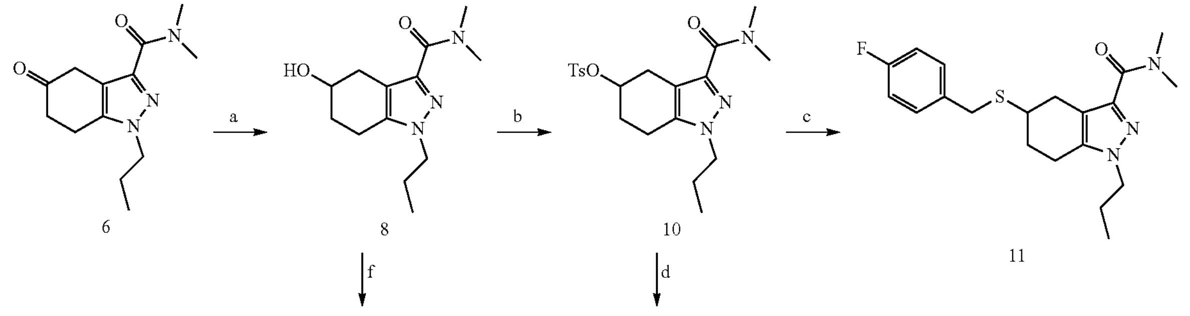

-continued

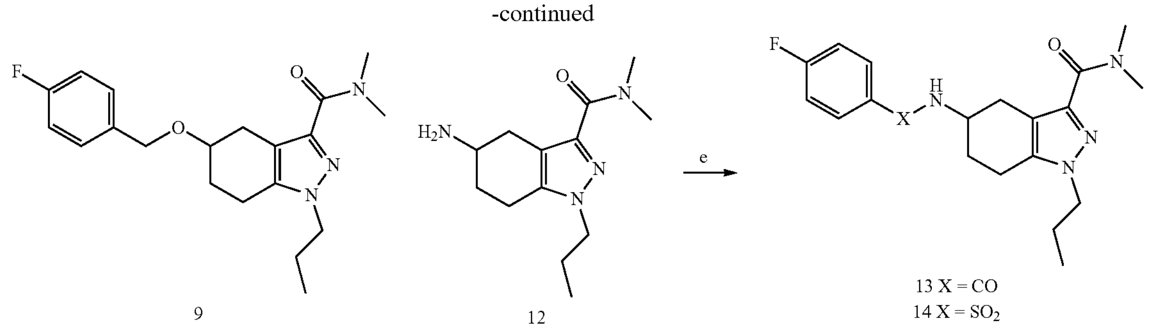

9 12 13 X = CO 14 X = $SO_2$

[a]Reagents and conditions: a) $NaBH_4$, MeOH; b) TsCl, DMAP, TEA, DCM; c) (4-fluorophenyl)methanethiol, NaOMe, EtOH; d) $NaN_3$, DMF, 70°C then Pd/C, EtOH; e) 4-fluorobenzoic acid, EDCl, DMAP, DCM OR 4-fluorobenzene-1-sulfonyl chloride, TEA, DCM; f) 1-(bromomethyl)-4-fluorobenzene, NaH, THF.

Synthesis of N-1 and N-2 aryl indazole regioisomers is shown in Scheme 3. Cyclization of 2 with hydrazine afforded the pyrazole 3a which was hydrolyzed to the acid 4a. Amidation with piperidine followed by Chan-Lam coupling afforded both stereoisomers 6a and 6b which were separable by prep LC. Removal of the ketal protecting group, followed by reductive amination gave the final compounds (Scheme 3).

Substituting an amide 13 (624) or a sulfonylamide 14 (629) did not restore the activity, thus highlighting the importance of a basic nitrogen for the activity of this class of compounds. Sticking with the amine at the C5 position of the indazole, the fluoro on the benzyl group was substituted with bulkier halogen Cl (875) and observed there was complete loss of activity against sigma-1 but moderate inhibition against sigma-2. Comparing 875 vs 874 and 878 vs 876, Scheme 3. Synthesis of *N*-1 and *N*-2 aryl indazole regioisomers[a]

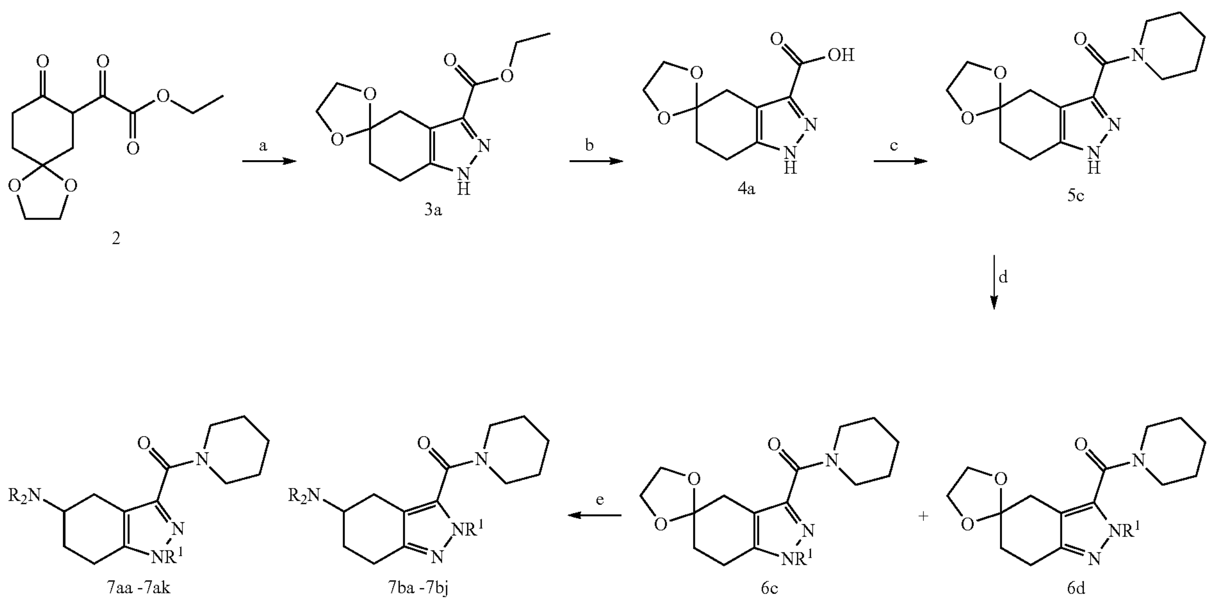

2 3a 4a 5c 7aa-7ak 7ba-7bj 6c 6d

[a]Reagents and conditions: a) $NH_2NH_2$, AcOH, EtOH, 100%; (b) NaOH, EtOH, 73%; (c) piperidine, EDCl, HOBt, TEA, DMF; (d) phenylboronic acid, $Cu(OAc)_2$, Py., TEA, DMF; (e) 3N HCl, THF, 50°C; then $R'NH_2$, AcOH, $NaBH(OAc)_3$, 1,2-DCE.

Structure-Activity Relationships. The initial ligand 7a (54121) inhibited sigma-1 and sigma-2 receptors with Ki of 1.5 and 2.1 μM respectively, showing slightly more selectivity for the sigma-1 receptor (Table 1). Initially, it was decided to focus on the connection between the indazole and the fluorobenzyl group. On substituting the nitrogen on the C5 position of the indazole with an oxygen and a sulfur 9 (622) and 11 (624) respectively, the activity of these indazoles against both sigma receptors was completely lost.

electron donating groups improved both activity and selectivity against sigma-2. Substituting the dimethyl amide for a piperidine amide and with an hydroxyl group on the benzyl group afforded 643, with about 8-fold more potent against sigma-2 and excellent selectivity. Replacing the benzyl group by a heteroaromatic ring 390 eliminated the activity against the sigma receptors. However, a piperidine ring on the benzyl group afforded the most potent and selective compounds in these series (Table II).

TABLE II
Dimethyl and piperidine amide
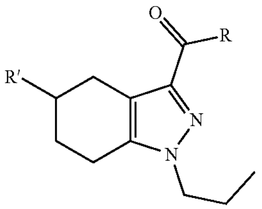
R = 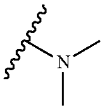
(A)
R = 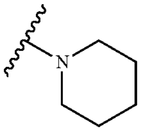
(B)
| ID | R | R' | $K_i$ (nM) Sigma-1 | Sigma-2 |
|---|---|---|---|---|
| 54121 | A | 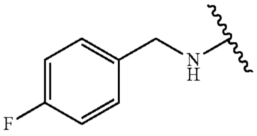 [SMILES: *NCc1ccc(F)cc1] | 1576 | 2193 |
| 200622 | A | 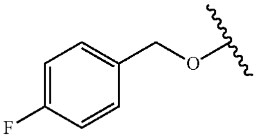 [SMILES: *OCc1ccc(F)cc1] | >10,000 | >10,000 |
| 200624 | A | 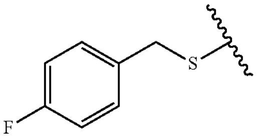 [SMILES: *SCc1ccc(F)cc1] | >10,000 | >10,000 |
| 2000623 | A | 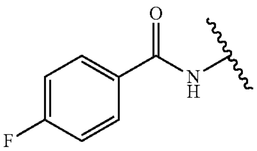 [SMILES: *NC(=O)c1ccc(F)cc1] | >10,000 | >10,000 |
| 200629 | A | 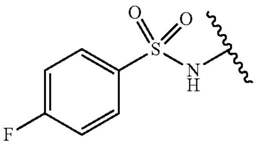 [SMILES: *NS(=O)(=O)c1ccc(F)cc1] | >10,000 | >10,000 |
| 200875 | A | 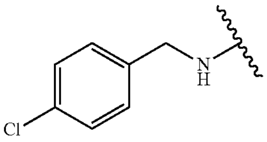 [SMILES: *NCc1ccc(Cl)cc1] | >10,000 | 1019 |
| 200878 | A | 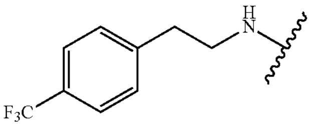 [SMILES: *NCCc1ccc(C(F)(F)F)cc1] | 1404 | 595 |
| 200874 | A | 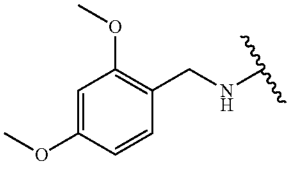 [SMILES: *NCc1ccc(OC)cc1OC] | >10,000 | 839 |

TABLE II-continued

Dimethyl and piperidine amide

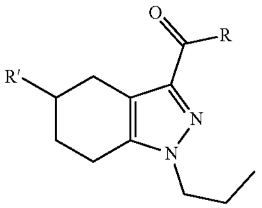

R = 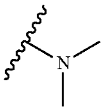

(A)

R = 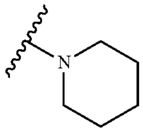

(B)

| | | | $K_i$ (nM) | |
|---|---|---|---|---|
| ID | R | R' | Sigma-1 | Sigma-2 |
| 200876 | A | 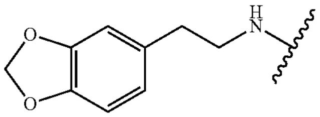 [SMILES: *NCCc1ccc2c(c1)OCO2] | >10,000 | 430 |
| 200643 | B | 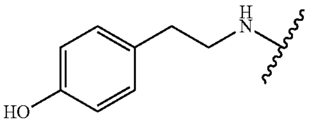 [SMILES: *NCCc1ccc(O)cc1] | >10,000 | 273 |
| 200646 | B | 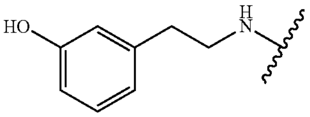 [SMILES: *NCCc1cccc(O)c1] | 872 | 612 |
| 200390 | B | 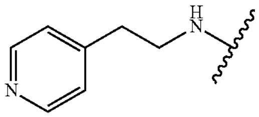 [SMILES: *NCCc1ccncc1] | >10,000 | >10,000 |
| 200652 | B | 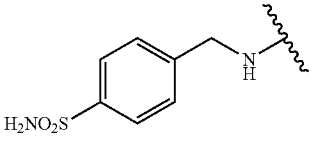 [SMILES: *NCc1ccc(S(N)(=O)=O)cc1] | >10,000 | 439 |
| 200647 | B | 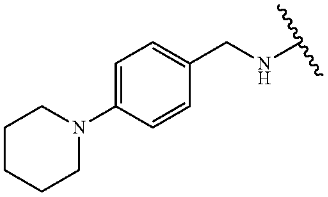 [SMILES: *NCc1ccc(N2CCCCC2)cc1] | >10,000 | 169 |
| 200637 | B | 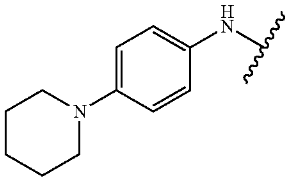 [SMILES: *Nc1ccc(N2CCCCC2)cc1] | >10,000 | 787 |
| 200702 | B | 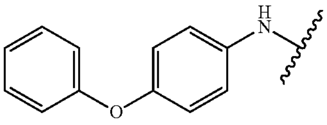 [SMILES: *Nc1ccc(Oc2ccccc2)cc1] | >10,000 | 310 |

Experiments were conducted to explore the effect of aliphatic acyclic and cyclic groups instead of the phenyl group. Substitution of a basic guanidine group 829 decreased activity against sigma-2 displaying similar inhibition to compound 7. Other aliphatic groups explored showed moderate activity and most notable, replacement with a dibasic N-methyl piperazine group 196337 showed great overall potency against sigma-2 but only about 5-fold selectivity over sigma-1. Compound 196338 with isoquinoline retained sigma-2 activity with excellent selectivity. Encouraged by the activity and selectivity of 196338, we explored other tertiary amines on the indazole C5 position, providing 196339 and 639 with Ki of 19 and 16 nM respectively against sigma-2 and excellent selectivity against sigma-1 representing our most potent and selective compound against sigma-2 receptor (Table III).

TABLE III

Piperidine amides

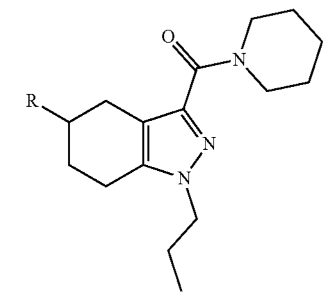

| ID | R | $K_i$ (nM) Sigma-1 | $K_i$ (nM) Sigma-2 |
|---|---|---|---|
| 200829 | 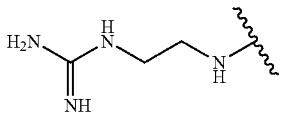 [SMILES: *NCCNC(=N)N] | >10,000 | 2156 |
| 200820 | 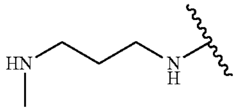 [SMILES: *NCCCNC] | >10,000 | 1987 |
| 54120 | 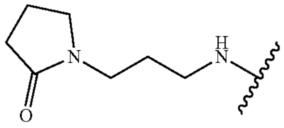 [SMILES: *NCCCN1CCCC1=O] | >10,000 | 673 |
| 200640 | 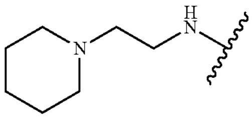 [SMILES: *NCCN1CCCCC1] | >10,000 | 434 |
| 200642 | 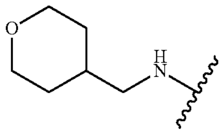 [SMILES: *NCC1CCOCC1] | >10,000 | 710 |
| 196331 | 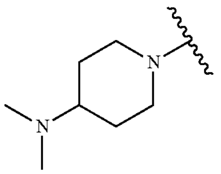 [SMILES: *N1CCC(N(C)C)CC1] | >10,000 | >10,000 |

TABLE III-continued

Piperidine amides

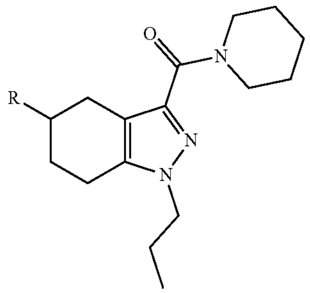

| ID | R | $K_i$ (nM) Sigma-1 | $K_i$ (nM) Sigma-2 |
|---|---|---|---|
| 196337 | 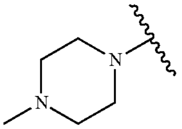 [SMILES: *N1CCN(C)CC1] | 192 | 34 |
| 196338 | 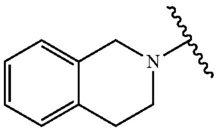 [SMILES: *N1CCc2ccccc2C1] | >10,000 | 31 |
| 196339 | 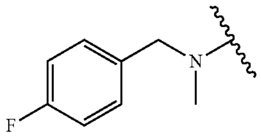 [SMILES: *N(C)Cc1ccc(F)cc1] | >10,000 | 19 |
| 200639 | 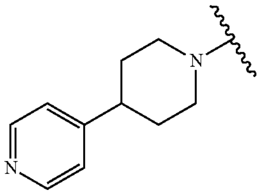 [SMILES: *N1CCC(c2ccncc2)CC1] | >10,000 | 16 |
| 200709 | 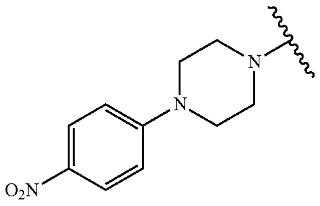 [SMILES: *N1CCN(c2ccc([N+](=O)[O-])cc2)CC1] | 1591 | 526 |
| 200641 | 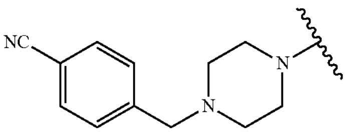 [SMILES: *N1CCN(Cc2ccc(C#N)cc2)CC1] | >10,000 | 1099 |

Encouraged by the active and selective sigma-2 inhibitors, experiments were conducted to optimize for potent and selective sigma-1 inhibitors by evaluating the essence of different substituents on the N-1 of the indazole as well as their regioisomers. Retaining the piperidine amide and with a basic tertiary amine on the C5 of the indazole but replaced the n-propyl with a phenyl group 1674 showed over 10-fold improved activity against sigma-1 receptor and about 5-fold selectivity over sigma-2 receptor. An aliphatic group on the C5 position of the indazole 1677 completely lost activity against both sigma receptors while the benzyl group 1665 had a Ki of 710 nM. The fluorobenzyl group 1685 showed over 4-fold improvement in potency over the benzyl group. Substitution of the fluoro group for other electron donating group did not yield any improved potency. Increasing the linker length between the amine on C5 position of the indazole and aromatic group with a methylene unit 1667 afforded equipotent inhibitor against both sigma receptors. Replacement of the phenyl group on the N-1 of the indazole with a phenyl group in compound 1115 afforded a compound with 70 nM Ki against sigma-1 inhibitor with excellent selectivity. Though the N-2 regioisomer was equally potent, however it was less selective until N-2 substitution with a p-fluoro phenyl group 1117 with 17 nM inhibitory constant (Table IV).

TABLE IV

N-1 and N-2 aryl tetrahydroindazole regioisomers

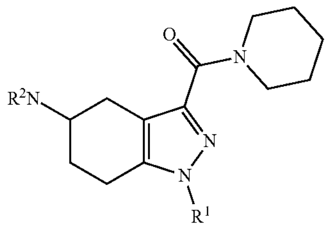

| ID | $R^1$ | $R^2$ | Sigma-1 Ki (nM) | Sigma-2 Ki (nM) |
|---|---|---|---|---|
| 2001685 | Ph | 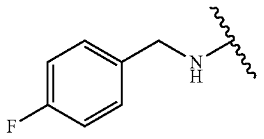 | 159 | >10,000 |
| 201665 | Ph | 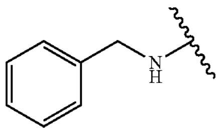 [SMILES: *NCc1ccccc1] | 710 | 492 |
| 201684 | Ph | 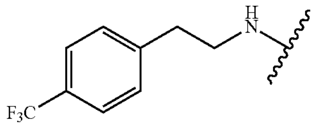 [SMILES: *NCCc1ccc(C(F)(F)F)cc1] | 337 | >10,000 |
| 201666 | Ph | 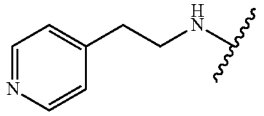 [SMILES: *NCCc1ccncc1] | 1032 | 517 |
| 201679 | Ph | 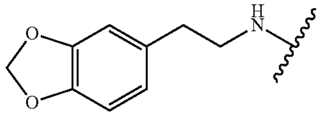 [SMILES: *NCCc1ccc2c(c1)OCO2] | 547 | 349 |
| 201667 | Ph | 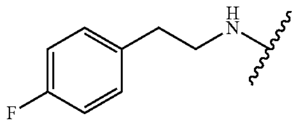 [SMILES: *NCCc1ccc(F)cc1] | 131 | 91 |
| 201681 | Ph | 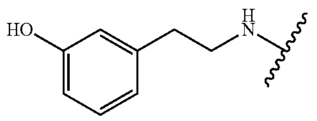 | 204 | >10,000 |

TABLE IV-continued
N-1 and N-2 aryl tetrahydroindazole regioisomers
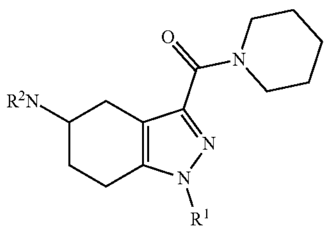
| ID | $R^1$ | $R^2$ | Sigma-1 Ki (nM) | Sigma-2 Ki (nM) |
|---|---|---|---|---|
| 201243 | $PhCONH_2$ | 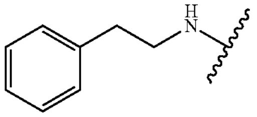 [SMILES: *NCCc1ccccc1] | 465 | 561 |
| 201244 | $Ph(CH_2{=}CH_2)$ | 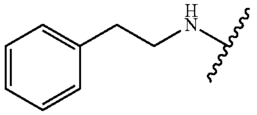 [SMILES: *NCCc1ccccc1] | 458 | 305 |
| 201114 | Bn | 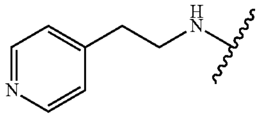 | 249 | >10,000 |
| 201115 | Bn | 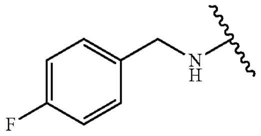 | 70 | >10,000 |
| 201678 | Ph | 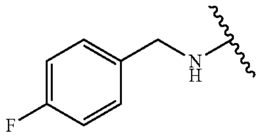 | 30 | 164 |
| 201676 | Ph | 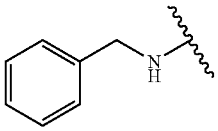 [SMILES: *NCc1ccccc1] | 38 | 139 |
| 201683 | Ph | 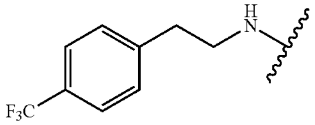 | 213 | >10,000 |
| 201670 | Ph | 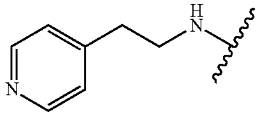 [SMILES: *NCCc1ccncc1] | 226 | 296 |
| 201671 | Ph | 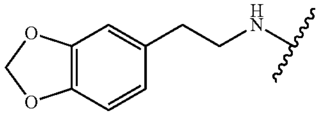 [SMILES: *NCCc1ccc2c(c1)OCO2] | 66 | 29 |

TABLE IV-continued

N-1 and N-2 aryl tetrahydroindazole regioisomers

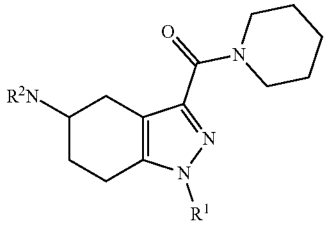

| ID | $R^1$ | $R^2$ | Sigma-1 Ki (nM) | Sigma-2 Ki (nM) |
|---|---|---|---|---|
| 201116 | p-F(Ph) | 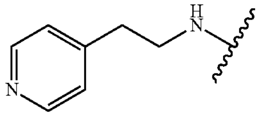 [SMILES: *NCCc1ccncc1] | 103 | 251 |
| 201117 | P-F(Ph) | 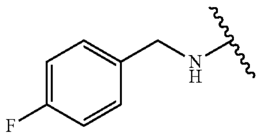 | 17 | >10,000 |
| 201242 | $PhCONH_2$ | 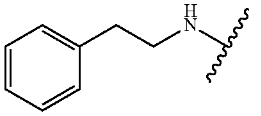 [SMILES: *NCCc1ccccc1] | 588 | >10,000 |
| 201591 | $Ph(CH_2{=}CH_2)$ | 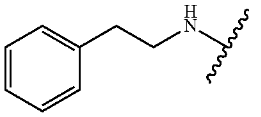 [SMILES: *NCCc1ccccc1] | 96 | 32 |
| 201592 | PhOH | 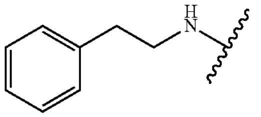 [SMILES: *NCCc1ccccc1] | 322 | 281 |

FIG. 1 shows additional representative tetrahydroindazole (or similar) compounds of the present invention and, where applicable, analytical data, sigma-1 receptor binding activity, and sigma-2 receptor binding activity (wheren Ki Legend: +++=<1 uM; ++=between 1-10 uM; Blank=>10 uM).

Synthesis of tricyclic analogs was accomplished according to the general procedure shown in Scheme 4.

Scheme 4. Synthesis N-2 tricyclic derivatives[a]
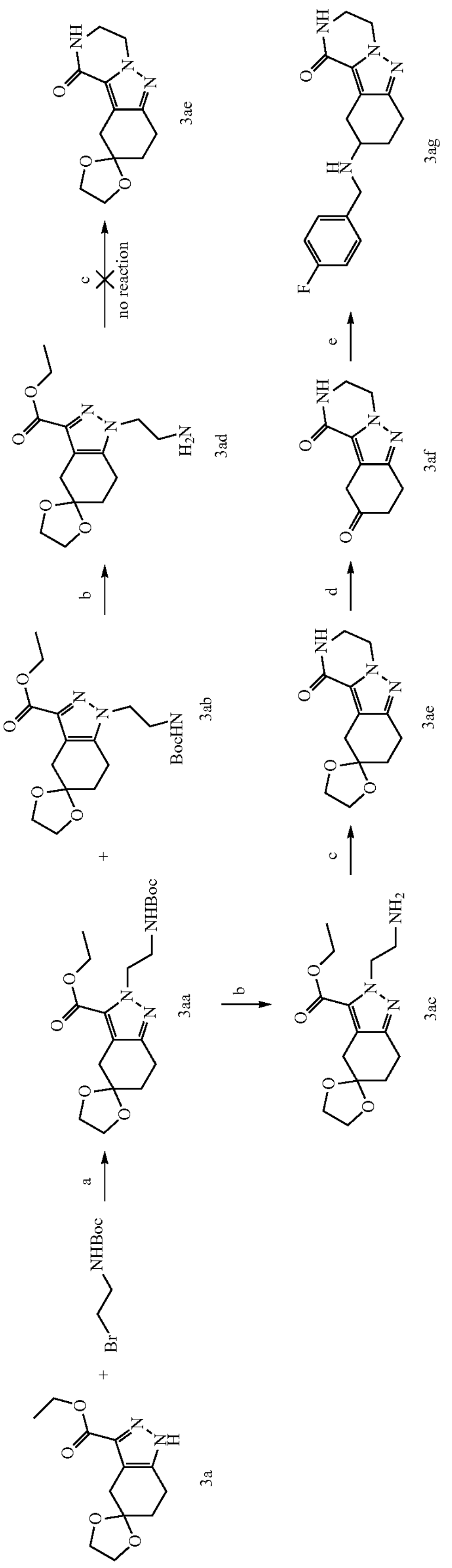
[a]Reagents and conditions: (a) Cs2CO3, DMF; (b) TFA, DCM,; (c) Na2CO3, dioxane/water; (d) HCl, THF; (e) NaBH(OAc)3, DCE, AcOH.

In order to synthesize the tricyclic analogs, experiments were conducted that envisaged alkylation of N-2 position in ethyl 1,4,6,7-tetrahydrospiro[indazole-5,2'-[1,3]dioxolane]-3-carboxylate 3a with 2-bromoethan-1-amine followed by hydrolysis of the ester group and subsequently, amidation of the amino and carboxylic acid functionalities on the pyrazole.

The pyrazole 3a was synthesized as previously described in scheme 3. N-alkylation of ethyl 1,4,6,7-tetrahydrospiro[indazole-5,2'-[1,3]dioxolane]-3-carboxylate 3a with tert-butyl (2-bromoethyl)carbamate using caesium carbonate as the base in DMF afforded stereoisomers with alkylation at both N-1 and N-2 positions of the pyrazole to afford 3aa and 3ab in quantitative yield in a ratio of 4:1 with 3aa as the major product. Interestingly, both stereoisomers were separable by flash chromatography with 3aa the more polar stereoisomer. The boc protecting group of both stereoisomers were removed by TFA to afford the free amines 3ac and 3ad from 3aa and 3ab respectively. Expectedly, treatment of 3ac with a base (sodium carbonate or DBU) in a mixture of dioxane and water afforded the tricyclic compound 3,4,7,8-tetrahydro-2H-spiro[pyrazino[1,2-b]indazole-9,2'-[1,3]dioxolan]-1(10H)-one 3ae in a single step with excellent yield confirming alkylation at the N-2 position of the pyrazole 3a. Subjecting the other stereoisomer 3ad to the same basic treatment gave no reaction further confirming the alkylation at the N-1 position, hence the inability of the amine to access the electrophilic carbon on the ester functionality of the C-3 position on the pyrazole due to the distance between both amine and ester groups. Removal of the ketal protecting group on 3ae with 3N HCl in THF afforded the ketone. Reductive amination of 3af with (4-fluorophenyl)methanamine afforded the tricyclic analog 3ag.

All other tricyclic analogs were synthesized via the same scheme.

Discussion From the identification of tetrahydroindazoles 54121 with moderate activity against sigma-1 and sigma-2 receptors, a SAR study was directed towards this new sigma receptor inhibitor to improve potency and tune for selectivity for both sigma receptors from this chemotype. The synthesized compounds successfully improved potency and selectivity towards sigma-2 receptor by substituting a dibasic amine on the C5 position of the indazole 196337-639 with 639 the most potent and selective (Ki-16 nM for sigma-2 and >10 μM for sigma-1) inhibitor for this chemotype after identifying the essential role of the basic amine for potency. The molecular docking studies buttress this finding from the binding energies of these compounds. To identify potent and selective sigma-2 inhibitor from this chemotype, experiments were conducted that substituted different aryl groups on the N-1 and N-2 of the tetrahydroindazole and identified 1117 with Ki of 17 nM against sigma-1 and over 500× selectivity against sigma-2 from the same chemotype. Interestingly we also discovered 1671 which is a pan-inhibitor of both sigma-1 and sigma-2 receptors. Such experiments resulted in identification of selective inhibitors for either sigma-1 and sigma-2 receptors as well as pan inhibitor of both receptors from a single chemotype. This class of compounds have good to excellent kinetic solubility and poor to very good thermodynamic solubility.

Chemistry. Unless otherwise noted, all materials for the synthetic chemistry portion were obtained from commercial suppliers (Combi-Blocks, CombiPhos, Fisher Scientific, Sigma-Aldrich, or VWR) and used without further purification. The $^{1}H$ and $^{13}C$ NMR spectra were recorded on a Bruker AVANCE 500 MHz spectrometer using $CDCl_3$ or $CD_3OD$ as the solvent. Chemical shifts are expressed in ppm (δ scale). When peak multiplicities are reported, the following abbreviations are used: s (singlet), d (doublet), t (triplet), q (quartet), m (multiplet), or br s (broad singlet). Thin layer chromatography (TLC) was performed on glass backed Merck silica gel 60 $F_{254}$ plates, column chromatography was performed using KP-SIL silica gel (Biotage, USA), and flash column chromatography was performed on Biotage pre-packed columns using the automated flash chromatography system Biotage Isolera One. The purities of all the final compounds were of >95% as determined by UPLC analysis unless otherwise indicated.

General Procedure A: Synthesis of Amides

To a solution carboxylic acid (1.0 equiv) in DCM (0.1M) was added EDC (1.1 equiv) and HOBT (1.0 equiv). The reaction mixture was stirred at RT for 30 min and then amine (1.0 equiv) and TEA (1.1 equiv) were added. The mixture was then stirred at RT for 12 h, diluted with DCM and washed with $H_2O$ and brine. The organic extract was dried over with anhydrous $Na_2SO_4$, filtered and concentrated in vacuo to give a residue which was purified by a short silica gel plug (10% MeOH in DCM) to give the amide.

General Procedure B: Removal of Ketal Protecting Group

Ketals (1.0 equiv) were dissolved in THF (0.8M) then 3N HCl (5.0 equiv) was added to the mixture. The resulting solution was heated at 50° C. for 2 h. The solvents were evaporated and EtOAc was added. The organic layer was washed with saturated $NaHCO_3$ and $H_2O$. The combined organic layer was dried over anhydrous $Na_2SO_4$ and evaporated in vacuo to give the crude product which was purified by a short silica gel plug using 0-10% MeOH in DCM to give the product.

General Procedure C: Reductive Amination

A solution of the ketone (1 eqiv) and acetic acid (1.5 eqiv) in DCE (1.5 mL) was stirred at room temperature. The amine (2 eqiv) was added, followed by $NaBH(OAc)_3$. The mixture was stirred at room temperature overnight, quenched with saturate $NaHCO_3$ aqueous solution (3 mL), and extracted with DCM (3 mL×3). The organic layers were combined, dried over $Na_2SO_4$, concentrated and further purified by and further purified by preparative HPLC, with $AcCN/H_2O$ (0.1% FA as additive), to provide the desired product as FA salt or free amine.

Ethyl 2-(8-hydroxy-1,4-dioxaspiro[4.5]dec-7-en-7-yl)-2-oxoacetate (2): To a solution of 1,4-dioxaspiro[4.5]decan-8-one 1 (7.81 g, 50 mmol) in anhydrous THF (75 mL) cooled to −78° C. under a $N_2$ atmosphere was added LDA (27.5 mL, 55 mmol). After stirring for 15 minutes, diethyl oxalate (7.47 mL, 55 mmol) was added in portions over 10 min. The reaction was gradually warmed to RT and stirred for 16 h. The reaction mixture was quenched with 1N HCl and the resulting mixture was extracted with EtOAc, washed with brine and dried over anhydrous $Na_2SO_4$, filtered and concentrated in vacuo. The residue was purified by silica gel flash chromatography (0-100% EtOAc in Hexanes) to yield the Ethyl 2-(8-hydroxy-1,4-dioxaspiro[4.5]dec-7-en-7-yl)-2-oxoacetate 2 (4.2 g, 33%) as a thick yellow oil. MS (ESI): mass calcd. for $C_{12}H_{16}O_6$, 256.09. m/z found, 257.16 [M+H]+; $^{1}H$ NMR (500 MHz, $CDCl_3$) δ 1.37 (t, J=7.17 Hz, 3H), 1.91 (t, J=6.87 Hz, 2H), 2.68 (t, J=6.87 Hz, 2H), 2.74 (s, 2H), 3.97-4.02 (m, 4H), 4.33 (q, J=7.22 Hz, 2H), 15.35 (s, 1H)

Ethyl 1'-propyl-1',4',6',7'-tetrahydrospiro[[1,3]dioxolane-2,5'-indazole]-3'-carboxylate (3): Propylhydrazine·2HCl (2 g, 13.6 mmol) was added to a solution of ethyl 2-oxo-2-(8-oxo-1,4-dioxaspiro[4.5]decan-7-yl)acetate 2 (3.49 g, 13.6 mmol) and $K_2CO_3$ (3.76 g, 27.2 mmol) in EtOH (84 ml). The reaction mixture was stirred at RT for 4 h and then concentrated in vacuo. The residue was re-dissolved in EtOAc and $H_2O$ and the layers separated. The aqueous layer was extracted with EtOAc and the combined organic layer was washed with brine, dried over anhydrous $Na_2SO_4$, filtered and concentrated in vacuo. The residue obtained was purified by silica gel chromatography (0-60% EtOAc in Hexanes) to give ethyl r-propyl-1',4',6',7'-tetrahydrospiro[[1, 3]dioxolane-2,5'-indazole]-3'-carboxylate 3 (3.3 g, 82%) as a thick oil. MS (ESI): mass calcd. for $C_{15}H_{22}N_2O_4$, 294.16. m/z found, 295.41 [M+H]+. $^1$H NMR (500 MHz, $CDCl_3$) δ 0.92 (t, J=7.48 Hz, 3H), 1.34-1.40 (m, 3H), 1.86 (m, 2H), 1.98 (t, J=6.56 Hz, 2H), 2.78 (t, J=6.56 Hz, 2H), 2.98 (s, 2H), 3.97-4.08 (m, 6H), 4.37 (q, J=7.22 Hz, 2H).

Ethyl 1,4,6,7-tetrahydrospiro[indazole-5,2'-[1,3]dioxolane]-3-carboxylate (3a). A solution of 2 (7.03 g, 27.4 mmol), hydrazine monohydare (2.7 mL, 64%, 34.9 mmol), and acetic acid (16 mL, 279 mmol) in ethanol (80) was heated to 65° C. for 90 min. After cooling down to room temperature, solvent was evaporated, residues dissolved in water (200 mL), neutralized with NaHCO3, and extracted with ethyl acetate (150 mL×4). The organic layers were combined, dried over $Na_2SO_4$, concentrated in vacuo to provide the product as light yellow oil (6.92 g, 100%), which was used in the next step without further purification.

1'-Propyl-1',4',6',7'-tetrahydrospiro[[1,3]dioxolane-2,5'-indazole]-3'-carboxylic acid (4): To a mixture of ethyl 1'-propyl-1',4',6',7'-tetrahydrospiro[[1,3]dioxolane-2,5'-indazole]-3'-carboxylate 3 (3.3 g, 11.21 mmol) in EtOH (50 ml) was added a 2M solution of NaOH (50 mL) and the reaction mixture stirred at RT for 4 h. The EtOH was evaporated and the aqueous mixture was washed with diethyl ether. The pH of the aqueous layer was adjusted to 5-6. The aqueous layer was then extracted with EtOAc (×3). The combined organic extract was dried using anhydrous Na2SO4, filtered and concentrated under educed pressure to yield r-propyl-1',4',6',7'-tetrahydrospiro[[1,3]dioxolane-2,5'-indazole]-3'-carboxylic acid 4 (2.5 g, 84%) as an off-white solid. MS (ESI): mass calcd. for $C_{13}H_{18}N_2O_4$, 266.13. m/z found, 267.37 [M+H]+. $^1$H NMR (500 MHz, $CD_3OD$) δ (t, J=7.32 Hz, 3H), 1.79-1.90 (m, 2H), 1.94-2.00 (m, 2H), 2.81 (t, J=6.56 Hz, 2H), 2.90 (s, 2H), 3.99-4.06 (m, 6H).

1,4,6,7-Tetrahydrospiro[indazole-5,2'-[1,3]dioxolane]-3-carboxylic acid (4a). A solution of 3a (6.92 g, 27.4 mmol) in ethanol (80 mL) was stirred at room temperature. NaOH (10%, 80 mL) aqueous solution was added, and the mixture was stirred at room temperature overnight. Ethanol was carefully evaporated, the resulting aqueous solution was acidified with concentrated HCl to pH~4. The white solid was collected by filtration, dried in vacuo to afford the product 5 (4.48 g, 73%).

Piperidin-1-yl(1,4,6,7-tetrahydrospiro[indazole-5,2'-[1,3]dioxolan]-3-yl)methanone (5c). A solution of 4a (3.4 g, 15.2 mmol), EDCI (3.3 g, 17.2 mmol), HOBt (2.3 g, 15.0 mmol) in dry DMF (25 mL) was stirred at room temperature for 30 min, then a solution of piperidine (3 mL, 30.4 mmol) and trimethylamine (4 mL, 28.7 mmol) in DMF (25 mL) was added. The mixture was stirred at room temperature overnight. The mixture was poured into water (150 mL) and extracted with ethyl acetate (150 mL×6). The organic layers were combined, washed with water (150 mL) and brine (150 mL) sequentially, dried over $Na_2SO_4$, concentrated and further purified by flash silica gel column, with EA/hex, (gradient up to 99:1), to provide the product as pale yellow solid (2.1 g, 48%).

N,N-dimethyl-1'-propyl-1',4',6',7'-tetrahydrospiro[[1,3]dioxolane-2,5'-indazole]-3'-carboxamide (5a): Prepared according to General procedure A using carboxylic acid 4 (0.3 g, 1.13 mmol) to afford N,N-dimethyl-r-propyl-1',4',6',7'-tetrahydrospiro[[1,3]dioxolane-2,5'-indazole]-3'-carboxamide 5 (145 mg, 44%) as a pale yellow solid. MS (ESI): mass calcd. for $C_{15}H_{23}N_3O_3$, 293.17. m/z found, 294.30 [M+H]+; $^1$H NMR (500 MHz, $CDCl_3$) δ 0.93 (t, J=7.32 Hz, 3H), 1.83 (sxt, J=7.32 Hz, 2H), 1.99 (t, J=6.56 Hz, 2H), 2.77 (t, J=6.56 Hz, 2H), 2.93 (s, 2H), 3.05 (br. s., 3H), 3.32 (br. s., 3H), 3.92 (t, J=7.32 Hz, 2H), 3.97-4.07 (m, 4H).

N,N-dimethyl-5-oxo-1-propyl-4,5,6,7-tetrahydro-1H-indazole-3-carboxamide (6a): Prepared according to General procedure B using 5a (320 mg, 1.1 mmol) to afford N,N-dimethyl-5-oxo-1-propyl-4,5,6,7-tetrahydro-1H-indazole-3-carboxamide 6a (230 mg, 85%) as yellow waxy solid. MS (ESI): mass calcd. for $C_{13}H_{19}N_3O_2$, 249.15. m/z found, 250.24 [M+H]+.

5-((4-Fluorobenzyl)amino)-N,N-dimethyl-1-propyl-4,5,6,7-tetrahydro-1H-indazole-3-carboxamide (7a, NUCC-0054121): Prepared according to General procedure C using 6 (150 mg, 0.6 mmol) to afford 7a (60 mg, 28%) as light pink solid (FA salt). MS (ESI): mass calcd. for $C_{20}H_{27}FN_4O$, 358.22. m/z found, 359.40 [M+H]+; $^1$H NMR (500 MHz, $CD_3OD$) δ 0.88-0.93 (m, 3H), 1.80-1.87 (m, 3H), 1.95 (s, 3H), 2.22-2.33 (m, 1H), 2.52 (dd, J=15.56, 9.46 Hz, 1H), 2.64-2.74 (m, 1H), 2.82-2.92 (m, 1H), 3.08 (s, 3H), 3.10-3.24 (m, 2H), 3.26 (s, 3H), 4.00 (t, J=7.02 Hz, 2H), 4.05 (s, 2H), 7.08-7.17 (m, 2H), 7.42-7.51 (m, 2H); $^{13}$CNMR (126 MHz, $CD_3OD$) δ 11.48, 20.67, 22.97, 24.50, 27.10, 27.95, 36.10, 39.60, 50.26, 51.86, 55.09, 116.12, 116.71, 116.88, 132.55, 132.61, 139.94, 143.29, 163.37, 167.02.

5-((4-chlorobenzyl)amino)-N,N-dimethyl-1-propyl-4,5,6,7-tetrahydro-1H-indazole-3-carboxamide 0200875 (7b): Prepared according to General procedure C using 6 (30 mg, 0.120 mmol) to afford 7b (27 mg, 60%) as white solid (FA salt). $^1$H NMR (500 MHz, $CDCl_3$) δ 9.33 (s, 3H), 8.30 (s, 1H), 7.38 (d, J=7.9 Hz, 2H), 7.25 (d, J=8.1 Hz, 2H), 4.11 (d, J=12.6 Hz, 1H), 4.01-3.85 (m, 3H), 3.31 (s, 3H), 3.27-3.15 (m, 2H), 3.02 (s, 3H), 2.76 (dd, J=15.1, 10.0 Hz, 1H), 2.63 (dd, J=16.5, 5.2 Hz, 1H), 2.54-2.42 (m, 1H), 2.09-1.94 (m, 1H), 1.79 (h, J=7.4 Hz, 2H), 1.66 (dp, J=12.1, 6.1 Hz, 1H), 0.89 (t, J=7.4 Hz, 3H). $^{13}$C NMR (126 MHz, $CDCl_3$) δ 167.13, 164.77, 141.95, 137.47, 134.98, 131.88, 130.61, 129.06, 114.91, 53.72, 51.04, 47.93, 39.20, 35.98, 25.73, 24.57, 23.49, 19.81, 11.28.

N,N-dimethyl-1-propyl-5-((4-(trifluoromethyl)phenethyl)amino)-4,5,6,7-tetrahydro-1H-indazole-3-carboxamide 0200878 (7c): Prepared according to General procedure C using 6 (30 mg, 0.120 mmol), to afford 7c (19 mg, 37%) as white solid (FA salt). $^1$H NMR (500 MHz, $CDCl_3$) δ 8.88 (s, 4H), 8.36 (s, 1H), 7.46 (d, J=7.7 Hz, 2H), 7.25 (d, J=7.8 Hz, 2H), 3.82 (t, J=7.5 Hz, 2H), 3.23 (d, J=15.7 Hz, 6H), 3.12-2.99 (m, 3H), 2.95 (s, 3H), 2.81-2.66 (m, 2H), 2.57 (q, J=11.1, 8.8 Hz, 1H), 2.38-2.29 (m, 1H), 1.93 (h, J=8.2, 6.5 Hz, 1H), 1.72 (h, J=7.6 Hz, 2H), 0.81 (t, J=7.5 Hz, 3H). $^{13}$C NMR (126 MHz, $CDCl_3$) δ 167.48, 164.72, 142.03, 141.21, 137.43, 129.63, 129.38, 129.27, 125.85, 125.82, 125.79, 125.76, 114.93, 54.36, 51.04, 46.35, 39.19, 36.00, 32.62, 25.97, 24.95, 23.46, 19.78, 11.23.

5-((2,4-dimethoxybenzyl)amino)-N,N-dimethyl-1-propyl-4,5,6,7-tetrahydro-1H-indazole-3-carboxamide 0200874 (7d): Prepared according to General procedure C using 6 (30 mg, 0.120 mmol), to afford 7d (23 mg, 47%) as white solid (FA salt). $^1$H NMR (500 MHz, $CDCl_3$) δ 8.90 (s, 3H), 8.31 (s, 1H), 7.25 (d, J=9.7 Hz, 1H), 6.59-6.14 (m, 2H), 4.15 (d, J=12.4 Hz, 1H), 4.01 (d, J=12.5 Hz, 1H), 3.89 (td, J=6.9, 2.9 Hz, 2H), 3.78 (s, 3H), 3.74 (s, 3H), 3.30 (s, 5H), 3.04 (s, 3H), 2.83 (dd, J=15.2, 9.2 Hz, 1H), 2.70 (d, J=16.2 Hz, 1H), 2.54 (t, J=11.2 Hz, 1H), 2.26-2.13 (m, 1H), 2.02-1.73 (m, 3H), 0.90 (t, J=7.5 Hz, 3H). $^{13}$C NMR (126 MHz, $CDCl_3$) δ 166.96, 164.79, 162.00, 159.00, 142.22, 137.40, 132.78, 114.77, 112.23, 104.68, 98.42, 55.57, 55.48, 53.25, 50.98, 43.80, 39.16, 35.89, 25.69, 24.61, 23.47, 19.57, 11.27.

5-((2-(benzo[d][1,3]dioxol-5-yl)ethyl)amino)-N,N-dimethyl-1-propyl-4,5,6,7-tetrahydro-1H-indazole-3-carboxamide 0200876 (7e): Prepared according to General procedure C using 6 (30 mg, 0.120 mmol), to afford 7d (17 mg, 36%) as white solid (FA salt). $^1$H NMR (500 MHz, $CDCl_3$) δ 9.02 (s, 4H), 8.41 (s, 2H), 6.68-6.62 (m, 3H), 3.89 (t, J=7.3 Hz, 2H), 3.41-3.26 (m, 4H), 3.26-3.17 (m, 1H), 3.12 (tt, J=10.7, 5.7 Hz, 1H), 3.03 (s, 3H), 2.93 (ddd, J=17.0, 10.9, 5.5 Hz, 2H), 2.86-2.72 (m, 2H), 2.63 (ddd, J=16.5, 10.5, 5.5 Hz, 1H), 2.45-2.35 (m, 1H), 2.00 (q, J=7.8, 7.4 Hz, 1H), 1.79 (h, J=7.4 Hz, 2H), 0.88 (t, J=7.3 Hz, 3H). $^{13}$C NMR (126 MHz, $CDCl_3$) δ 167.39, 164.74, 147.99, 146.66, 142.04, 137.47, 130.58, 121.89, 114.88, 109.24, 108.60, 101.11, 54.27, 51.03, 46.91, 39.20, 36.01, 32.45, 25.90, 24.75, 23.46, 19.76, 11.26.

5-((4-fluorobenzyl)oxy)-N,N-dimethyl-1-propyl-4,5,6,7-tetrahydro-1H-indazole-3-carboxamide. 0200622 (9) To a solution of 5-hydroxy-N,N-dimethyl-1-propyl-4,5,6,7-tetrahydro-1H-indazole-3-carboxamide 8 (50 mg, 0.199 mmol) in DMF was added 50% NaH in mineral oil (11.94 mg, 0.298 mmol) and 1-(bromomethyl)-4-fluorobenzene (0.037 ml, 0.298 mmol). The reaction mixture was heated to 80° C. overnight. The reaction was cooled to room temperature, quenched with saturated $NH_4Cl$, and extracted with EtOAc (3×). The organic layers were combined, washed with brine and dried over $Na_2SO_4$, concentrated and purified by preparative HPLC to afford 9 (35 mg, 49%) as a light yellow solid. $^1$H NMR (500 MHz, $CDCl_3$) δ 7.32-7.27 (m, 2H), 7.04-6.96 (m, 2H), 4.61 (d, J=11.9 Hz, 1H), 4.51 (d, J=11.9 Hz, 1H), 3.92 (dd, J=7.8, 6.5 Hz, 2H), 3.90-3.78 (m, 1H), 3.31 (s, 3H), 3.16-3.01 (m, 4H), 2.87-2.70 (m, 2H), 2.58 (dt, J=15.8, 6.8 Hz, 1H), 2.08-1.94 (m, 2H), 1.82 (q, J=7.3 Hz, 2H), 0.91 (t, J=7.4 Hz, 3H). $^{13}$C NMR (126 MHz, $CDCl_3$) δ 165.25, 163.33, 161.38, 142.62, 137.93, 134.61, 134.58, 129.39, 129.33, 116.01, 115.39, 115.22, 73.51, 69.61, 50.86, 39.13, 35.80, 27.92, 27.33, 23.61, 18.87, 11.32.

5-((4-fluorobenzyl)thio)-N,N-dimethyl-1-propyl-4,5,6,7-tetrahydro-1H-indazole-3-carboxamide 0200624 (11). A solution of NaOEt (70.5 mg, 1.036 mmol) in ethanol (3 ml) was heated at 70° C. until a clear solution was formed. (4-fluorophenyl)methanethiol (0.064 ml, 0.518 mmol) was then added and was stirred for 10 mins before addition of 3-(dimethylcarbamoyl)-1-propyl-4,5,6,7-tetrahydro-1H-indazol-5-yl 4-methylbenzenesulfonate 10 (140 mg, 0.345 mmol) in ethanol (3 ml). The temperature was reduced to 40° C. and stirring was continued overnight. The reaction was cooled to room temperature, quenched with saturated $NH_4Cl$, and extracted with EtOAc (3×). The organic layers were combined, washed with brine and dried over $Na_2SO_4$, concentrated and purified by preparative HPLC to afford 11 (18 mg, 22%) as a clear oil. $^1$H NMR (500 MHz, $CDCl_3$) δ 7.39-7.28 (m, 2H), 7.13-6.75 (m, 2H), 3.91 (t, J=7.2 Hz, 2H), 3.78 (s, 2H), 3.30 (s, 3H), 3.18 (dd, J=16.2, 5.1 Hz, 1H), 3.07 (s, 3H), 2.93 (tdd, J=8.0, 6.5, 2.8 Hz, 1H), 2.71 (dq, J=16.4, 5.0, 4.1 Hz, 2H), 2.60-2.43 (m, 1H), 2.10 (dq, J=10.8, 2.7 Hz, 1H), 1.82 (dq, J=14.6, 7.4 Hz, 3H), 0.90 (t, J=7.4 Hz, 3H). $^{13}$C NMR (126 MHz, $CDCl_3$) δ 165.17, 162.93, 160.98, 142.35, 137.73, 134.28, 134.25, 130.48, 130.42, 116.89, 115.57, 115.40, 50.86, 39.32, 39.11, 35.81, 34.34, 28.78, 28.48, 23.61, 20.48, 11.33.

5-(4-fluorobenzamido)-N,N-dimethyl-1-propyl-4,5,6,7-tetrahydro-1H-indazole-3-carboxamide (13): Prepared according to General procedure A using 12 (25 mg, 0.1 mmol) to afford 13 (18 mg, 48%) as white solid. $^1$H NMR (500 MHz, $CDCl_3$) δ 8.06 (td, J=7.9, 1.8 Hz, 1H), 7.44 (tdd, J=7.4, 5.2, 1.9 Hz, 1H), 7.24 (d, J=7.5 Hz, 1H), 7.08 (dd, J=12.1, 8.3 Hz, 1H), 6.72 (dd, J=12.8, 7.5 Hz, 1H), 4.45 (ddt, J=9.8, 4.8, 2.4 Hz, 1H), 3.96 (t, J=7.1 Hz, 2H), 3.31 (s, 3H), 3.15 (dd, J=16.0, 5.2 Hz, 1H), 3.06 (s, 3H), 2.79-2.60 (m, 3H), 2.22 (dq, J=10.0, 3.0 Hz, 1H), 2.05-1.92 (m, 1H), 1.83 (q, J=7.3 Hz, 2H), 1.74 (q, J=6.9, 6.5 Hz, 1H), 0.91 (t, J=7.4 Hz, 3H). $^{13}$C NMR (126 MHz, $CDCl_3$) δ 164.99, 163.03, 161.63, 159.66, 142.77, 137.76, 133.35, 133.28, 132.04, 124.93, 124.90, 121.42, 121.33, 116.21, 116.01, 115.95, 50.93, 46.08, 39.07, 35.80, 29.83, 28.20, 27.89, 23.60, 19.40, 11.25.

5-((4-fluorophenyl)sulfonamido)-N,N-dimethyl-1-propyl-4,5,6,7-tetrahydro-1H-indazole-3-carboxamide 0200629 (14). Triethyamine (0.056 ml, 0.399 mmol) was added to a solution of 5-amino-N,N-dimethyl-1-propyl-4,5,6,7-tetrahydro-1H-indazole-3-carboxamide (20 mg, 0.080 mmol) in dichloromethane (1 ml). The reaction mixture was cooled to 0° C. and then 4-fluorobenzene-1-sulfonyl chloride (15.55 mg, 0.080 mmol) was added in portions. The reaction was warmed to room temperature and stirred until completion. The reaction mixture was washed with 1 M HCl and water, dried, concentrated and purified by prep LC to afford 14 (18 mg 55%) as a white solid. $^1$H NMR (500 MHz, $CDCl_3$) δ 8.08-7.91 (m, 2H), 7.26 (t, J=8.6 Hz, 2H), 4.00 (t, J=7.1 Hz, 2H), 3.71-3.59 (m, 1H), 3.38 (s, 3H), 3.13 (s, 3H), 2.92 (dd, J=16.2, 5.1 Hz, 1H), 2.81 (dt, J=16.5, 6.3 Hz, 1H), 2.69 (td, J=15.7, 15.2, 6.8 Hz, 2H), 2.15-2.05 (m, 2H), 1.89 (p, J=7.3 Hz, 2H), 1.00 (t, J=7.4 Hz, 3H). $^{13}$C NMR (126 MHz, $CDCl_3$) δ 166.12, 164.81, 164.10, 142.51, 137.57, 136.90, 136.88, 129.85, 129.78, 116.55, 116.37, 115.25, 50.93, 49.35, 39.12, 35.93, 28.98, 28.72, 23.53, 18.71, 11.30.

(5-((4-Hydroxyphenethyl)amino)-1-propyl-4,5,6,7-tetrahydro-1H-indazol-3-yl)(piperidin-1-yl)methanone 0200643 (7f). Prepared according to General procedure C to afford 7f (38%) as a colorless oil (38%). 1H NMR (500 MHz, $CDCl_3$) δ 8.44 (s, 1H, FA), 7.09-7.00 (m, 2H), 6.81-6.71 (m, 2H), 3.93 (dd, J=7.8, 6.4 Hz, 2H), 3.88-3.74 (m, 2H), 3.74-3.46 (m, 2H), 3.40-3.28 (m, 1H), 3.26-3.05 (m, 3H), 3.01-2.75 (m, 3H), 2.66 (tt, J=15.1, 7.9 Hz, 2H), 2.42-2.28 (m, 1H), 2.02-1.91 (m, 1H), 1.81 (q, J=7.3 Hz, 2H), 1.75-1.48 (m, 6H), 0.91 (t, J=7.4 Hz, 3H); 13C NMR (126 MHz, $CDCl_3$) δ 169.21, 165.08, 157.47, 143.42, 139.15, 131.22, 128.93, 117.20, 115.54, 55.34, 54.98, 52.40, 51.48, 49.94, 48.25, 45.02, 33.29, 28.19, 27.39, 27.23, 26.07, 25.80, 24.84, 21.02, 12.54.

(5-((3-Hydroxyphenethyl)amino)-1-propyl-4,5,6,7-tetrahydro-1H-indazol-3-yl)(piperidin-1-yl)methanone 0200646 (7g). Prepared according to General procedure C to afford 7g as colorless oil (57%). 1H NMR (500 MHz, $CDCl_3$) δ 8.29 (s, 2H, FA), 7.00 (t, J=7.8 Hz, 1H), 6.70 (s, 1H), 6.65 (dd, J=8.1, 2.1 Hz, 1H), 6.56 (d, J=7.5 Hz, 1H), 3.80 (dt, J=20.9, 6.6 Hz, 4H), 3.58 (t, J=5.2 Hz, 2H), 3.35 (q, J=10.2, 9.5 Hz, 1H), 3.18 (ddt, J=32.9, 15.1, 6.5 Hz, 3H), 2.86 (dq, J=14.1, 7.5, 6.5 Hz, 2H), 2.78-2.62 (m, 2H), 2.55 (ddd, J=16.2, 9.8, 5.5 Hz, 1H), 2.32 (d, J=12.4 Hz, 1H), 1.93 (dd, J=13.2, 7.4 Hz, 1H), 1.73 (h, J=7.3 Hz, 2H), 1.59 (ddq, J=24.1, 12.6, 6.2 Hz, 6H), 0.85 (t, J=7.4 Hz, 3H); 13C NMR (126 MHz, $CDCl_3$) δ 167.24, 163.35, 157.64, 141.67, 137.76, 137.52, 129.87, 119.64, 115.91, 114.51, 114.17, 54.32, 53.43, 50.87, 48.41, 46.46, 43.62, 32.29, 26.66, 25.73, 25.40, 24.57, 24.28, 23.28, 19.50, 11.13.

Piperidin-1-yl(1-propyl-5-((2-(pyridin-4-yl)ethyl)amino)-4,5,6,7-tetrahydro-1H-indazol-3-yl)methanone (7 h): Prepared according to General procedure C to afford 7g as white solid (57%). $^1$H NMR (500 MHz, $CDCl_3$) δ 0.90 (t, J=7.48 Hz, 3H), 1.21 (t, J=7.02 Hz, 1H), 1.56 (br. s., 2H), 1.63-1.69 (m, 3H), 1.71-1.77 (m, 1H), 1.80 (q, J=7.32 Hz, 2H), 2.05 (s, 3H), 2.41 (dd, J=15.56, 8.54 Hz, 1H), 2.53-2.62 (m, 1H), 2.63-2.72 (m, 1H), 2.79-2.88 (m, 2H), 2.94-3.00 (m, 3H), 3.03-3.09 (m, 4H), 3.42-3.53 (m, 1H), 3.67 (br. s., 2H), 3.78 (br. s., 2H), 3.90 (td, J=7.17, 1.53 Hz, 2H), 7.11-7.22 (m, 2H), 8.47-8.58 (m, 2H); $^{13}$C NMR (126 MHz, $CDCl_3$) δ 11.34, 19.93, 21.49, 23.60, 24.92, 27.74, 28.86, 35.53, 43.41, 47.16, 48.34, 50.87, 53.80, 115.97, 124.35, 137.95, 142.56, 149.06, 149.70, 163.89, 174.96.

4-(((3-(Piperidine-1-carbonyl)-1-propyl-4,5,6,7-tetrahydro-1H-indazol-5-yl)amino)methyl)benzenesulfonamide 0200652. (7i). Prepared according to General procedure C to afford 7i as colorless oil (39%). 1H NMR (500 MHz, $CD_3OD$) δ 8.22 (s, 2H, FA), 7.91 (d, J=8.1 Hz, 2H), 7.60 (d, J=8.0 Hz, 2H), 4.23 (d, J=13.3 Hz, 1H), 4.15 (d, J=13.3 Hz, 1H), 3.98-3.88 (m, 2H), 3.81 (q, J=5.7 Hz, 2H), 3.68 (t, J=5.3 Hz, 2H), 3.33-3.22 (m, 1H), 3.17 (dd, J=15.3, 5.1 Hz, 1H), 2.81 (ddd, J=16.2, 5.8, 3.2 Hz, 1H), 2.67 (dd, J=15.3, 9.4 Hz, 2H), 2.36-2.27 (m, 1H), 2.02-1.87 (m, 1H), 1.82 (q, J=7.3 Hz, 2H), 1.74-1.56 (m, 6H), 0.92 (t, J=7.4 Hz, 3H); 13C NMR (126 MHz, $CD_3OD$) δ 165.62, 163.60, 143.21, 141.79, 137.68, 129.92, 126.69, 114.28, 53.22, 50.81, 48.39, 48.29, 43.46, 26.62, 26.33, 25.65, 24.86, 24.48, 23.26, 19.48, 10.96.

Piperidin-1-yl(5-((4-(piperidin-1-yl)benzyl)amino)-1-propyl-4,5,6,7-tetrahydro-1H-indazol-3-yl)methanone 0200647 (7j). Prepared according to General procedure C to afford 7j as colorless oil (65%). 1H NMR (500 MHz, $CDCl_3$) δ 8.27 (s, 2H, FA), 7.33-7.15 (m, 2H), 6.81 (d, J=8.6 Hz, 2H), 4.03 (d, J=13.0 Hz, 1H), 3.93 (d, J=13.1 Hz, 1H), 3.89-3.72 (m, 4H), 3.62 (q, J=6.1 Hz, 2H), 3.29-3.15 (m, 2H), 3.09 (t, J=5.4 Hz, 4H), 2.80 (dd, J=14.8, 9.1 Hz, 1H), 2.69 (ddd, J=16.5, 5.8, 3.0 Hz, 1H), 2.52 (ddd, J=16.6, 10.7, 5.9 Hz, 1H), 2.23 (dd, J=12.1, 5.8 Hz, 1H), 1.97-1.85 (m, 1H), 1.76 (h, J=7.3 Hz, 2H), 1.70-1.46 (m, 12H), 0.87 (t, J=7.4 Hz, 3H); 13C NMR (126 MHz, $CDCl_3$) δ 166.59, 163.31, 152.32, 141.98, 137.35, 131.08, 120.28, 115.92, 114.24, 52.38, 50.85, 49.77, 48.31, 47.87, 43.49, 26.73, 25.76, 25.57, 24.69, 24.22, 24.12, 23.33, 19.51, 11.17.

Piperidin-1-yl(5-((4-(piperidin-1-yl)phenyl)amino)-1-propyl-4,5,6,7-tetrahydro-1H-indazol-3-yl)methanone 0200637 (7k). Prepared according to General procedure C to afford 7k as colorless oil (37%). 1H NMR (500 MHz, $CDCl_3$) δ 8.31 (d, J=32.0 Hz, 1H, FA), 7.09 (d, J=8.3 Hz, 2H), 6.57 (d, J=8.3 Hz, 2H), 3.92 (t, J=7.2 Hz, 2H), 3.84-3.52 (m, 5H), 3.27-2.92 (m, 6H), 2.59 (dq, J=56.7, 7.0 Hz, 3H), 2.20-2.00 (m, 1H), 1.84 (dp, J=29.4, 7.3, 6.3 Hz, 7H), 1.62 (dddd, J=29.1, 24.0, 12.2, 5.8 Hz, 10H), 0.90 (t, J=7.4 Hz, 3H); 13C NMR (126 MHz, $CDCl_3$) δ 165.72, 163.82, 144.40, 142.62, 138.84, 137.68, 122.18, 120.82, 116.53, 115.47, 114.05, 77.28, 77.03, 76.78, 54.79, 50.77, 50.03, 49.83, 48.92, 48.23, 43.33, 28.36, 27.56, 26.81, 25.71, 25.48, 24.73, 24.67, 23.47, 22.96, 19.23, 11.20.

5-((4-Phenoxyphenyl)amino)-1-propyl-4,5,6,7-tetrahydro-1H-indazol-3-yl)(piperidin-1-yl)methanone 0200702 (7l). Prepared according to General procedure C to afford 7l as colorless oil (32%). 1H NMR (500 MHz, $CDCl_3$) δ 7.33-7.20 (m, 2H), 6.98 (tt, J=7.2, 1.2 Hz, 1H), 6.94-6.89 (m, 2H), 6.89-6.83 (m, 2H), 6.66-6.53 (m, 2H), 3.92 (t, J=7.2 Hz, 2H), 3.84-3.70 (m, 3H), 3.66 (d, J=6.3 Hz, 2H), 3.13 (dd, J=15.9, 5.0 Hz, 1H), 2.78-2.60 (m, 2H), 2.56 (dd, J=15.9, 7.5 Hz, 1H), 2.22-2.06 (m, 1H), 1.94-1.76 (m, 4H), 1.70-1.46 (m, 6H), 0.91 (t, J=7.4 Hz, 3H); 13C NMR (126 MHz, $CDCl_3$) δ 163.74, 159.07, 147.55, 143.75, 142.76, 137.65, 129.48, 121.91, 121.32, 117.10, 115.70, 114.27, 50.85, 50.77, 49.13, 48.19, 43.25, 28.56, 27.84, 26.84, 25.73, 24.78, 23.50, 19.37, 11.22.

2-(2-((3-(Piperidine-1-carbonyl)-1-propyl-4,5,6,7-tetrahydro-1H-indazol-5-yl)amino)ethyl)guanidine 0200829 (7m). Prepared according to General procedure C to afford 7m as colorless glassy solid (95%). 1H NMR (500 MHz, $CD_3OD$) δ 4.07 (t, J=6.9 Hz, 2H), 3.83-3.59 (m, 7H), 3.41 (d, J=6.4 Hz, 2H), 3.23 (dd, J=15.4, 4.7 Hz, 1H), 3.00 (d, J=16.7 Hz, 1H), 2.92-2.70 (m, 2H), 2.47 (d, J=12.6 Hz, 1H), 2.11 (dd, J=12.0, 6.0 Hz, 1H), 1.87 (q, J=7.2 Hz, 2H), 1.75 (q, J=5.6 Hz, 2H), 1.70-1.55 (m, 6H), 0.94 (t, J=7.1 Hz, 3H); 13C NMR (126 MHz, $CD_3OD$) δ 157.45, 140.84, 113.11, 65.49, 54.67, 50.51, 43.82, 37.76, 33.39, 24.82, 24.02, 23.69, 22.81, 18.81, 14.05, 9.92.

(5-((3-(Methylamino)propyl)amino)-1-propyl-4,5,6,7-tetrahydro-1H-indazol-3-yl)(piperidin-1-yl)methanone 0200820 (7n). Prepared according to General procedure C to afford 7n as colorless glassy solid (88%). 1H NMR (500 MHz, $CDCl_3$) δ 3.87 (td, J=7.0, 2.2 Hz, 1H), 3.75 (dq, J=10.7, 6.8, 5.9 Hz, 1H), 3.69-3.53 (m, 1H), 3.07 (d, J=23.9 Hz, 1H), 2.78 (dd, J=17.7, 7.0 Hz, 1H), 2.65 (q, J=6.7, 4.3 Hz, 1H), 2.45-2.30 (m, 1H), 1.78 (p, J=7.3 Hz, 1H), 1.70-1.49 (m, 2H), 0.89 (q, J=7.5 Hz, 1H).

Piperidin-1-yl(5-((2-(piperidin-1-yl)ethyl)amino)-1-propyl-4,5,6,7-tetrahydro-1H-indazol-3-yl)methanone 0200640 (7p). Prepared according to General procedure C to afford 7p as colorless oil (49%). $^1$H NMR (500 MHz, $CDCl_3$) δ 8.69 (s, 4H), 8.39 (s, 2H), 3.88 (t, J=7.2 Hz, 2H), 3.78 (t, J=5.4 Hz, 2H), 3.63 (d, J=5.7 Hz, 2H), 3.36-3.14 (m, 4H), 3.14-2.95 (m, 2H), 2.86 (d, J=10.6 Hz, 4H), 2.78-2.49 (m, 3H), 2.31-2.17 (m, 1H), 2.05-1.89 (m, 1H), 1.85-1.36 (m, 14H), 0.87 (t, J=7.4 Hz, 3H); $^{13}$C NMR (126 MHz, $CDCl_3$) δ 167.69, 163.42, 142.23, 137.48, 114.52, 77.30, 77.04, 76.79, 54.66, 53.82, 53.78, 50.81, 48.23, 43.32, 40.57, 26.78, 25.75, 24.95, 24.72, 23.53, 23.38, 22.56, 19.37, 11.16.

Piperidin-1-yl(1-propyl-5-(((tetrahydro-2H-pyran-4-yl)methyl)amino)-4,5,6,7-tetrahydro-1H-indazol-3-yl)methanone 0200642 (7q). Prepared according to General procedure C to afford 7q as colorless oil (45%). $^1$H NMR (500 MHz, $CDCl_3$) δ 3.98-3.72 (m, 6H), 3.62 (dt, J=16.9, 5.9 Hz, 2H), 3.40-3.10 (m, 4H), 2.90 (dd, J=12.1, 7.5 Hz, 1H), 2.85-2.68 (m, 3H), 2.62 (dt, J=10.7, 5.5 Hz, 1H), 2.48-2.29 (m, 1H), 2.08-1.87 (m, 2H), 1.86-1.48 (m, 10H), 1.29 (dtd, J=12.9, 7.2, 3.5 Hz, 2H), 0.88 (t, J=7.4 Hz, 3H); $^{13}$C NMR (126 MHz, $CDCl_3$) δ 167.37, 163.25, 142.05, 137.32, 114.63, 67.23, 67.19, 54.85, 50.89, 48.28, 43.43, 32.80, 30.66, 26.74, 25.94, 25.78, 24.69, 24.43, 23.37, 19.94, 11.16.

(5-(4-(dimethylamino)piperidin-1-yl)-1-propyl-4,5,6,7-tetrahydro-1H-indazol-3-yl)(piperidin-1-yl)methanone 196331 (7r) Prepared according to General procedure C to afford 7r as colorless oil (45%). $^1$H NMR (500 MHz, $CDCl_3$) δ 3.90 (td, J=7.25, 1.37 Hz, 2H), 3.77 (s, 2H), 3.63-3.70 (m, 2H), 3.05-3.13 (m, 2H), 2.91 (d, J=14.95 Hz, 2H), 2.70-2.76 (m, 1H), 2.54-2.64 (m, 3H), 2.44 (s, 6H), 2.38 (s, 1H), 2.32-2.37 (m, 1H), 1.92-1.97 (m, 2H), 1.70-1.87 (m, 4H), 1.61-1.70 (m, 6H), 1.56 (br. s., 2H), 0.90 (t, J=7.48 Hz, 3H). $^{13}$C NMR (126 MHz, $CDCl_3$) δ 163.92, 142.66, 138.10, 116.67, 62.02, 60.79, 50.88, 49.23, 48.34, 46.90, 44.01, 39.95, 26.98, 26.92, 26.88, 26.65, 26.33, 24.92, 23.61, 22.79, 22.10, 21.40, 11.32.

(5-(4-methylpiperazin-1-yl)-1-propyl-4,5,6,7-tetrahydro-1H-indazol-3-yl)(piperidin-1-yl)methanone 196337 (7s): Prepared according to General procedure C to afford 7s as colorless oil (45%). $^1$H NMR (500 MHz, $CDCl_3$) 3.87-3.95 (m, 2H), 3.72 (br. s., 2H), 3.67 (br. s., 2H), 2.93 (dd, J=15.41, 4.73 Hz, 1H), 2.65-2.77 (m, 5H), 2.40-2.62 (m, 4H), 2.29 (s, 3H), 2.16 (dt, J=9.84, 2.25 Hz, 1H), 1.75-1.94 (m, 4H), 1.59-1.75 (m, 6H), 1.55 (br. s., 2H), 0.87-0.96 (m, 3H); $^{13}$C NMR (126 MHz, $CDCl_3$) δ 164.11, 142.80, 138.17, 116.64, 60.95, 55.59, 50.87, 46.11, 25.96, 24.94, 23.64, 23.54, 21.26, 11.35.

(5-(3,4-dihydroisoquinolin-2(1H)-yl)-1-propyl-4,5,6,7-tetrahydro-1H-indazol-3-yl)(piperidin-1-yl)methanone 196338 (7t): Prepared according to General procedure C to afford 7t as colorless oil (45%). $^1$H NMR (500 MHz, $CDCl_3$) δ 7.08-7.14 (m, 3H), 7.00-7.05 (m, 1H), 3.89-3.94 (m, 2H), 3.77 (br. s., 2H), 3.69 (br. s., 2H), 3.04 (dd, J=15.26, 4.58 Hz, 1H), 2.89-2.96 (m, 4H), 2.75-2.83 (m, 1H), 2.59-2.70 (m, 2H), 2.18-2.28 (m, 1H), 1.79-1.91 (m, 3H), 1.60-1.70 (m, 7H), 1.57 (br. s., 2H), 0.92 (t, J=7.48 Hz, 3H); NMR (126 MHz, $CDCl_3$) δ 164.11, 142.78, 138.29, 134.68, 128.84, 126.89, 126.14, 125.67, 116.94, 60.55, 52.38, 50.89, 47.10, 29.86, 26.67, 24.96, 23.66, 22.71, 21.38, 11.37.

(5-((4-fluorobenzyl)(methyl)amino)-1-propyl-4,5,6,7-tetrahydro-1H-indazol-3-yl)(piperidin-1-yl)methanone 196339 (7u) Prepared according to General procedure C to afford 7u as colorless oil (45%). $^1$H NMR (500 MHz, $CDCl_3$) δ 7.28 (dd, J=8.54, 5.49 Hz, 2H), 6.95-7.01 (m, 2H), 3.91 (t, J=7.17 Hz, 2H), 3.78 (br. s., 2H), 3.69 (br. s., 2H), 3.57-3.66 (m, 2H), 2.88-2.96 (m, 2H), 2.73-2.79 (m, 1H), 2.55-2.69 (m, 2H), 2.24 (s, 3H), 2.11 (dd, J=12.51, 3.36 Hz, 1H), 1.79-1.83 (m, 2H), 1.66 (br. s., 4H), 1.57 (br. s., 2H), 0.91 (t, J=7.32 Hz, 3H); $^{13}$C NMR (126 MHz, $CDCl_3$) δ 164.08, 142.73, 138.26, 130.25, 130.19, 117.28, 115.20, 115.04, 59.81, 57.37, 50.87, 48.35, 43.35, 37.60, 27.00, 26.48, 25.91, 24.96, 23.65, 21.82, 21.51, 11.35.

Piperidin-1-yl(1-propyl-5-(4-(pyridin-4-yl)piperidin-1-yl)-4,5,6,7-tetrahydro-1H-indazol-3-yl)methanone 200639 (7v). Prepared according to General procedure C to afford 7v as colorless oil (34%). $^1$H NMR (500 MHz, $CDCl_3$) δ 8.58 (s, 2H), 7.24 (d, J=5.3 Hz, 2H), 3.94 (tt, J=7.9, 4.1 Hz, 4H), 3.71 (t, J=5.2 Hz, 2H), 3.57 (dddd, J=24.6, 12.6, 5.6, 2.8 Hz, 3H), 3.21 (dd, J=15.1, 4.8 Hz, 1H), 3.09 (td, J=12.3, 2.8 Hz, 1H), 2.95-2.62 (m, 5H), 2.55 (ddd, J=12.6, 5.3, 2.5 Hz, 1H), 2.32 (tt, J=12.8, 9.2 Hz, 2H), 2.11-1.99 (m, 2H), 1.94 (dq, J=11.9, 6.2 Hz, 1H), 1.84 (h, J=7.3 Hz, 2H), 1.77-1.52 (m, 6H), 0.93 (t, J=7.4 Hz, 3H); $^{13}$C NMR (126 MHz, $CDCl_3$) δ 166.37, 163.05, 153.03, 149.42, 142.23, 137.43, 122.45, 115.16, 77.30, 77.04, 76.79, 61.44, 51.12, 50.95, 48.21, 45.78, 43.47, 40.44, 29.84, 29.58, 26.79, 25.81, 25.12, 24.72, 23.38, 20.79, 20.72, 11.14.

(5-(4-(4-Nitrophenyl)piperazin-1-yl)-1-propyl-4,5,6,7-tetrahydro-1H-indazol-3-yl)(piperidin-1-yl)methanone 200709 (7w). Prepared according to General procedure C to afford 7w as colorless oil (41%). $^1$H NMR (500 MHz, $CDCl_3$) δ 8.20 (s, 2H, FA), 8.16-8.03 (m, 2H), 6.92-6.69 (m, 2H), 4.00-3.72 (m, 4H), 3.62 (dt, J=25.0, 5.3 Hz, 6H), 3.34-3.19 (m, 1H), 3.12 (ddq, J=21.5, 11.0, 5.1 Hz, 5H), 2.87-2.54 (m, 3H), 2.46-2.26 (m, 1H), 1.94-1.71 (m, 3H), 1.71-1.46 (m, 6H), 0.88 (t, J=7.4 Hz, 3H); $^{13}$C NMR (126 MHz, $CDCl_3$) δ 165.35, 163.38, 154.11, 142.16, 139.39, 137.56, 125.94, 115.47, 113.43, 61.22, 50.90, 48.29, 47.85, 45.90, 43.50, 26.78, 25.75, 25.11, 24.68, 23.41, 21.63, 20.77, 11.15.

4-((4-(3-(Piperidine-1-carbonyl)-1-propyl-4,5,6,7-tetrahydro-1H-indazol-5-yl)piperazin-1-yl)methyl)benzonitrile 200641 (7x). Prepared according to General procedure C to afford 7w as colorless oil (32%). $^1$H NMR (500 MHz, $CDCl_3$) δ 8.33 (s, 2H), 7.61 (d, J=7.9 Hz, 2H), 7.41 (d, J=8.0 Hz, 2H), 3.88 (tt, J=9.2, 4.6 Hz, 4H), 3.72-3.53 (m, 4H), 3.48-3.34 (m, 1H), 3.13 (dq, J=26.5, 11.2, 8.4 Hz, 5H), 2.84-2.57 (m, 7H), 2.50-2.37 (m, 1H), 1.98 (s, 1H), 1.80 (dq, J=21.9, 7.3, 6.8 Hz, 3H), 1.72-1.44 (m, 6H), 0.88 (t, J=7.4 Hz, 3H); $^{13}$C NMR (126 MHz, $CDCl_3$) δ 166.36, 163.13, 142.89, 142.27, 137.39, 132.34, 129.46, 118.73, 115.15, 111.46, 61.43, 61.08, 50.93, 50.33, 48.20, 43.43, 26.80, 25.79, 24.89, 24.73, 23.39, 21.08, 20.71, 11.14. ESIMS m/z 475 [MH]+.

Procedure for preparation of 6c and 6d. A solution of 5a (1.00 g, 3.46 mmol), phenylboronic acid (0.87 g, 7.14 mmol), copper acetate (648 mg, 3.57 mmol), pyridine (0.58 mL, 7.2 mmol) and TEA (0.98 mL, 7.03 mmol) in dry DMF (8 mL) was stirred at room temperature for 48 h. The mixture was poured into water (50 mL) and extracted with ethyl acetate (50 mL×4). The organic layers were combined, washed with water (50 mL) and brine (50 mL) sequentially, dried over $Na_2SO_4$, concentrated and further purified by flash silica gel column, with EA/hex, (gradient up to 99:1), to provide a mixture of 6c and 6d as light yellow oil. The mixture was separated by preparative HPLC, with AcCN/$H_2O$ (0.1% FA as additive), to first provide 6d and then 6c.

(1-Phenyl-1,4,6,7-tetrahydrospirolindazole-5,2'-[1,3]dioxolan]-3-yl)(piperidin-1-yl)methanone (6c). Pale yellow oil (476 mg, 37.5%). $^1$H NMR (500 MHz, $CDCl_3$) δ 7.29 (d, J=7.6 Hz, 2H), 7.24 (t, J=7.8 Hz, 2H), 7.13 (t, J=7.4 Hz, 1H), 3.93-3.76 (m, 4H), 3.68 (t, J=5.3 Hz, 2H), 3.50 (t, J=5.1 Hz, 2H), 2.78 (s, 2H), 2.73 (t, J=6.5 Hz, 2H), 1.78 (t, J=6.5 Hz, 2H), 1.53-1.31 (m, 6H).

(2-Phenyl-2,4,6,7-tetrahydrospiro[indazole-5,2'-[1,3]dioxolan]-3-yl)(piperidin-1-yl)methanone (6d). Pale yellow oil (466 mg, 36.7%). $^1$H NMR (500 MHz, $CDCl_3$) δ 7.33 (dd, J=7.9, 1.6 Hz, 2H), 7.24 (t, J=7.9 Hz, 2H), 7.13 (dd, J=13.9, 6.4 Hz, 1H), 3.96-3.78 (m, 4H), 3.58 (s, 1H), 3.29 (s, 1H), 2.99-2.68 (m, 5H), 2.52 (d, J=16.1 Hz, 1H), 1.87 (t, J=6.5 Hz, 2H), 1.40 (s, 1H), 1.32 (q, J=5.7 Hz, 2H), 1.25 (s, 1H), 1.10 (s, 1H), 0.65 (s, 1H).

(5-((4-Fluorobenzyl)amino)-1-phenyl-4,5,6,7-tetrahydro-1H-indazol-3-yl)(piperidin-1-yl)methanone (7aa). Prepared according to General procedure B followed by C to afford lac as a colorless oil (84%). $^1$H NMR (500 MHz, $CDCl_3$) δ 8.09 (s, 1H, FA), 7.36-7.20 (m, 6H), 7.20-7.11 (m, 1H), 6.80 (t, J=8.4 Hz, 2H), 3.96 (d, J=12.9 Hz, 1H), 3.85 (d, J=12.9 Hz, 1H), 3.70 (t, J=5.3 Hz, 2H), 3.47 (t, J=5.3 Hz, 2H), 3.15 (q, J=8.3, 5.2 Hz, 2H), 2.80-2.66 (m, 1H), 2.57 (dq, J=9.7, 5.4, 4.4 Hz, 2H), 2.00 (d, J=12.5 Hz, 1H), 1.64 (dd, J=11.9, 6.9 Hz, 1H), 1.55-1.32 (m, 6H); $^{13}$C NMR (126 MHz, $CDCl_3$) δ 166.77, 163.98, 162.83, 162.00, 143.84, 139.14, 137.92, 132.14, 132.07, 129.30, 127.69, 127.66, 127.63, 123.24, 116.33, 115.96, 115.79, 52.89, 48.36, 47.77, 43.51, 26.76, 26.00, 25.79, 24.66, 24.45, 21.53.

(5-(Benzylamino)-1-phenyl-4,5,6,7-tetrahydro-1H-indazol-3-yl)(piperidin-1-yl)methanone (7ab). Prepared according to General procedure B followed by C to afford lad as a colorless oil (61%). $^1$H NMR (500 MHz, $CDCl_3$) δ 8.12 (s, 1H, FA), 7.35-7.19 (m, 6H), 7.19-7.09 (m, 3H), 7.08 (d, J=7.1 Hz, 1H), 3.93 (d, J=13.0 Hz, 1H), 3.83 (d, J=13.0 Hz, 1H), 3.68 (t, J=5.3 Hz, 2H), 3.47 (t, J=5.4 Hz, 2H), 3.20-3.07 (m, 2H), 2.79-2.66 (m, 1H), 2.57 (qd, J=10.8, 4.7 Hz, 2H), 2.12-1.99 (m, 1H), 1.78-1.63 (m, 1H), 1.57-1.35 (m, 6H); $^{13}$C NMR (126 MHz, $CDCl_3$) δ 167.08, 162.87, 143.97, 139.21, 137.99, 132.09, 129.98, 129.27, 128.92, 128.87, 127.60, 123.24, 116.44, 52.54, 48.45, 48.32, 43.44, 26.77, 26.14, 25.78, 24.69, 24.54, 21.58.

(1-Phenyl-5-((4-(trifluoromethyl)phenethyl)amino)-4,5,6,7-tetrahydro-1H-indazol-3-yl)(piperidin-1-yl)methanone (7ac). Prepared according to General procedure B followed by C to afford 7af as a colorless oil (72%). $^1$H NMR (500 MHz, $CDCl_3$) δ 8.21 (s, 1H, FA), 7.35 (d, J=7.9 Hz, 2H), 7.30-7.21 (m, 4H), 7.21-7.12 (m, 3H), 3.70 (t, J=5.3 Hz, 2H), 3.46 (q, J=4.4 Hz, 2H), 3.34 (q, J=9.3, 7.8 Hz, 1H), 3.15 (td, J=12.6, 10.4, 5.5 Hz, 2H), 3.01 (dtd, J=50.4, 13.0, 12.0, 5.3 Hz, 3H), 2.82-2.61 (m, 3H), 2.21 (d, J=12.3 Hz, 1H), 1.91-1.76 (m, 1H), 1.47 (dq, J=25.6, 5.4, 5.0 Hz, 6H); $^{13}$C NMR (126 MHz, $CDCl_3$) δ 167.08, 162.79, 143.84, 140.91, 139.06, 137.90, 129.31, 129.16, 127.75, 125.75, 125.72, 125.70, 125.67, 123.21, 116.18, 54.04, 48.35, 46.30, 43.49, 32.43, 26.73, 25.98, 25.77, 24.65, 24.61, 21.47.

(1-Phenyl-5-((2-(pyridin-4-yl)ethyl)amino)-4,5,6,7-tetrahydro-1H-indazol-3-yl)(piperidin-1-yl)methanone (7ad). Prepared according to General procedure B followed by C to afford 7ak as a colorless oil (75%). $^1$H NMR (500 MHz, $CDCl_3$) δ 8.32 (d, J=5.1 Hz, 2H), 7.32-7.21 (m, 4H), 7.21-7.14 (m, 1H), 7.02 (d, J=5.3 Hz, 2H), 3.70 (t, J=5.2 Hz, 2H), 3.46 (d, J=5.7 Hz, 2H), 3.29 (tt, J=8.6, 4.4 Hz, 1H), 3.21-3.09 (m, 2H), 3.05 (td, J=11.0, 5.5 Hz, 1H), 2.90 (td, J=10.2, 5.7 Hz, 2H), 2.79-2.56 (m, 3H), 2.16 (dd, J=12.3, 6.2 Hz, 1H), 1.80 (ddd, J=12.9, 6.8, 3.0 Hz, 1H), 1.47 (ddt, J=31.3, 10.9, 5.9 Hz, 6H); $^{13}$C NMR (126 MHz, $CDCl_3$) δ 166.75, 162.81, 149.43, 146.80, 143.85, 139.09, 137.92, 129.32, 127.74, 124.27, 123.21, 116.27, 53.99, 48.34, 45.61, 43.49, 32.19, 26.74, 26.11, 25.78, 24.93, 24.61, 21.46.

(5-((2-(Benzo[d][1,3]dioxol-5-yl)ethyl)amino)-1-phenyl-4,5,6,7-tetrahydro-1H-indazol-3-yl)(piperidin-1-yl)methanone (7ae). Prepared according to General procedure B followed by C to afford 7ah as a colorless oil (82%). $^1$H NMR (500 MHz, $CDCl_3$) δ 8.23 (s, 1H, FA), 7.29-7.20 (m, 4H), 7.20-7.13 (m, 1H), 6.61-6.35 (m, 3H), 5.73 (s, 2H), 3.69 (t, J=5.3 Hz, 2H), 3.47 (p, J=6.5, 5.2 Hz, 2H), 3.35-3.21 (m, 1H), 3.13 (dd, J=15.6, 5.1 Hz, 1H), 3.06 (td, J=11.0, 5.9 Hz, 1H), 2.96 (td, J=11.1, 5.3 Hz, 1H), 2.87-2.61 (m, 5H), 2.27-2.15 (m, 1H), 1.91-1.73 (m, 1H), 1.46 (dq, J=27.9, 6.0, 5.3 Hz, 6H); $^{13}$C NMR (126 MHz, $CDCl_3$) δ 167.29, 162.80, 147.88, 146.54, 143.93, 139.15, 137.95, 130.50, 129.28, 127.64, 123.24, 121.77, 121.66, 116.31, 109.12, 108.49, 108.43, 100.98, 53.87, 48.32, 46.86, 43.44, 32.47, 26.75, 26.19, 25.77, 24.66, 24.59, 21.57.

(5-((4-Fluorophenethyl)amino)-1-phenyl-4,5,6,7-tetrahydro-1H-indazol-3-yl)(piperidin-1-yl)methanone (7af). Prepared according to General procedure B followed by C to afford Taj as a colorless oil (78%). $^1$H NMR (500 MHz, $CDCl_3$) δ 8.24 (s, 1H, FA), 7.33-7.21 (m, 4H), 7.21-7.14 (m, 1H), 6.98 (dd, J=8.4, 5.2 Hz, 2H), 6.77 (t, J=8.4 Hz, 2H), 3.70 (t, J=5.2 Hz, 2H), 3.46 (q, J=4.6 Hz, 2H), 3.30 (q, J=7.2, 6.4 Hz, 1H), 3.18-3.05 (m, 2H), 3.05-2.94 (m, 1H), 2.86 (t, J=12.2 Hz, 2H), 2.78-2.58 (m, 3H), 2.20 (d, J=11.3 Hz, 1H), 1.81 (t, J=9.5 Hz, 1H), 1.47 (dq, J=24.9, 5.7, 5.2 Hz, 6H); $^{13}$C NMR (126 MHz, $CDCl_3$) δ 167.35, 162.84, 162.79, 160.89, 143.89, 139.12, 137.92, 132.57, 132.54, 130.31, 130.25, 129.29, 127.69, 123.23, 116.30, 115.70, 115.53, 53.94, 48.32, 46.72, 43.45, 31.94, 26.74, 26.13, 25.77, 24.64, 21.55.

(5-((3-Hydroxyphenethyl)amino)-1-phenyl-4,5,6,7-tetrahydro-1H-indazol-3-yl)(piperidin-1-yl)methanone (7ag). Prepared according to General procedure B followed by C to afford 7ag as a colorless oil (55%). $^1$H NMR (500 MHz, $CDCl_3$) δ 8.32 (s, 1H, FA), 7.47-7.28 (m, 5H), 6.97 (t, J=7.8 Hz, 1H), 6.75 (s, 1H), 6.69-6.62 (m, 1H), 6.57 (d, J=7.4 Hz, 1H), 3.81 (q, J=4.8 Hz, 2H), 3.66-3.51 (m, 2H), 3.51-3.40 (m, 1H), 3.32-3.13 (m, 3H), 2.89 (dq, J=35.3, 9.6, 8.4 Hz, 3H), 2.74 (t, J=4.8 Hz, 2H), 2.33 (d, J=12.1 Hz, 1H), 2.02-1.81 (m, 1H), 1.60 (dq, J=27.6, 6.9, 6.2 Hz, 6H); $^{13}$C NMR (126 MHz, $CDCl_3$) δ 167.81, 162.86, 157.77, 143.59, 139.01, 138.10, 137.82, 129.86, 129.28, 127.69, 123.20, 119.59, 116.14, 115.99, 114.52, 54.10, 48.44, 46.53, 43.61, 32.40, 26.68, 25.75, 25.56, 24.55, 24.40, 21.50.

4-(5-(Phenethylamino)-3-(piperidine-1-carbonyl)-4,5,6,7-tetrahydro-1H-indazol-1-yl)benzamide (7ah). Prepared according to General procedure B followed by C to afford lap as a colorless oil (29.7 mg, 57%). $^1$H NMR (500 MHz, $CDCl_3$) δ 7.84 (d, J=8.2 Hz, 2H), 7.37 (d, J=8.2 Hz, 2H), 7.26-7.19 (m, 2H), 7.16 (t, J=6.4 Hz, 3H), 3.76 (q, J=7.3, 5.9 Hz, 2H), 3.62 (tq, J=13.5, 7.5, 6.4 Hz, 2H), 3.48 (s, 1H), 3.29 (p, J=5.6 Hz, 1H), 3.20 (dd, J=15.6, 6.1 Hz, 2H), 3.06 (q, J=15.6, 12.3 Hz, 2H), 2.90 (dd, J=15.8, 9.0 Hz, 1H), 2.75 (s, 2H), 2.35-2.19 (m, 1H), 1.96 (d, J=13.8 Hz, 1H), 1.72-1.42 (m, 6H); $^{13}$C NMR (126 MHz $CDCl_3$) δ 168.91, 167.03, 162.63, 144.60, 141.68, 138.12, 136.57, 131.93, 128.88, 128.83, 128.70, 127.10, 122.17, 116.47, 53.61, 48.35, 46.73, 43.49, 32.57, 26.72, 25.75, 24.53, 24.14, 21.52.

(5-(Phenethylamino)-1-(4-vinylphenyl)-4,5,6,7-tetrahydro-1H-indazol-3-yl)(piperidin-1-yl)methanone (7ai). Prepared according to General procedure B followed by C to afford Tao as a colorless oil (33.9 mg, 71%). $^1$H NMR (500 MHz, $CDCl_3$) δ 8.48 (s, 1H, FA), 7.50 (d, J=8.3 Hz, 2H), 7.42 (d, J=8.3 Hz, 2H), 7.35-7.27 (m, 2H), 7.24 (dd, J=8.8, 6.8 Hz, 3H), 6.76 (dd, J=17.6, 10.9 Hz, 1H), 5.81 (d, J=17.6 Hz, 1H), 5.35 (d, J=10.9 Hz, 1H), 3.90 (t, J=5.3 Hz, 2H), 3.68 (dt, J=10.7, 5.1 Hz, 2H), 3.51 (dq, J=11.2, 6.6, 5.2 Hz, 1H), 3.34 (ddd, J=17.0, 10.8, 5.4 Hz, 2H), 3.23 (td, J=11.3, 5.2 Hz, 1H), 3.11 (ddt, J=21.3, 12.0, 4.9 Hz, 2H), 3.01-2.82 (m, 3H), 2.51-2.36 (m, 1H), 2.12-1.96 (m, 1H), 1.75-1.57 (m, 6H); $^{13}$C NMR (126 MHz $CDCl_3$) δ 167.46. 162.77, 143.97, 138.45, 137.93, 136.94, 136.88, 135.62, 128.79, 128.72, 126.98, 123.16, 116.41, 114.02, 53.83, 48.31, 46.66, 43.43, 32.73, 26.74, 26.17, 25.76, 24.65, 24.57, 21.63. ESIMS m/z 455 [MH]+.

(1-benzyl-5-((2-(pyridin-4-yl)ethyl)amino)-4,5,6,7-tetrahydro-1H-indazol-3-yl)(piperidin-1-yl)methanone (7aj) $^1$H NMR (500 MHz, $CDCl_3$) δ 8.60-8.47 (m, 2H), 8.24 (s, 3H), 7.33-7.27 (m, 3H), 7.23-7.19 (m, 2H), 7.15-7.06 (m, 2H), 3.85 (qt, J=12.6, 5.0 Hz, 2H), 3.64 (pt, J=12.6, 5.2 Hz, 2H), 3.40-3.17 (m, 4H), 3.06 (dddd, J=20.6, 13.2, 10.3, 5.3 Hz, 2H), 2.83 (dd, J=15.4, 9.6 Hz, 1H), 2.69 (ddd, J=16.6, 6.0, 3.2 Hz, 1H), 2.48 (ddd, J=16.7, 10.4, 5.9 Hz, 1H), 2.29 (d, J=13.4 Hz, 1H), 2.03-1.88 (m, 1H), 1.74-1.54 (m, 7H). $^{13}$C NMR (126 MHz, $CDCl_3$) δ 165.76, 163.03, 148.99, 147.00, 142.24, 137.68, 135.76, 128.91, 128.13, 127.16, 124.43, 115.09, 54.36, 53.59, 48.37, 45.51, 43.57, 31.94, 26.71, 25.77, 25.59, 24.68, 24.61, 19.56.

(1-benzyl-5-((4-fluorobenzyl)amino)-4,5,6,7-tetrahydro-1H-indazol-3-yl)(piperidin-1-yl)methanone (7ak) $^1$H NMR (500 MHz, $CDCl_3$) δ 8.24 (s, 1H), 7.49-7.38 (m, 2H), 7.35-7.27 (m, 4H), 7.17-7.08 (m, 2H), 7.04-6.92 (m, 2H), 4.08 (d, J=13.0 Hz, 1H), 3.93 (d, J=13.0 Hz, 1H), 3.85 (q, J=6.3 Hz, 2H), 3.65 (dq, J=13.5, 8.0, 6.7 Hz, 2H), 3.28 (dd, J=15.3, 5.1 Hz, 1H), 3.20-3.08 (m, 1H), 2.78 (dd, J=15.3, 9.7 Hz, 1H), 2.57 (ddd, J=16.5, 5.9, 2.8 Hz, 1H), 2.37 (ddd, J=16.5, 10.6, 5.8 Hz, 1H), 2.13-1.99 (m, 1H), 1.82-1.49 (m, 8H). $^{13}$C NMR (126 MHz, $CDCl_3$) δ 166.56, 164.01, 163.28, 142.53, 137.91, 136.08, 132.19, 132.12, 129.01, 128.41, 128.18, 127.34, 116.00, 115.83, 115.60, 53.68, 53.22, 48.45, 48.08, 43.58, 26.89, 26.07, 25.92, 24.85, 24.75, 19.84.

(5-((4-Fluorobenzyl)amino)-2-phenyl-4,5,6,7-tetrahydro-2H-indazol-3-yl)(piperidin-1-yl)methanone (7ba). Prepared according to General procedure B followed by C to afford 7bd as a colorless oil (59%). $^1$H NMR (500 MHz, $CDCl_3$) δ 8.23 (s, 2H, FA), 7.42 (dt, J=21.7, 7.7 Hz, 8H), 7.35-7.27 (m, 1H), 4.21-3.90 (m, 2H), 3.86-3.63 (m, 1H), 3.48-3.10 (m, 3H), 3.10-2.79 (m, 5H), 2.79-2.59 (m, 2H), 2.22 (d, J=13.1 Hz, 1H), 1.90 (d, J=15.1 Hz, 1H), 1.55 (s, 1H), 1.44 (p, J=5.8 Hz, 2H), 1.35 (s, 1H), 1.21 (d, J=24.9 Hz, 1H), 0.63

(s, 1H); $^{13}$C NMR (126 MHz, $CDCl_3$) δ 166.43, 162.12, 161.17, 148.36, 139.57, 133.63, 131.99, 131.93, 129.33, 127.75, 12 7.39, 122.77, 116.17, 116.00, 114.10, 53.28, 47.97, 47.46, 42.86, 26.78, 25.55, 25.07, 24.10, 23.54, 21.51.

(5-(Benzylamino)-2-phenyl-4,5,6,7-tetrahydro-2H-indazol-3-yl)(piperidin-1-yl)methanone (7bb). Prepared according to General procedure B followed by C to afford 7bc as a colorless oil (40%). $^1$H NMR (500 MHz, $CDCl_3$δ 8.32 (s, 1H, FA), 7.62-7.18 (m, 10H), 4.24-4.07 (m, 1H), 3.77 (tt, J=18.0, 8.4 Hz, 1H), 3.48-3.30 (m, 2H), 3.28-3.07 (m, 1H), 3.07-2.82 (m, 4H), 2.82-2.56 (m, 2H), 2.31 (d, J=16.8 Hz, 1H), 2.09-1.82 (m, 1H), 1.56 (s, 1H), 1.47 (p, J=6.2 Hz, 2H), 1.36 (s, 1H), 1.32-1.16 (m, 1H), 0.67 (s, 1H); $^{13}$C NMR (126 MHz, $CDCl_3$) δ 166.88, 161.24, 148.64, 139.24, 129.38, 129.26, 129.07, 128.91, 128.02, 122.80, 114.55, 52.92, 47.54, 42.91, 26.70, 25.52, 24.98, 24.22, 23.91, 21.22.

(2-Phenyl-5-((4-(trifluoromethyl)phenethyl)amino)-4,5,6,7-tetrahydro-2H-indazol-3-yl)(piperidin-1-yl)methanone (7bc) Prepared according to General procedure B followed by C to afford 7ba as a colorless oil (63%). $^1$H NMR (500 MHz, $CDCl_3$) δ 8.39 (s, 1H, FA), 7.54 (d, J=7.9 Hz, 2H), 7.44 (d, J=8.2 Hz, 2H), 7.39 (t, J=7.8 Hz, 2H), 7.36-7.27 (m, 3H), 3.88-3.66 (m, 1H), 3.47-3.23 (m, 3H), 3.23-3.05 (m, 4H), 3.04-2.58 (m, 5H), 2.52-2.30 (m, 1H), 2.12-1.89 (m, 1H), 1.52 (d, J=13.3 Hz, 1H), 1.41 (qd, J=8.0, 5.2 Hz, 2H), 1.32 (s, 1H), 1.21 (d, J=15.7 Hz, 1H), 0.59 (s, 1H); $^{13}$C NMR (126 MHz, $CDCl_3$) δ 167.37, 161.15, 148.43, 141.10, 139.57, 133.67, 129.33, 129.07, 127.74, 125.77, 125.13, 12 2.97, 122.73, 114.58, 114.25, 54.45, 47.42, 46.48, 42.80, 32.80, 27.34, 25.50, 25.02, 24.07, 23.91, 21.66, 21.51.

(2-Phenyl-5-((2-(pyridin-4-yl)ethyl)amino)-4,5,6,7-tetrahydro-2H-indazol-3-yl)(piperidin-1-yl)methanone (7bd) Prepared according to General procedure B followed by C to afford 7bb as a colorless oil (53%). $^1$H NMR (500 MHz, $CDCl_3$) δ 8.53 (d, J=5.0 Hz, 2H), 7.41 (dt, J=15.6, 8.1 Hz, 4H), 7.36-7.28 (m, 1H), 7.22 (d, J=15.3 Hz, 2H), 3.77 (d, J=15.7 Hz, 1H), 3.50-3.03 (m, 6H), 3.03-2.57 (m, 6H), 2.37 (d, J=23.2 Hz, 1H), 2.01 (q, J=14.3, 11.3 Hz, 1H), 1.53 (s, 1H), 1.42 (p, J=5.9 Hz, 2H), 1.33 (s, 1H), 1.21 (d, J=16.4 Hz, 1H), 0.60 (s, 1H); $^{13}$C NMR (126 MHz, $CDCl_3$) δ 166.25, 161.14, 149.39, 148.36, 146.84, 139.54, 133.66, 129.36, 127.79, 124.25, 122.74, 11 4.17, 77.28, 77.02, 76.77, 54.62, 54.42, 47.45, 45.71, 42.85, 32.35, 27.33, 25.50, 25.03, 24.07, 21.62.

(5-((2-(Benzo[d][1,3]dioxol-5-yl)ethyl)amino)-2-phenyl-4,5,6,7-tetrahydro-2H-indazol-3-yl)(piperidin-1-yl)methanone (7be). Prepared according to General procedure B followed by C to afford 7bj as a colorless oil (74%). $^1$H NMR (500 MHz, $CDCl_3$) δ 8.40 (s, 1H, FA), 7.45 (d, J=7.8 Hz, 2H), 7.39 (dd, J=8.7, 7.0 Hz, 2H), 7.34-7.27 (m, 1H), 6.77-6.56 (m, 3H), 5.91 (d, J=4.6 Hz, 2H), 3.79 (dd, J=14.0, 6.6 Hz, 1H), 3.31 (q, J=14.1, 10.9 Hz, 2H), 3.24-3.01 (m, 3H), 3.01-2.82 (m, 5H), 2.82-2.62 (m, 2H), 2.41 (d, J=14.0 Hz, 1H), 2.12-1.86 (m, 1H), 1.53 (s, 1H), 1.47-1.38 (m, 2H), 1.33 (s, 1H), 1.27-1.12 (m, 1H), 0.61 (d, J=13.0 Hz, 1H); $^{13}$C NMR (126 MHz, $CDCl_3$) δ 167.33, 161.15, 148.49, 147.95, 146.59, 139.63, 133.71, 130.58, 129.29, 127.66, 122.73, 12 1.72, 121.66, 114.26, 109.05, 108.55, 108.43, 101.03, 100.97, 54.32, 47.42, 47.04, 42.79, 39.37, 35.22, 32.66, 27.27, 25.56, 25.06, 24.11, 23.85, 21.64.

(2-(4-fluorophenyl)-5-((2-(pyridin-4-yl)ethyl)amino)-4,5,6,7-tetrahydro-2H-indazol-3-yl)(piperidin-1-yl)methanone (7bf) $^1$H NMR (500 MHz, $CDCl_3$) δ 8.55 (s, 2H), 8.18 (s, 1H), 7.57-7.32 (m, 4H), 7.08 (t, J=8.3 Hz, 2H), 3.78 (d, J=26.7 Hz, 1H), 3.55-3.10 (m, 7H), 3.10-2.61 (m, 6H), 2.52 (s, 1H), 2.21-1.88 (m, 1H), 1.64-1.03 (m, 6H), 0.56 (d, J=26.5 Hz, 1H).

(5-((4-fluorobenzyl)amino)-2-(4-fluorophenyl)-4,5,6,7-tetrahydro-2H-indazol-3-yl)(piperidin-1-yl)methanone (7bg) $^1$H NMR (500 MHz, $CDCl_3$) δ 8.20 (s, 1H), 7.64-7.51 (m, 2H), 7.49-7.34 (m, 2H), 7.16-7.07 (m, 2H), 7.01 (q, J=9.7, 8.3 Hz, 2H), 4.31-4.05 (m, 2H), 3.88-3.59 (m, 1H), 3.42-3.11 (m, 2H), 3.09-2.73 (m, 4H), 2.73-2.58 (m, 1H), 2.37 (s, 1H), 2.16-1.87 (m, 1H), 1.47 (p, J=6.4, 6.0 Hz, 3H), 1.27 (d, J=57.1 Hz, 2H). $^{13}$C NMR (126 MHz, $CDCl_3$) δ 165.59, 162.87, 162.22, 161.12, 160.90, 148.51, 135.96, 133.82, 132.30, 132.23, 127.20, 124.67, 116.45, 116.27, 116.15, 114.29, 52.95, 47.89, 47.63, 43.02, 26.54, 25.89, 25.27, 24.17, 23.65, 21.68.

4-(5-(Phenethylamino)-3-(piperidine-1-carbonyl)-4,5,6,7-tetrahydro-2H-indazol-2-yl)benzamide (7bh). Prepared according to General procedure B followed by C to afford 7bg as a colorless oil (17.6 mg, 63%). $^1$H NMR (500 MHz, $CDCl_3$) δ 8.35 (s, 1H, FA), 8.06-7.55 (m, 2H), 7.41 (dd, J=40.7, 8.2 Hz, 2H), 7.33-7.09 (m, 4H), 6.70 (s, 1H), 3.68 (ddd, J=35.5, 14.8, 8.2 Hz, 1H), 3.58-3.34 (m, 2H), 3.34-3.06 (m, 5H), 3.06-2.86 (m, 3H), 2.86-2.66 (m, 2H), 2.40 (d, J=47.7 Hz, 1H), 2.14 (d, J=16.0 Hz, 1H), 1.63-1.14 (m, 5H), 0.84 (d, J=14.5 Hz, 1H); $^{13}$C NMR (126 MHz, $CDCl_3$) δ 168.86, 166.93, 160.88, 148.94, 142.18, 136.73, 136.55, 133.70, 131.80, 128.89, 128.76, 12 8.67, 127.17, 121.83, 121.57, 114.60, 54.25, 47.45, 46.79, 42.92, 32.58, 26.46, 26.02, 25.15, 24.01, 23.54, 21.31, 20.73.

(5-(phenethylamino)-2-(4-vinylphenyl)-4,5,6,7-tetrahydro-2H-indazol-3-yl)(piperidin-1-yl)methanone (7bi)$^1$H NMR (500 MHz, $CDCl_3$) δ 8.60-8.47 (m, 2H), 8.24 (s, 3H), 7.33-7.27 (m, 3H), 7.23-7.19 (m, 2H), 7.15-7.06 (m, 2H), 3.85 (qt, J=12.6, 5.0 Hz, 2H), 3.64 (pt, J=12.6, 5.2 Hz, 2H), 3.40-3.17 (m, 4H), 3.06 (dddd, J=20.6, 13.2, 10.3, 5.3 Hz, 2H), 2.83 (dd, J=15.4, 9.6 Hz, 1H), 2.69 (ddd, J=16.6, 6.0, 3.2 Hz, 1H), 2.48 (ddd, J=16.7, 10.4, 5.9 Hz, 1H), 2.29 (d, J=13.4 Hz, 1H), 2.03-1.88 (m, 1H), 1.74-1.54 (m, 7H). $^{13}$C NMR (126 MHz, $CDCl_3$) δ 165.76, 163.03, 148.99, 147.00, 142.24, 137.68, 135.76, 128.91, 128.13, 127.16, 124.43, 115.09, 54.36, 53.59, 48.37, 45.51, 43.57, 31.94, 26.71, 25.77, 25.59, 24.68, 24.61, 19.56.

(2-(4-Hydroxyphenyl)-5-(phenethylamino)-4,5,6,7-tetrahydro-2H-indazol-3-yl)(piperidin-1-yl)methanone (7bj). Prepared according to General procedure B followed by C to afford 7be as a colorless oil (24.3 mg, 76%). $^1$H NMR (500 MHz, $CDCl_3$) δ 8.36 (s, 1H, FA), 7.31 (dd, J=8.5, 6.4 Hz, 2H), 7.28-7.15 (m, 5H), 6.85 (d, J=8.5 Hz, 2H), 3.71 (h, J=8.2, 6.0 Hz, 1H), 3.41-3.31 (m, 2H), 3.21 (qd, J=13.0, 11.7, 6.7 Hz, 2H), 3.00 (tt, J=45.0, 20.9 Hz, 6H), 2.82-2.54 (m, 2H), 2.35 (d, J=12.5 Hz, 1H), 2.09-1.87 (m, 1H), 1.61-1.41 (m, 3H), 1.41-1.16 (m, 2H), 0.76 (s, 1H); $^{13}$C NMR (126 MHz, $CDCl_3$) δ 166.81, 161.19, 157.24, 147.64, 136.46, 133.70, 131.38, 128.83, 128.57, 127.13, 124.49, 11 5.90, 113.28, 54.17, 53.90, 47.56, 46.41, 42.88, 32.47, 26.25, 25.55, 24.98, 23.89, 23.47, 21.17, 20.92.

Synthesis of ethyl 2-(2-((tert-butoxycarbonyl)amino)ethyl)-2,4,6,7-tetrahydrospirolindazole-5,2'-[1,3]dioxolane]-3-carboxylate (3aa) and ethyl 1-(2-((tert-butoxycarbonyl)amino)ethyl)-1,4,6,7-tetrahydrospiro[indazole-5,2'-[1,3]dioxolane]-3-carboxylate (3ab)

To a solution of 3a (650 mg, 2.58 mmol) and tert-butyl (2-bromoethyl)carbamate (1155 mg, 5.15 mmol) in DMF (20 ml) was added $Cs_2CO_3$ (2519 mg, 7.73 mmol). The reaction mixture was stirred at room temperature overnight. The reaction was quenched with water. The organic layer was separated and the aqueous one was extracted with EtOAc (3×30 mL). The combined organic layers were washed with brine and dried over anhydrous $Na_2SO_4$. Solvent was then removed under reduced pressure and the residue was purified by silica gel chromatography (n-hexanes/ethyl acetate=0:1 to 1:1) providing compound 3ab (204 mg, 20% yield) followed by 3aa as a light oil (795 mg, 78% yield).

ethyl 2-(2-((tert-butoxycarbonyl)amino)ethyl)-2,4,6,7-tetrahydrospirolindazole-5,2'-[1,3]dioxolane]-3-carboxylate (3aa) $^1$H NMR (500 MHz, $CDCl_3$) δ 4.55 (t, J=5.6 Hz, 2H), 4.28 (q, J=7.1 Hz, 2H), 3.98 (t, J=5.0 Hz, 4H), 3.49 (t, J=6.0 Hz, 2H), 2.92 (s, 2H), 2.81 (t, J=6.7 Hz, 2H), 1.91 (t, J=6.7 Hz, 2H), 1.36 (s, 9H), 1.32 (t, J=7.1 Hz, 3H). $^{13}$C NMR (126 MHz, $CDCl_3$) δ 160.18, 155.75, 147.03, 129.29, 120.33, 108.50, 79.18, 64.71, 60.87, 51.31, 40.95, 33.54, 31.44, 28.40, 27.94, 21.14, 14.33.

ethyl 1-(2-((tert-butoxycarbonyl)amino)ethyl)-1,4,6,7-tetrahydrospiro[indazole-5,2'-[1,3]dioxolane]-3-carboxylate (3ab) $^1$H NMR (500 MHz, $CDCl_3$) δ 4.57 (t, J=5.6 Hz, 2H), 4.29 (q, J=7.1 Hz, 2H), 4.01 (tt, J=6.4, 3.1 Hz, 4H), 3.51 (q, J=5.6 Hz, 2H), 2.93 (s, 2H), 2.83 (t, J=6.7 Hz, 2H), 1.92 (t, J=6.7 Hz, 2H), 1.38 (s, 9H), 1.33 (t, J=7.1 Hz, 3H). $^{13}$C NMR (126 MHz, $CDCl_3$) δ 160.21, 155.78, 147.06, 129.35, 120.37, 108.53, 79.24, 64.75, 60.92, 51.35, 40.98, 33.57, 31.47, 28.43, 21.17, 14.37.

Synthesis of ethyl 2-(2-aminoethyl)-2,4,6,7-tetrahydrospiro[indazole-5,2'-[1,3]dioxolane]-3-carboxylate (3ac)

TFA (1 ml, 12.98 mmol) was added to a solution of 3aa (680 mg, 1.720 mmol) in dichloromethane (Volume: 10 ml). The reaction was stirred at room temperature until the reaction was complete. The solvent was removed under reduced pressure and the residue was washed with 10% NaOH to afford the free amine which was used without further purification.

Synthesis of 3,4,7,8-tetrahydro-2H-spiro[pyrazino[1,2-b]indazole-9,2'-[1,3]dioxolan]-1(10H)-one (3ae)

To a solution of 3ac (535 mg, 1.812 mmol) in dioxane/water (10 ml) was added sodium carbonate (1152 mg, 10.87 mmol). The reaction mixture was stirred at room temperature overnight. The solvent was removed under reduced pressure and the residue was extracted with EtOAc (3×30 mL). The combined organic layers were dried over anhydrous $Na_2SO_4$. Solvent was then removed under reduced pressure and the residue was purified by silica gel chromatography (DCM/MeOH=0-10% MeOH) providing compound 3ae (384 mg, 85% yield) as a yellow solid, $^1$H NMR (500 MHz, $CDCl_3$) δ 4.26 (t, J=6.1 Hz, 2H), 3.99 (s, 4H), 3.76-3.66 (m, 2H), 2.99 (s, 2H), 2.88 (t, J=6.6 Hz, 2H), 1.97 (t, J=6.7 Hz, 2H). $^{13}$C NMR (126 MHz, $CDCl_3$) δ 160.94, 148.05, 129.75, 118.51, 108.41, 64.78, 46.13, 40.13, 32.08, 31.84, 21.32.

Synthesis of 3,4,7,8-tetrahydropyrazino[1,2-b]indazole-1,9(2H,10H)-dione (3af)

To a solution of 3ae (300 mg, 1.204 mmol) in THF (6 ml) was added 3N HCl (2.006 ml, 6.02 mmol). The reaction was heated to 50° C. for 2 hrs. The organic solvent was removed, and the aqueous solvent was neutralized with 10% NaOH and then extracted with DCM (3×10 mL). The combined organic layers were dried over anhydrous $Na_2SO_4$. Solvent was then removed under reduced pressure and the residue was used without further purification.

Synthesis of 9-((4-fluorobenzyl)amino)-3,4,7,8,9,10-hexahydropyrazino[1,2-b]indazol-1(2H)-one (3ag)

A mixture of 3af (30 mg, 0.146 mmol), (4-fluorophenyl)methanamine (0.020 ml, 0.175 mmol) and acetic acid (0.013 ml, 0.219 mmol) in 1,2-dichloroethane (1 ml) was stirred at room temperature for 30 mins, then sodium triacetoxyhydroborate (46.5 mg, 0.219 mmol) was added and stirring was continued overnight. The reaction was diluted with DCM, quenched with $NaHCO_3$, extracted with DCM (3×10 mL). The combined organic layers were dried over anhydrous $Na_2SO_4$. Solvent was then removed under reduced pressure and the residue was purified by prep HPLC (5-95% ACN) to afford 3af (20 mg, 44% yield) as a yellow solid. $^1$H NMR (500 MHz, DMSO-d6) δ 8.24 (s, 1H), 8.03 (t, J=2.8 Hz, 1H), 7.48-7.41 (m, 2H), 7.16 (t, J=8.8 Hz, 2H), 4.16 (dd, J=7.1, 5.0 Hz, 2H), 3.89 (s, 2H), 3.53 (td, J=6.1, 5.2, 2.8 Hz, 2H), 3.08 (dd, J=16.2, 5.0 Hz, 1H), 2.95 (tdd, J=8.3, 5.1, 2.4 Hz, 1H), 2.71 (dt, J=16.3, 4.9 Hz, 1H), 2.57-2.51 (m, 1H), 2.47 (d, J=8.8 Hz, 1H), 2.05 (dd, J=12.8, 6.3 Hz, 1H), 1.65 (dtd, J=12.9, 10.1, 5.4 Hz, 1H). $^{13}$C NMR (126 MHz, DMSO-d6) δ 164.09, 162.30, 159.40, 147.10, 134.97, 130.44, 129.47, 116.30, 114.99, 52.40, 48.65, 45.76, 39.02, 27.63, 26.88, 20.80.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound described by Formulas I, II, III, IV, V, or VI:

(Formula I)

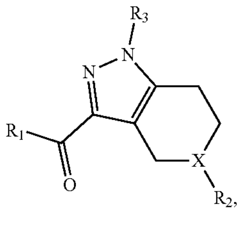

-continued
(Formula II)
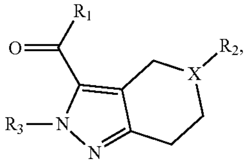
(Formula III)
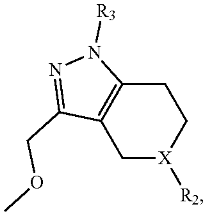
(Formula IV)
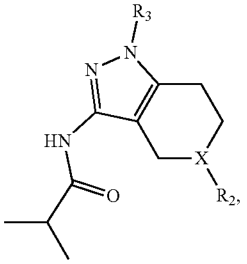
(Formula V)
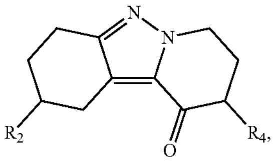
and
(Formula VI)
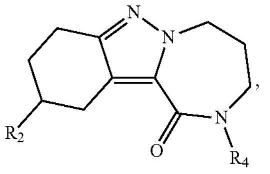
including pharmaceutically acceptable salts, solvates, and/or prodrugs thereof;
wherein X is either CH or Nitrogen;
wherein $R_1$ is selected from
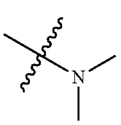
,
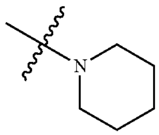
,
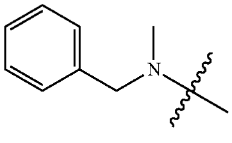
,
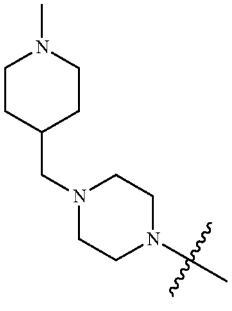
,
-continued
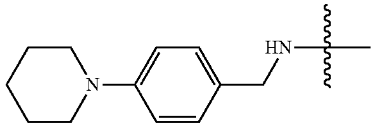
,
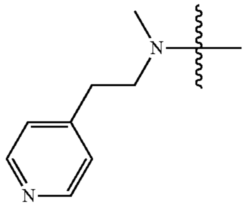
,
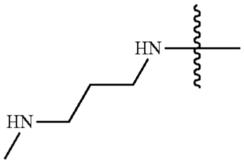
,
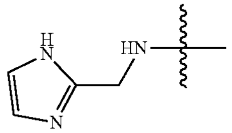
,
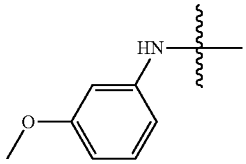
,
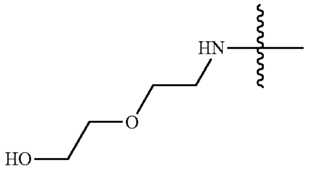
,
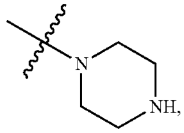
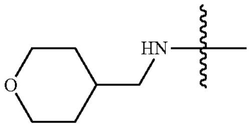
,
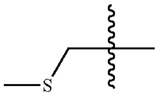
,
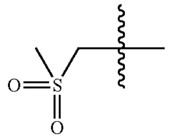
, and
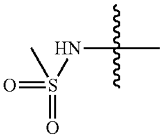
;
wherein $R_2$ is selected from Hydrogen,
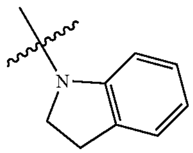
,
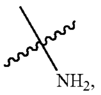
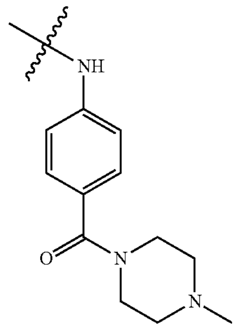
,
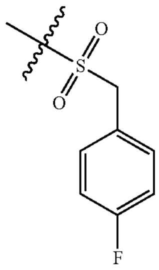
,
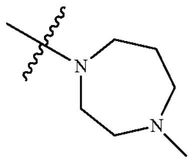
, -continued
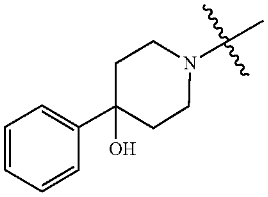,
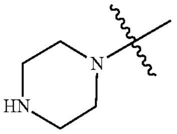,
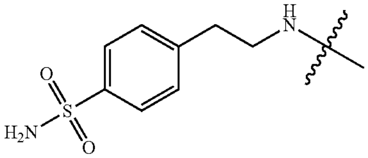,
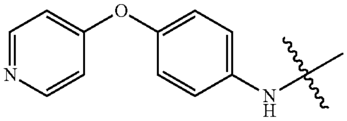,
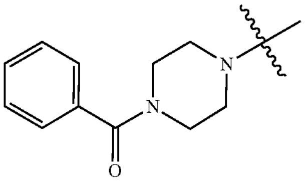,
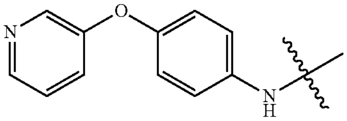,
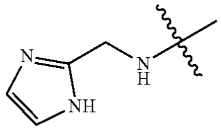,
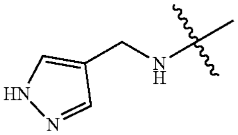,
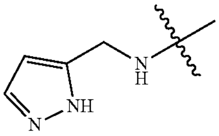,
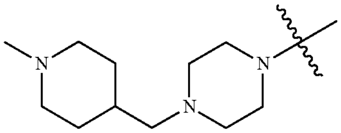,
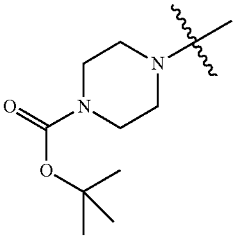,
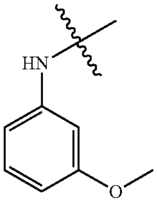,
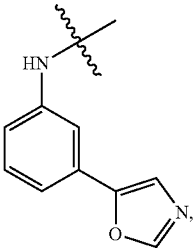
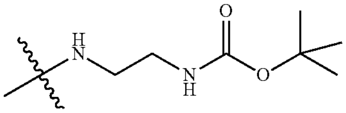,
-continued
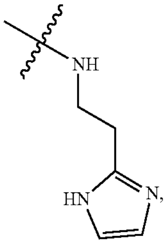
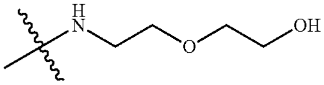,
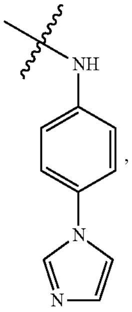
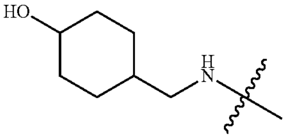,
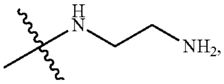
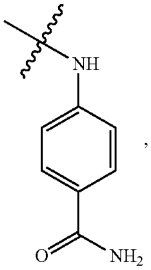,
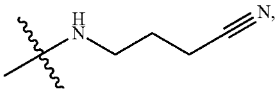
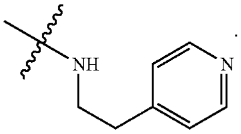.
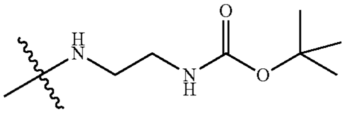,
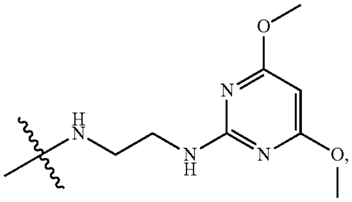
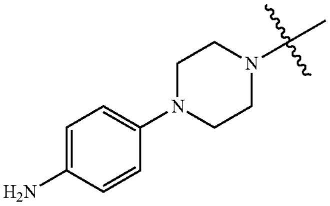,
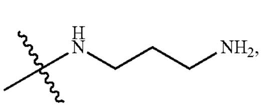
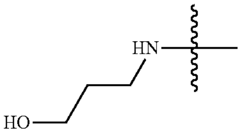,
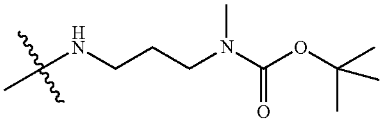, -continued
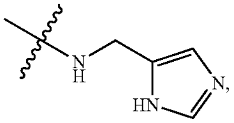
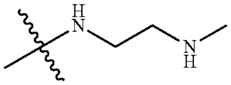
,
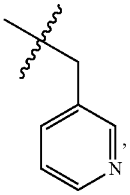
,
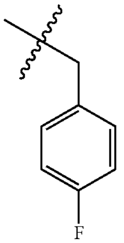
,
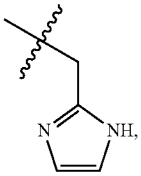
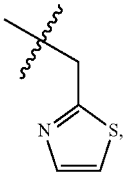
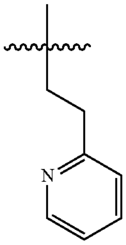
,
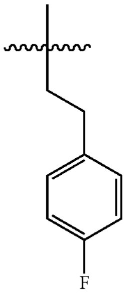
,
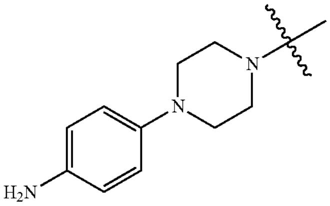
,
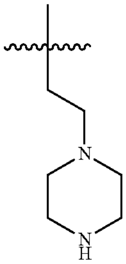
,
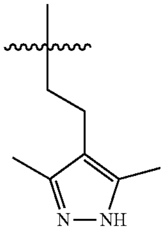
,
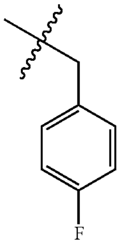
,
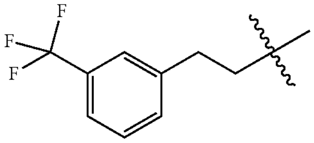
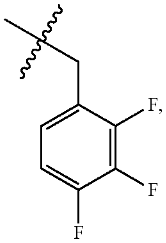
,
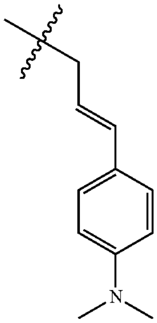
,
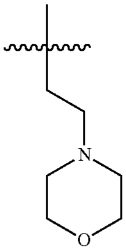
,
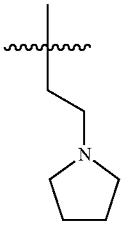
,
-continued
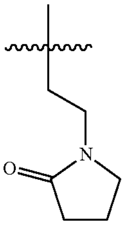
,
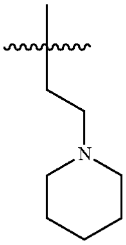
,
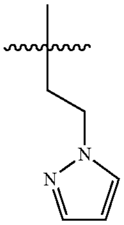
,
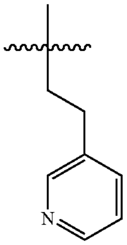
,
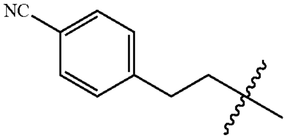
,
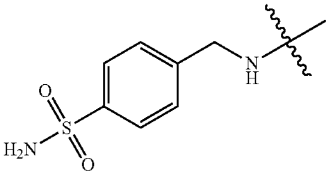
,
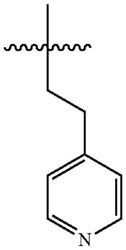
,
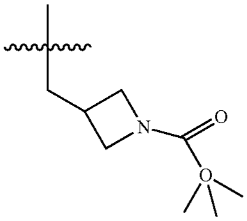
,
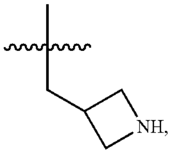
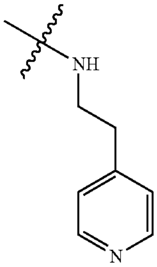
,
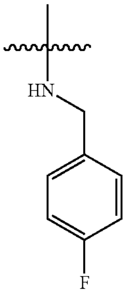
,
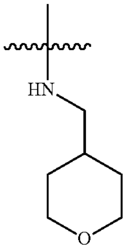
,
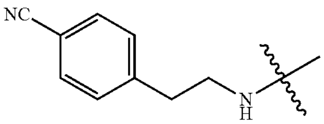
,
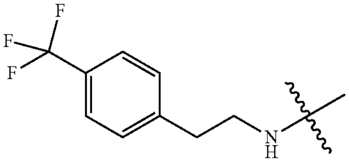
,
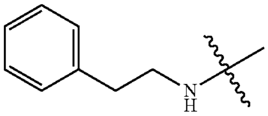
, -continued
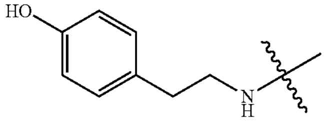,
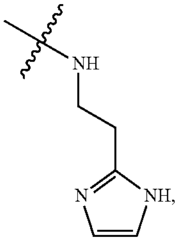
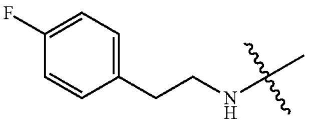,
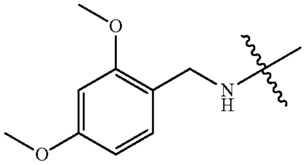,
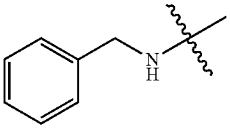,
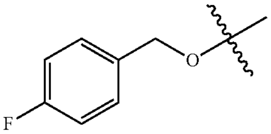,
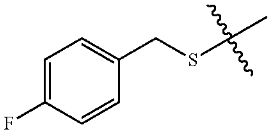,
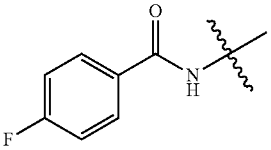,
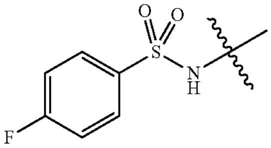,
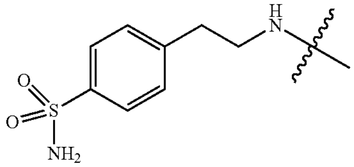,
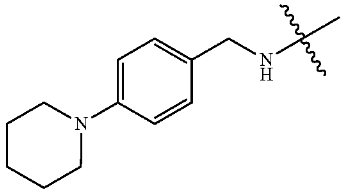,
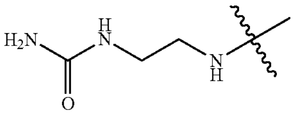,
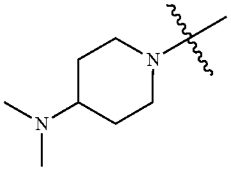,
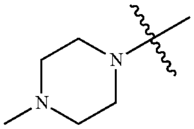,
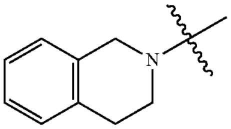,
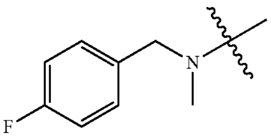,
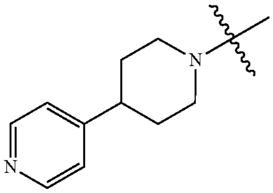,
-continued
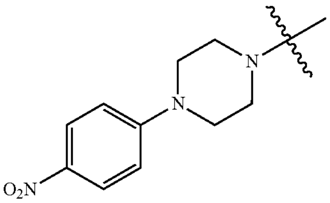,
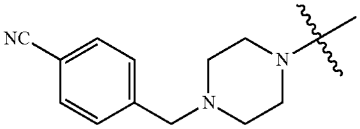,
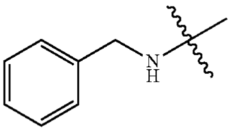,
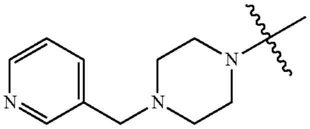,
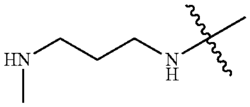,
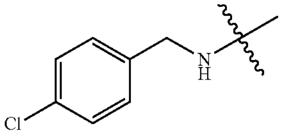,
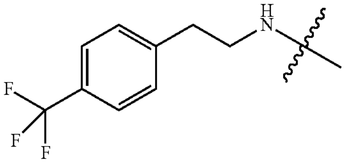,
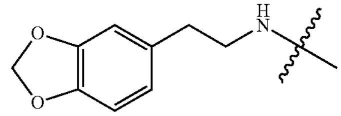,
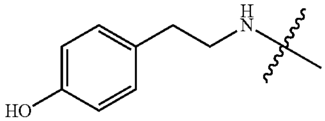,
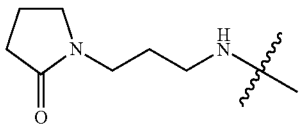,
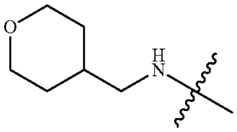,
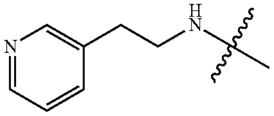,
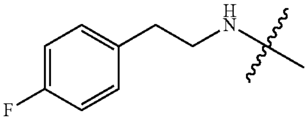,
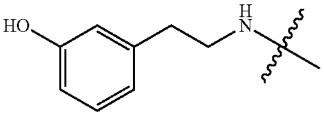, and
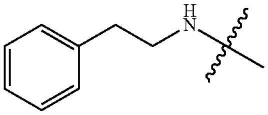;

wherein $R_3$ is selected from
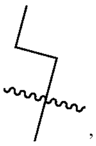,
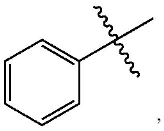,
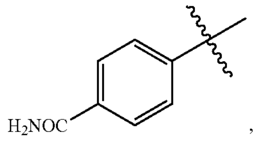,
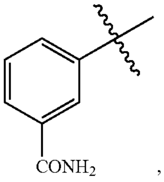,
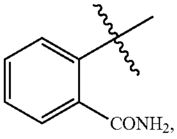,
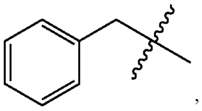,
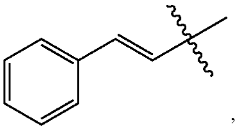,
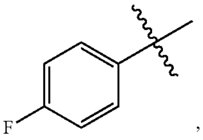, and
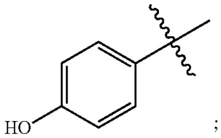;
wherein $R_4$ is Hydrogen or methyl;
wherein if the compound is described by Formula I
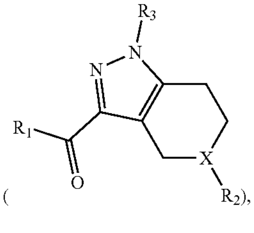
then $R_2$ cannot be
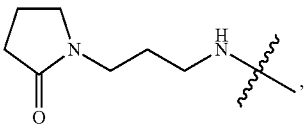,
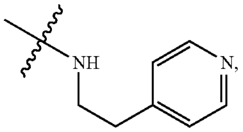
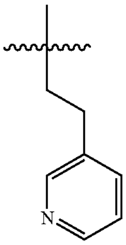, or
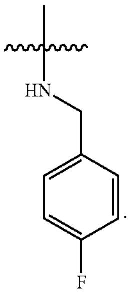.
2. The compound of claim 1, wherein the compound is selected from the group consisting of:
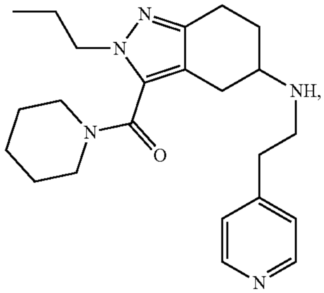
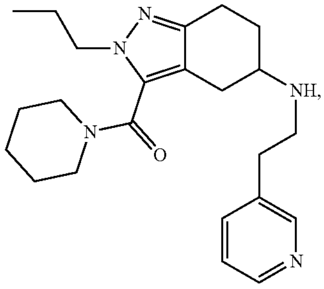
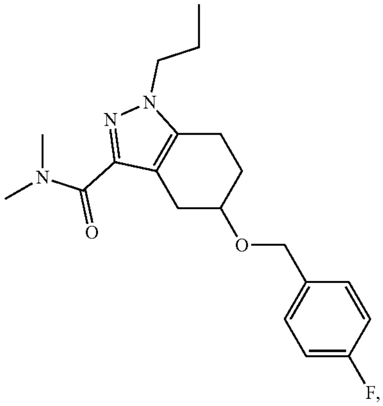
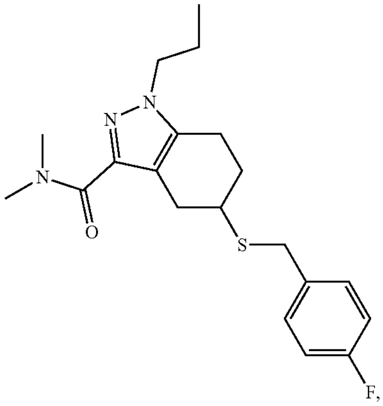

-continued
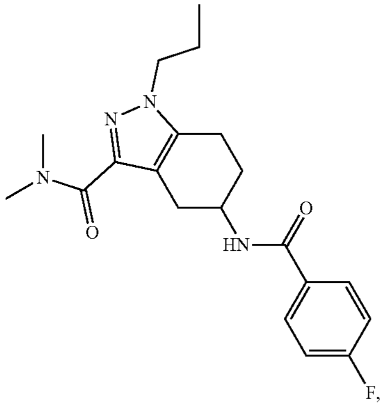
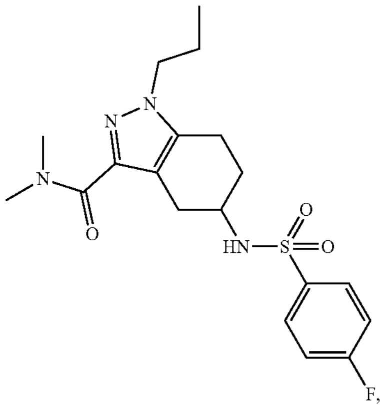
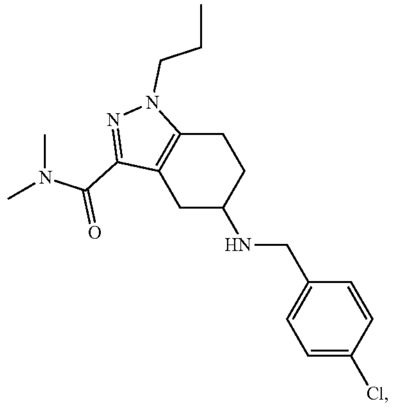
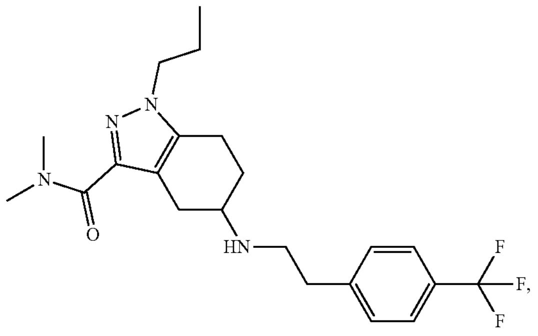
-continued
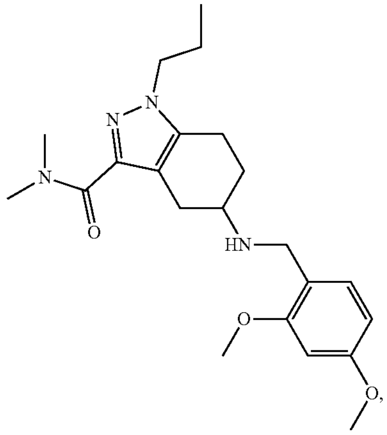
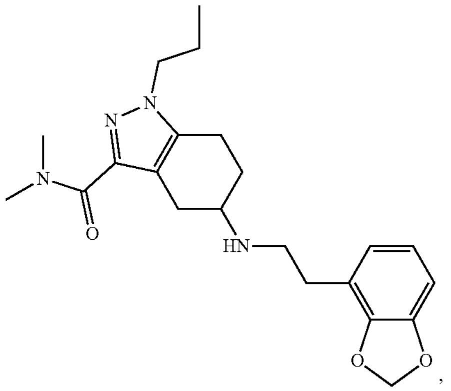
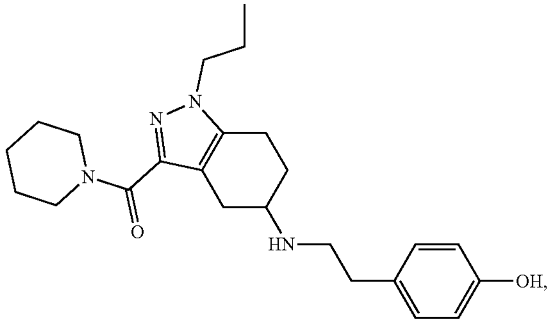
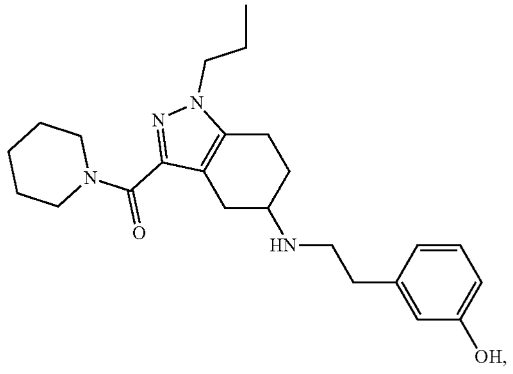

-continued
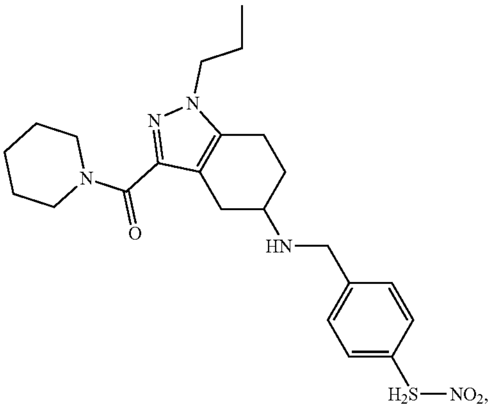
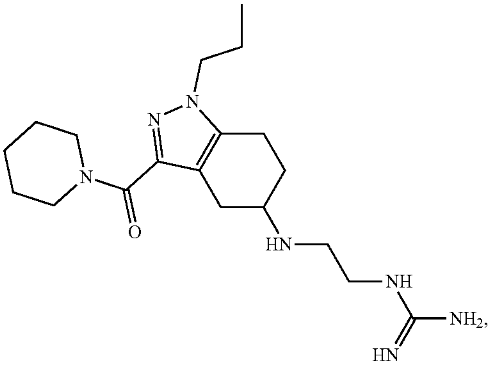
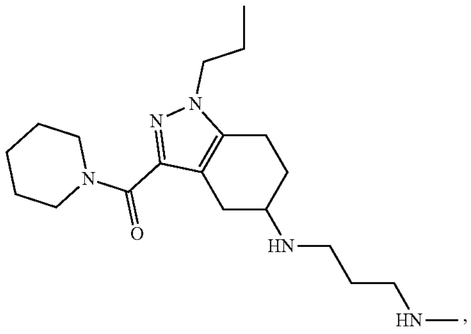
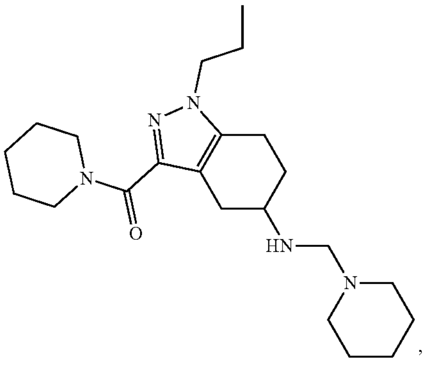
-continued
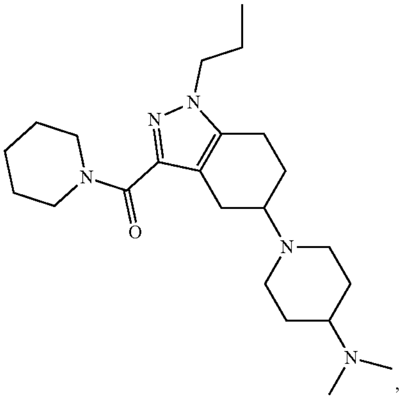
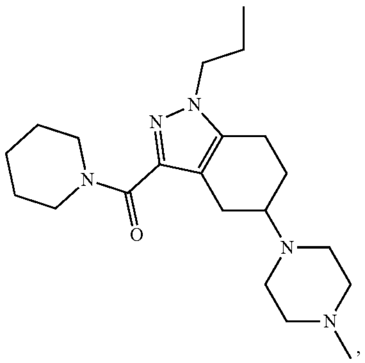
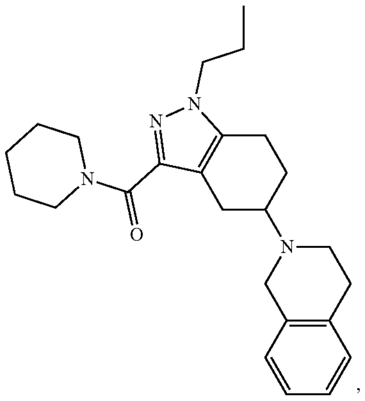
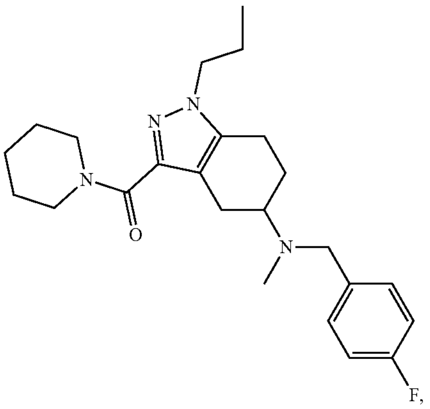

-continued
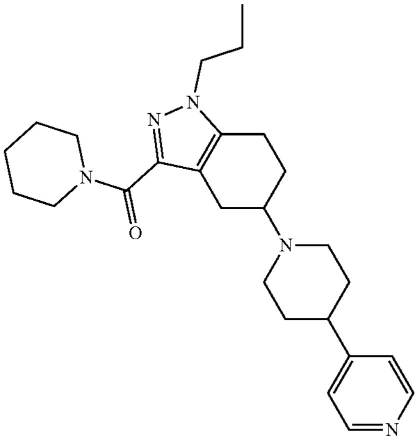
,
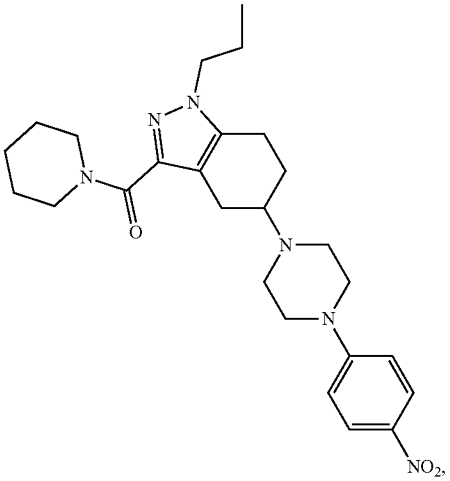
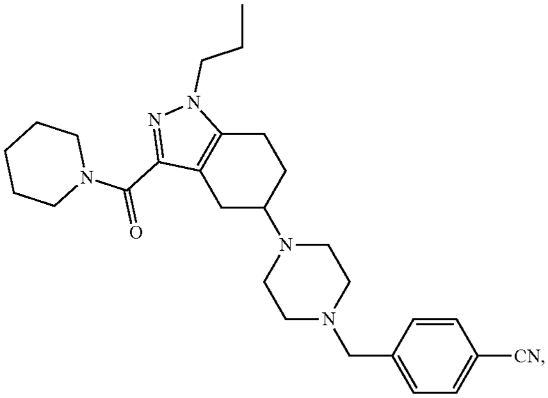
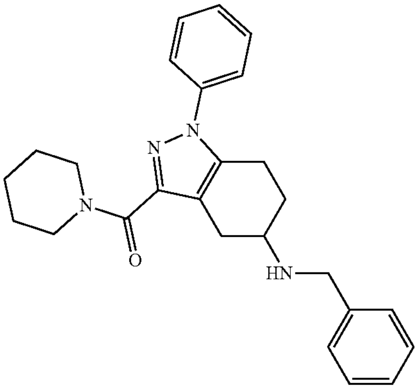
,
-continued
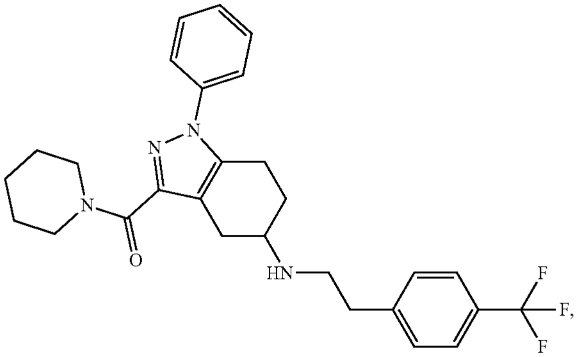
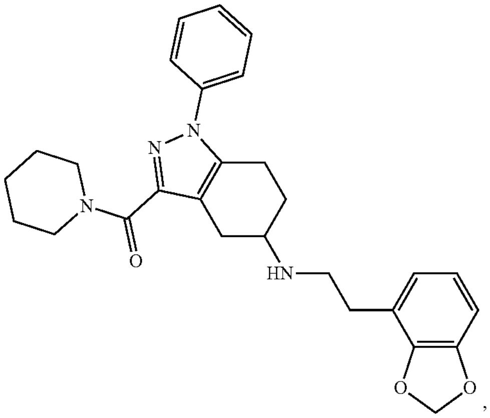
,
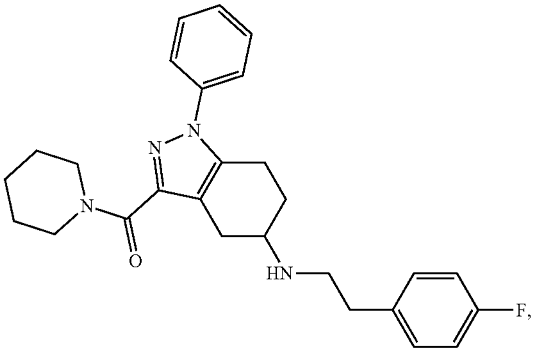
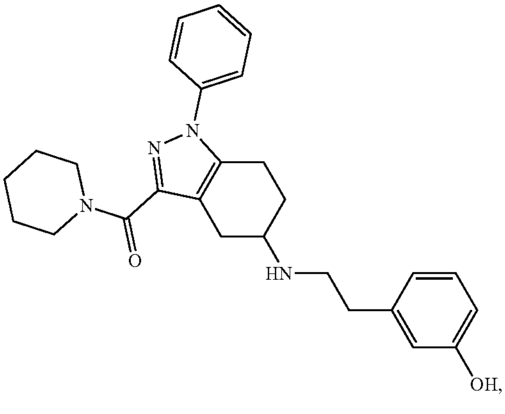

-continued
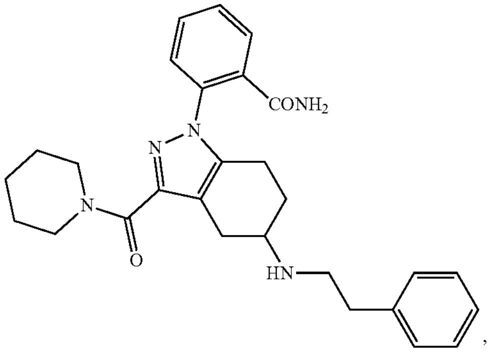
,
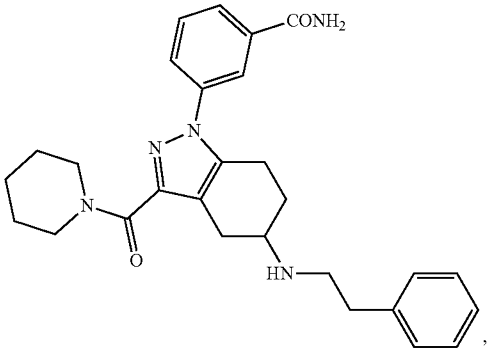
,
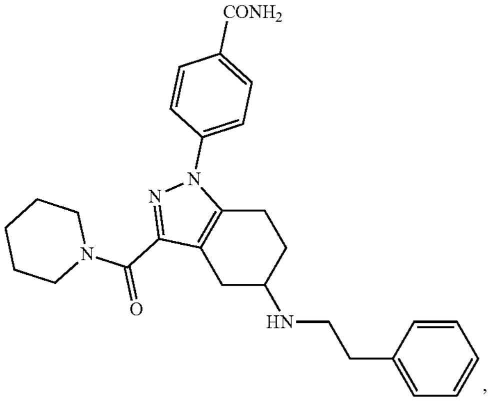
,
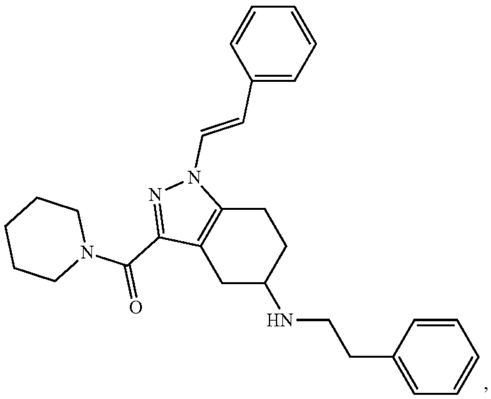
,
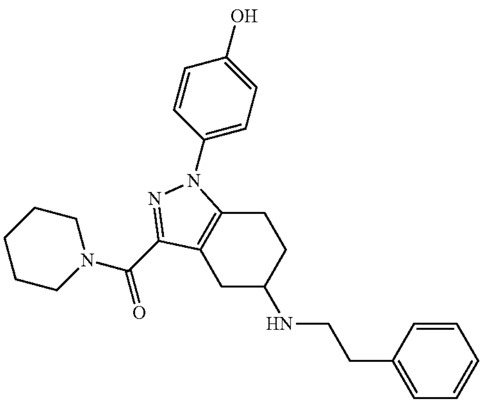
,
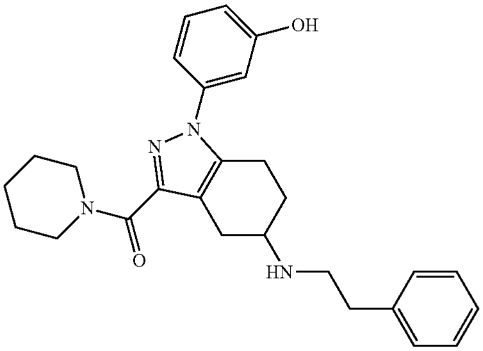
,
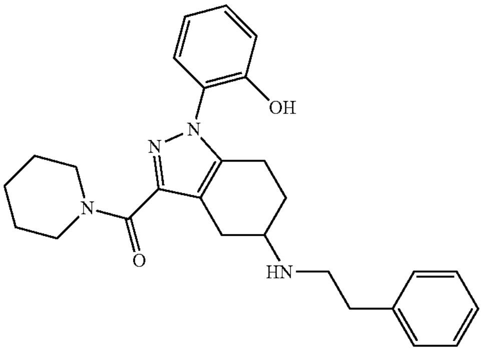
,
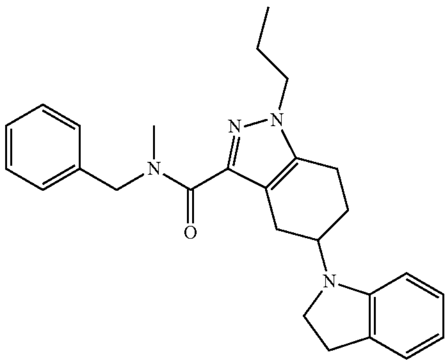
, -continued
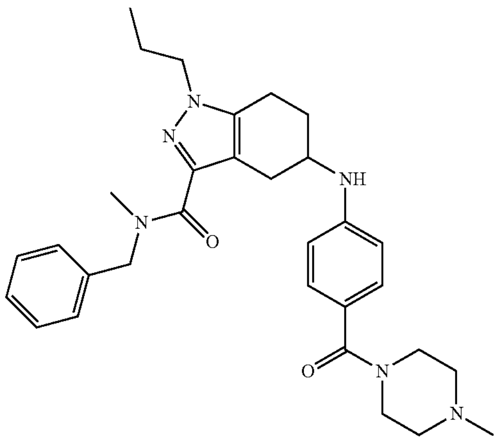
,
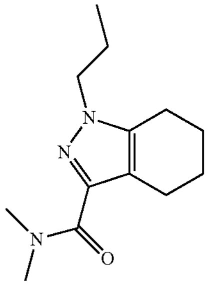
,
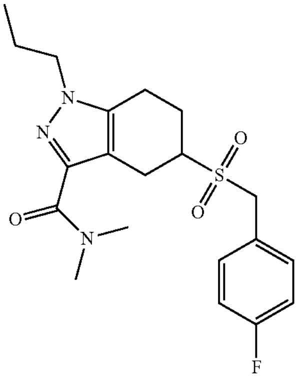
,
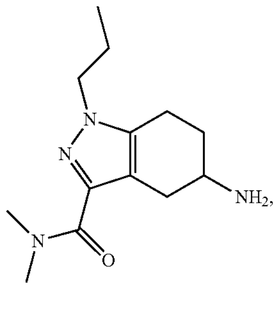
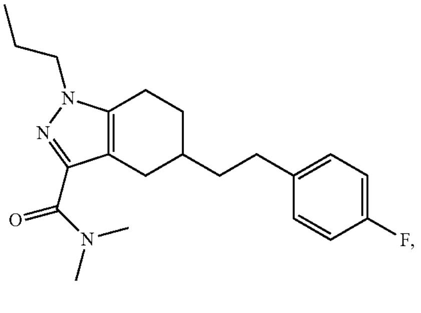
-continued
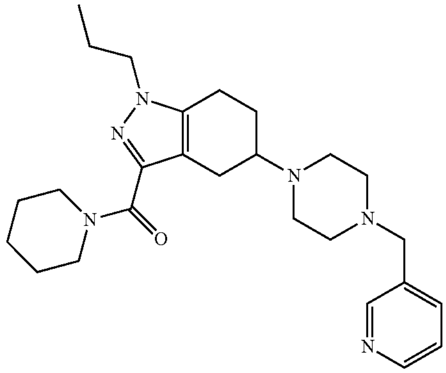
,
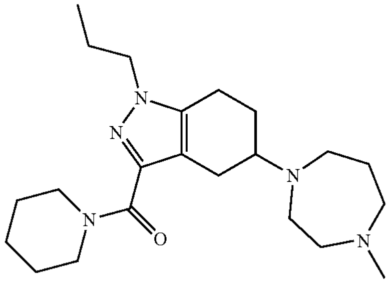
,
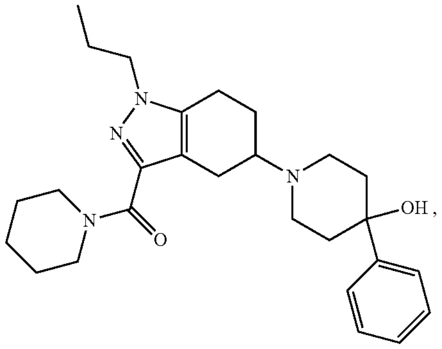
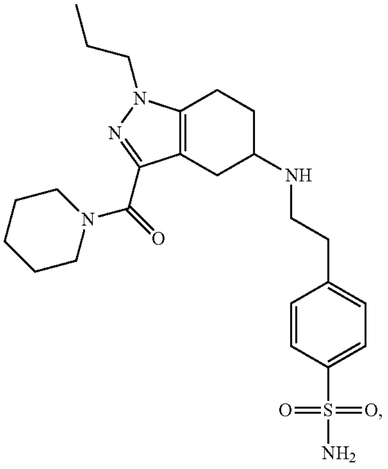

-continued
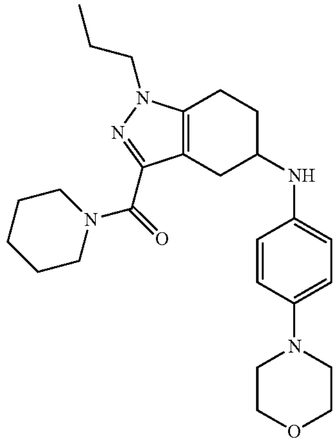
,
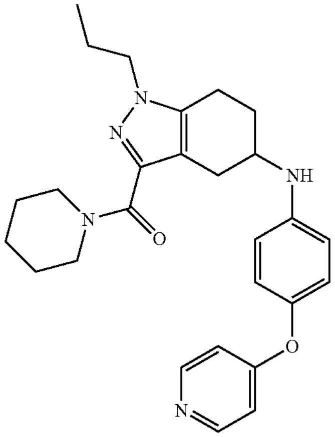
,
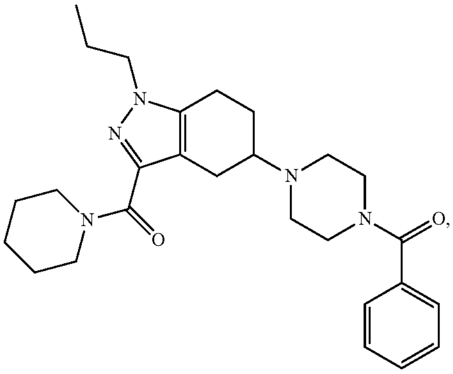
,
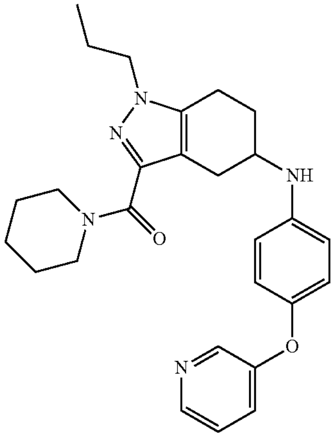
,
-continued
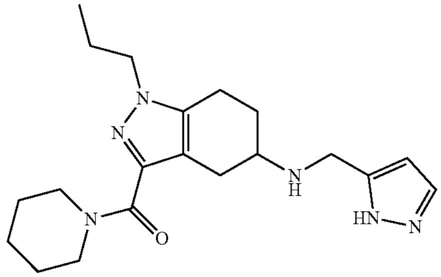
,
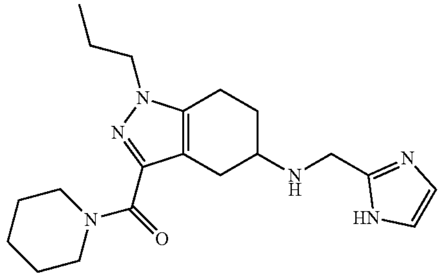
,
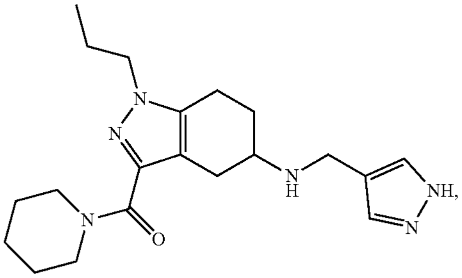
,
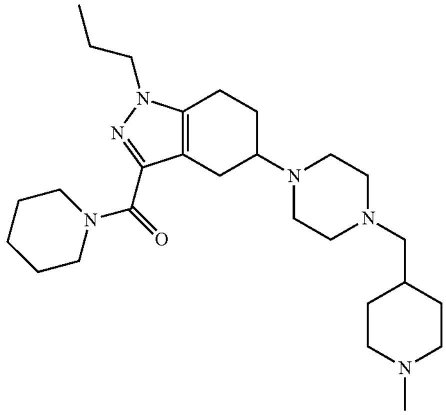
,
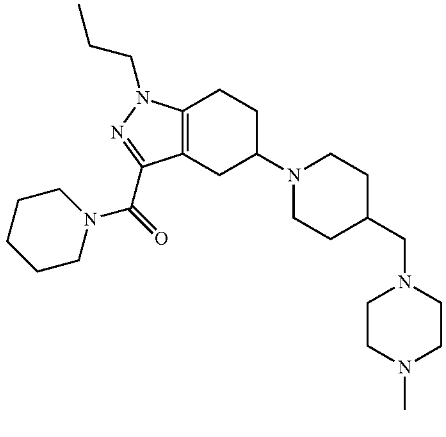
, -continued
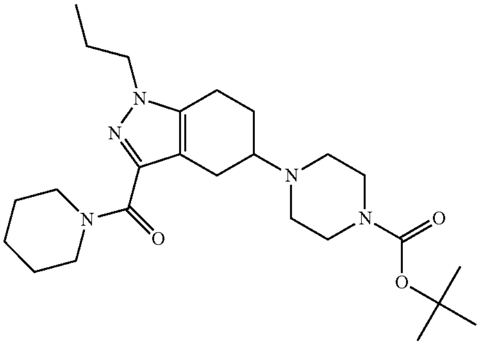
,
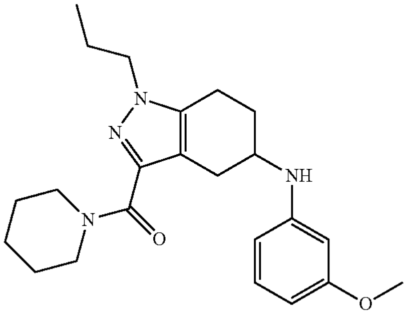
,
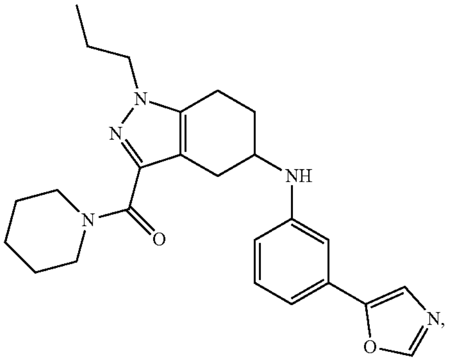
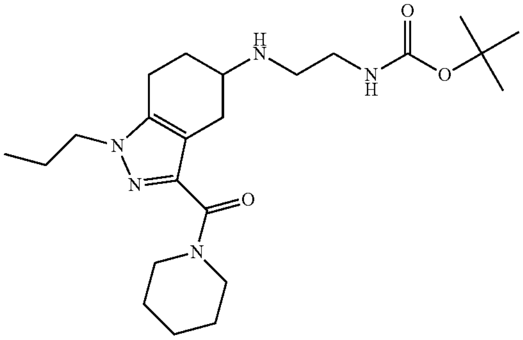
,
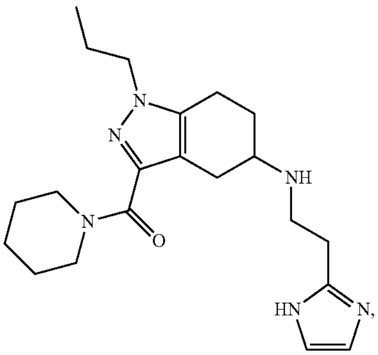
-continued
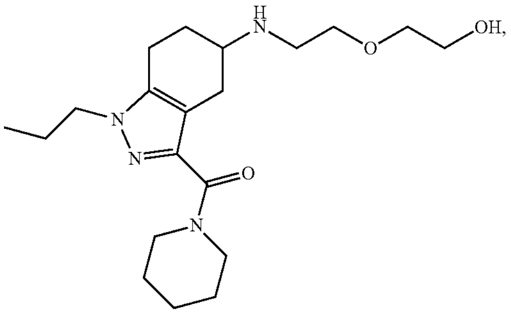
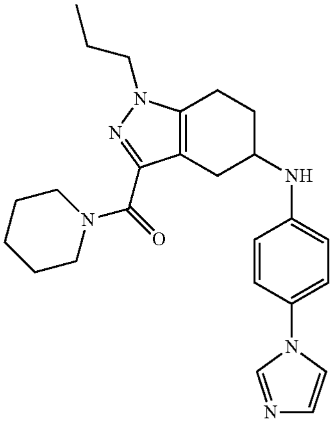
,
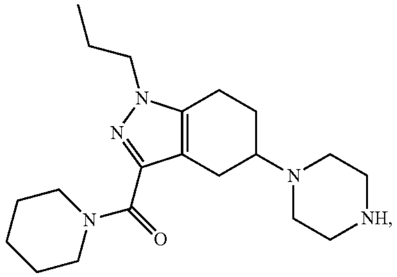
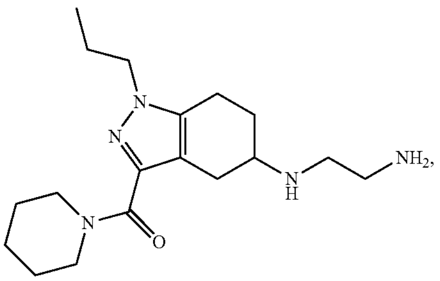
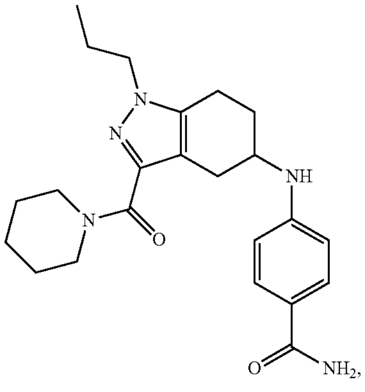

-continued
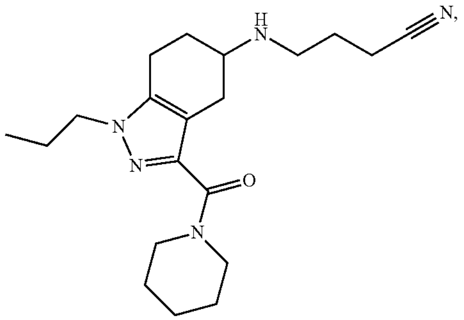
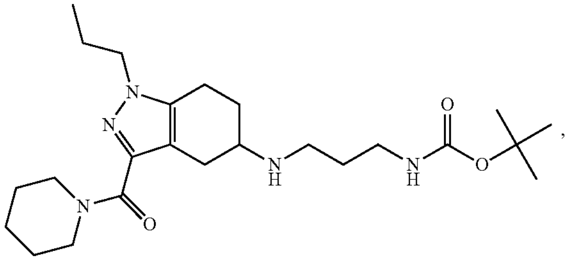
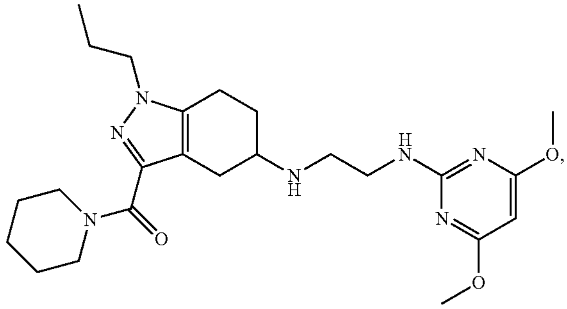
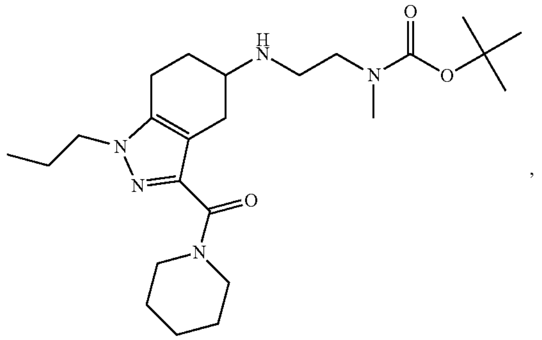
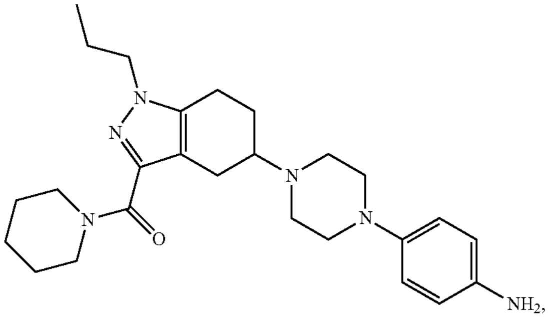
-continued
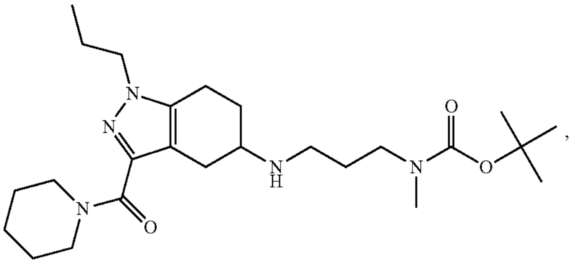
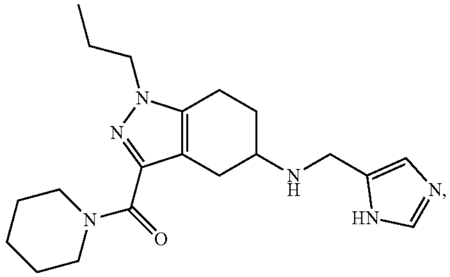
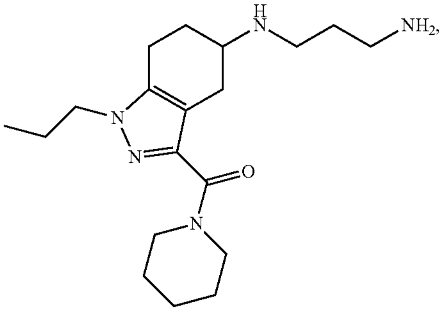
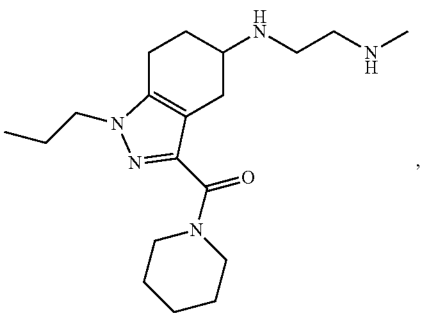
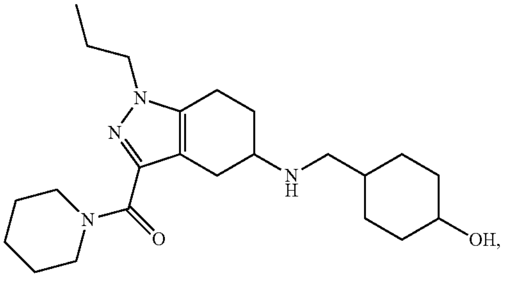

-continued
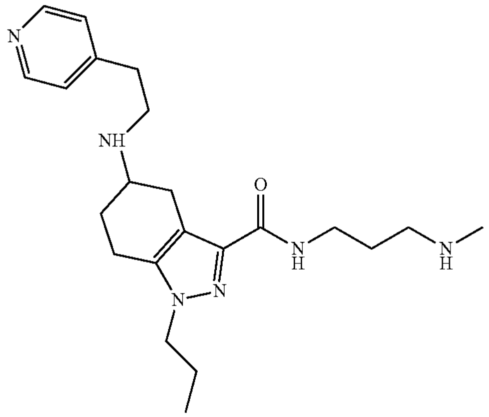
,
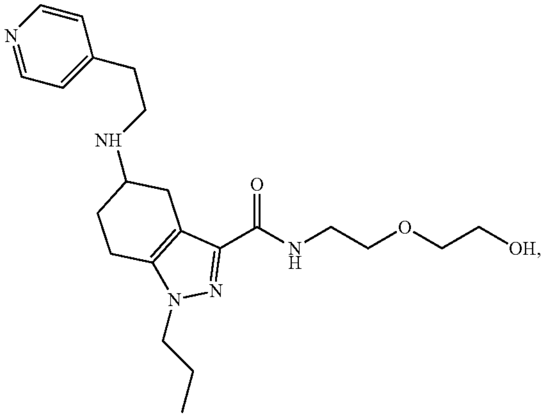 [SMILES: CCCn1nc(C(=O)NCCOCCO)c2c1CCC(NCCc1ccncc1)C2]
OH,
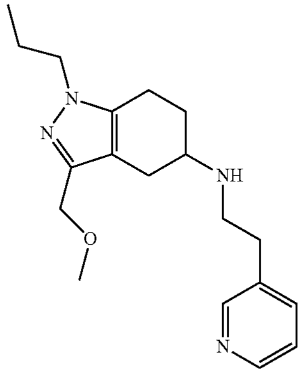
,
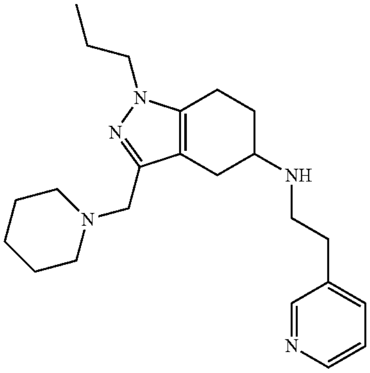
,
-continued
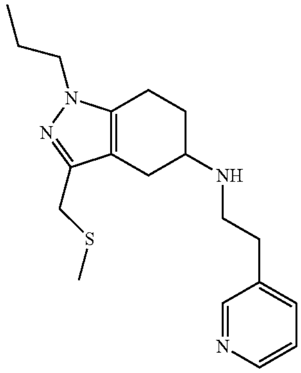
,
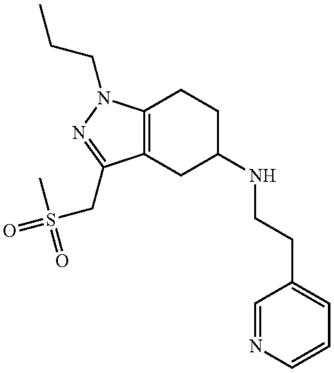
,
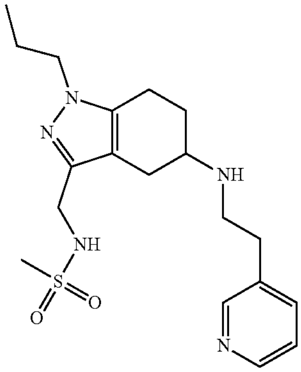
,
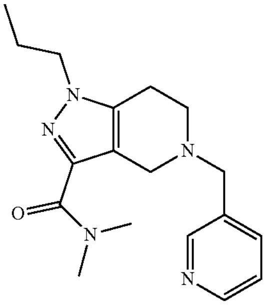
, -continued
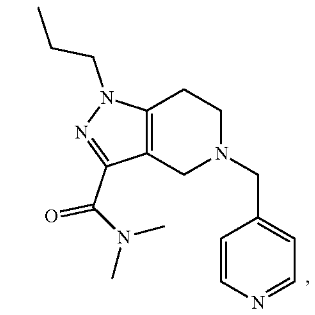
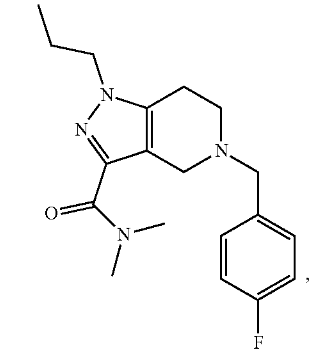
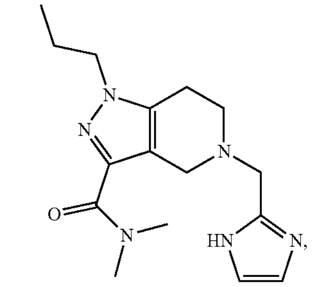
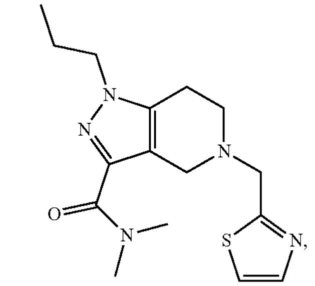
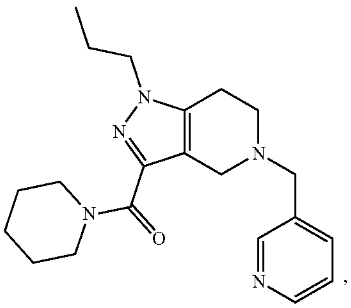
-continued
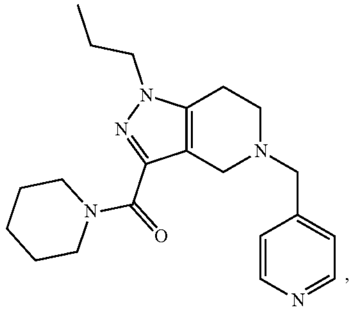
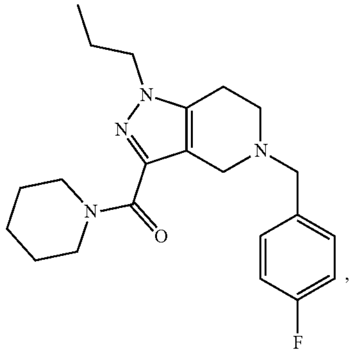
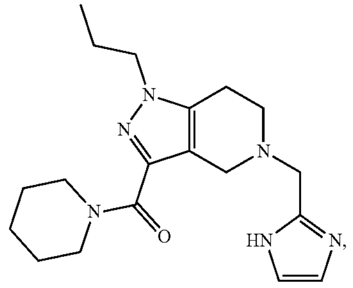
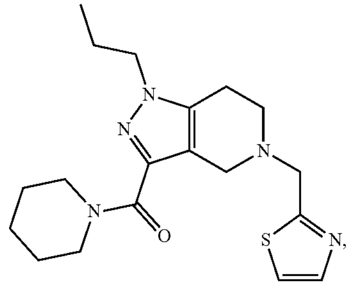
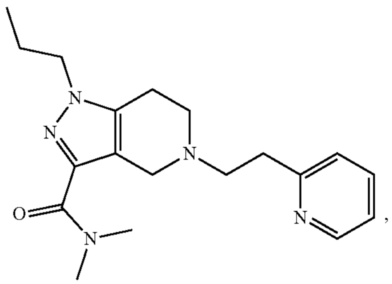

-continued
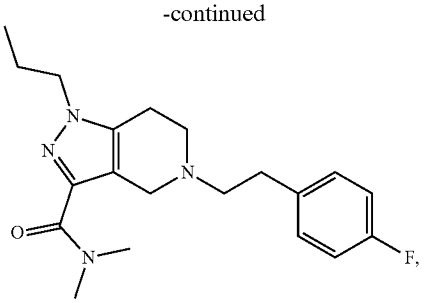
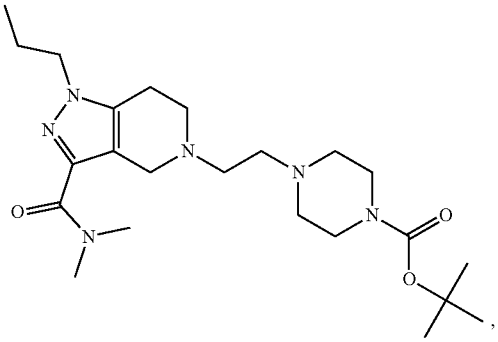
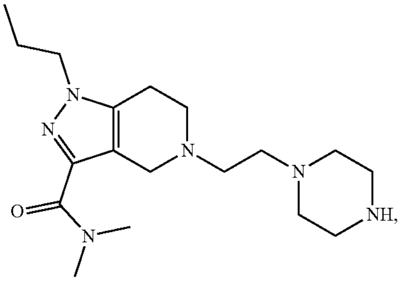
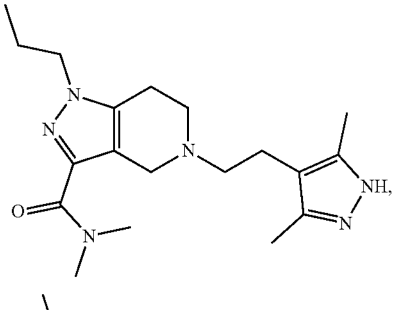
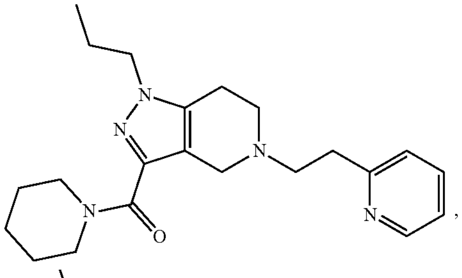
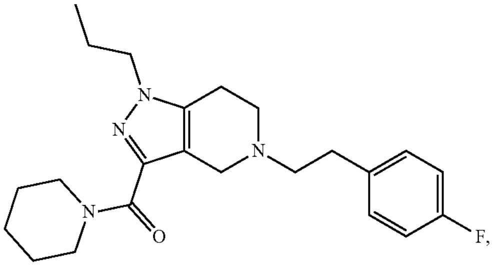
-continued
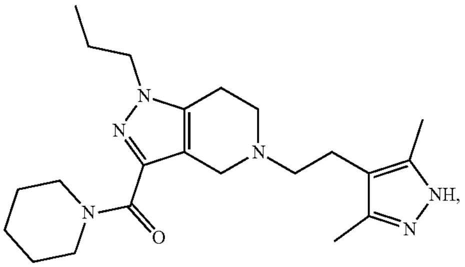
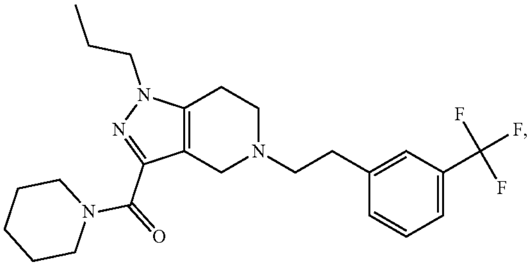
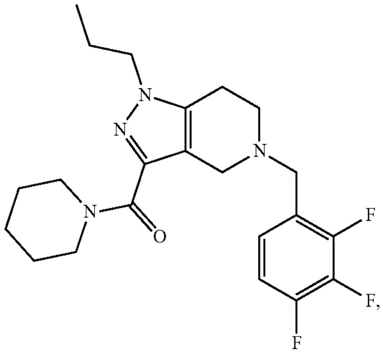
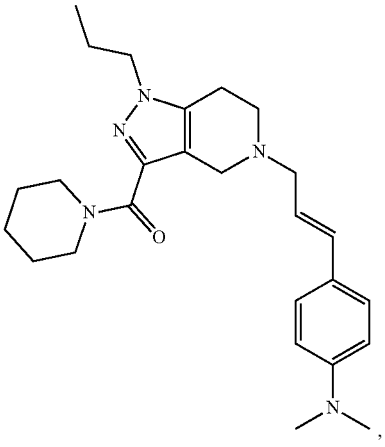
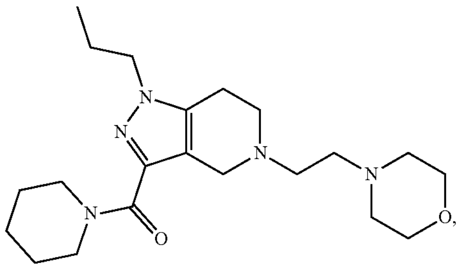

-continued
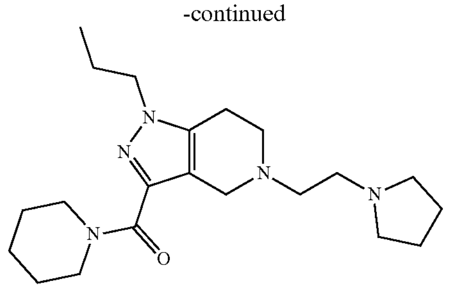
,
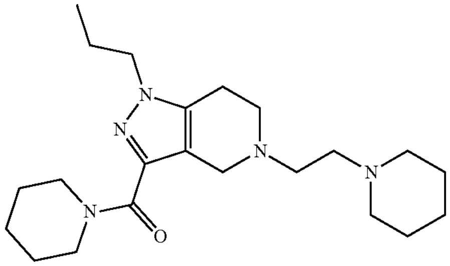
,
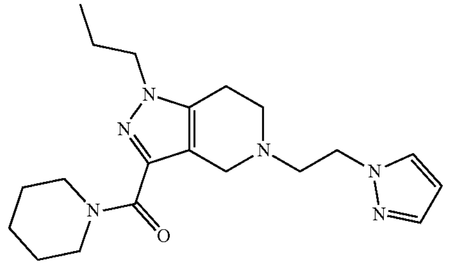
,
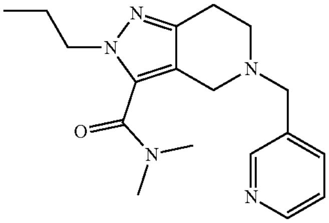
,
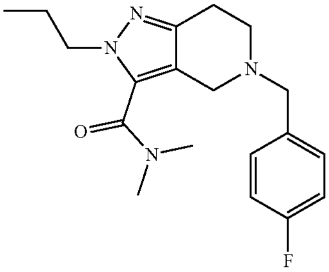
,
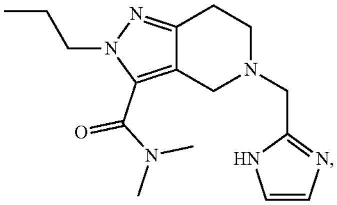
,
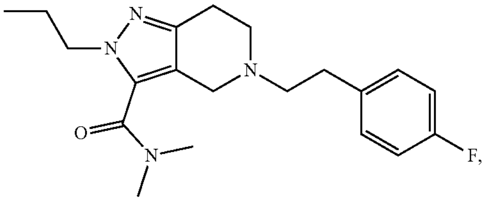
,
-continued
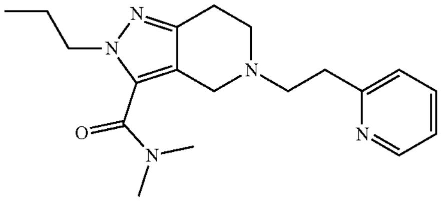
,
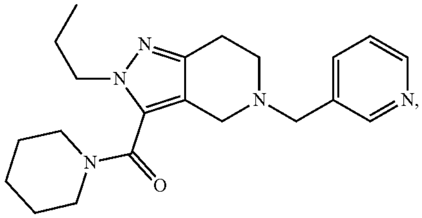
,
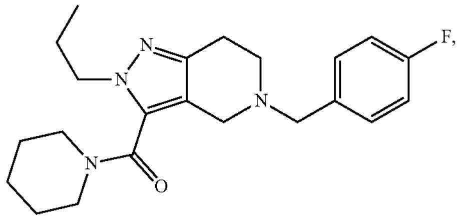
,
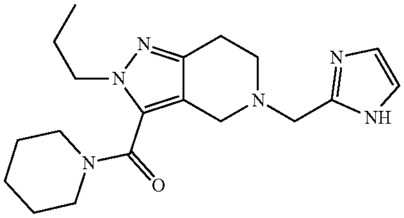
,
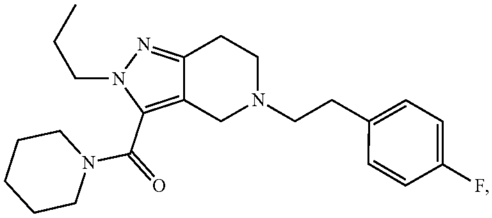
,
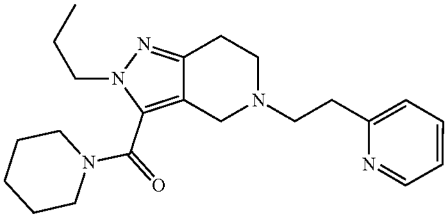
, -continued
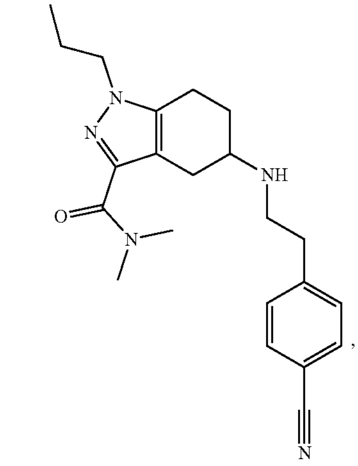
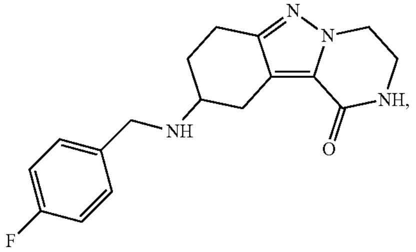
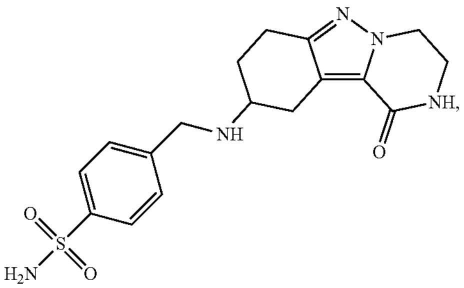
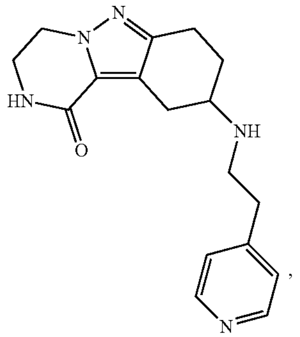
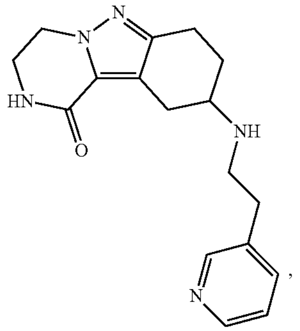
-continued
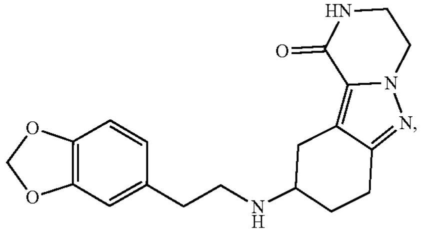
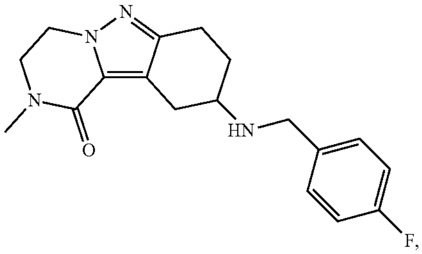
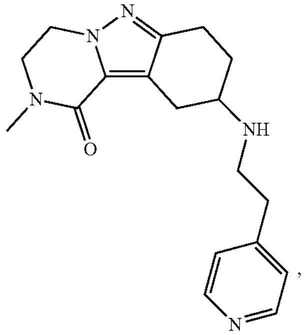
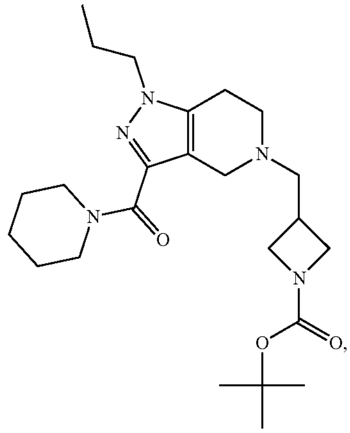
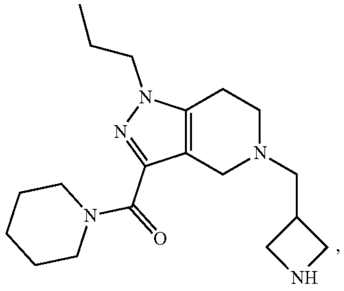

-continued
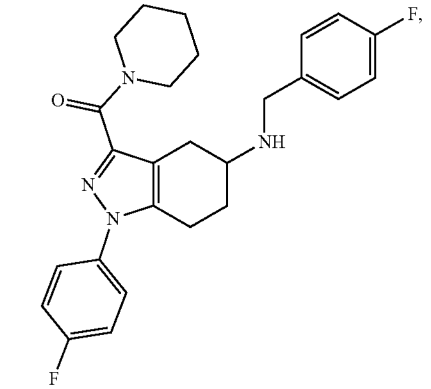
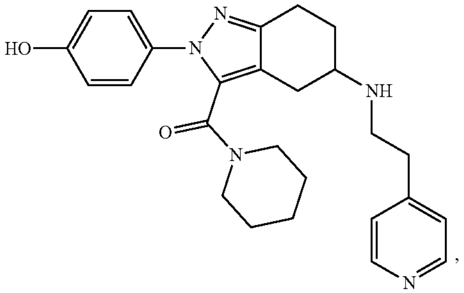
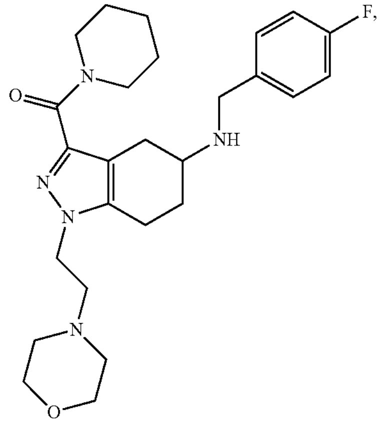 [SMILES: O=C(c1nn(CCN2CCOCC2)c2c1CC(NCc1ccc(F)cc1)CC2)N1CCCCC1]
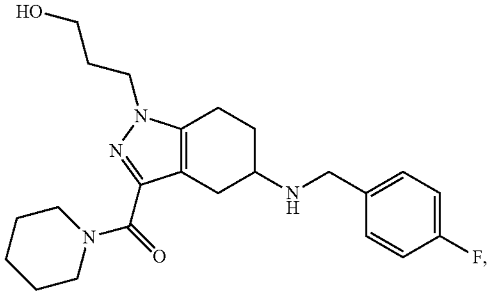
-continued
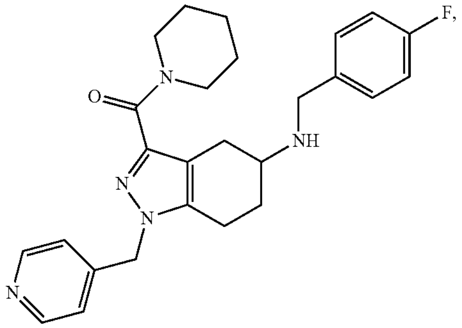
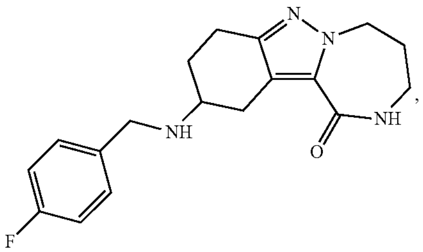
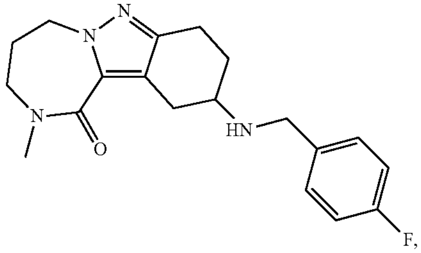
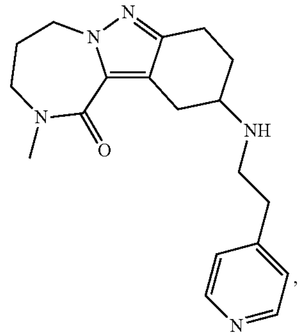
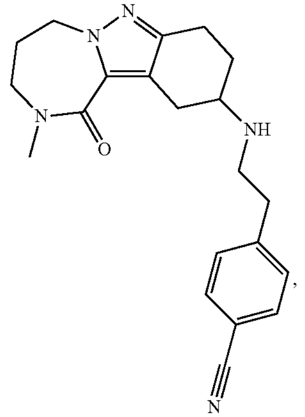

-continued
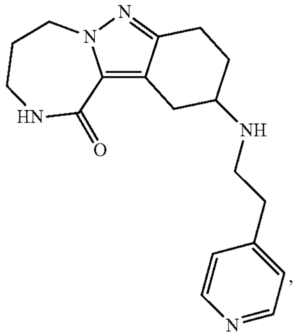
,
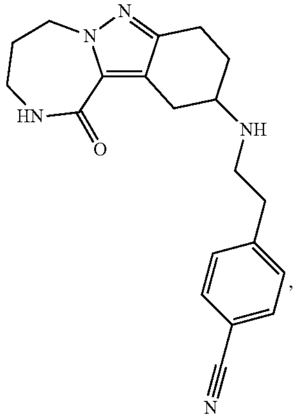
,
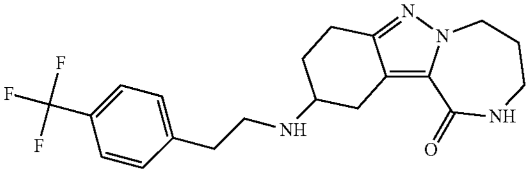
,
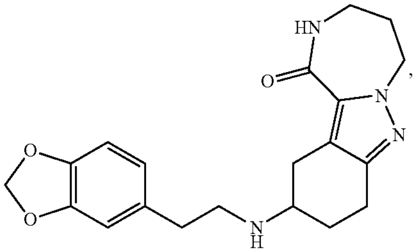
,
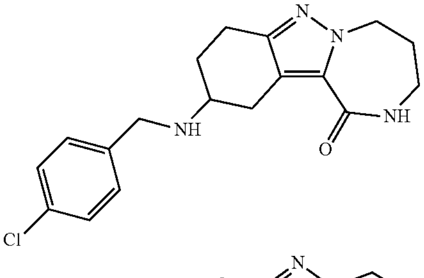
,
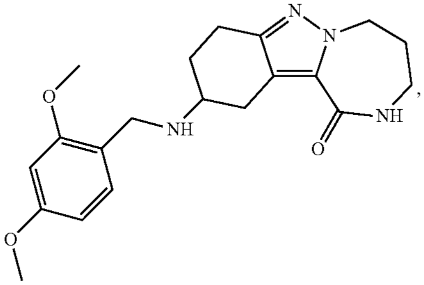
,
-continued
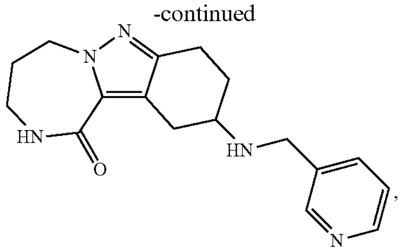
,
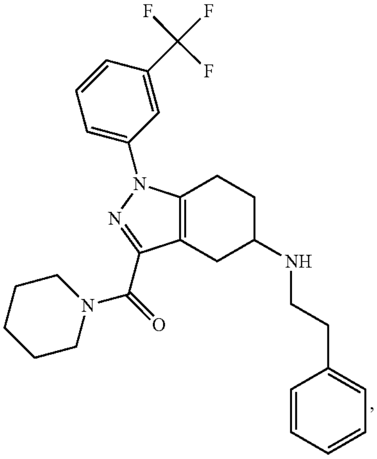
,
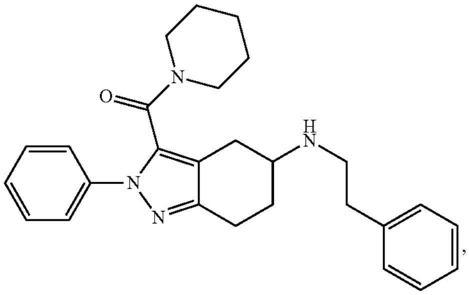
,
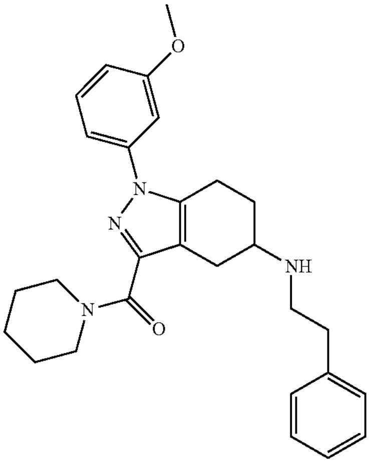
,
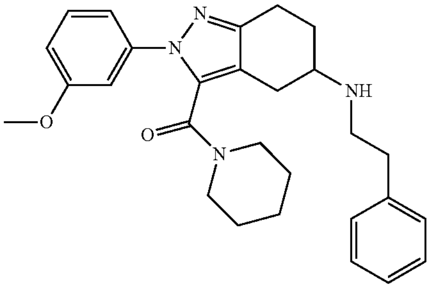
, -continued
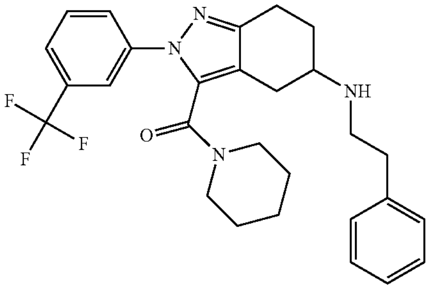
,
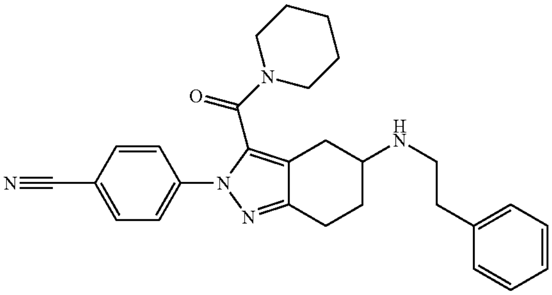
,
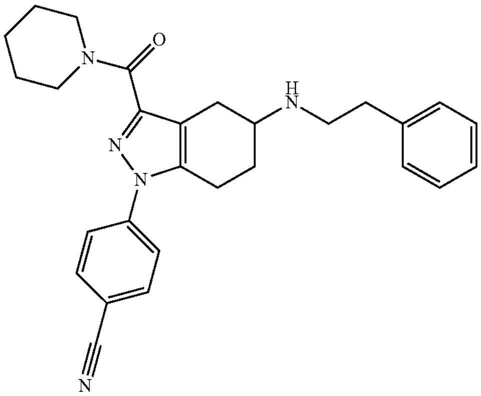
,
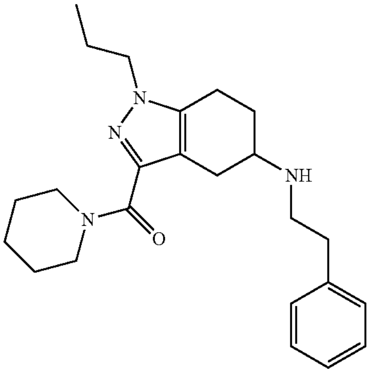
,
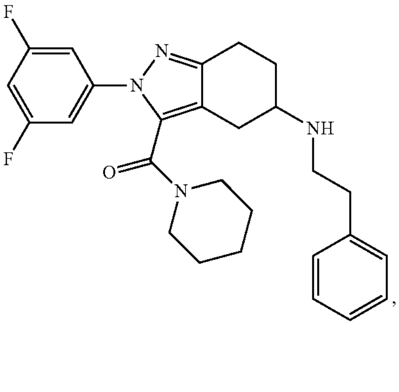
,
-continued
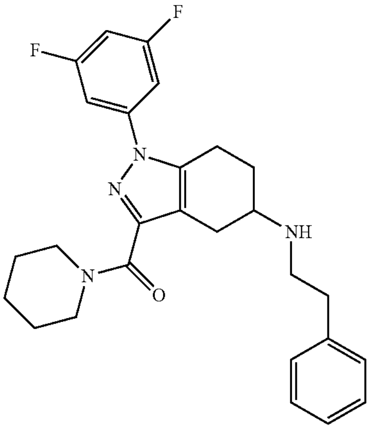
,
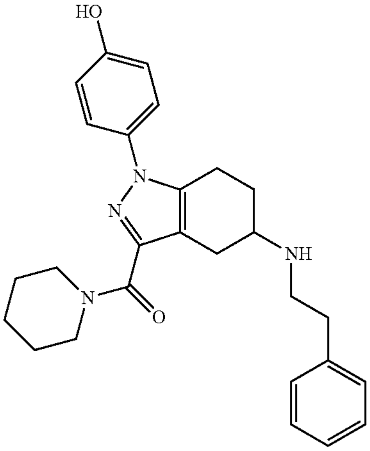
,
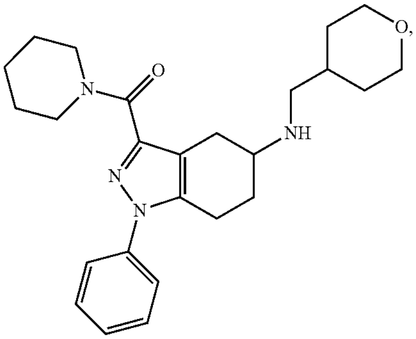
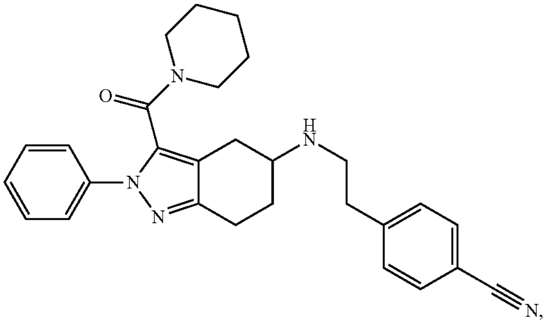

-continued

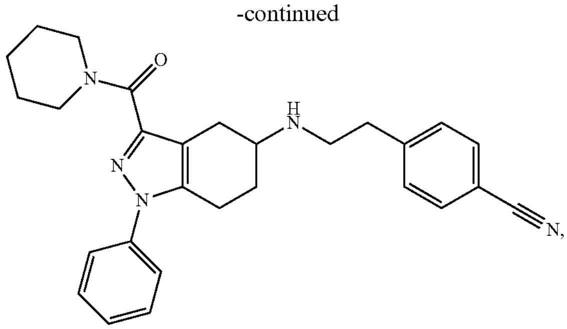

,

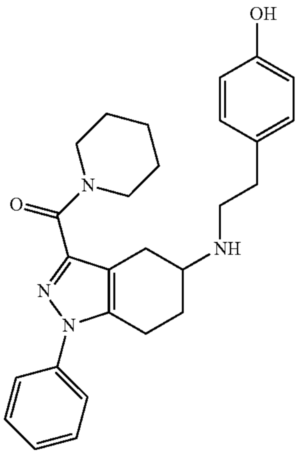

,

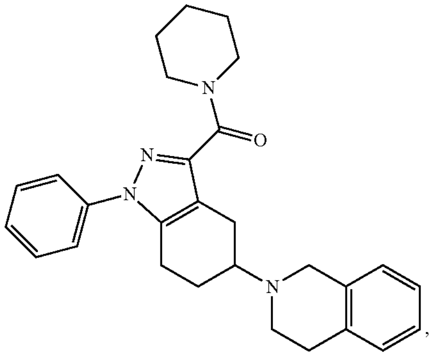

,

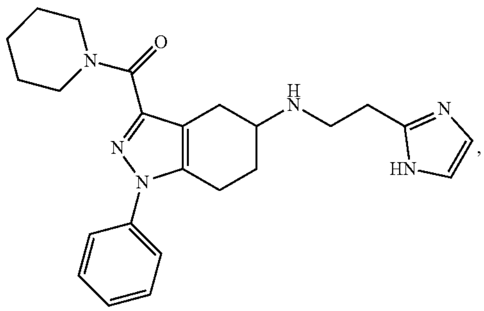

,

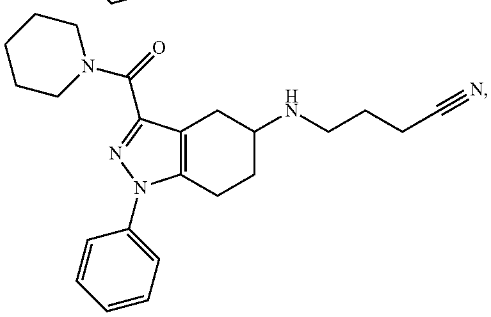

,

-continued

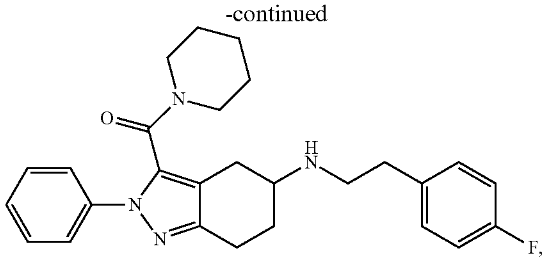

,

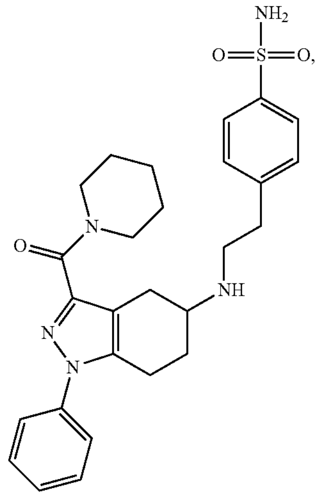

, and

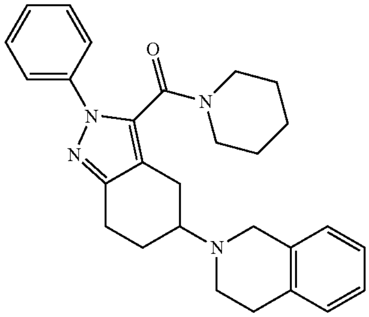

, or a pharmaceutically acceptable salt, solvate, or prodrug thereof, and a pharmaceutically acceptable carrier.

3. The compound of claim 1, wherein the compound is comprised within a pharmaceutical composition.

4. A method of treating, ameliorating, or preventing a disease or condition characterized with sigma-1 receptor activity, sigma-2 receptor activity or both sigma-1 receptor activity and sigma-2 receptor activity, comprising administering to a patient a therapeutically effective amount of a compound of claim 1;

wherein the disease or condition is a neurological or CNS disease or condition, or a hyperproliferative disease or condition, wherein the neurological or CNS disease or condition is one or more of traumatic brain injury, depression, stroke, pain, alcohol addiction, substance abuse, ALS, and Alzheimer's disease, wherein the hyperproliferative disease is any type of cancer characterized with sigma-1 and/or sigma-2 receptor activity selected from liver cancer, esophageal cancer, prostate cancer, breast cancer, pancreatic cancer, and colon cancer.

5. The method of claim 4, wherein the patient is a human patient.

6. The method of claim 4, further comprising administering to said patient one or more anticancer agents, wherein said anticancer agent is selected from one or more of a chemotherapeutic agent and radiation therapy.
7. A compound selected from the group consisting of:
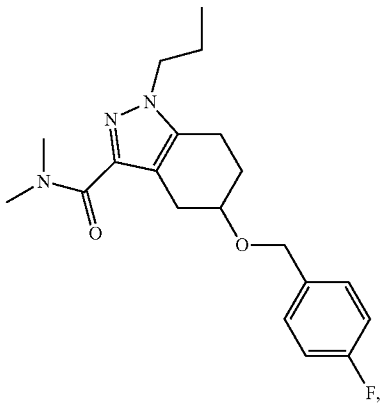
,
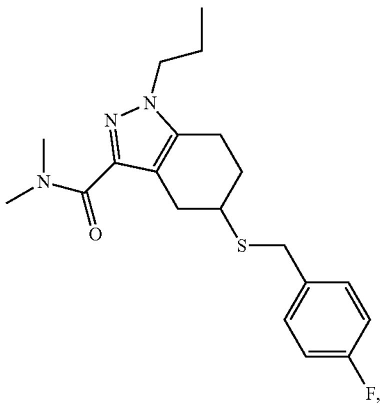
,
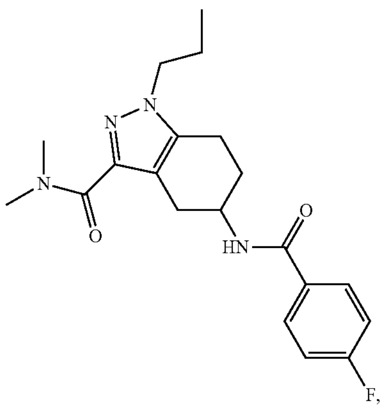
,
-continued
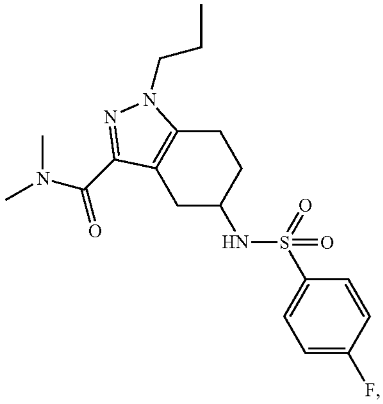
,
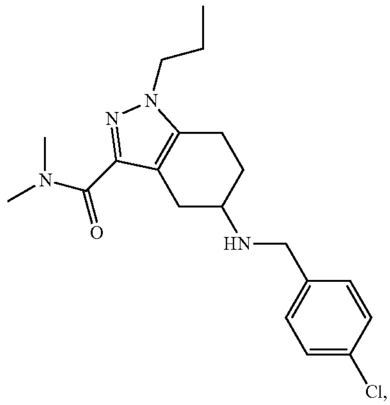
,
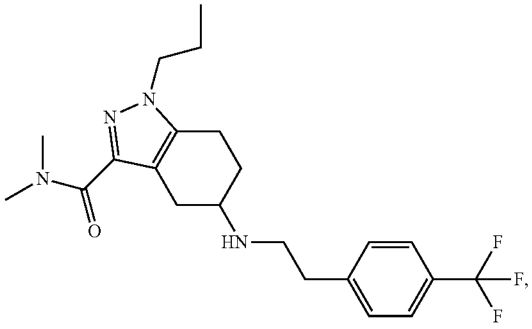
,
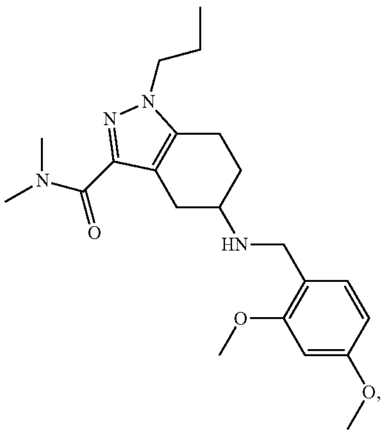
, -continued
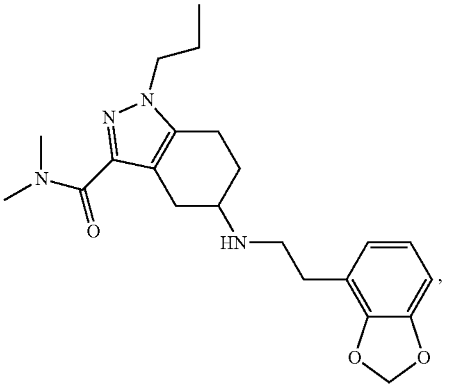
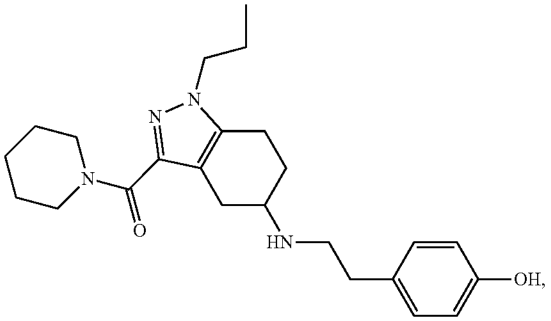
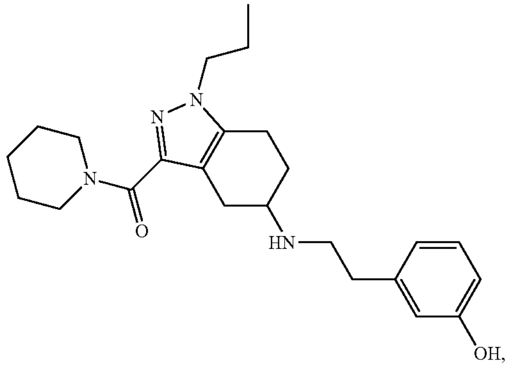
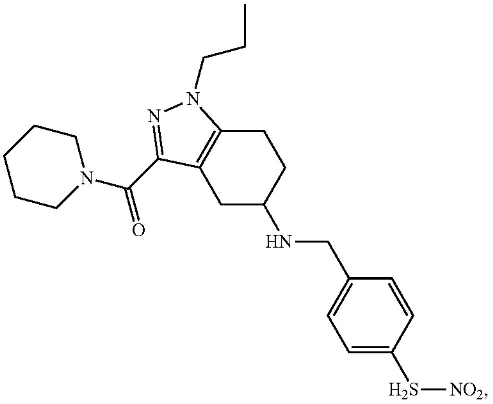
-continued
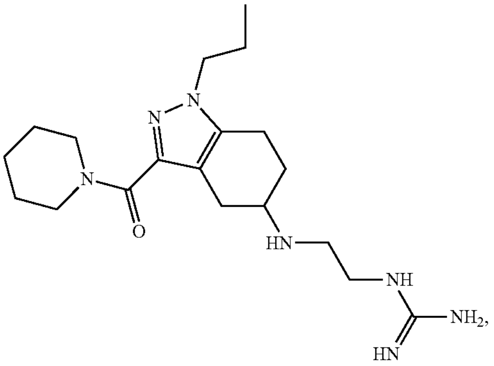
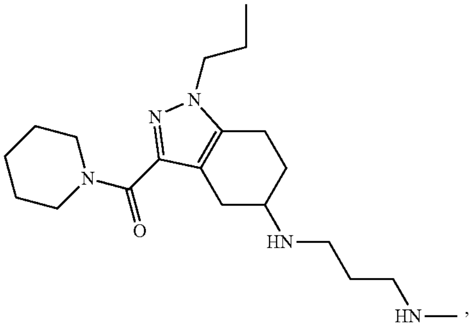
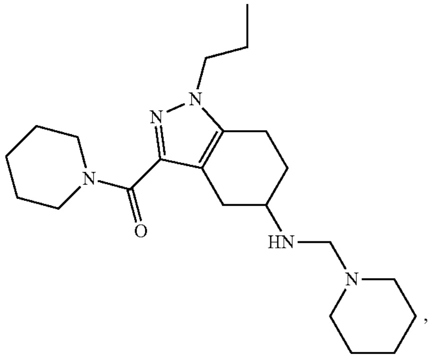
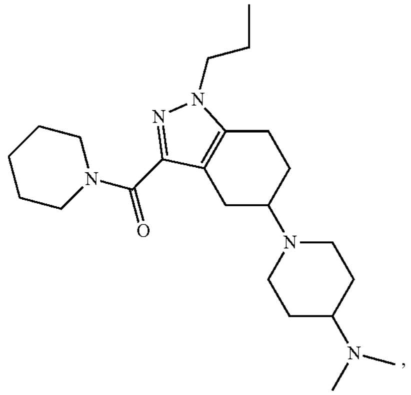

-continued
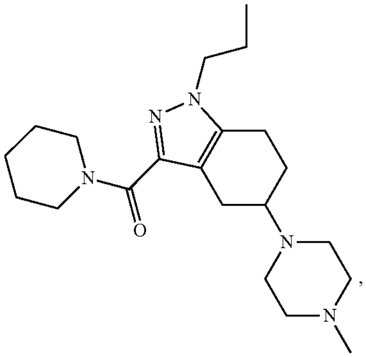
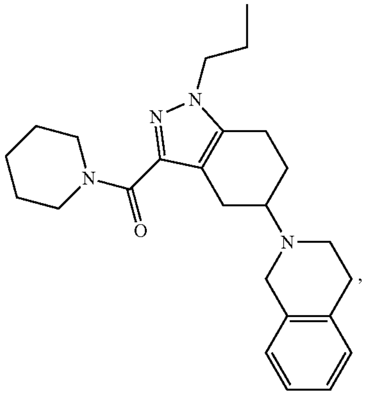
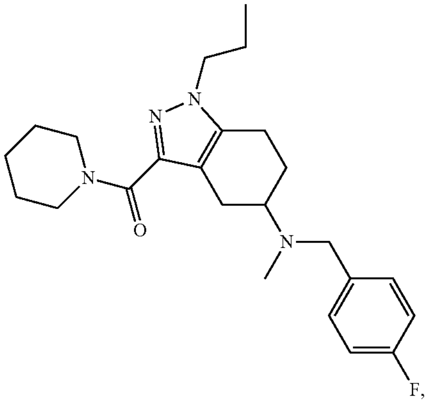
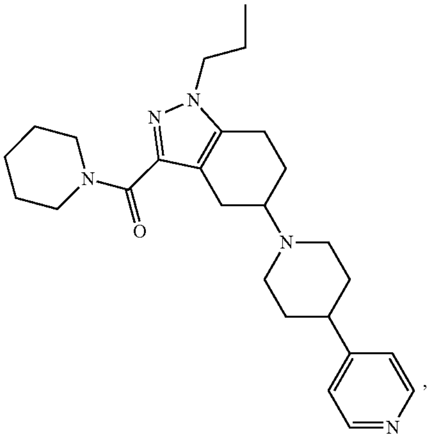
-continued
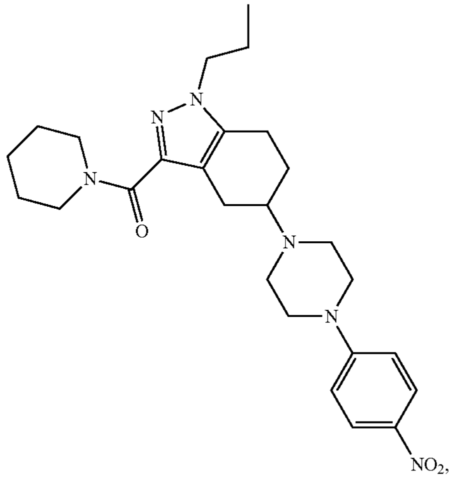
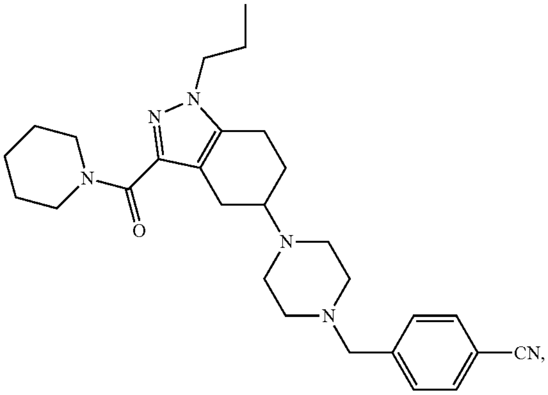
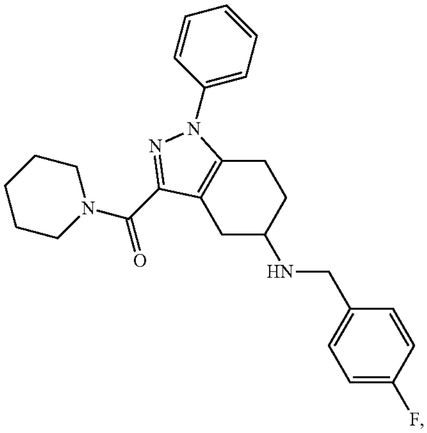
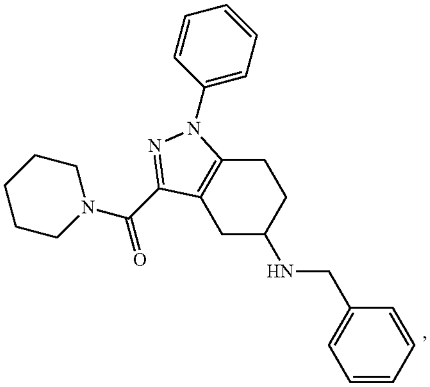

-continued
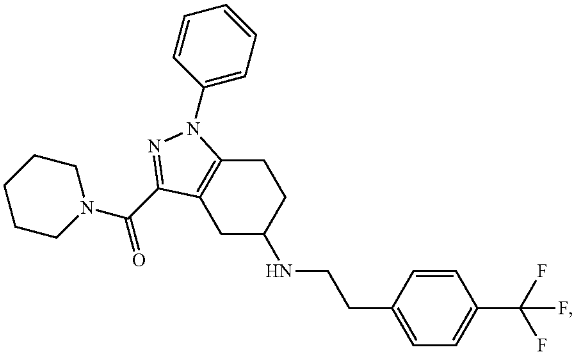
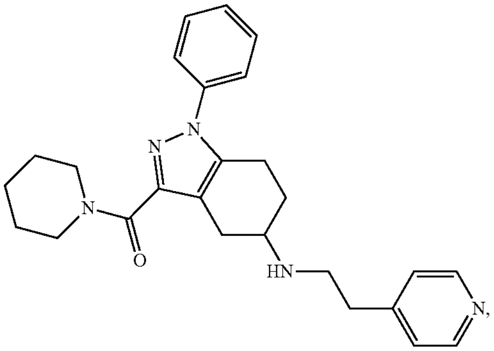
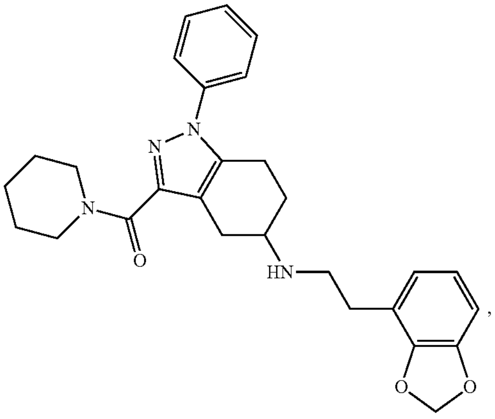
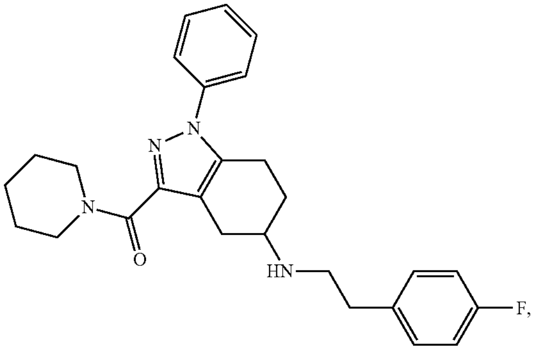
-continued
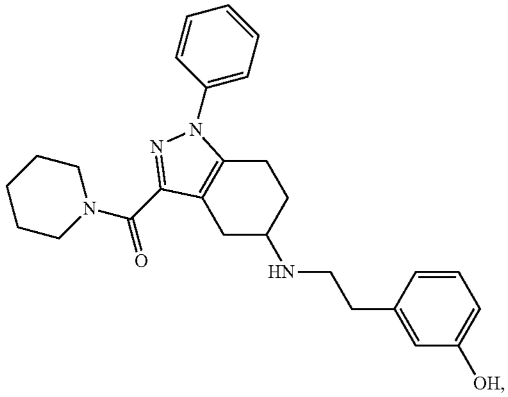
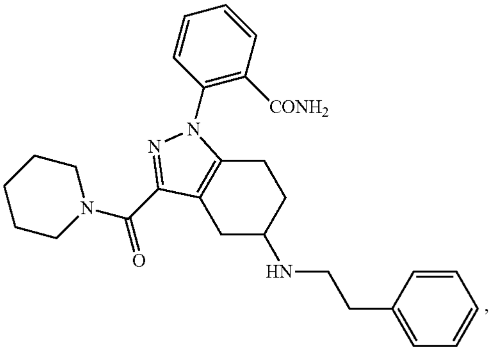
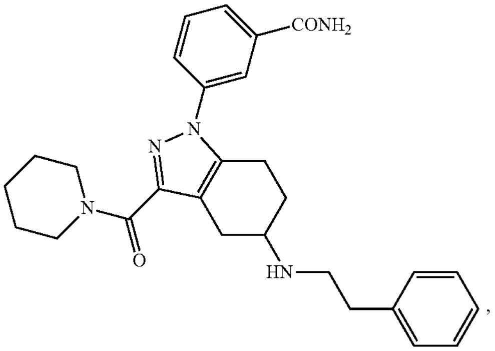
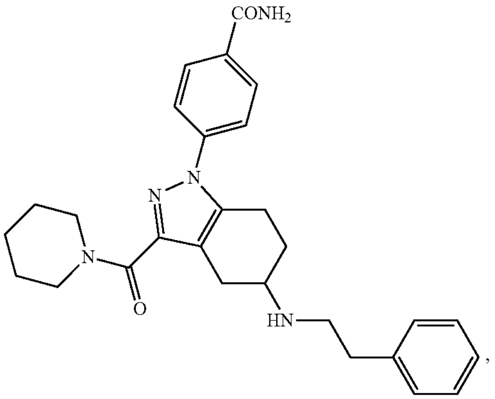

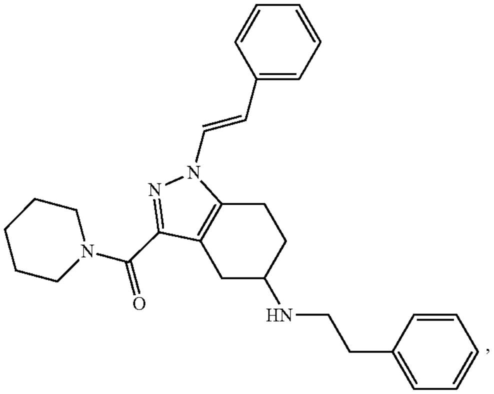
,
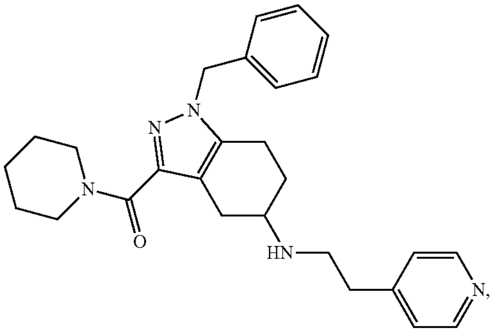 [SMILES: O=C(c1nn(Cc2ccccc2)c2c1CC(NCCc1ccncc1)CC2)N1CCCCC1]
,
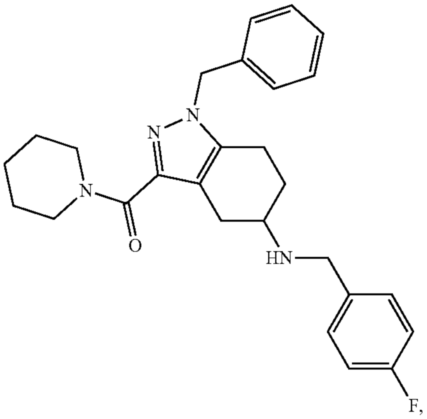
,
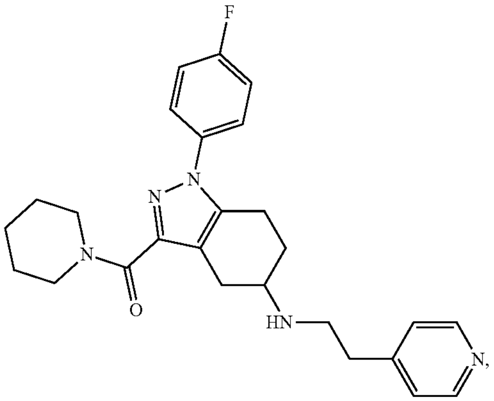
,
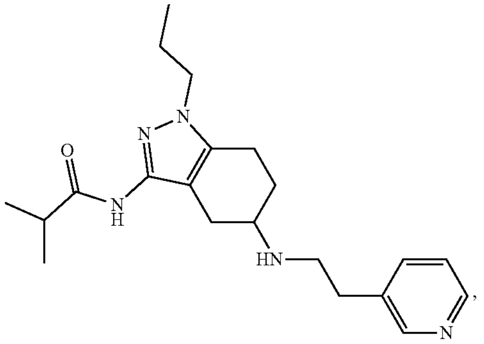
,
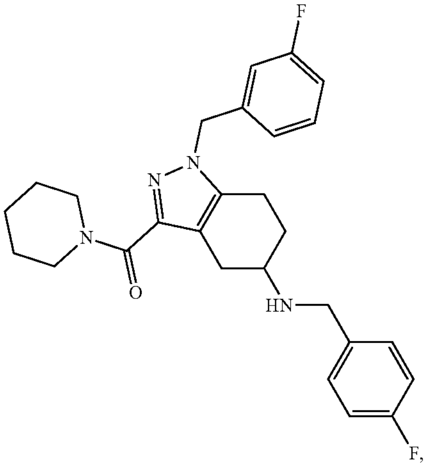
,
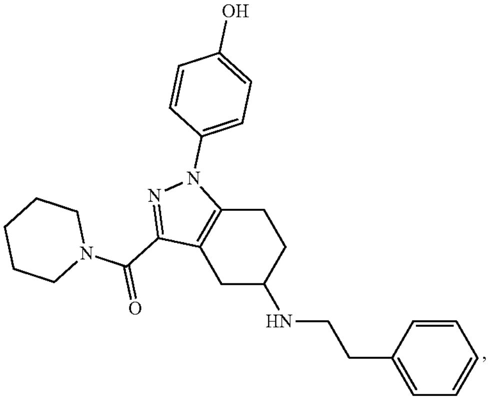
,
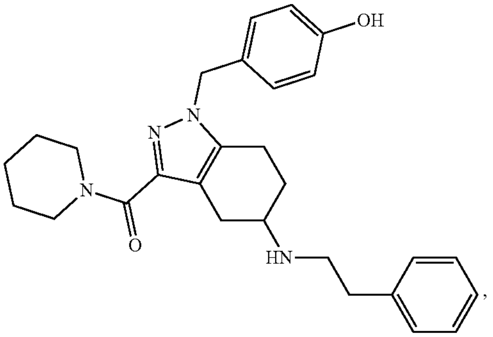
, -continued
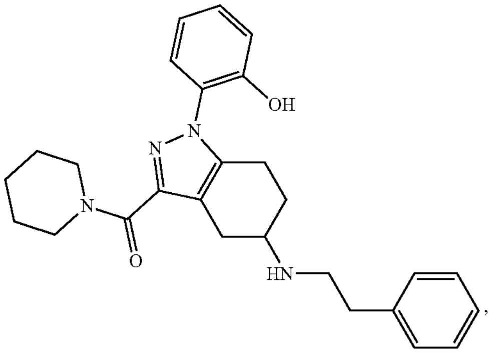
,
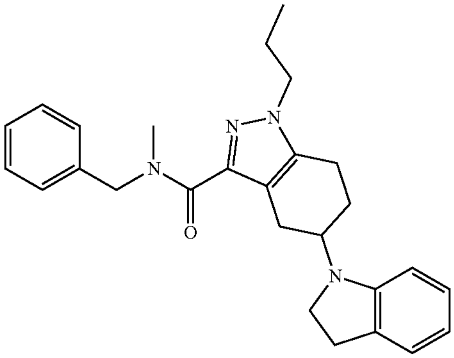
,
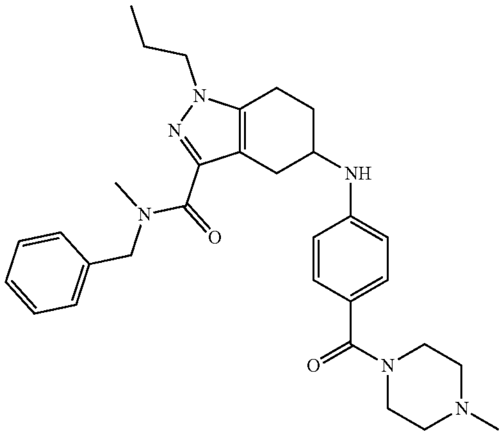
,
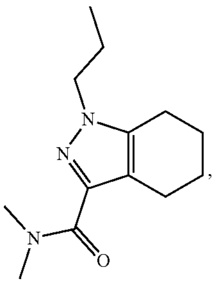
,
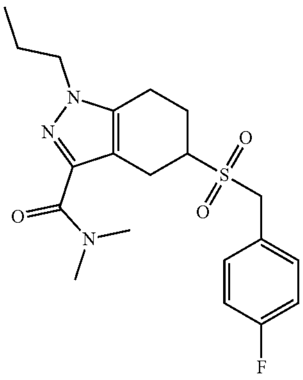
,
-continued
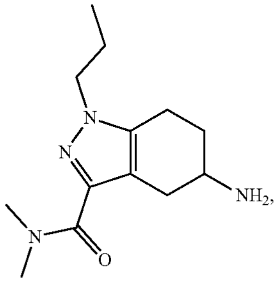
,
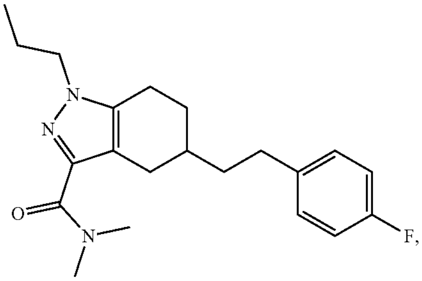
,
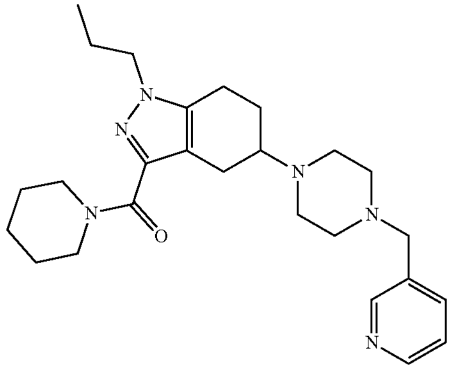
,
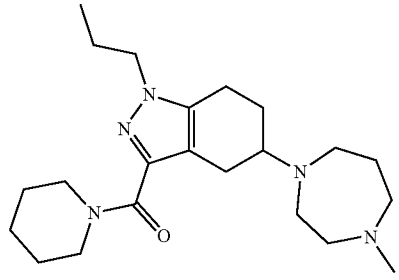
,
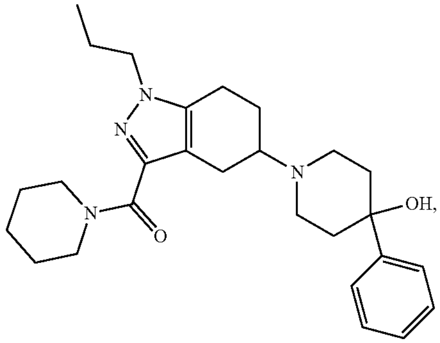
, -continued
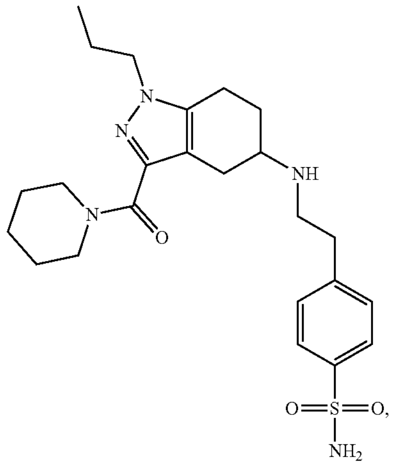
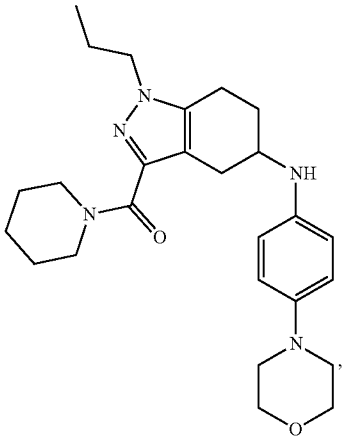
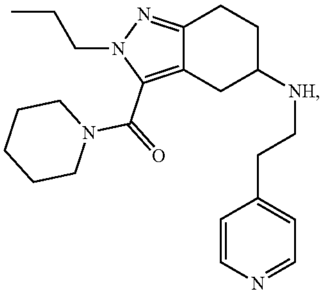
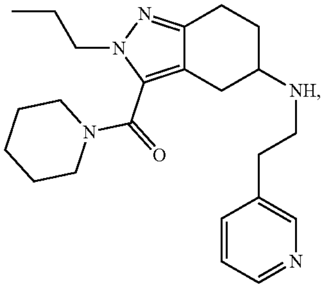
-continued
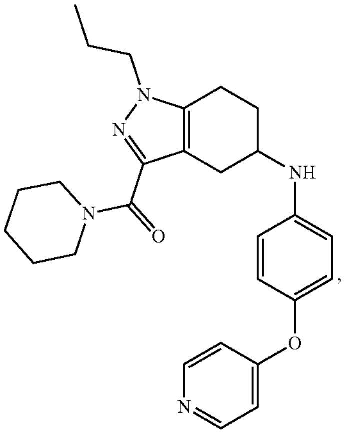
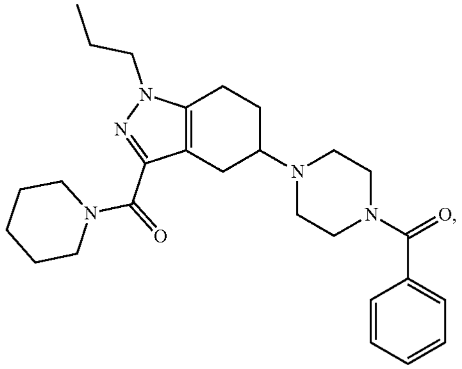
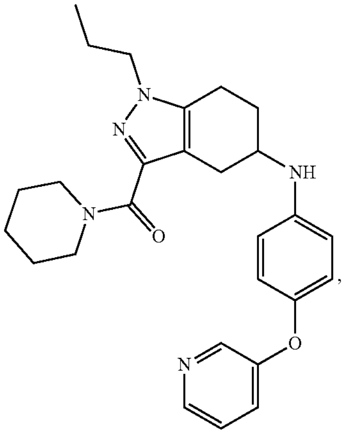
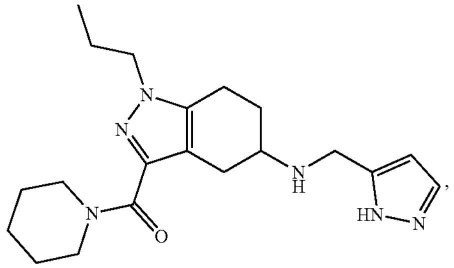

-continued
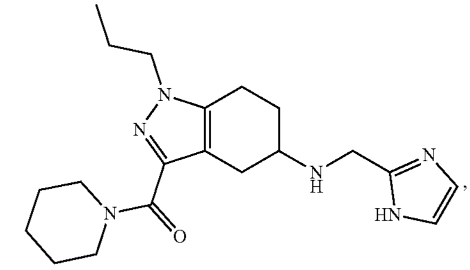,
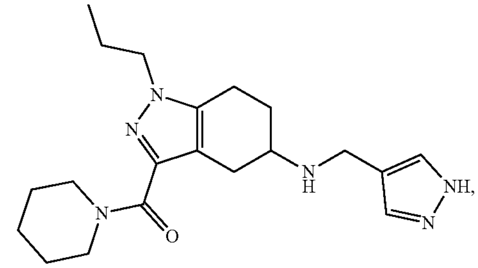,
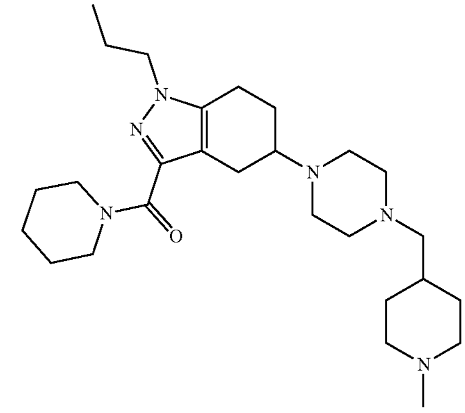,
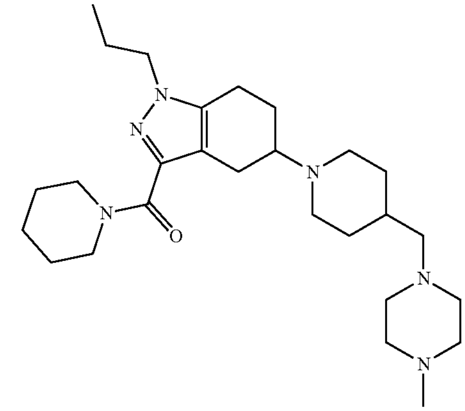,
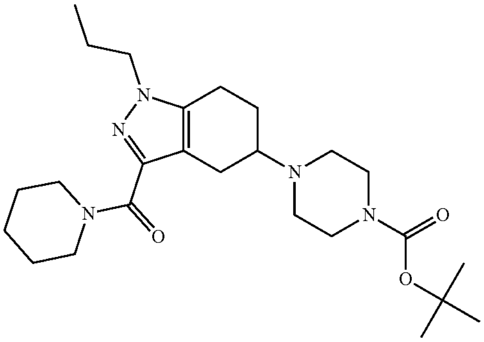,
-continued
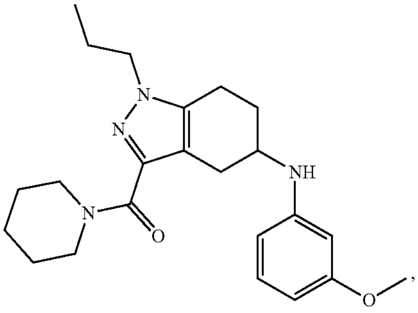,
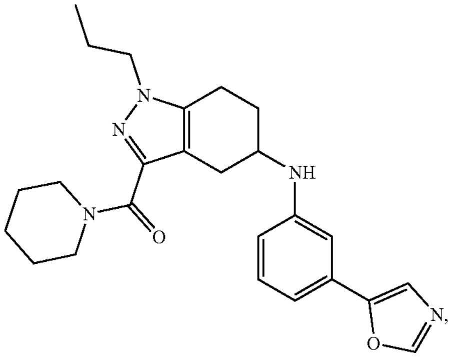,
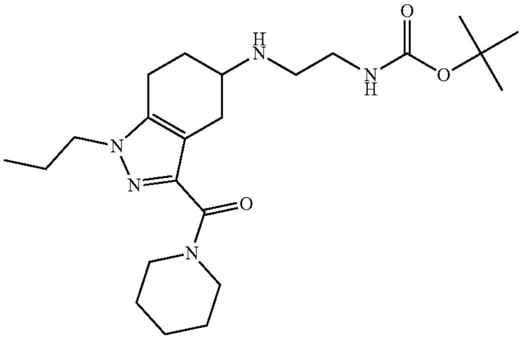,
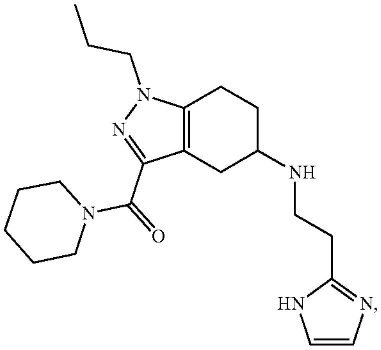,
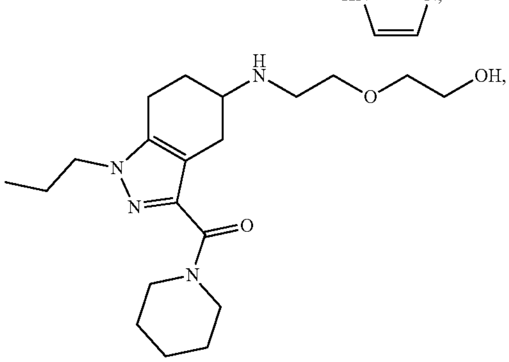, -continued
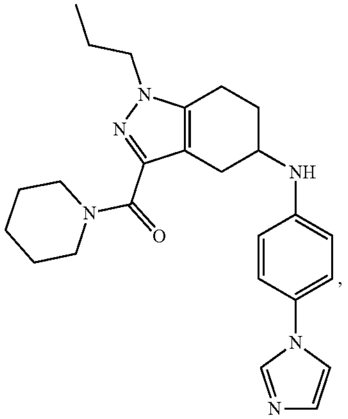
,
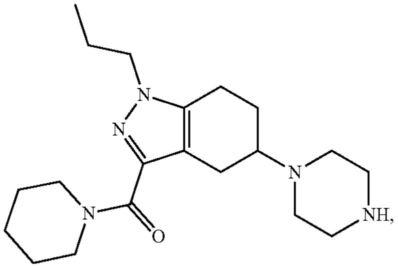
,
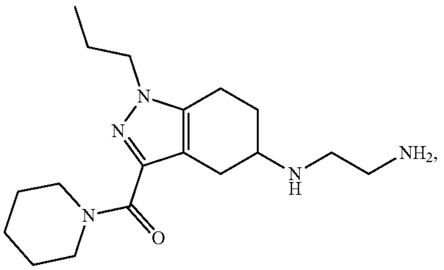
,
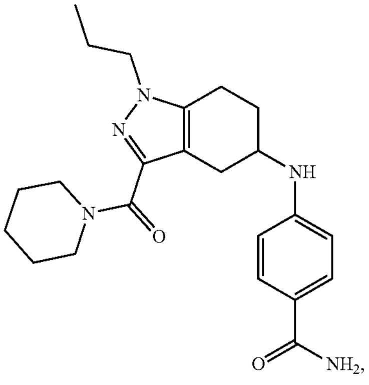
,
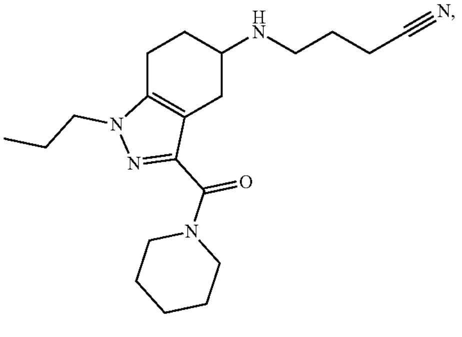
,
-continued
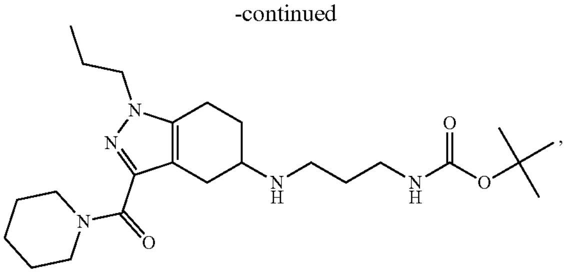
,
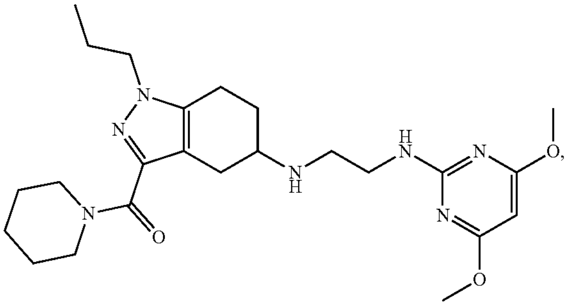
,
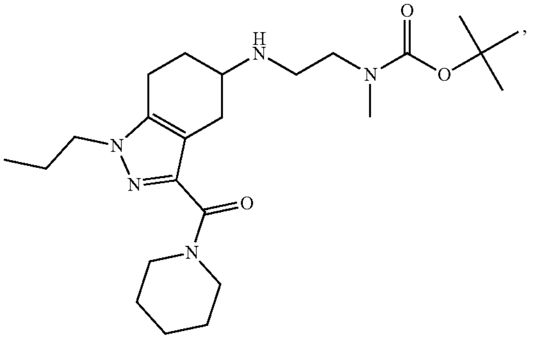
,
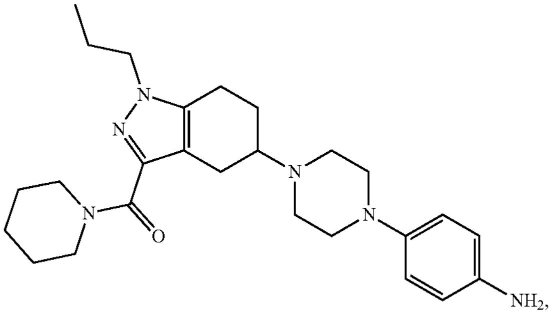
,
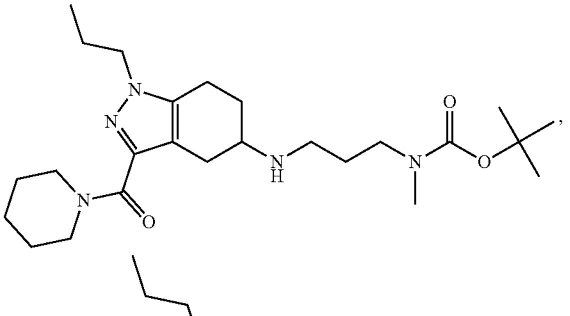
,
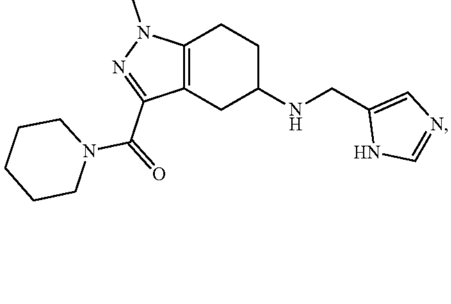
, -continued
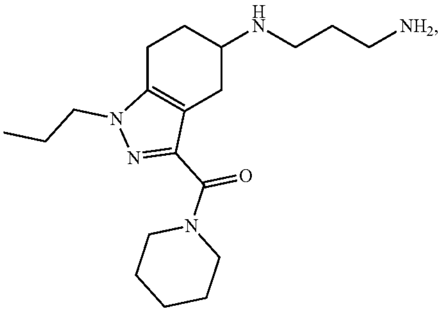
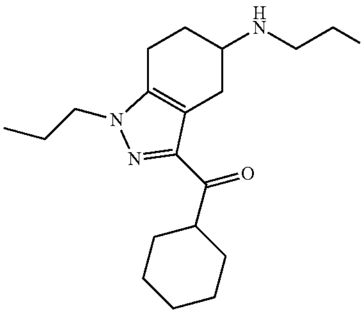
,
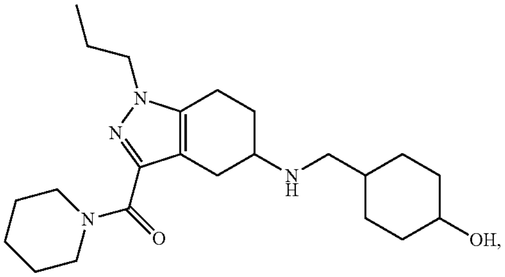
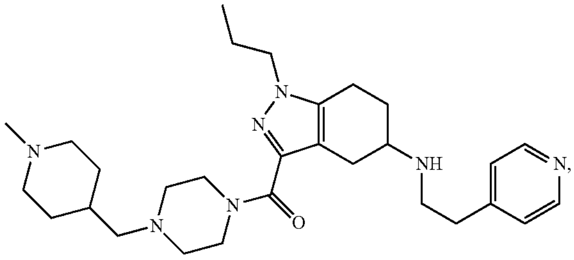
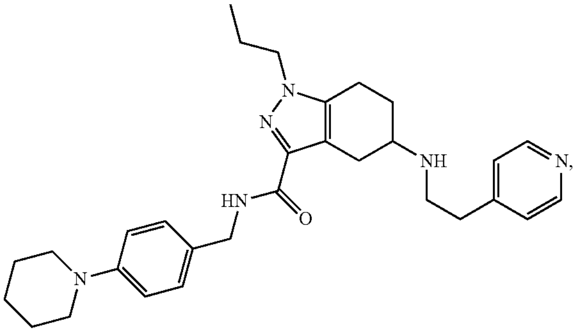
-continued
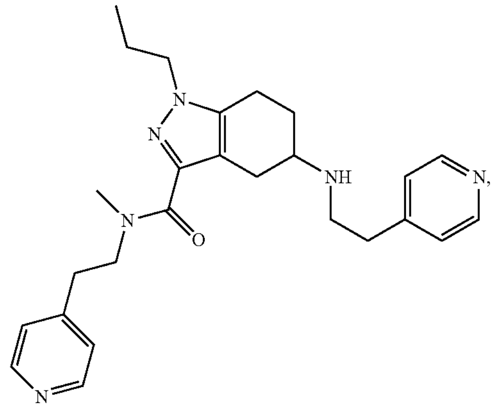
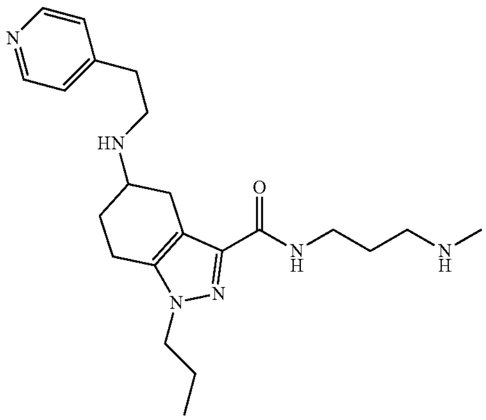
,
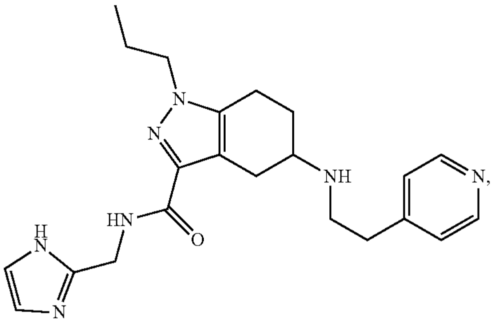
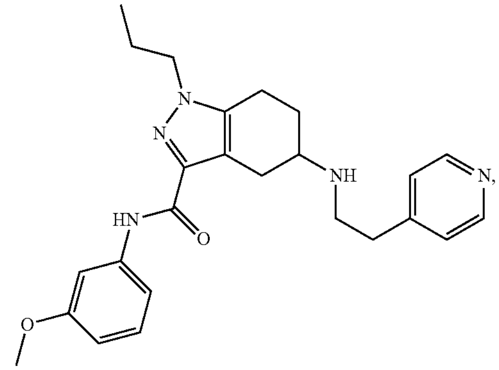

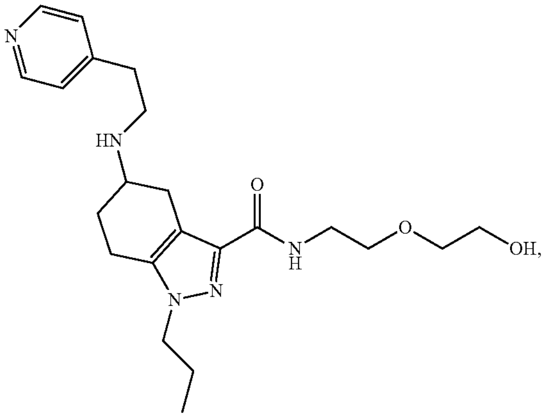
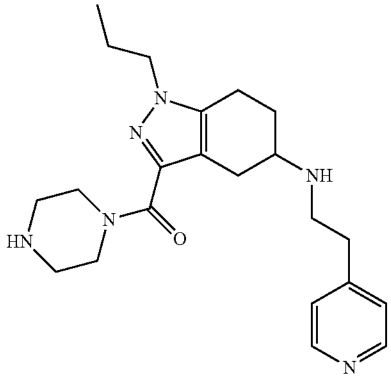
,
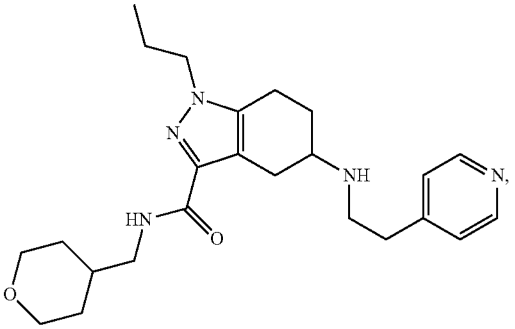
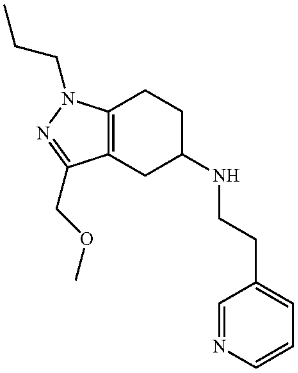
,
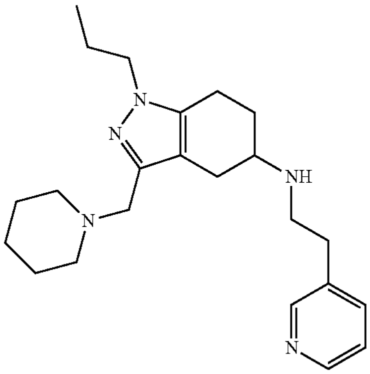
,
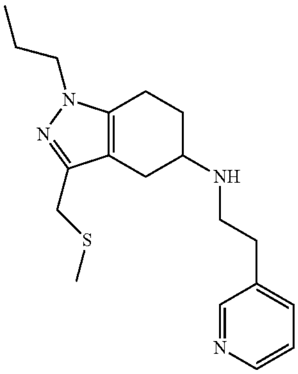
,
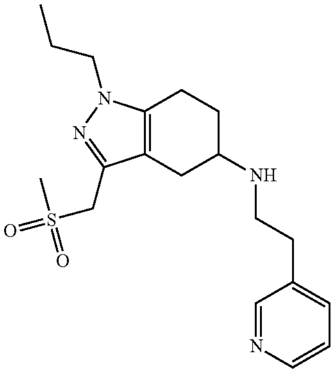
,
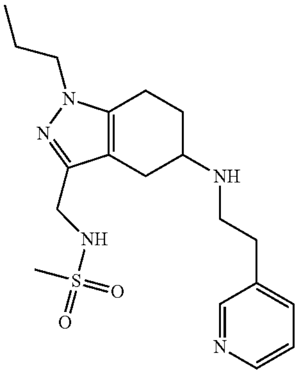
, -continued
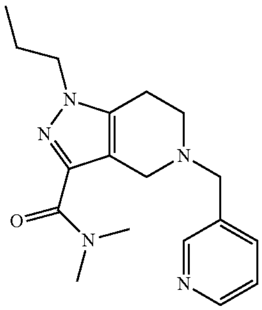
,
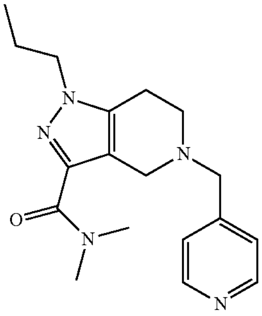
,
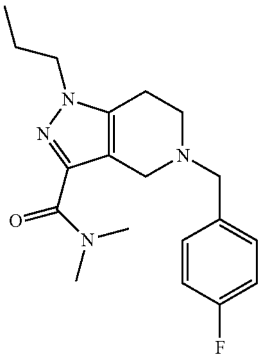
,
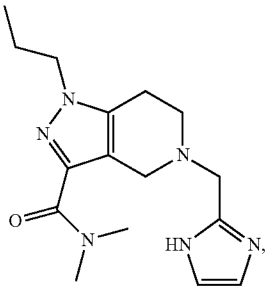
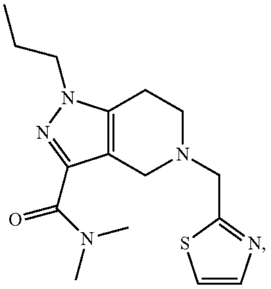
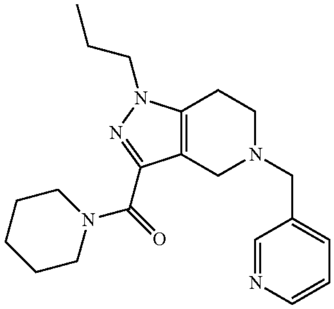
,
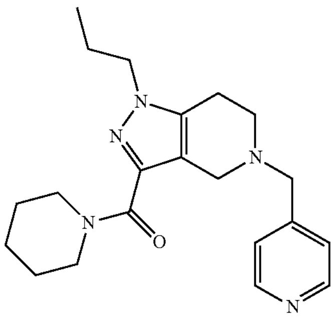
,
-continued
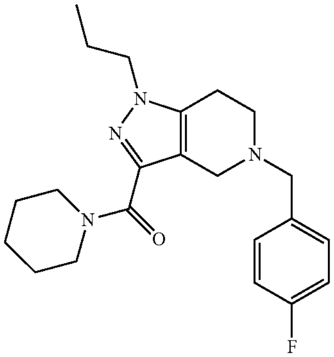
,
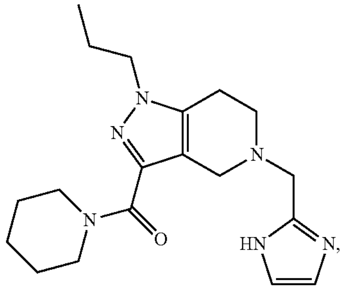
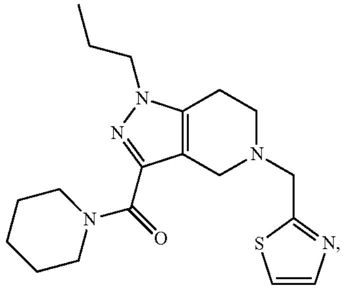
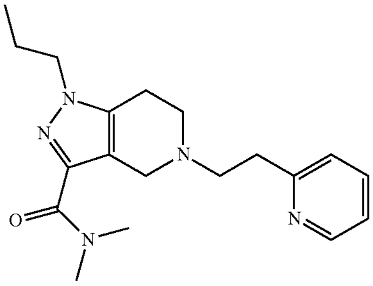
,
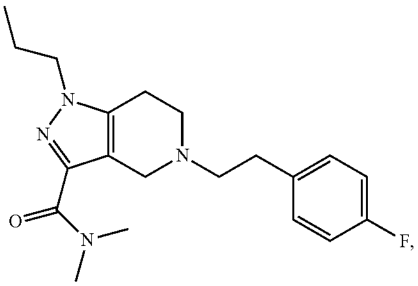

-continued
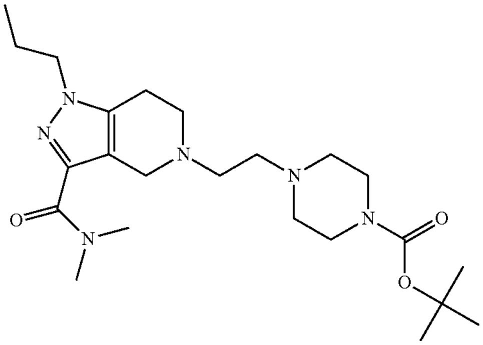
,
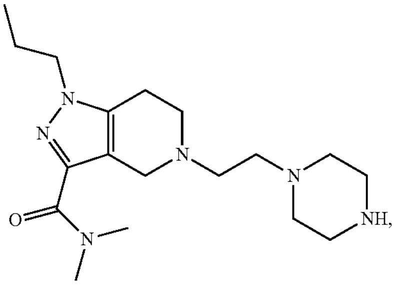
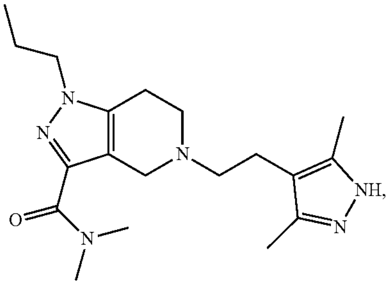
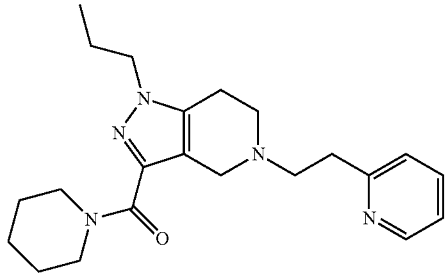
,
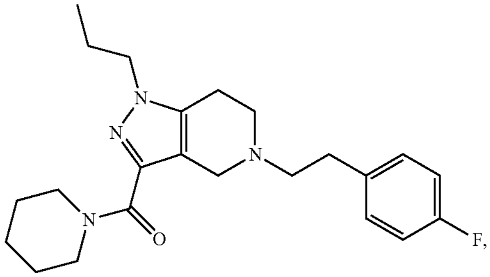
-continued
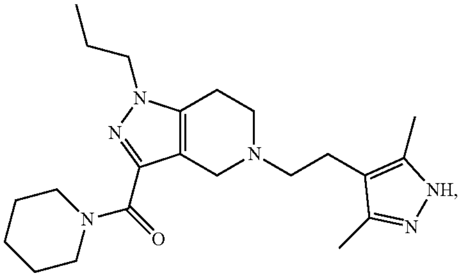
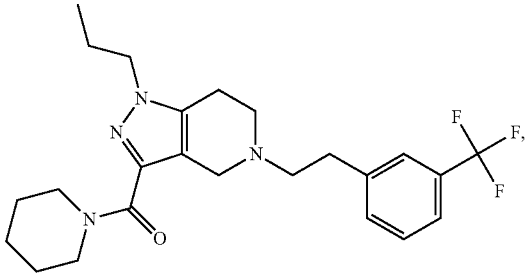
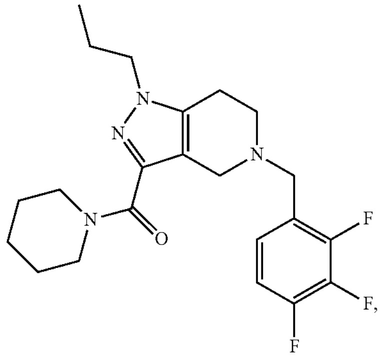
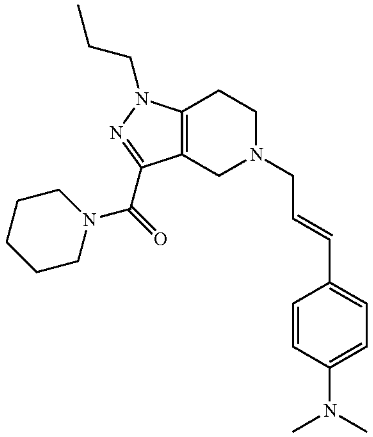
,
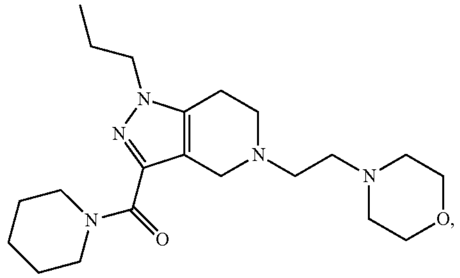

-continued
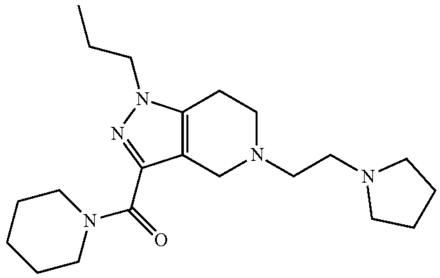
,
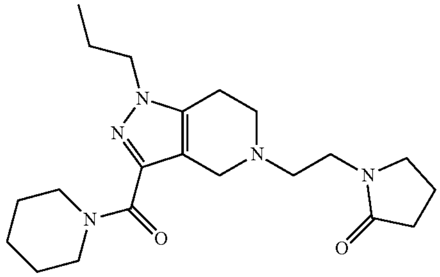
,
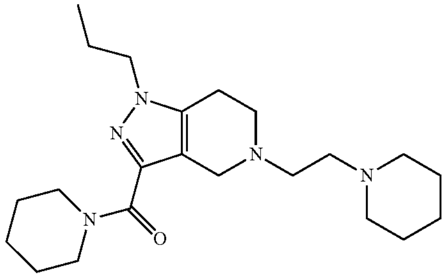
,
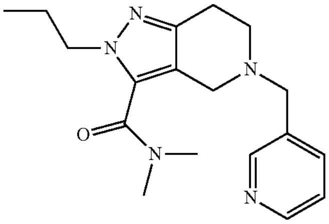
,
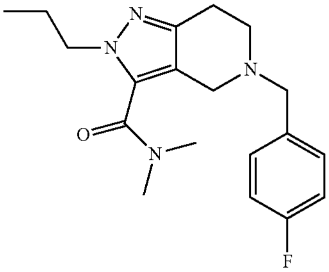
,
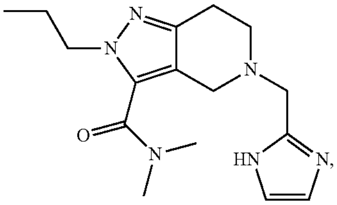
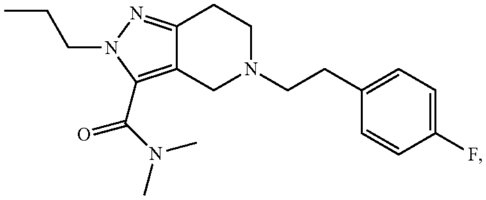
-continued
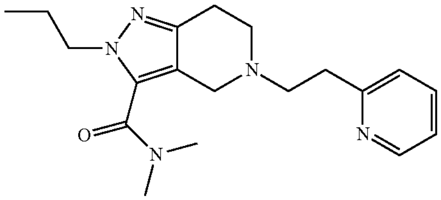
,
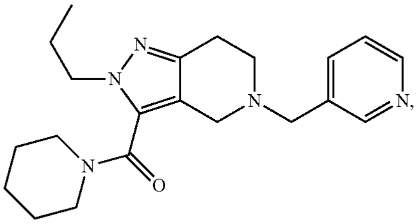
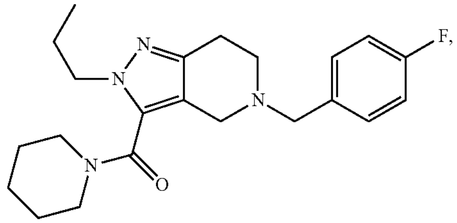
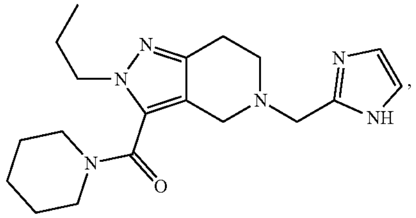
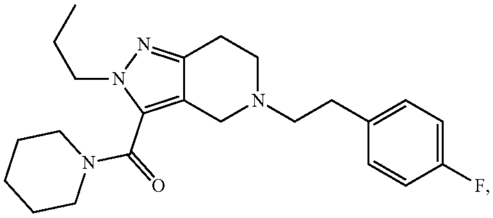
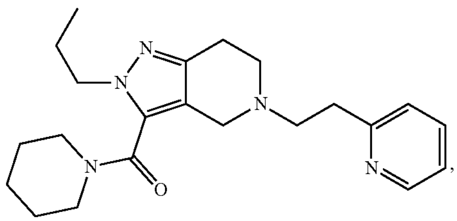
,

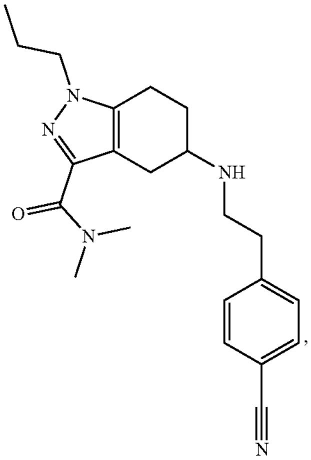
,
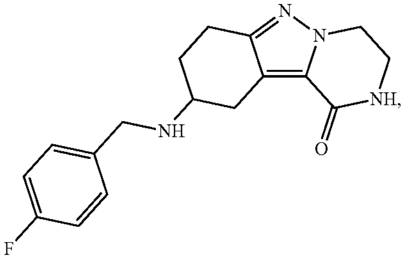
,
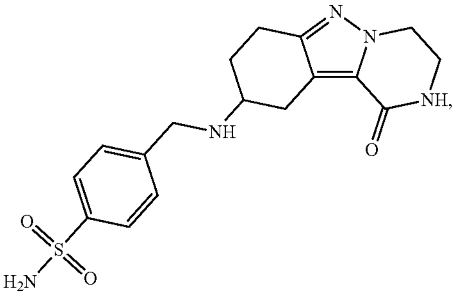
,
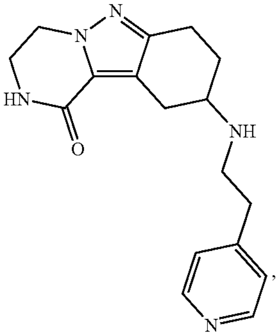
,
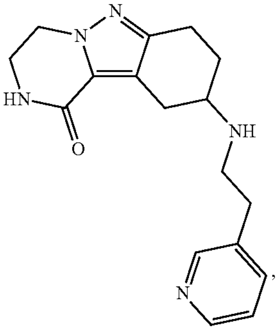
,
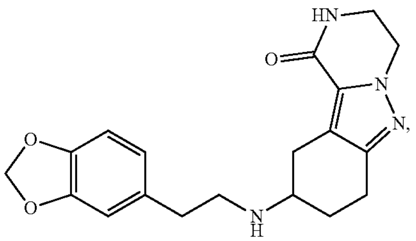
,
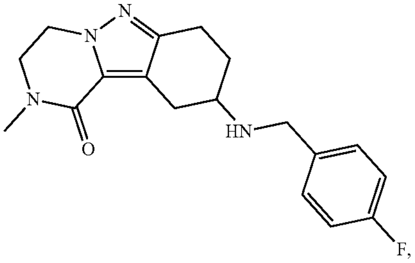
,
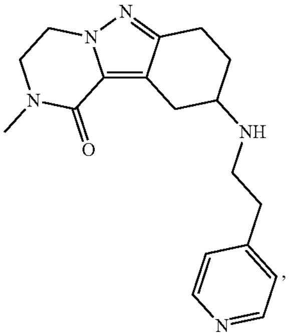
,
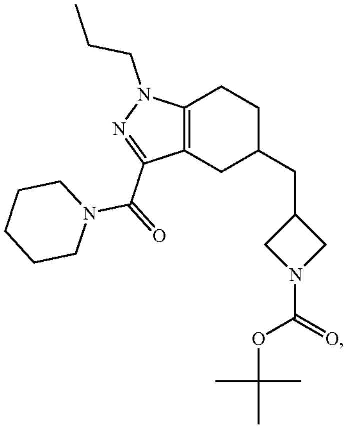
,
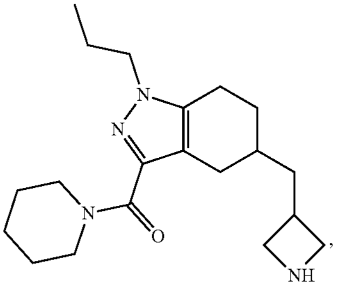
,
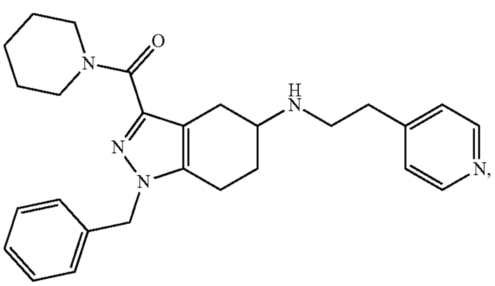
, -continued
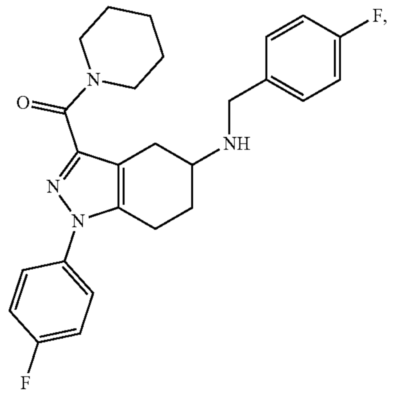
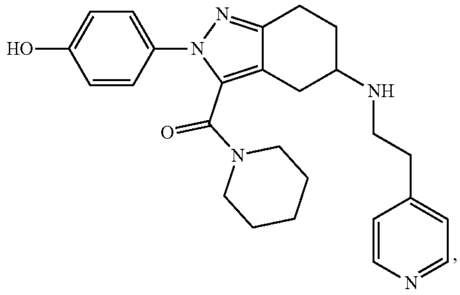
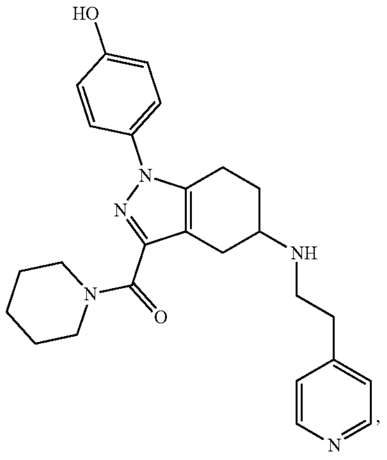
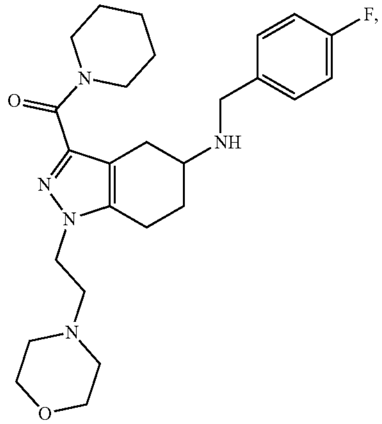
-continued
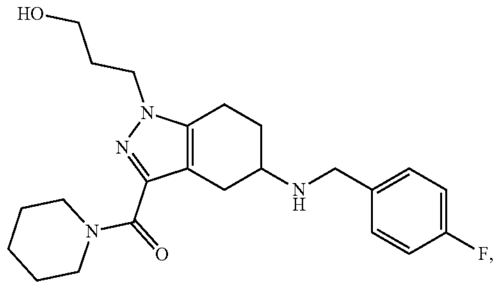
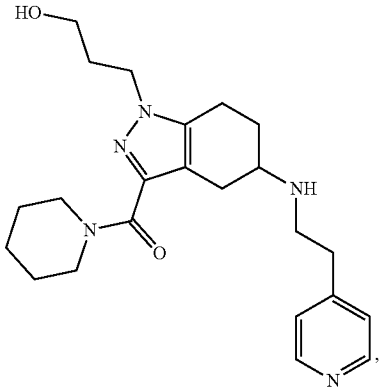
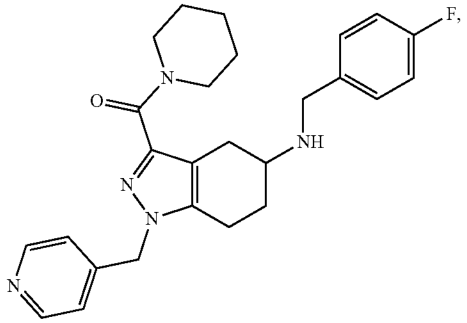
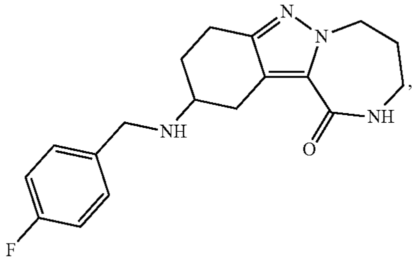
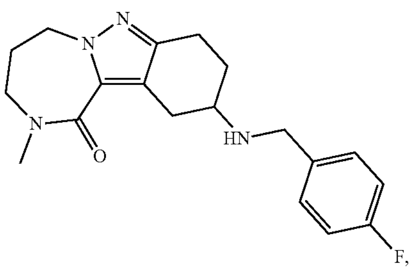 [SMILES: CN1CCCn2nc3c(c2C1=O)CC(NCc1ccc(F)cc1)CC3]

-continued
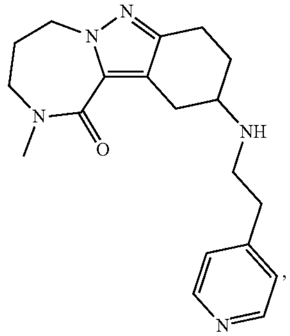
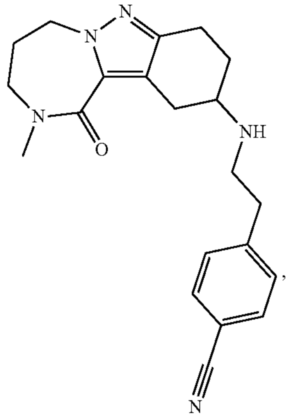
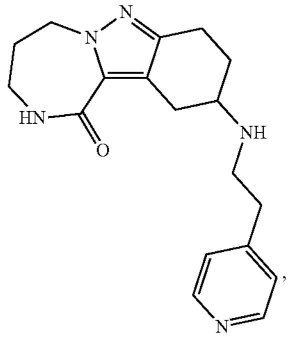
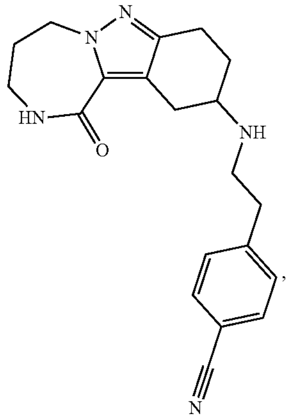
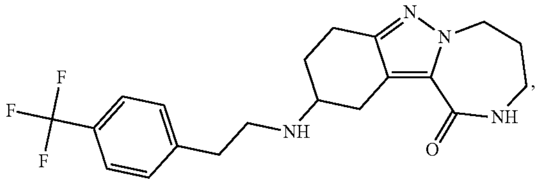
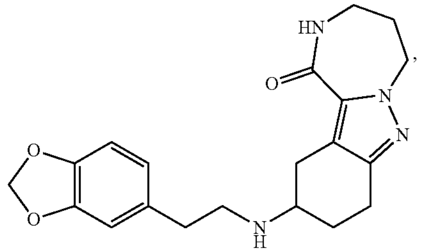
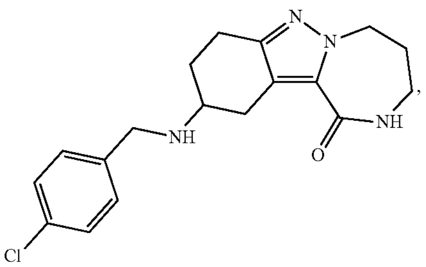
-continued
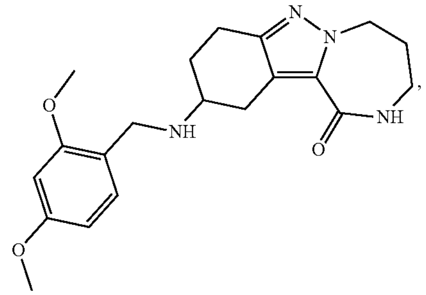
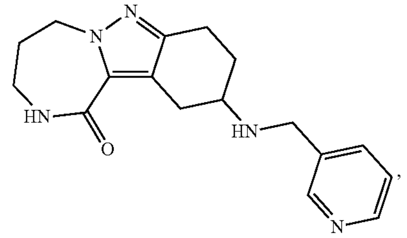
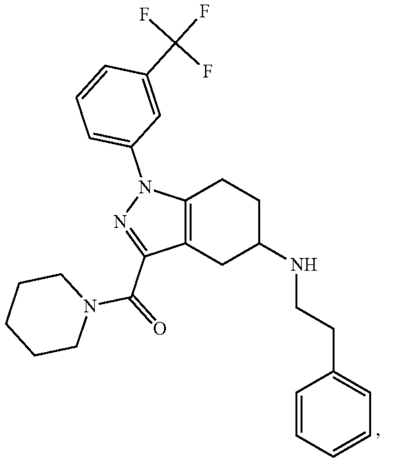
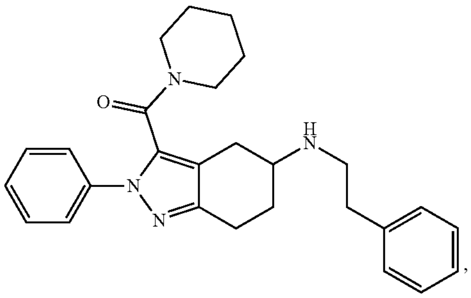

-continued
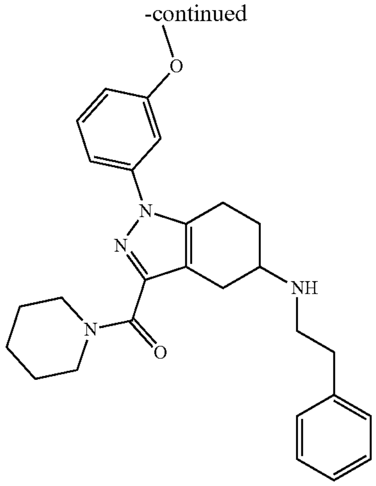
,
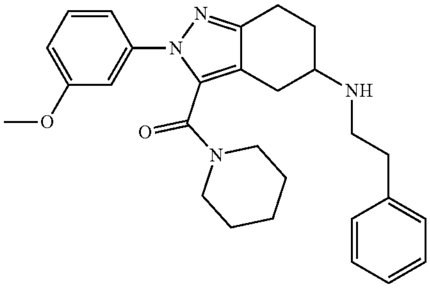
,
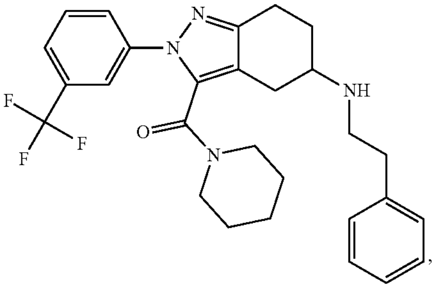
,
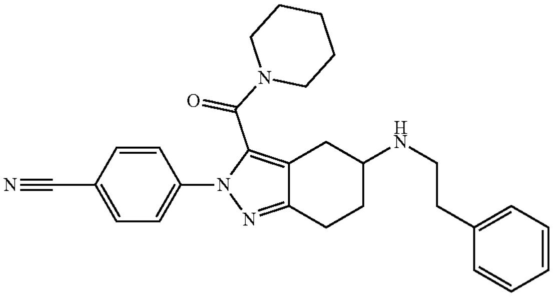
,
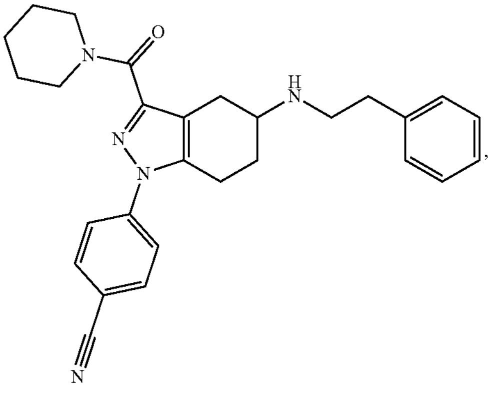
,
-continued
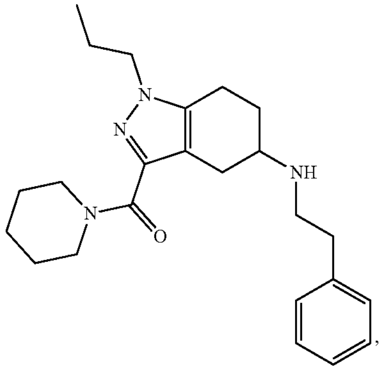
,
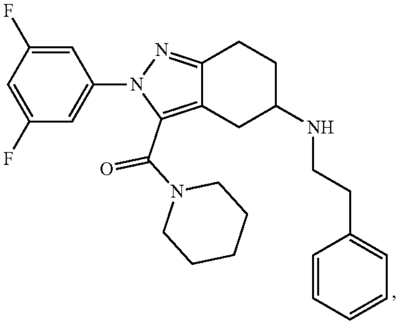
,
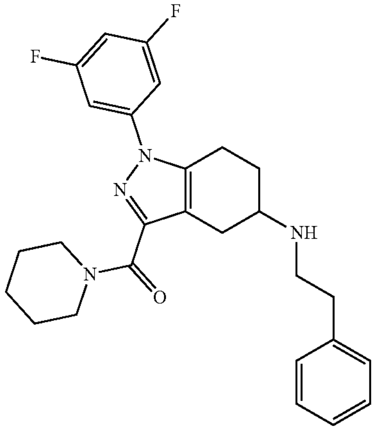
,
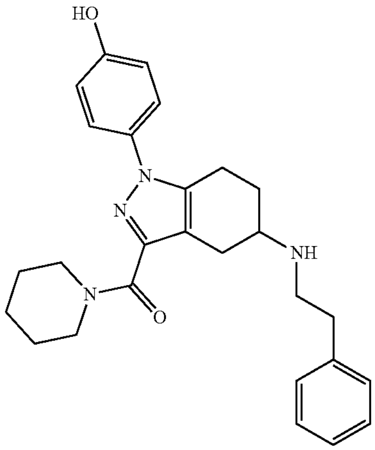
, -continued
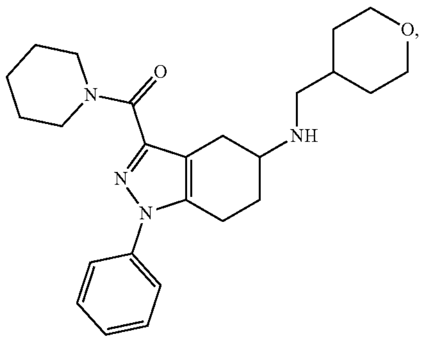
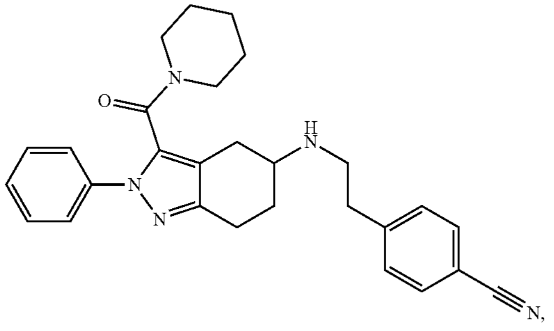
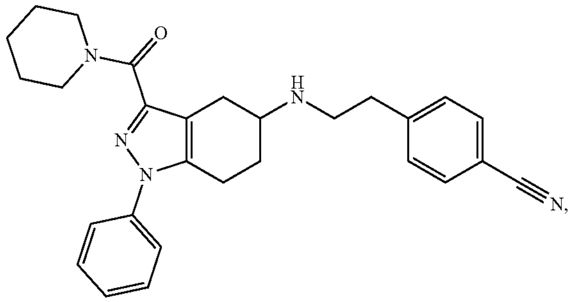
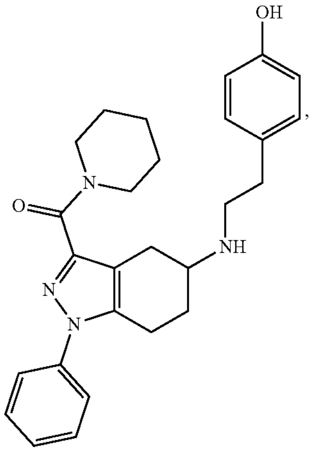
-continued
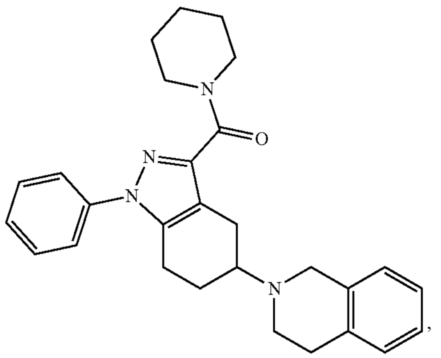
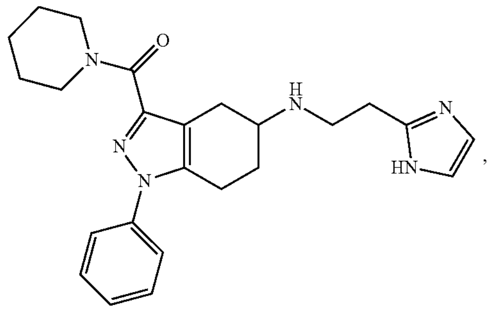
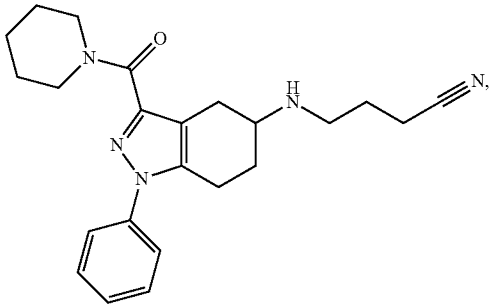
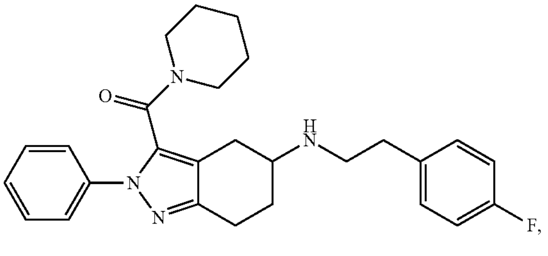

-continued
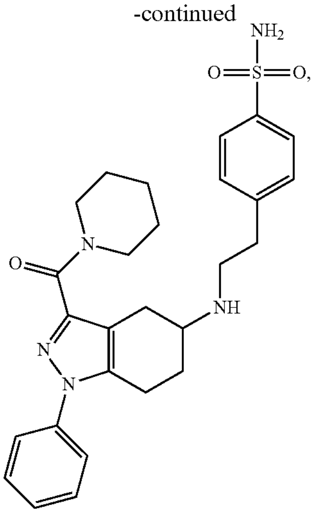
and
-continued
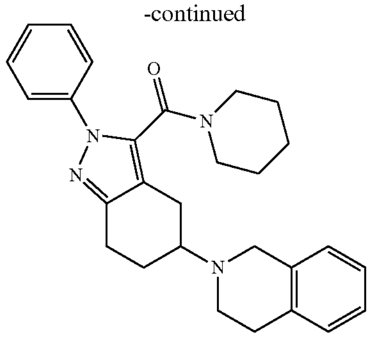
,
or a pharmaceutically acceptable salt, solvate, or prodrug thereof, and a pharmaceutically acceptable carrier.
* * * * *